US011066447B2

(12) United States Patent
Wuts et al.

(10) Patent No.: US 11,066,447 B2
(45) Date of Patent: Jul. 20, 2021

(54) AUREOBASIDIUM DERIVATIVES AND METHODS OF SYNTHESIS

(71) Applicant: AureoGen Biosciences, Inc., Kalamazoo, MI (US)

(72) Inventors: Peter Wuts, Kalamazoo, MI (US); Ake P. Elhammer, Kalamazoo, MI (US)

(73) Assignee: AueroGen Biosciences, Inc., Kalamazoo, MI (US)

( * ) Notice: Subject to any disclaimer, the term of this patent is extended or adjusted under 35 U.S.C. 154(b) by 38 days.

(21) Appl. No.: 16/323,601

(22) PCT Filed: Aug. 8, 2017

(86) PCT No.: PCT/US2017/045851
§ 371 (c)(1),
(2) Date: Feb. 6, 2019

(87) PCT Pub. No.: WO2018/031521
PCT Pub. Date: Feb. 15, 2018

(65) Prior Publication Data
US 2019/0292225 A1    Sep. 26, 2019

Related U.S. Application Data

(60) Provisional application No. 62/371,936, filed on Aug. 8, 2016.

(51) Int. Cl.
*C07K 11/02* (2006.01)
*A61K 38/00* (2006.01)
*A61P 31/10* (2006.01)
*A01N 43/72* (2006.01)
*A01N 43/90* (2006.01)

(52) U.S. Cl.
CPC .............. *C07K 11/02* (2013.01); *A01N 43/72* (2013.01); *A01N 43/90* (2013.01); *A61P 31/10* (2018.01); *A61K 38/00* (2013.01)

(58) Field of Classification Search
None
See application file for complete search history.

(56) References Cited

U.S. PATENT DOCUMENTS

2014/0024578 A1* 1/2014 Wuts ...................... A61P 43/00
514/3.6

FOREIGN PATENT DOCUMENTS

| EP | 0510271 | 10/1992 | |
|----|---------|---------|---|
| EP | 0581429 | 2/1994 | |
| EP | 0687686 | 12/1995 | |
| WO | 2012/134989 | 10/2012 | |
| WO | WO-2012134989 A1 * | 10/2012 | ............. C07K 11/02 |

OTHER PUBLICATIONS

Ikai, Katsushige, et al., "Structures of Aureobasidins B to R", The Journal of Antibiotics, Japan Antibiotics Research Association, vol. 44, No. 11, Nov. 1, 1991, pp. 1187-1198.
International Search Report for PCT/US2012/030269 dated Jul. 6, 2012.
Kurome, Toru, et al., "Structure-Activity Relationship of Antifungal Aureobasidin A, Inhibitor of Sphingolipid Biosynthesis: Synthesis of New Active Aureobasidins against Aspergillus fumigatus", Peptide Science, vol. 36, Dec. 31, 1999, pp. 197-200.
Meyer, Falco-Magnus, et al., "Functionalization of Aromatic Amino Acids via Direct C-H Activation: Generation of Versatile Building Blocks for Accessing Novel Peptide Space", Organic Letters, vol. 12, No. 17, Sep. 3, 2010, pp. 3870-3873.
Tiberghien, Françoise, et al. "Aureobasidins: Structure-Activity Relationships for the Inhibition of the Human MDR1 P-Glycoprotein ABC-Transporter", Journal of Medicinal Chemistry, vol. 43, No. 13, 200-06-01, pp. 2547-2556.

\* cited by examiner

*Primary Examiner* — Julie Ha
*Assistant Examiner* — Kristina M Hellman
(74) *Attorney, Agent, or Firm* — Honigman LLP; Andrew N. Weber; Jonathan P. O'Brien

(57) ABSTRACT

In general, the invention relates to AbA derivatives that are useful for treating infection. These novel compounds are shown to be effective in treating various fungal infections. The invention also provides pharmaceutically acceptable compositions comprising said compounds and methods of using the compositions in the treatment of various fungal infections.

30 Claims, 66 Drawing Sheets

AUREOBASIDIUM DERIVATIVES AND METHODS OF SYNTHESIS

CROSS REFERENCE TO RELATED APPLICATION

This patent application is the U.S. national phase of PCT application no. PCT/US2017/045851, filed on Aug. 8, 2017 which claims priority to U.S. Provisional Patent Application No. 62/371,936 filed on Aug. 8, 2016. The contents of the aforementioned applications are hereby incorporated by reference in their entireties.

FIELD OF THE INVENTION

The present invention provides novel broad spectrum antibiotic compounds, e.g., *Aureobasidium* A derivatives, that are useful for preventing and/or treating infections.

BACKGROUND

As the population of cancer, transplantation, abdominal surgery, and other immunocompromized patients continues to grow, there is a concomitant increase in the number of patients needing treatment for systemic fungal infections. Traditionally, systemic mycoses antibiotics are dominated by just three classes of drugs, polyenes, most notably amphotericin B and Nystatin; azoles, such as Flucanazole, Itraconazole, Ketoconazole, and Voriconazole; and echinocandins, such as Caspofungin, Micafungin, and Anidulafungin. Each of these drug classes possess significant limitations in terms of efficacy, toxicity, drug-drug interactions, and the generation of resistant organisms (e.g., Barrett, 2002; Fishman, 2002; Girmenia and Martino, 2003; Gupta and Thomas, 2003; Park et al., 2005; Pavie et al., 2005; Balashov et al., 2006; Perlin et al., 2007; Choi et al., 2008). Consequently, there is an urgent need for new drugs with novel modes of action to treat of systemic mycoses.

The *Aureobasidium pullulans* strain BP-1938 produces a 9-amino acid cyclic peptide, referred to as Aureobasidin A ("AbA"). This compound is a potent, fungicidal drug that is very well tolerated in animals and humans (Takesako et al., 1993). AbA also has a unique mode of action that targets inositol phosphorylceramide (IPC) synthase; an enzyme in the fungal sphingolipid biosynthesis pathway. Attempts to develop spontaneous resistance mutants to AbA has, to date, been unsuccessful, suggesting that resistance development in clinical settings with this compound will be very slow (Heidler et al., 1995; Hashida-Okado et al., 1996). Unfortunately, native AbA does not have a perfect target spectrum: it is very efficacious against virtually all *Candida* species, including *C. albicans*. It is also efficacious against most *Cryptococcus* species, including *C. neoformans*. However, it shows little activity towards most Aspergilli, and most notably *A. fumigatus*. Since *Candida* and *Aspergillus* are the two most common human pathogens and broad-spectrum antibiotics are preferred in the clinic, AbA's lack of efficacy against aspergilli has hampered its development into a marketed drug (Takesako et al., 1993). The reason for *A. fumigatus*' resistance to AbA is not that the target enzyme, inositol phosphorylceramide (IPC) synthase in *A. fumigatus* is resistant to the compound, but rather that this organism has pumps capable of efficiently clearing the drug (Ogawa et al., 1998; Zhong et al., 2000). Thus, the development of AbA derivatives capable of avoiding or blocking the *A. fumigatus* pumps would greatly enhance the development potential and marketability of the compound.

A small number of AbA derivatives have been prepared using recombinant techniques or synthetic chemistry (reviewed in Kurome and Takesako, 2000) and evaluation of these compounds has demonstrated that AbA's pharmacological properties can be altered significantly by modifying and/or exchanging amino acids in the sequence. Most importantly, AbA derivatives have been generated that appear to have similar antifungal activity against *A. fumigatus* and *C. albicans* (Kurome and Takesako, 2000). Specifically, substitution of the N-methyl-L-phenylalanine residue at position 4 with a N-methyl-D-alanine or a sarcosine residue results in a compound with significant activity against *A. fumigatus*; and combining this substitution with substitution of the L-phenylalanine residue at position 3 with derivatized L-tyrosine, phenylalanine or alanine residues, results in compounds with *A. fumigatus* minimum inhibitory concentrations (MICs) in the single digit microgram/ml range. Importantly, while gaining considerable activity against *A. fumigatus*, these compounds retain their activity against *C. albicans* and *Cryptococcus neoformans*. Nonetheless, there is a need for additional AbA derivatives that can be formulated into drug products for the treatment of fungal infections.

SUMMARY OF THE INVENTION

In general, the invention relates to novel AbA derivatives that are useful for treating infection and amenable to further chemical elaboration. The novel compounds presented herein are useful for treating fungal infections.

One aspect of the present invention provides novel Aureobasidin derivatives that are useful for the treatment of infections (e.g., fungal infections). These compounds are generally described by a compound of Formula I-P1:

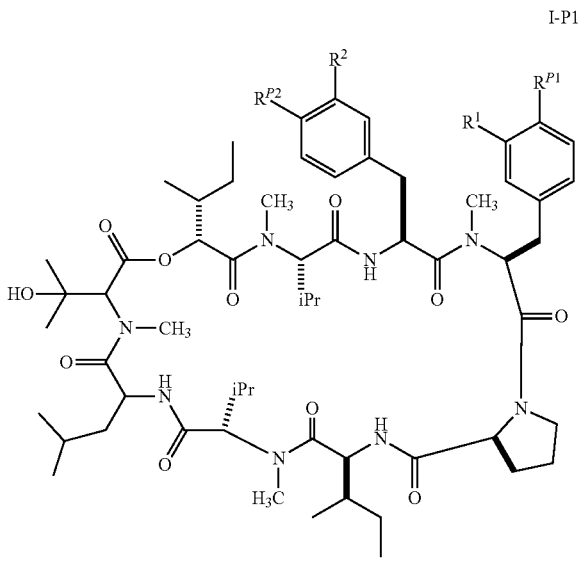

I-P1 or a pharmaceutically acceptable salt thereof, wherein

Each of $R^1$ and $R^{P1}$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^1$ and $R^{P1}$ are each independently and optionally substituted with x instances of $R^3$;

x is independently 1, 2, or 3;

Each $R^3$ is independently —$L^1$-$R^4$, wherein if $R^1$ is phenyl or a 5 to 6 membered monocyclic heteroaryl, at least one $R^3$ is other than —H;

Each $L^1$ is independently a bond or an optionally substituted branched or straight $C_{1-4}$ aliphatic chain, wherein up to two carbon atoms of $L^1$ are optionally and independently replaced by —$NR^A$—, —S—, —O—, —OC(O)—, —C(O)O—, —C(O)—, —C(O)C(O)—, —C(O)$NR^A$—, —$NR^A$C(O)—, —$NR^A$C(O)O—, —S(O)$_2NR^A$—, —$NR^A$S(O)$_2$—, —C(O)$NR^ANR^A$—, —$NR^A$C(O)$NR^A$—, —OC(O)$NR^A$—, —$NR^ANR^A$—, —$NR^A$S(O)$_2NR^A$—, —S(O)—, or —S(O)$_2$—;

Each $R^4$ is independently selected from $R^A$, halo, or —$CF_3$;

Each $R^A$ is independently selected from —H, or an optionally substituted group selected from a $C_{1-6}$ alkyl group, a 3 to 8 membered saturated, partially unsaturated, or fully unsaturated monocyclic ring having 0-3 heteroatoms independently selected from nitrogen, oxygen, or sulfur; an 8-12 membered saturated, partially unsaturated, or fully unsaturated bicyclic ring system having 0-5 heteroatoms independently selected from nitrogen, oxygen, or sulfur; or a 13 to 14 membered saturated, partially unsaturated, or fully unsaturated tricyclic ring system having 0 to 5 heteroatoms independently selected from N, O, or S, wherein each of the $C_{1-6}$ alkyl, the monocyclic ring, the bicycling ring system, or the tricyclic ring system is optionally substituted with up to 2 occurrences of $R^5$;

Each $R^5$ is independently —$L^2$-$R^6$;

Each $L^2$ is independently a bond or an optionally substituted branched or straight $C_{1-6}$ aliphatic chain, wherein up to two carbon atoms of $L^2$ are optionally and independently replaced by —$NR^B$—, —O—, —OC(O)—, —C(O)O—, —C(O)—, —C(O)C(O)—, —C(O)$NR^B$—, —$NR^B$C(O)—, or —$NR^B$C(O)O—; and Each $R^6$ is independently selected from $R^B$, halo, —$CF_3$, or Boc;

Each $R^B$ is independently selected from —H, $C_{1-3}$ alkyl, or phenyl;

Each of $R^2$ and $R^{P2}$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^2$ and $R^{P2}$ is independently and optionally substituted with x instances of $R^3$ Each $R^{P2}$ is $R^{P1}$, provided that i) at least one of $R^1$ and $R^{P1}$ is hydrogen;
ii) at least one of $R^2$ and $R^{P2}$ is hydrogen;
iii) at least one of $R^1$, $R^2$, $R^{P1}$, and $R^{P2}$ is not hydrogen;
iv) when $R^1$ is phenyl or pyridinyl, x is 1, and each of $R^2$, $R^{P1}$, and $R^{P2}$ is hydrogen, then $R^3$ is not chloro;
v) when $R^1$ is phenyl or pyridinyl, x is 1, and each of $R^2$, $R^{P1}$, and $R^{P2}$ is hydrogen, then $R^3$ is not unsubstituted phenyl;
vi) when $R^1$ is phenyl, x is 1, and each of $R^2$, $R^{P1}$, and $R^{P2}$ is hydrogen, then $R^3$ is not —N(H)C(O)$CH_3$ or —C(O)$NH_2$; and vii) when $R^1$ is furyl or thiophenyl, x is 1, and each of $R^2$, $R^{P1}$, and $R^{P2}$ is hydrogen, then $R^3$ is not —$CH_3$.

In some embodiments, $R^2$ and $R^{P2}$ are both —H.

In some embodiments, one of $R^1$ and $R^{P1}$ is hydrogen and the other is phenyl substituted with x occurrences of $R^3$. In some of these embodiments, x is 1 and $R^3$ is selected from halo, an optionally substituted $C_{1-6}$alkyl group, an optionally substituted 3 to 8 membered saturated, partially unsaturated, or fully unsaturated monocyclic ring having 0-3 heteroatoms independently selected from nitrogen, oxygen, or sulfur, a 13 to 14 membered saturated, partially unsaturated, or fully unsaturated tricyclic ring system having 0 to 5 heteroatoms independently selected from N, O, or S, or —O—($C_{1-3}$ alkyl)-phenyl, wherein each $R^3$ is substituted with up to 2 occurrences of $R^5$ at any chemically feasible position. In other embodiments, $R^3$ is selected from halo, an unsubstituted $C_{1-6}$ alkyl group, a halo-substituted $C_{1-6}$ alkyl group, an optionally substituted 5 to 6 membered saturated, partially unsaturated, or fully unsaturated monocyclic ring having 0-3 heteroatoms independently selected from nitrogen, oxygen, or sulfur; or —O—$(CH_2)_{1-2}$ phenyl. And, in some embodiments, $R^3$ is selected from —Cl, —F, —I, —$CH_3$, —$CF_3$, —$CH_2CH_3$, or —$CH_2CF_3$.

In some embodiments, $R^3$ is selected from piperidine, piperazine, morpholine, pyrrolidine, imidazolidine, pyrrole, thiophene, furan, oxazole, pyridine, pyrimidine, or pyrazine, wherein $R^3$ is substituted with $C_{1-6}$ alkyl. In some of these embodiments, $R^3$ is selected from piperidine or piperazine, either of which is optionally substituted with $C_{1-6}$ alkyl. In other embodiments, $R^3$ is selected from

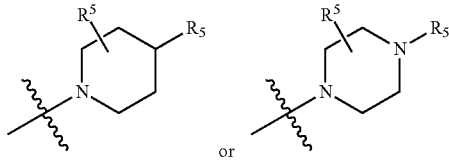

wherein each $R^5$ is independently —H or $C_{1-6}$ alkyl.

In some embodiments, $R^3$ is BOC. For example, x is 1 and $R^3$ is BOC.

In some embodiments, x is 2, and at least one occurrence of $R^3$ is halogen. For example, x is 2, and each $R^3$ is halogen.

In some embodiments, one of $R^1$ and $R^{P1}$ is hydrogen and the other is naphthyl substituted with x occurrences of $R^3$. For example, one of $R^1$ and $R^{P1}$ is hydrogen and the other is selected from

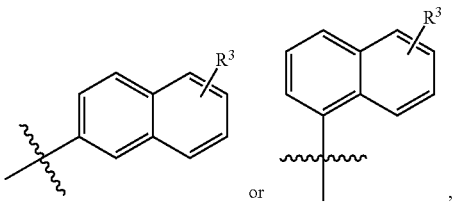

wherein $R^3$ is —H or $C_{1-6}$ alkyl.

In some embodiments, one of $R^1$ and $R^{P1}$ is hydrogen and the other is a 5 to 6 membered monocyclic heteroaryl having 1 to 3 nitrogen atoms, wherein the monocyclic heteroaryl is substituted with x occurrences of $R^3$. For example, one of $R^1$ and $R^{P1}$ is hydrogen and the other is selected from pyrazole, pyridine, pyrazine, or pyrimidine, and x is 1 or 2. In other examples, one of $R^1$ and $R^{P1}$ hydrogen and the other is

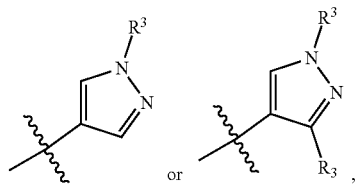

wherein $R^3$ is hydrogen, —$CF_3$, $C_{1-6}$ alkyl, or a 5 to 6 membered cycloaliphatic group. And, in some examples, each $R^3$ is independently selected from hydrogen, methyl, trifluoromethyl, ethyl, propyl, cyclopentyl, or cyclohexyl.

In some embodiments, one of $R^1$ and $R^{P1}$ is hydrogen and the other is selected from

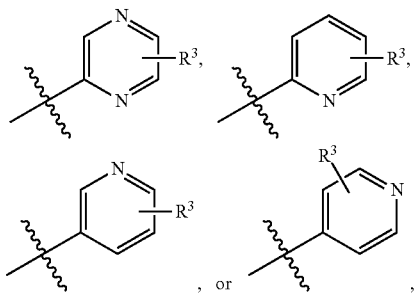

wherein each $R^3$ is hydrogen, a $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of the $C_{1-6}$ alkyl, the monocyclic ring, or the bicycling ring system is optionally substituted with up to 2 occurrences of $R^5$. For example, one of $R^1$ and $R^{P1}$ is hydrogen and the other is

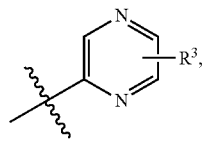

wherein $R^3$ is an optionally substituted 5 to 6 membered saturated, partially unsaturated, or fully unsaturated monocyclic ring having 0-2 heteroatoms independently selected from nitrogen or oxygen, and the other is hydrogen. In other examples, one of $R^1$ and $R^{P1}$ is hydrogen and the other is

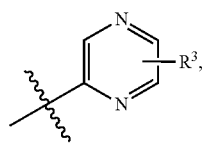

wherein $R^3$ is piperidine-1-yl optionally substituted with $C_{1-6}$ alkyl. And, in some examples, one of $R^1$ and $R^{P1}$ is hydrogen and the other is selected from

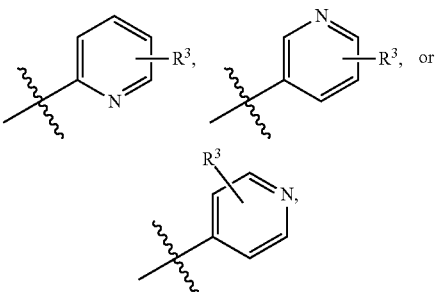

wherein each $R^3$ is —H, $C_{1-6}$ alkyl, or an optionally substituted 5 to 6 membered, saturated, or fully unsaturated monocyclic ring having 0-2 heteroatoms independently selected from nitrogen or oxygen, wherein the monocyclic ring is optionally substituted with up to 2 occurrences of $R^5$. In some examples, $R^3$ is selected from —H, $C_{1-4}$ alkyl,

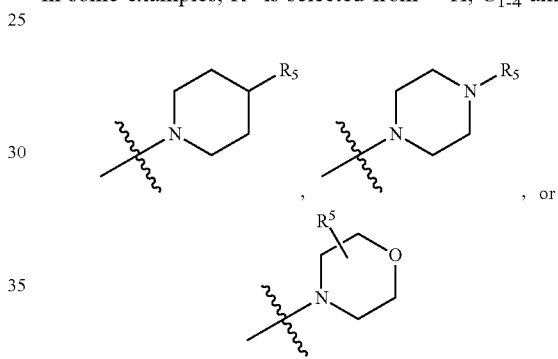

And, in other examples, each $R^5$ is independently selected from —H, $C_{1-4}$ alkyl, —$N(CH_3)_2$, —C(O)—$CH_3$, —C(O)—$CH_2$—$CH_3$, or —C(O)—O—$C(CH_3)_3$.

In some embodiments, one of $R^1$ and $R^{P1}$ is hydrogen and the other is a 9 to 10 membered bicyclic heteroaryl having 1 to 3 heteroatoms independently selected from N, O, or S, wherein the bicyclic heteroaryl is substituted with x occurrences of $R^3$.

In some embodiments, one of $R^1$ and $R^{P1}$ is hydrogen and the other is selected from

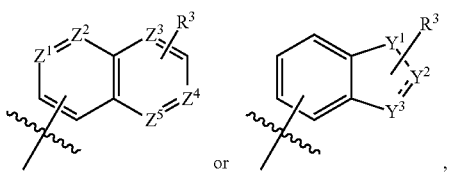

wherein
  Each of $Z^1$, $Z^2$, $Z^3$, $Z^4$, and $Z^5$ is independently $CR^3$ or N, wherein at least one of $Z^1$, $Z^2$, $Z^3$, $Z^4$, and $Z^5$ is N;
  Each of $Y^1$, $Y^2$, and $Y^3$ is independently CH, $CR^3$, N, $NR^3$, or O, wherein at least one of $Y^1$, $Y^2$, and $Y^3$ are N, $NR^3$, or O; and --- is a bond or absent, provided that i) No more than three of $Z^1$, $Z^2$, $Z^3$, $Z^4$, and $Z^5$ is N;

ii) $R^1$ is substituted with no more than three occurrences of $R^3$;

iii) If either of $Y^2$ or $Y^3$ is —O—, then --- is absent; and iv) If --- is bond, then $Y^2$ is N, CH, or $CR^3$, and $Y^3$ is N, CH, or $CR^3$.

In some embodiments, one of $R^1$ and $R^{P1}$ is hydrogen and the other is selected from

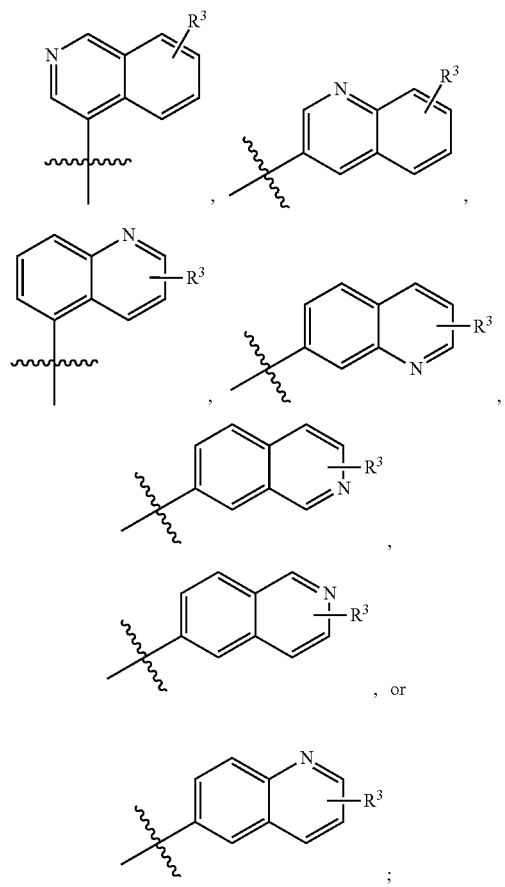

wherein $R^3$ is —H or $C_{1-6}$ alkyl.

In some embodiments, one of $R^1$ and $R^{P1}$ is hydrogen and the other is selected from

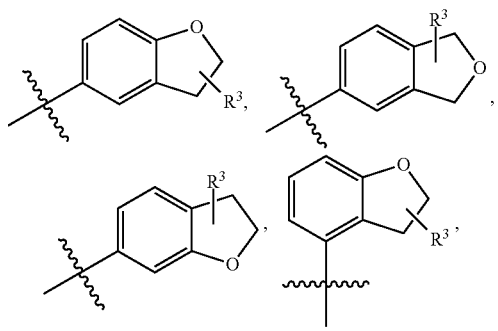

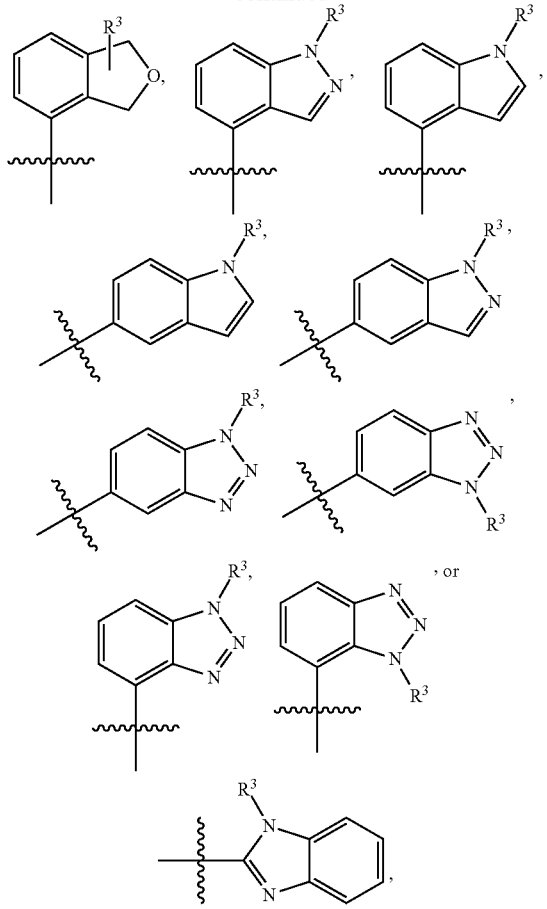

wherein $R^3$ is —H or $C_{1-6}$ alkyl.

In some embodiments, $R^1$ and $R^{P1}$ are both —H.

In some embodiments, one of $R^2$ and $R^{P2}$ is hydrogen and the other is phenyl substituted with x occurrences of $R^3$. For example, x is 1 and $R^3$ is selected from halo, an optionally substituted $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur, a 13 to 14 membered saturated, partially unsaturated, or fully unsaturated tricyclic ring system having 0 to 5 heteroatoms independently selected from N, O, or S, or —O—($C_{1-3}$ alkyl)-phenyl, wherein each $R^3$ is substituted with up to 2 occurrences of $R^5$ at any chemically feasible position. In other examples, $R^3$ is selected from halo, an unsubstituted $C_{1-6}$ alkyl group, a halo-substituted $C_{1-6}$ alkyl group, an optionally substituted 5 to 6 membered saturated, partially unsaturated, or fully unsaturated monocyclic ring having 0-3 heteroatoms independently selected from nitrogen, oxygen, or sulfur; or —O—$(CH_2)_{1-2}$phenyl. And, in some examples, $R^3$ is selected from —Cl, —F, —I, —CH$_3$, —CF$_3$, —CH$_2$CH$_3$, or —CH$_2$CF$_3$.

In some embodiments, $R^3$ is selected from piperidine, piperazine, morpholine, pyrrolidine, imidazolidine, pyrrole, thiophene, furan, oxazole, pyridine, pyrimidine, or pyrazine, wherein $R^3$ is substituted with $C_{1-6}$ alkyl.

In some embodiments, $R^3$ is selected from piperidine or piperazine, either of which is optionally substituted with $C_{1-6}$ alkyl. For example, $R^3$ is selected from

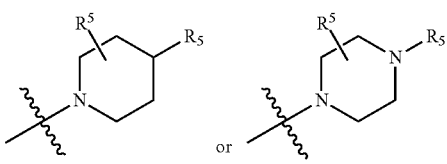

wherein each $R^5$ is independently —H or $C_{1-6}$ alkyl.

In some embodiments, $R^3$ is BOC.

In some embodiments, x is 2, and at least one occurrence of $R^3$ is halogen. For example, x is 2, and each $R^3$ is halogen.

In some embodiments, one of $R^2$ and $R^{P2}$ is hydrogen and the other is naphthyl substituted with x occurrences of $R^3$. For example, one of $R^2$ and $R^{P2}$ is hydrogen and the other is selected from

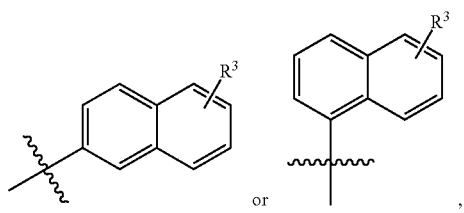

wherein $R^3$ is —H or $C_{1-6}$ alkyl.

In some embodiments, one of $R^2$ and $R^{P2}$ is hydrogen and the other is a 5 to 6 membered monocyclic heteroaryl having 1 to 3 nitrogen atoms, wherein the monocyclic heteroaryl is substituted with x occurrences of $R^3$.

In some embodiments, one of $R^2$ and $R^{P2}$ is hydrogen and the other is selected from pyrazole, pyridine, pyrazine, or pyrimidine, and x is 1 or 2. For example, one of $R^2$ and $R^{P2}$ hydrogen and the other is

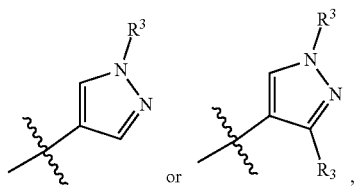

wherein $R^3$ is hydrogen, —CF$_3$, $C_{1-6}$ alkyl, or a 5 to 6 membered cycloaliphatic group. In other examples, each $R^3$ is independently selected from hydrogen, methyl, trifluoromethyl, ethyl, propyl, cyclopentyl, or cyclohexyl. In some examples, one of $R^2$ and $R^{P2}$ is hydrogen and the other is selected from

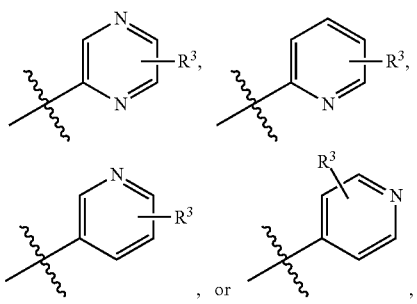

wherein each $R^3$ is hydrogen, a $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of the $C_{1-6}$ alkyl, the monocyclic ring, or the bicycling ring system is optionally substituted with up to 2 occurrences of $R^5$. In other examples, one of $R^2$ and $R^{P2}$ is hydrogen and the other is

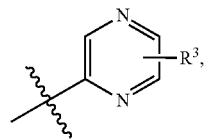

wherein $R^3$ is an optionally substituted 5 to 6 membered saturated, partially unsaturated, or fully unsaturated monocyclic ring having 0-2 heteroatoms independently selected from nitrogen or oxygen, and the other is hydrogen. In some examples, one of $R^2$ and $R^{P2}$ is hydrogen and the other is

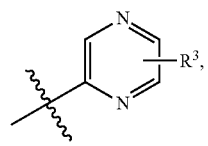

wherein $R^3$ is piperidine-1-yl optionally substituted with $C_{1-6}$ alkyl. In some examples, one of $R^2$ and $R^{P2}$ is hydrogen and the other is selected from

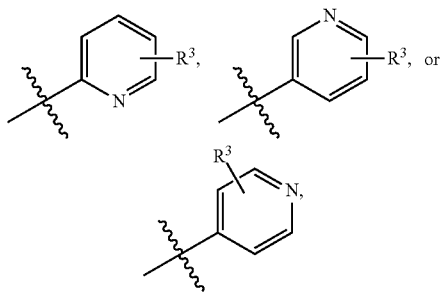

wherein each $R^3$ is —H, $C_{1-6}$ alkyl, or an optionally substituted 5 to 6 membered, saturated, or fully unsaturated monocyclic ring having 0-2 heteroatoms independently selected from nitrogen or oxygen, wherein the monocyclic ring is optionally substituted with up to 2 occurrences of $R^5$.

In some embodiments, $R^3$ is selected from —H, $C_{1-4}$ alkyl,

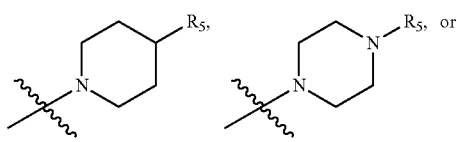

-continued

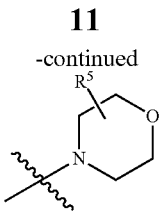

In some embodiments, each $R^5$ is independently selected from —H, $C_{1-4}$ alkyl, —N(CH$_3$)$_2$, —C(O)—CH$_3$, —C(O)—CH$_2$—CH$_3$, or —C(O)—O—C(CH$_3$)$_3$.

In some embodiments, one of $R^2$ and $R^{P2}$ is hydrogen and the other is a 9 to 10 membered bicyclic heteroaryl having 1 to 3 heteroatoms independently selected from N, O, or S, wherein the bicyclic heteroaryl is substituted with x occurrences of $R^3$.

In some embodiments, one of $R^2$ and $R^{P2}$ is hydrogen and the other is selected from

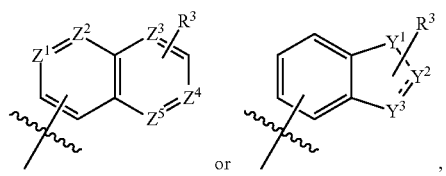

or wherein

Each of $Z^1$, $Z^2$, $Z^3$, $Z^4$, and $Z^5$ is independently $CR^3$ or N, wherein at least one of $Z^1$, $Z^2$, $Z^3$, $Z^4$, and $Z^5$ is N;

Each of $Y^1$, $Y^2$, and $Y^3$ is independently CH, $CR^3$, N, $NR^3$, or O, wherein at least one of $Y^1$, $Y^2$, and $Y^3$ are N, $NR^3$, or O; and --- is a bond or absent, provided that i) No more than three of $Z^1$, $Z^2$, $Z^3$, $Z^4$, and $Z^5$ is N;
ii) $R^1$ is substituted with no more than three occurrences of $R^3$;
iii) If either of $Y^2$ or $Y^3$ is —O—, then --- is absent; and
iv) If --- is bond, then $Y^2$ is N, CH, or $CR^3$, and $Y^3$ is N, CH, or $CR^3$.

In some embodiments, one of $R^2$ and $R^{P2}$ is hydrogen and the other is selected from

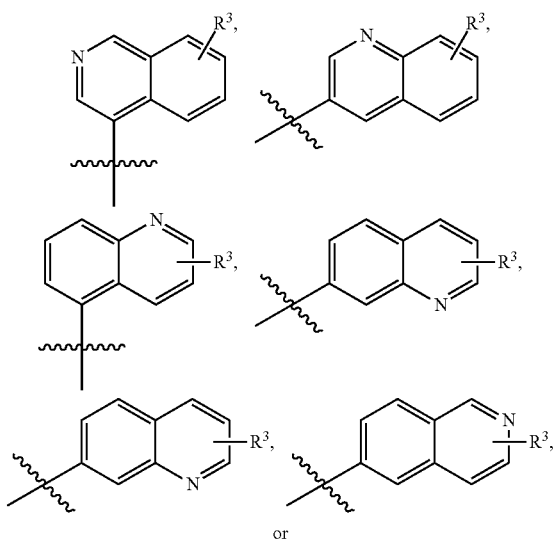

or

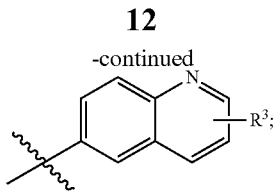

wherein $R^3$ is —H or $C_{1-6}$ alkyl.

In some embodiments, one of $R^2$ and $R^{P2}$ is hydrogen and the other is selected from

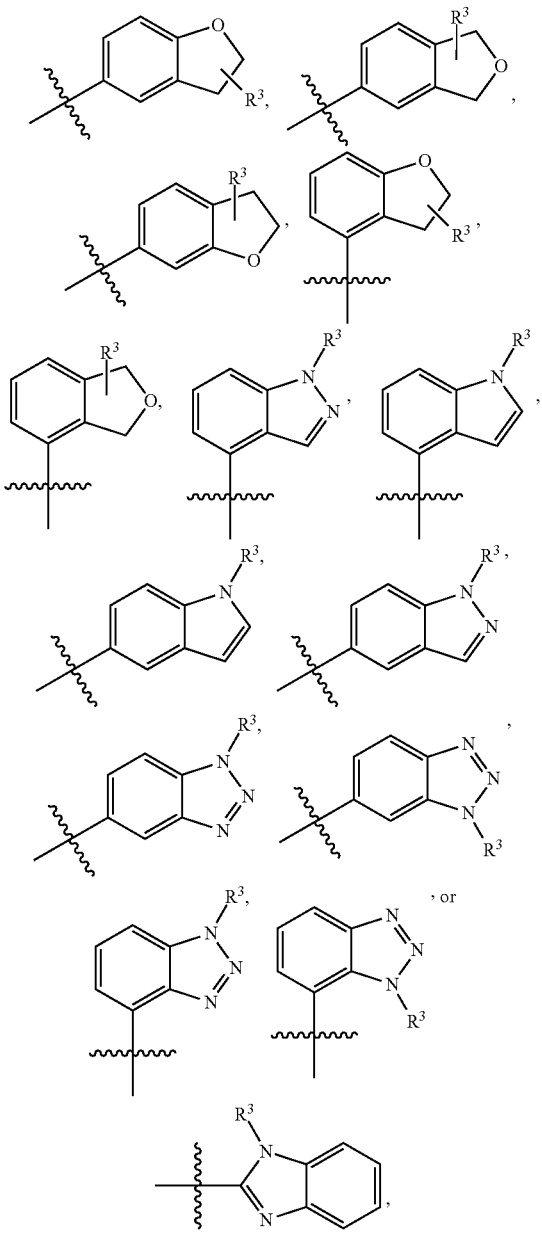

wherein $R^3$ is —H or $C_{1-6}$ alkyl.

Another aspect of the invention provides a compound selected from the compounds in Table 1, or a pharmaceutically acceptable salt thereof.

Another aspect of the invention provides a pharmaceutical composition comprising a compound, such as any of the compounds described herein, and a pharmaceutically acceptable carrier, vehicle, or adjuvant.

Another aspect of the invention provides a method of treating a fungal infection (e.g., a mycoses) in a patient, comprising administering to the patient an effective amount of a compound according to any one of the compounds disclosed herein or a pharmaceutical composition as disclosed herein.

Another aspect of the invention provides a method of reducing the number of fungi in a biological sample, comprising administering to the biological sample an effective amount of a compound disclosed herein or a pharmaceutical composition disclosed herein.

In further embodiments the fungi is *Aspergillus, Candida, Cryptococcus, Issatchenkia, Saccharomyces, Emericella, Coccidiodes,* or *Trichophyton*.

BRIEF DESCRIPTION OF THE DRAWINGS

The following figures are provided by way of example and are not intended to limit the scope of the claimed invention.

DETAILED DESCRIPTION

Figure 1A:
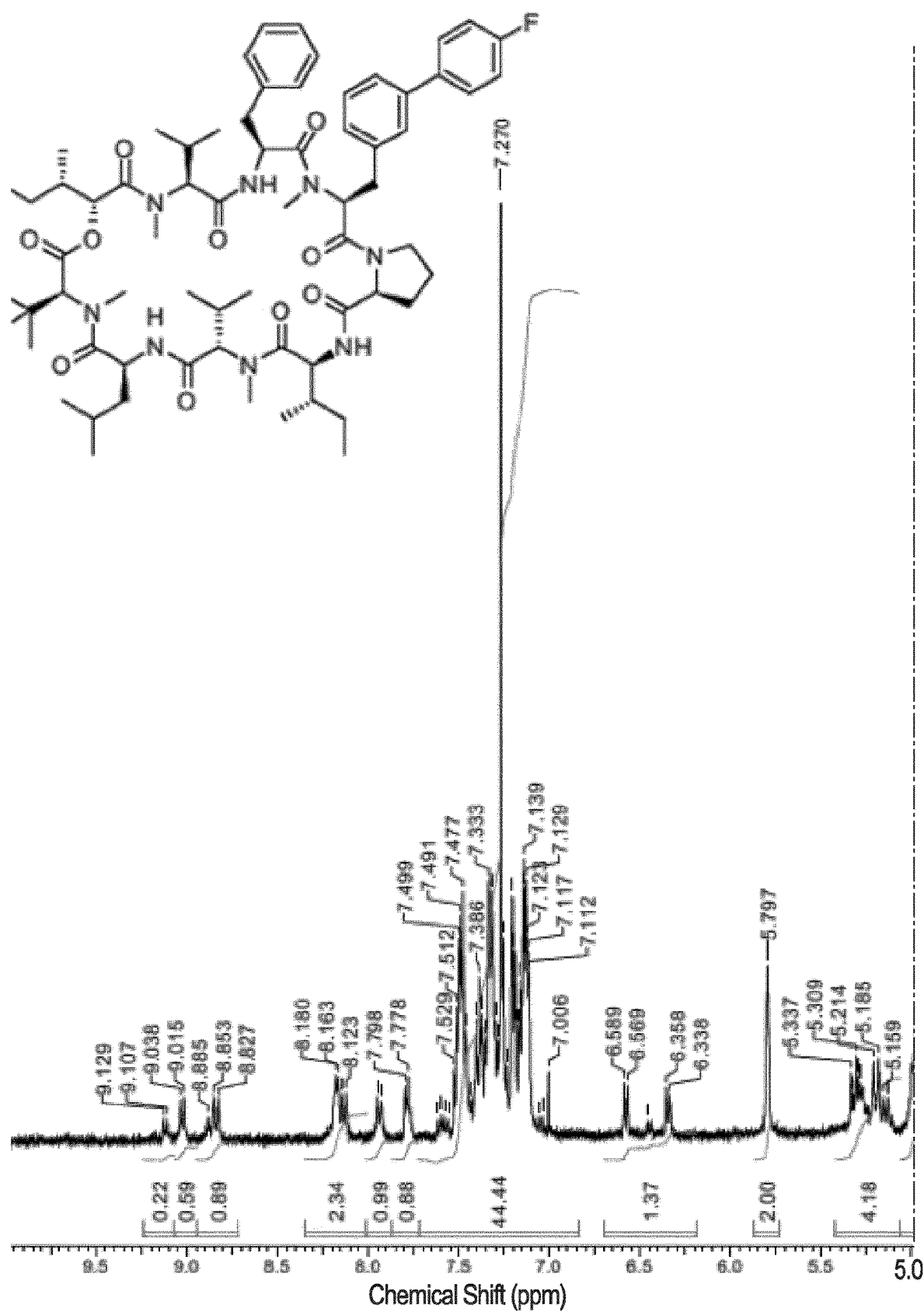
FIG. 1A and FIG. 1B presents a $^1$H NMR spectrum for Example 1.
Figure 1B:
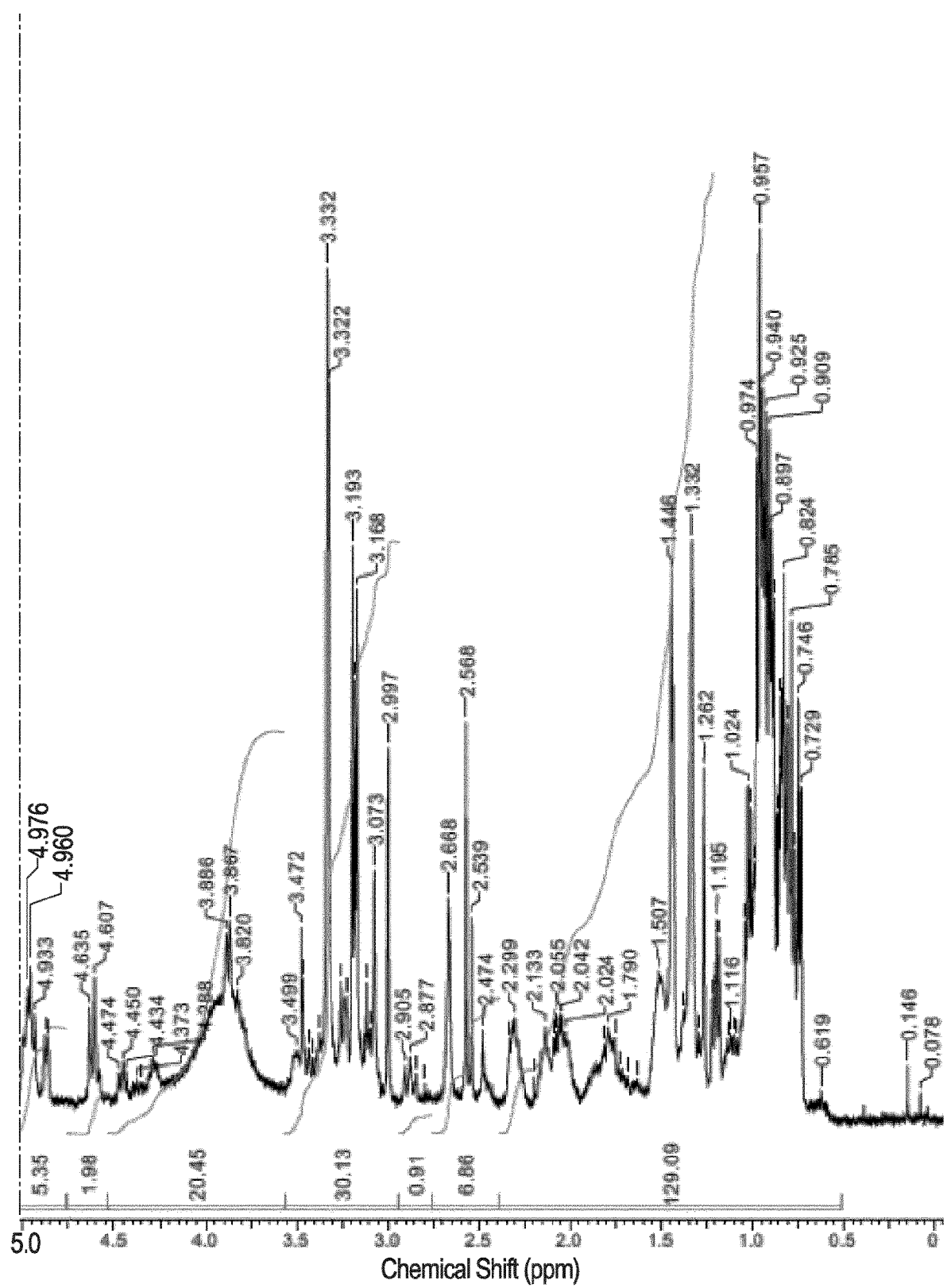
Figure 2A:
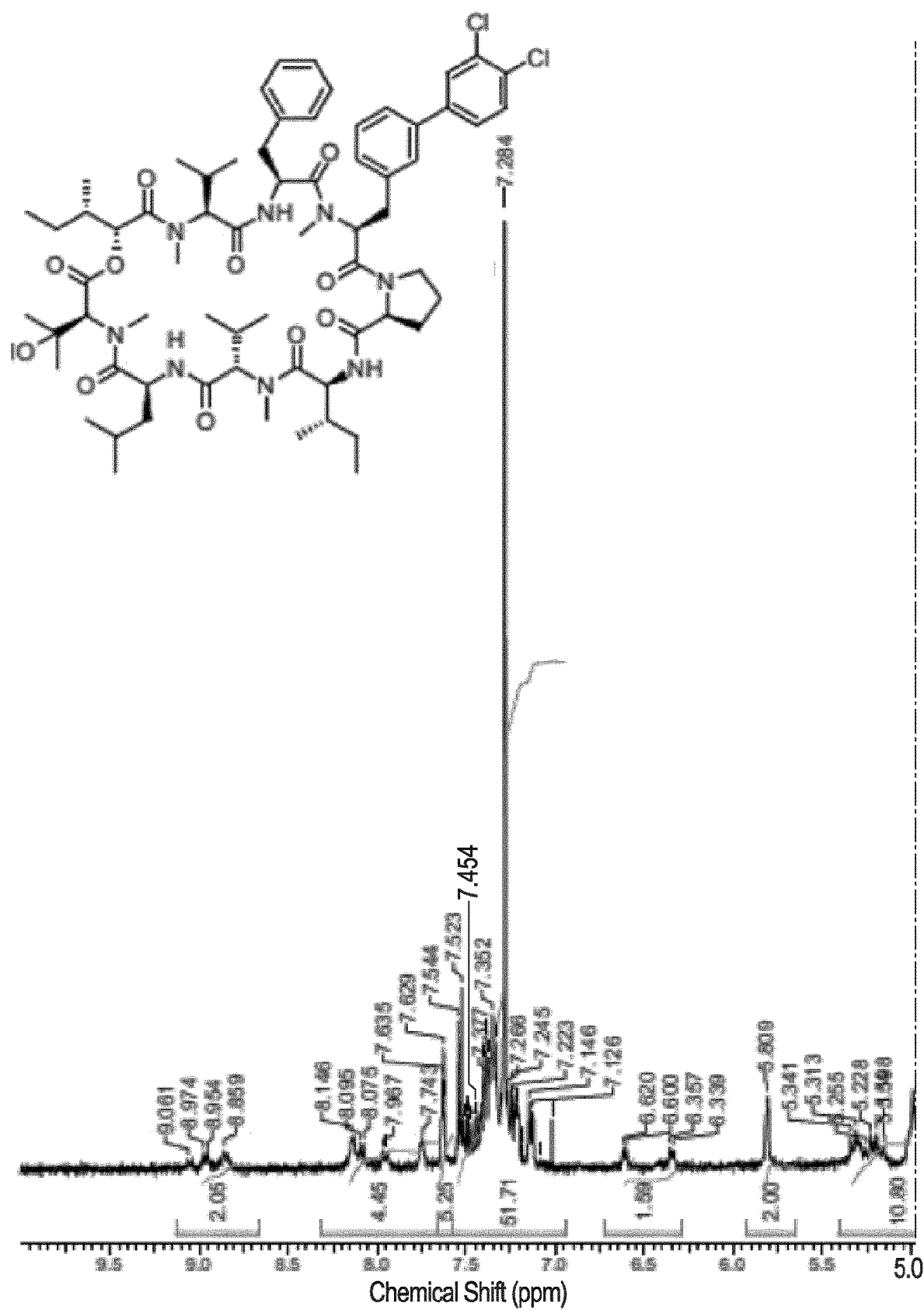
FIG. 2A and FIG. 2B presents a $^1$H NMR spectrum for Example 2.
Figure 2B:
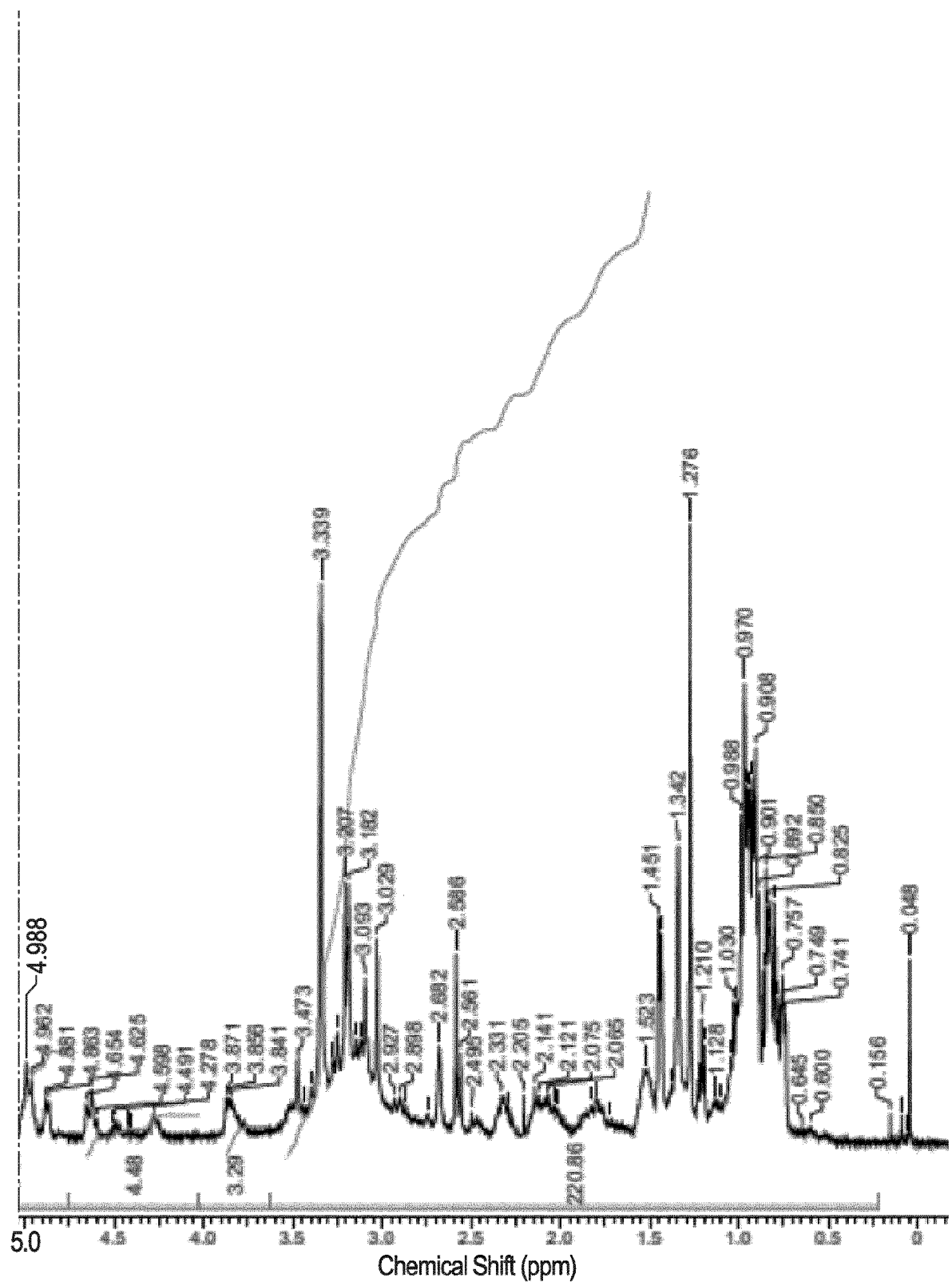
Figure 3A:
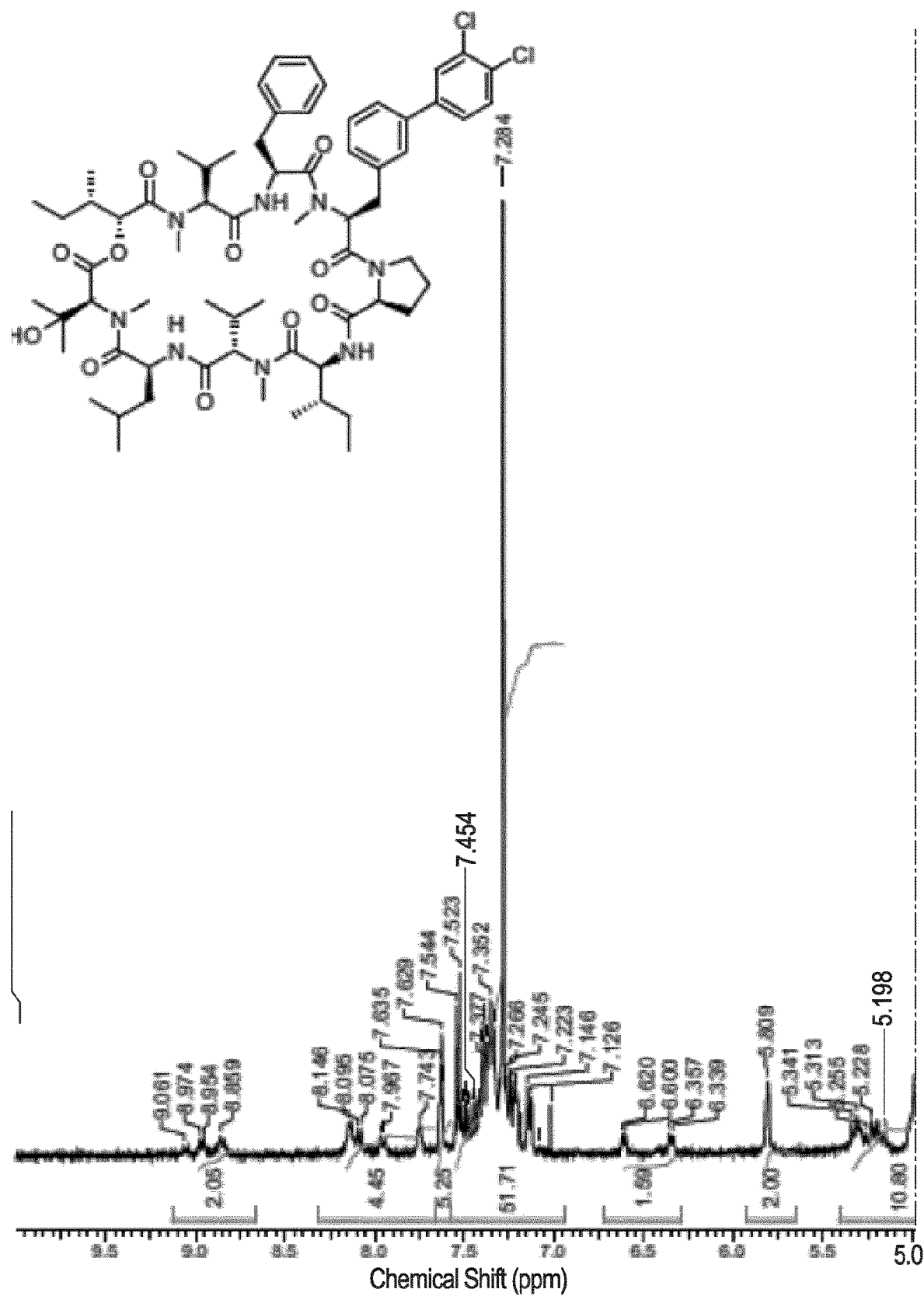
FIG. 3A and FIG. 3B presents a $^1$H NMR spectrum for Example 3.
Figure 3B:
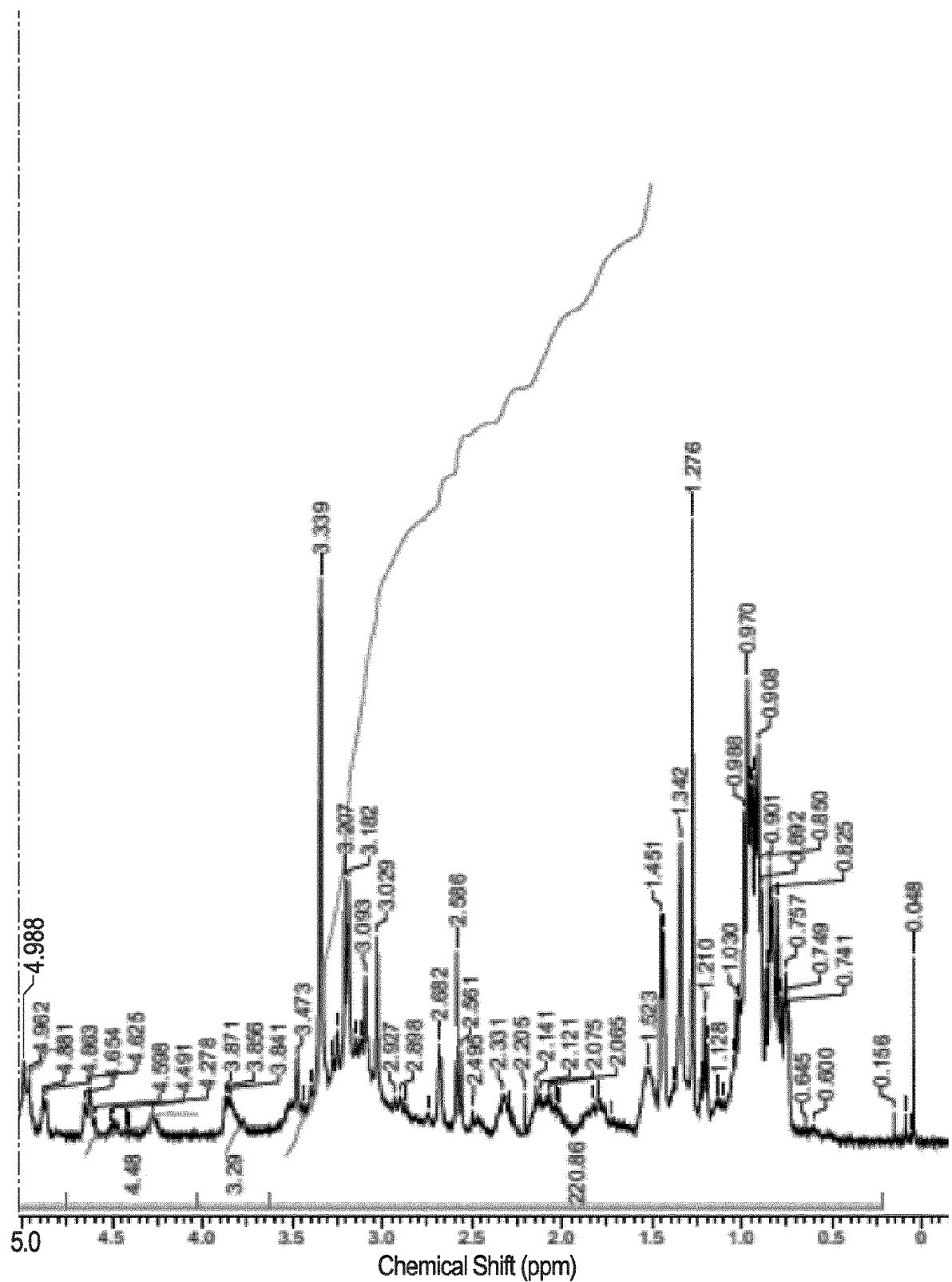
Figure 4A:
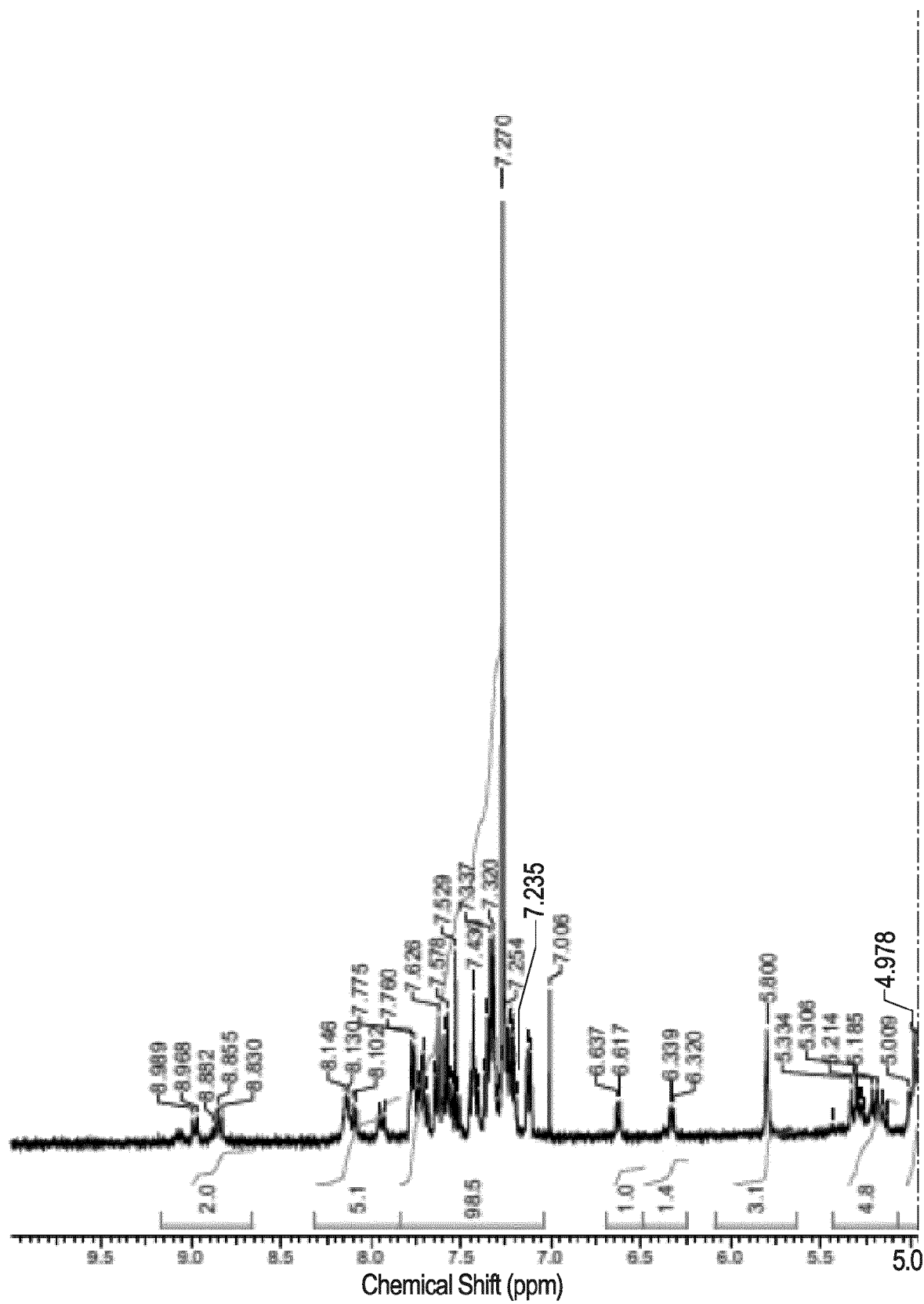
FIG. 4A and FIG. 4B presents a $^1$H NMR spectrum for Example 4.
Figure 4B:
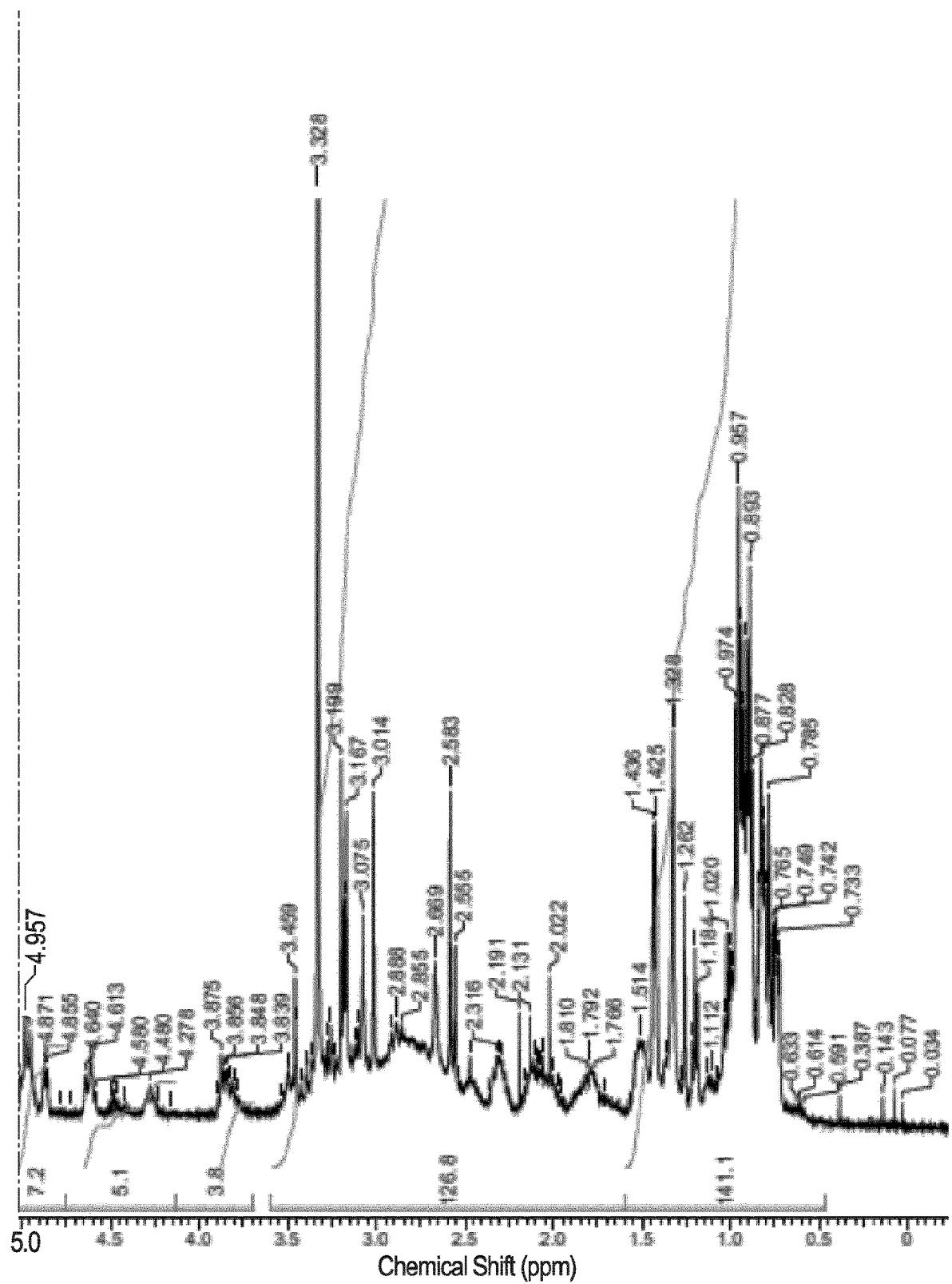
Figure 5A:
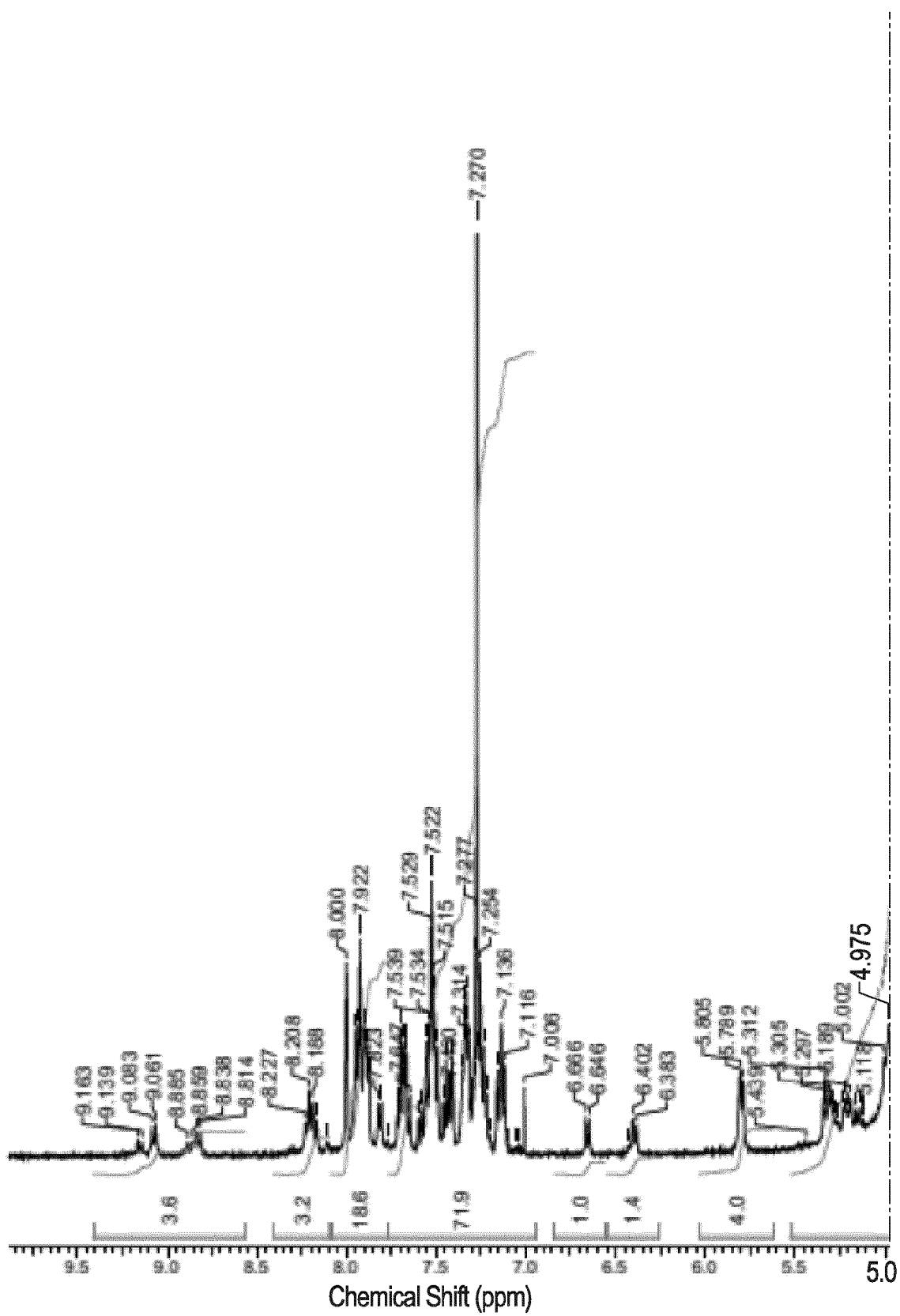
FIG. 5A and FIG. 5B presents a $^1$H NMR spectrum for Example 5.
Figure 5B:
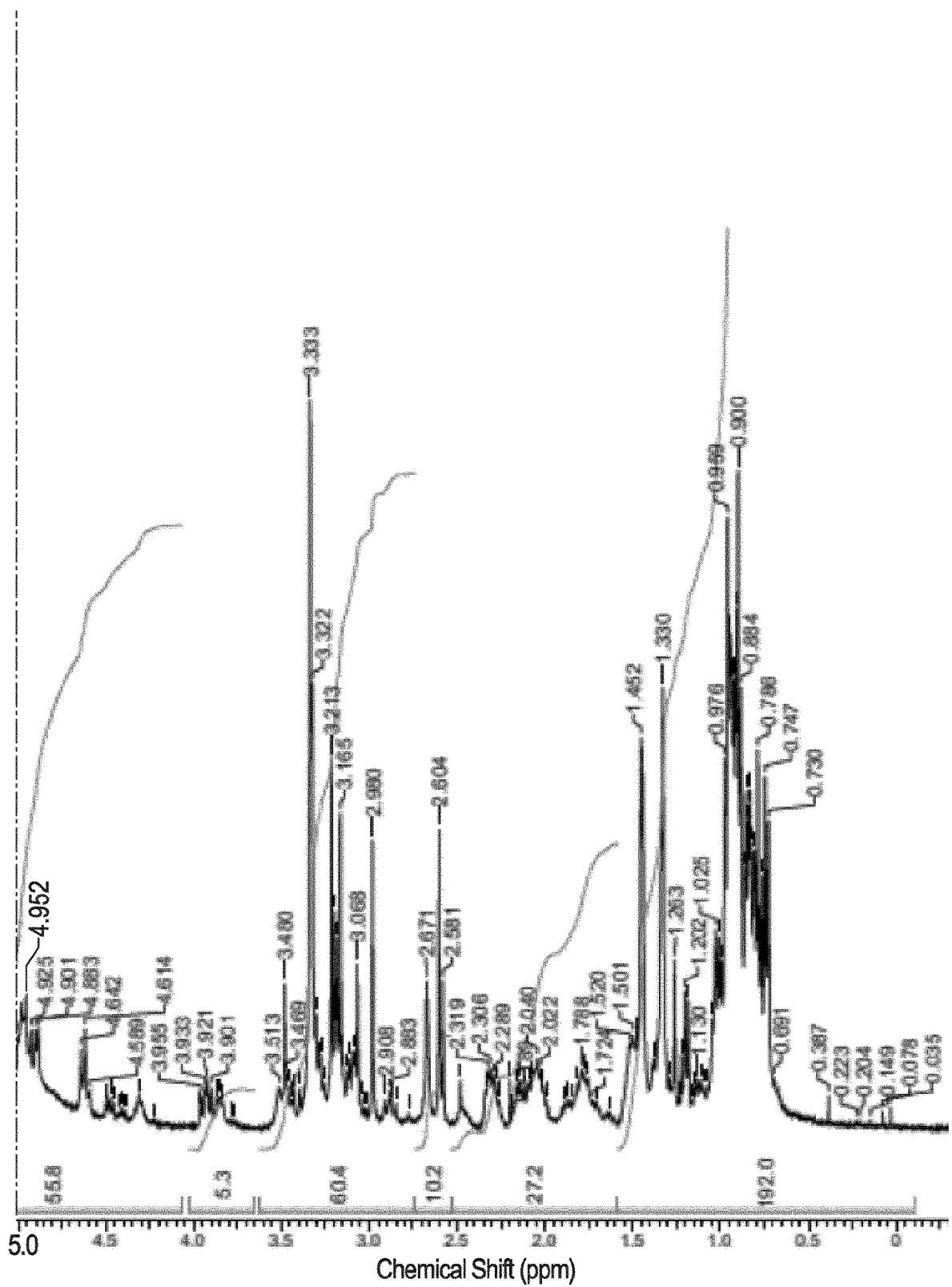
Figure 6A:
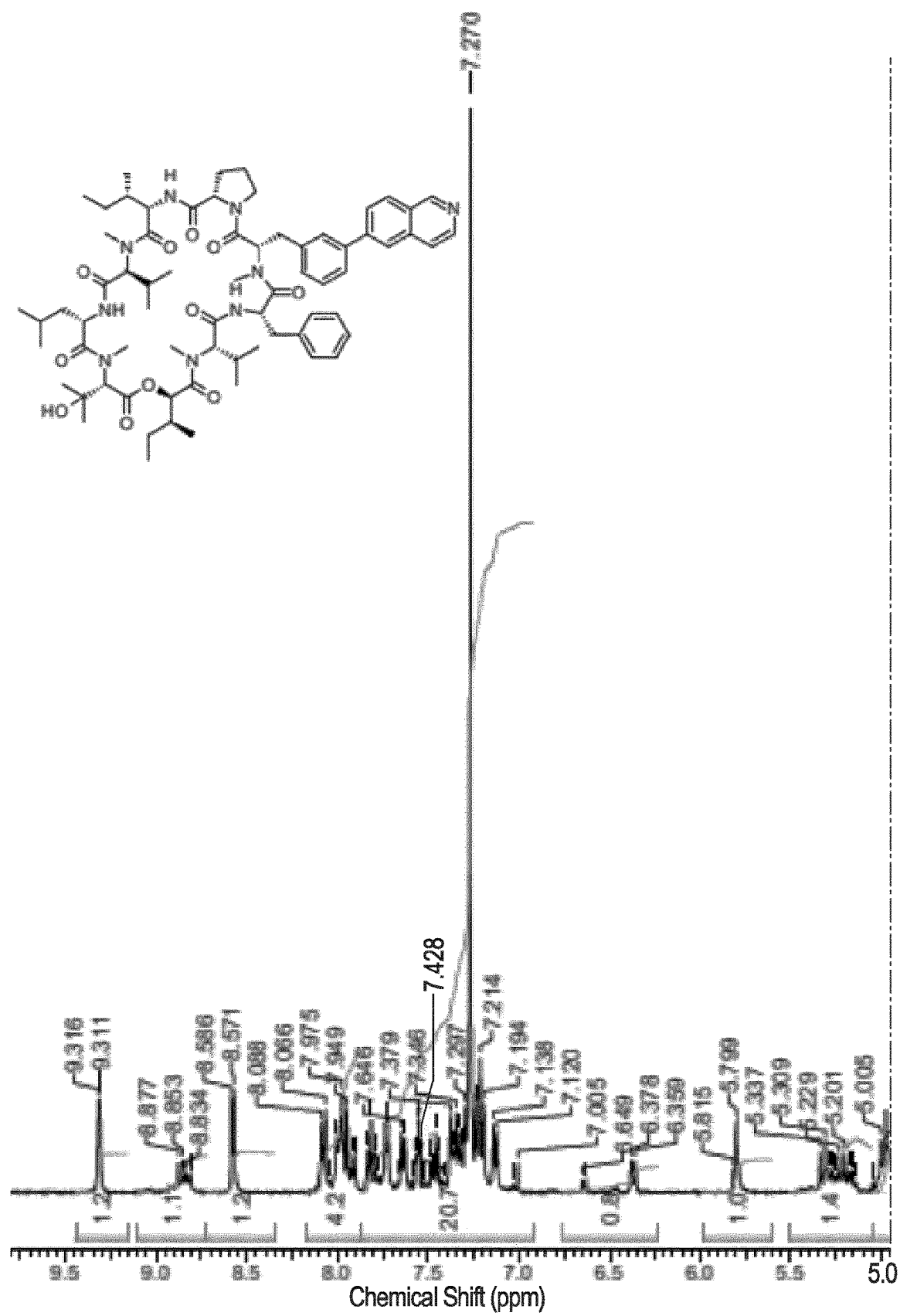
FIG. 6A and FIG. 6B presents a $^1$H NMR spectrum for Example 6.
Figure 6B:
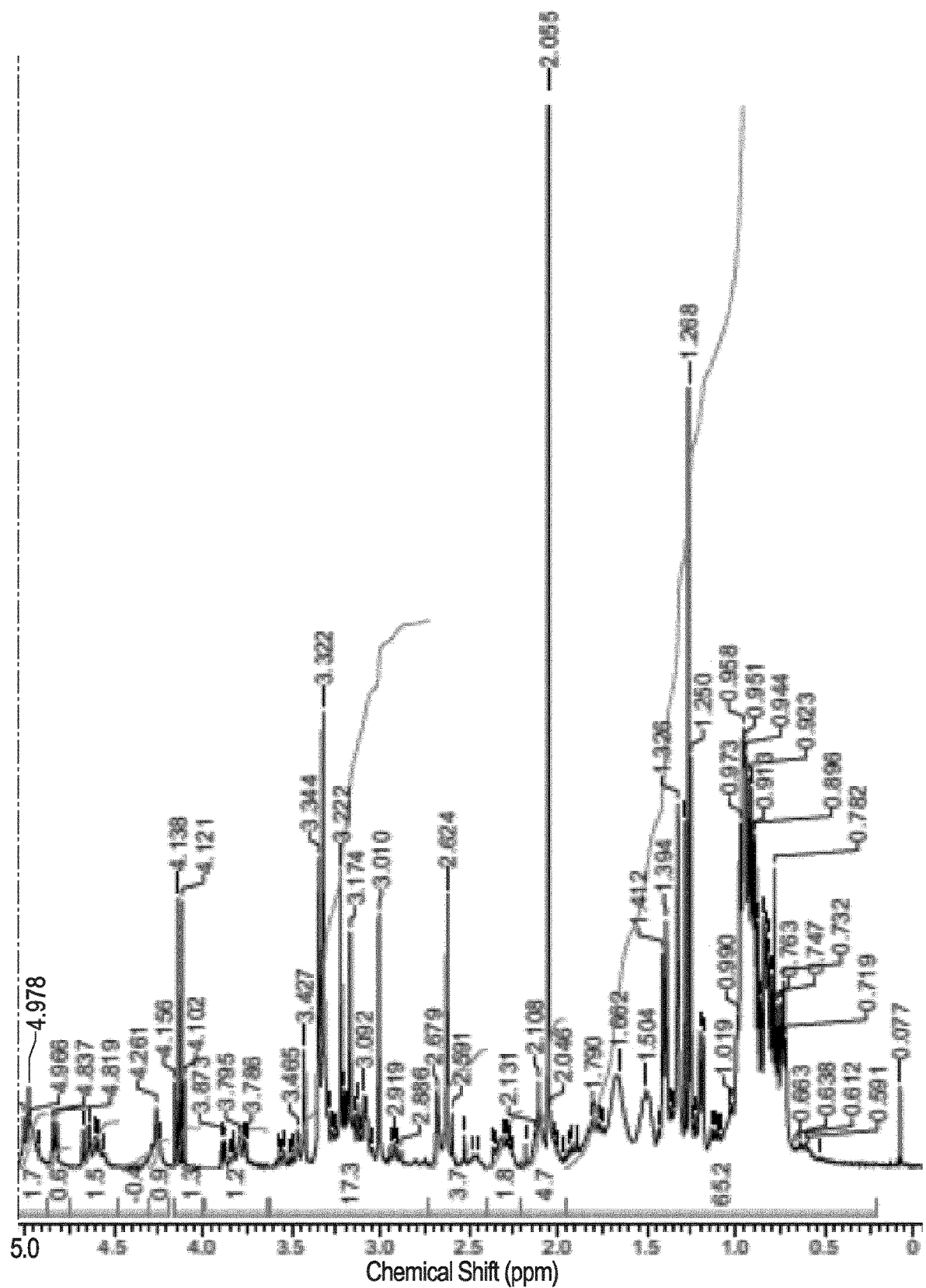
Figure 7A:
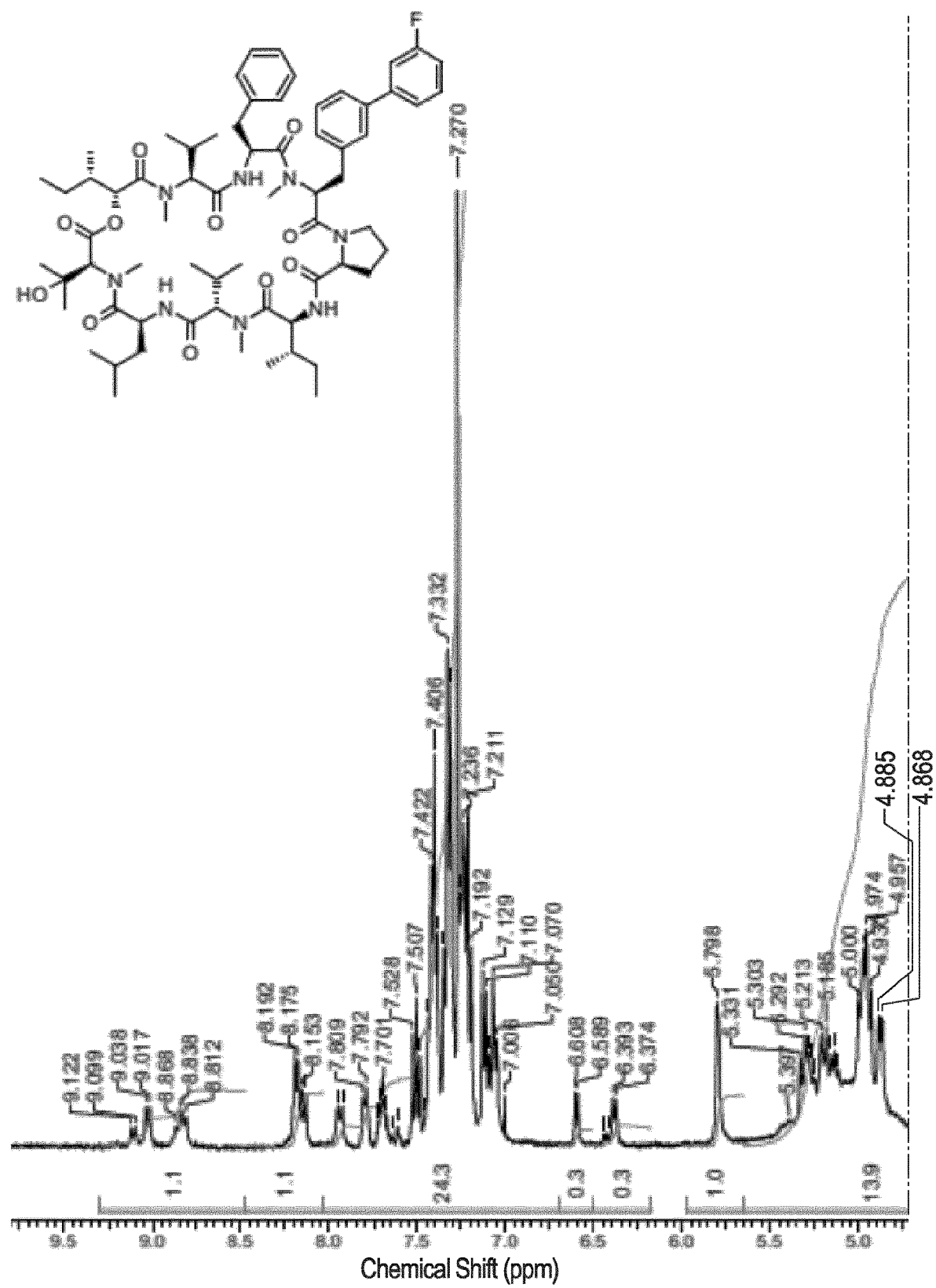
FIG. 7A and FIG. 7B presents a $^1$H NMR spectrum for Example 7.
Figure 7B:
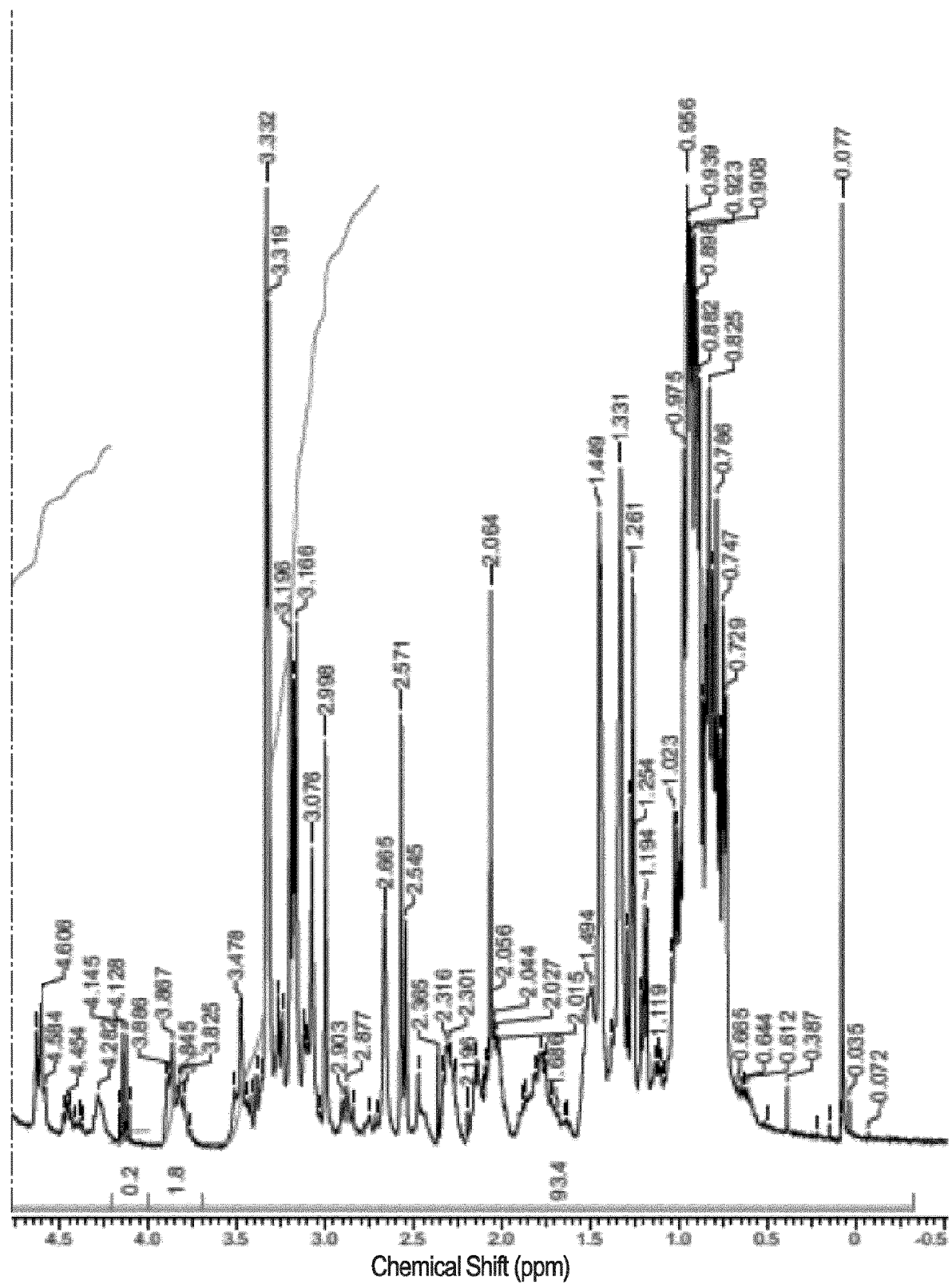
Figure 8A:
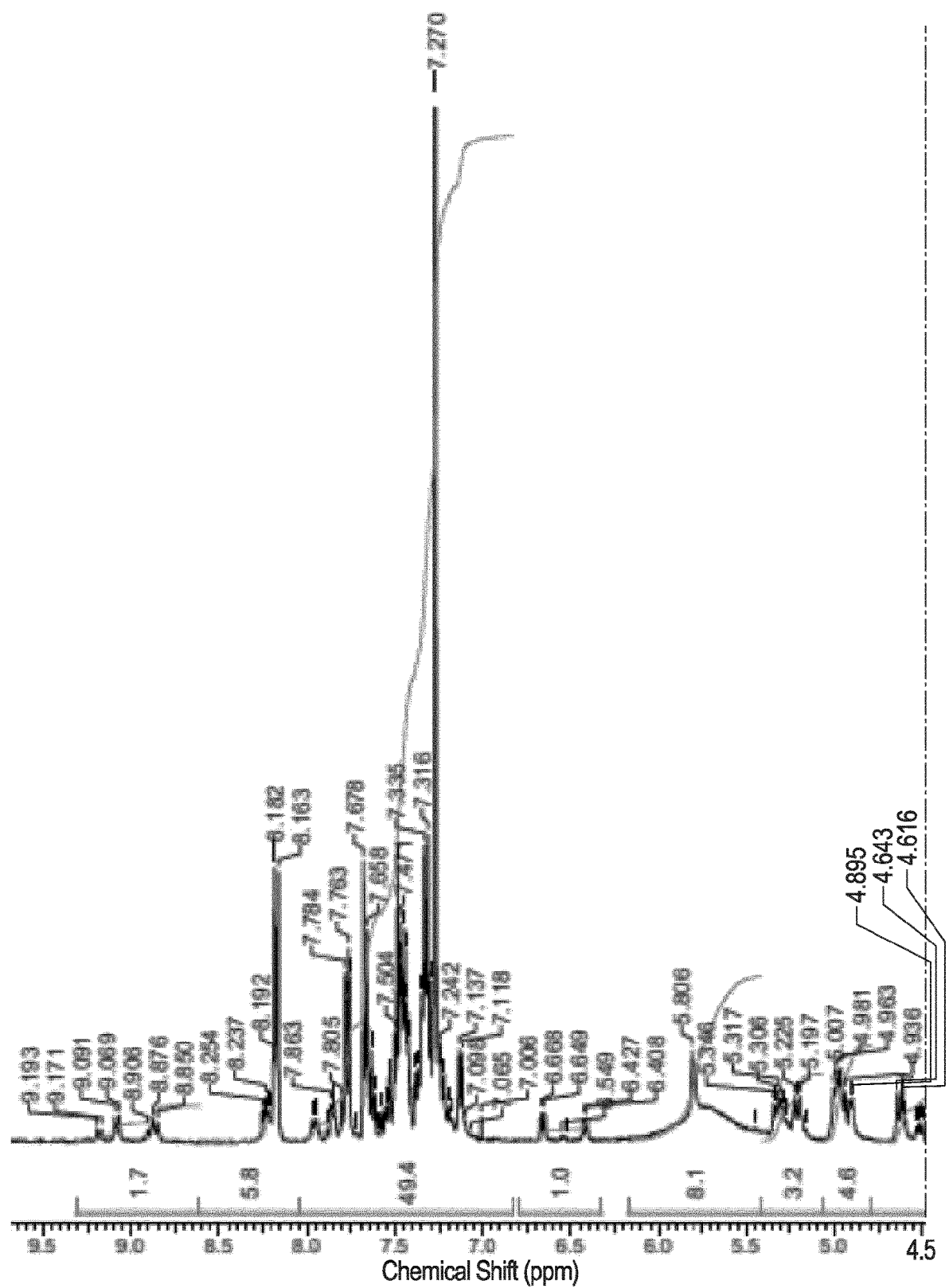
FIG. 8A and FIG. 8B presents a $^1$H NMR spectrum for Example 8.
Figure 8B:
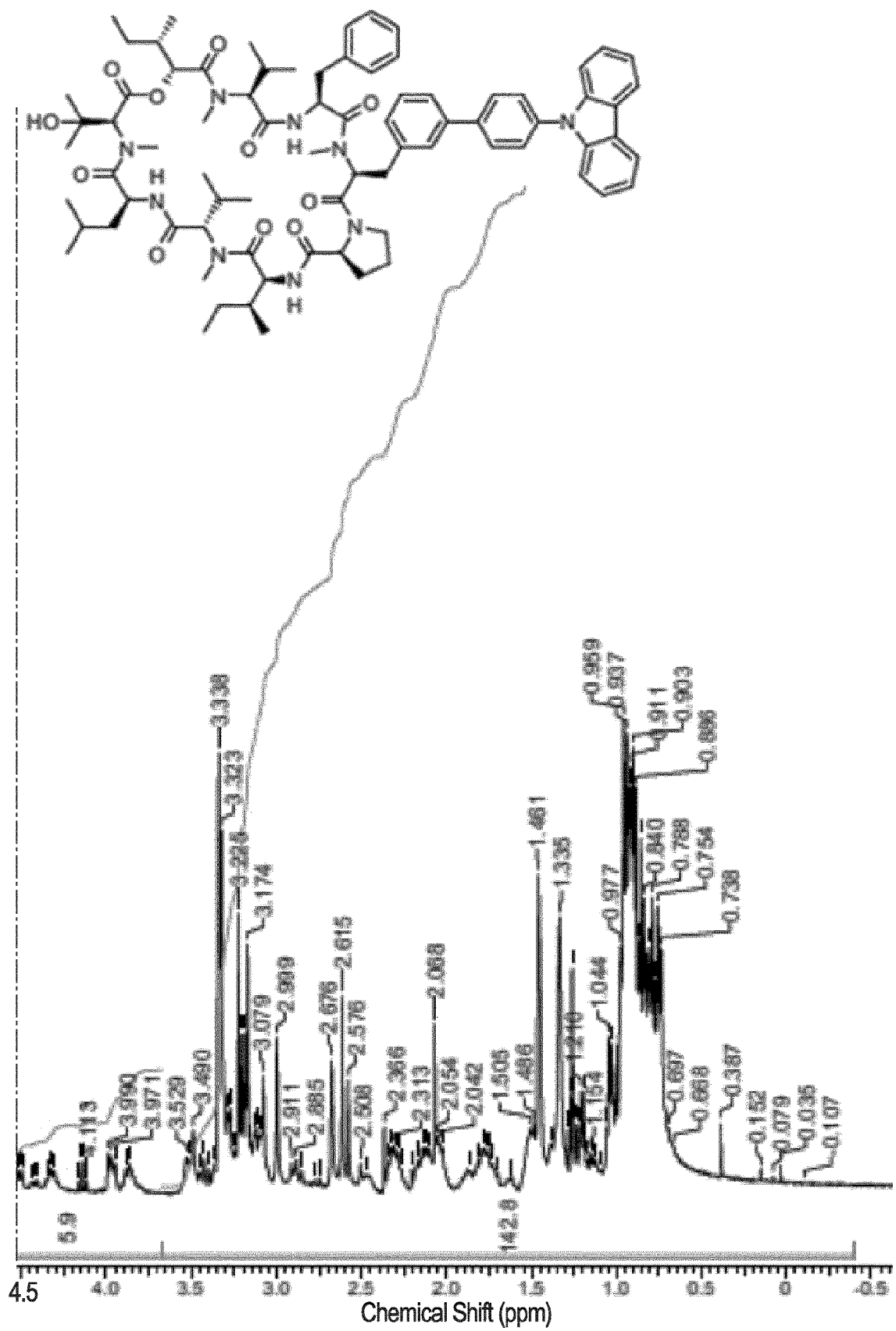
Figure 9A:
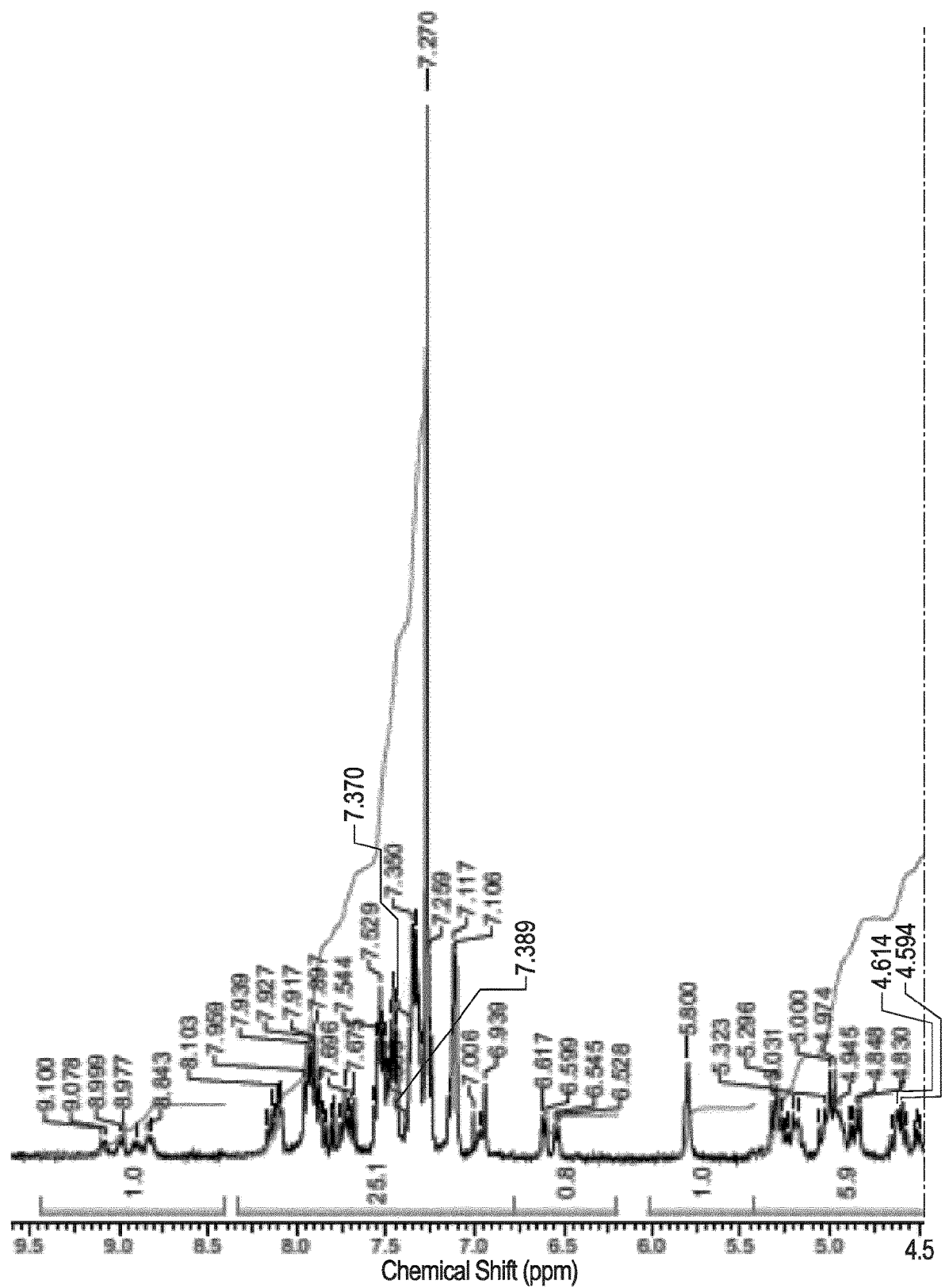
FIG. 9A and FIG. 9B presents a $^1$H NMR spectrum for Example 9.
Figure 9B:
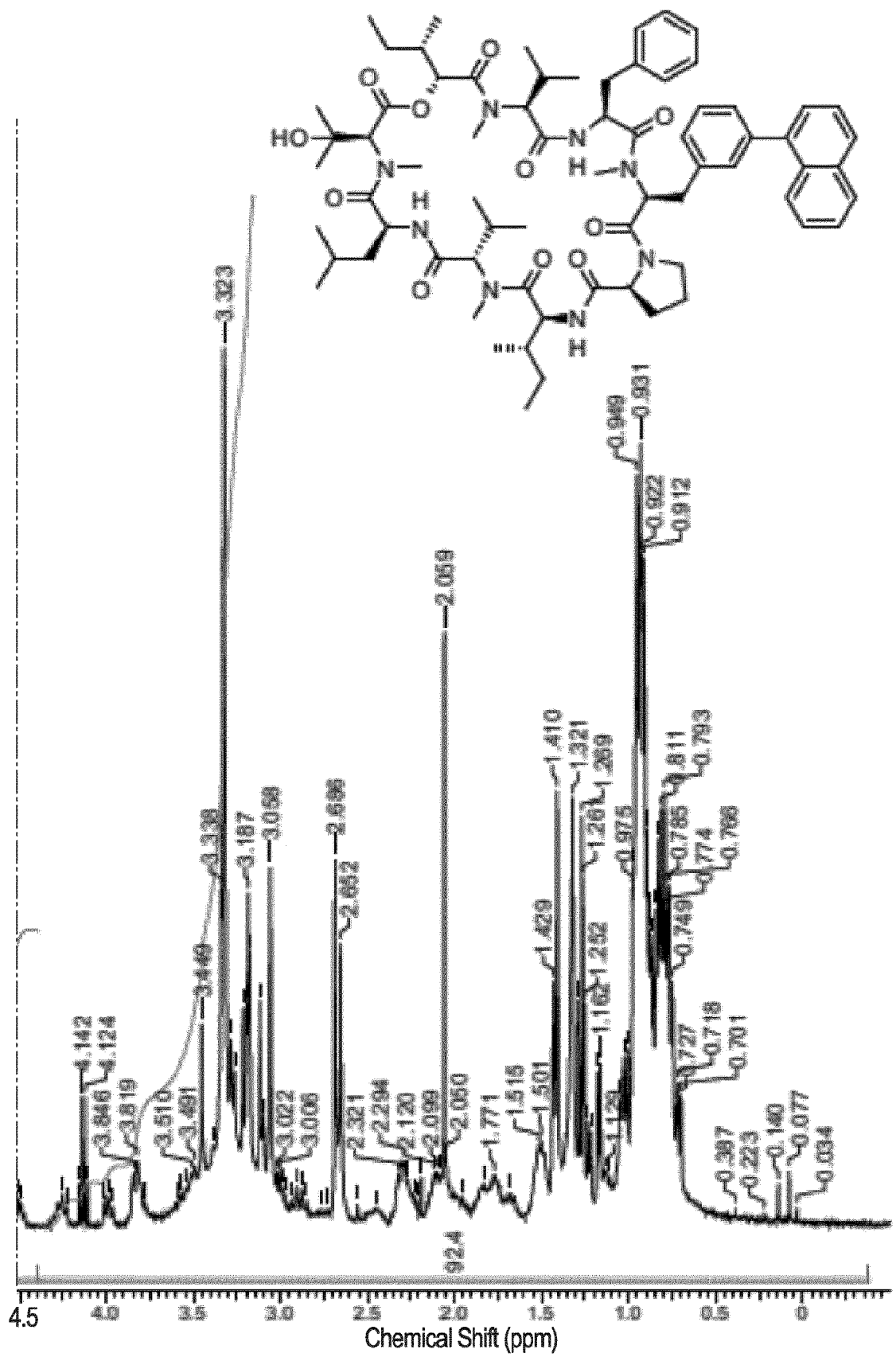
Figure 10A:
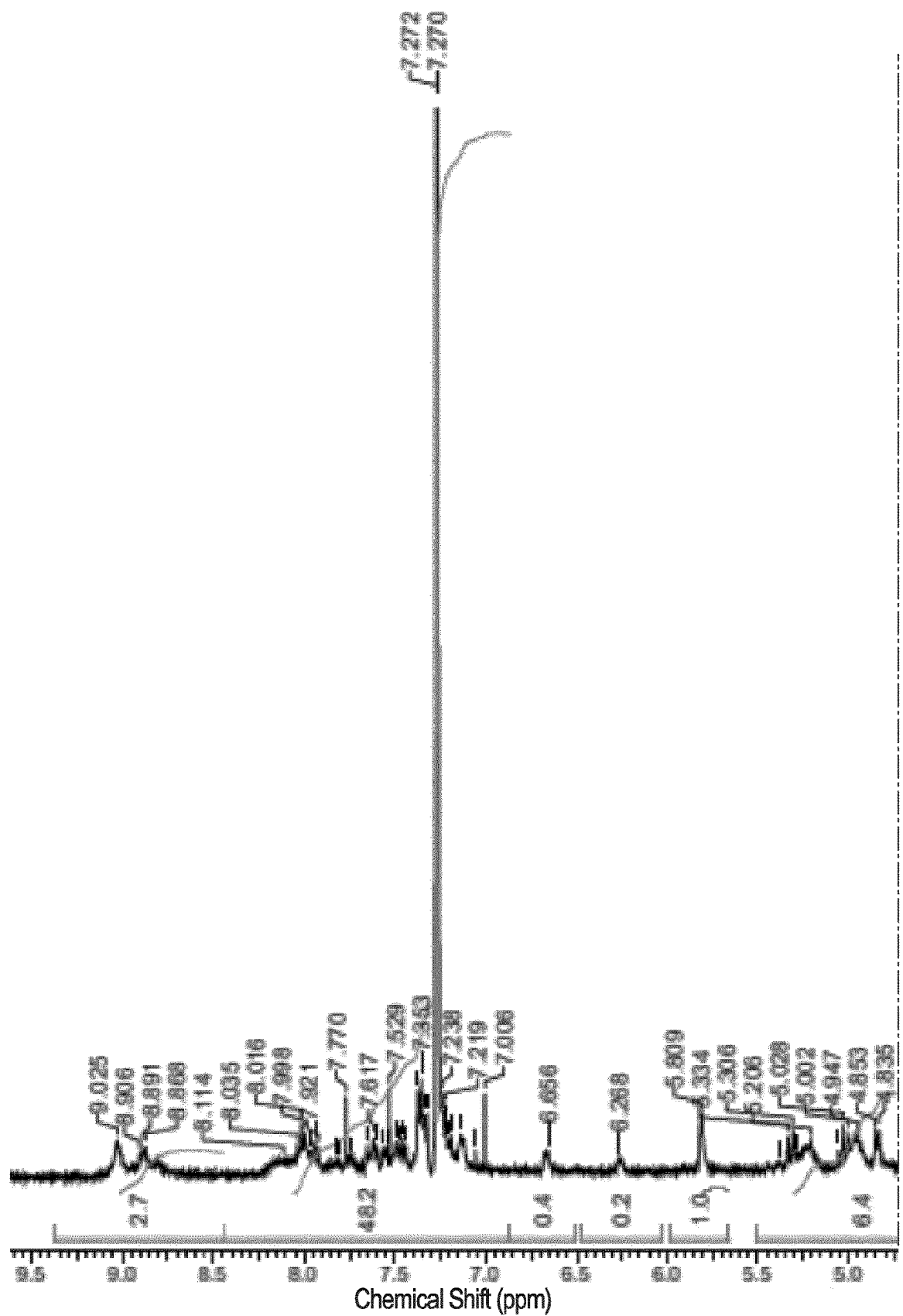
FIG. 10A and FIG. 10B presents a $^1$H NMR spectrum for Example 10.
Figure 10B:
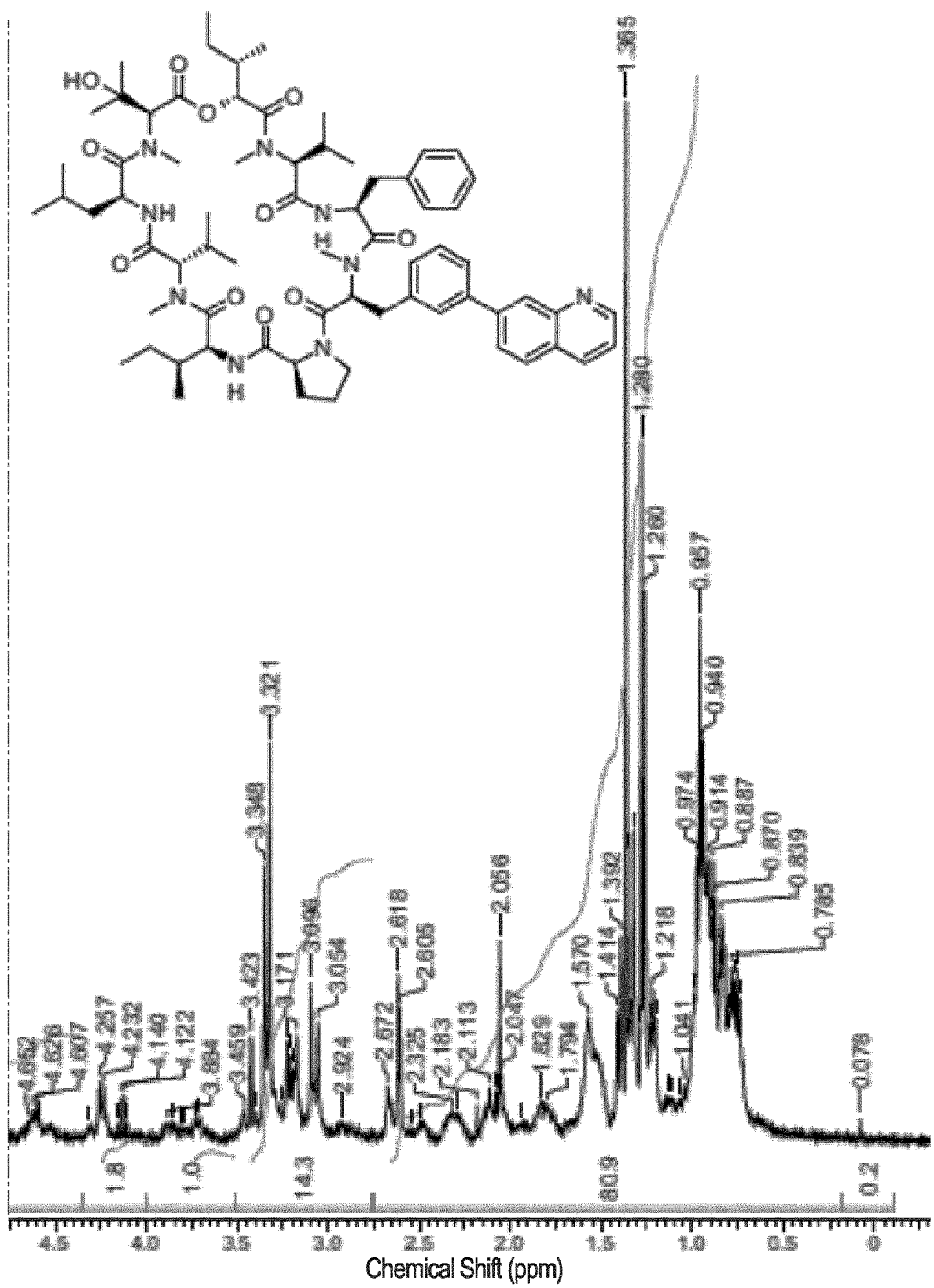
Figure 11A:
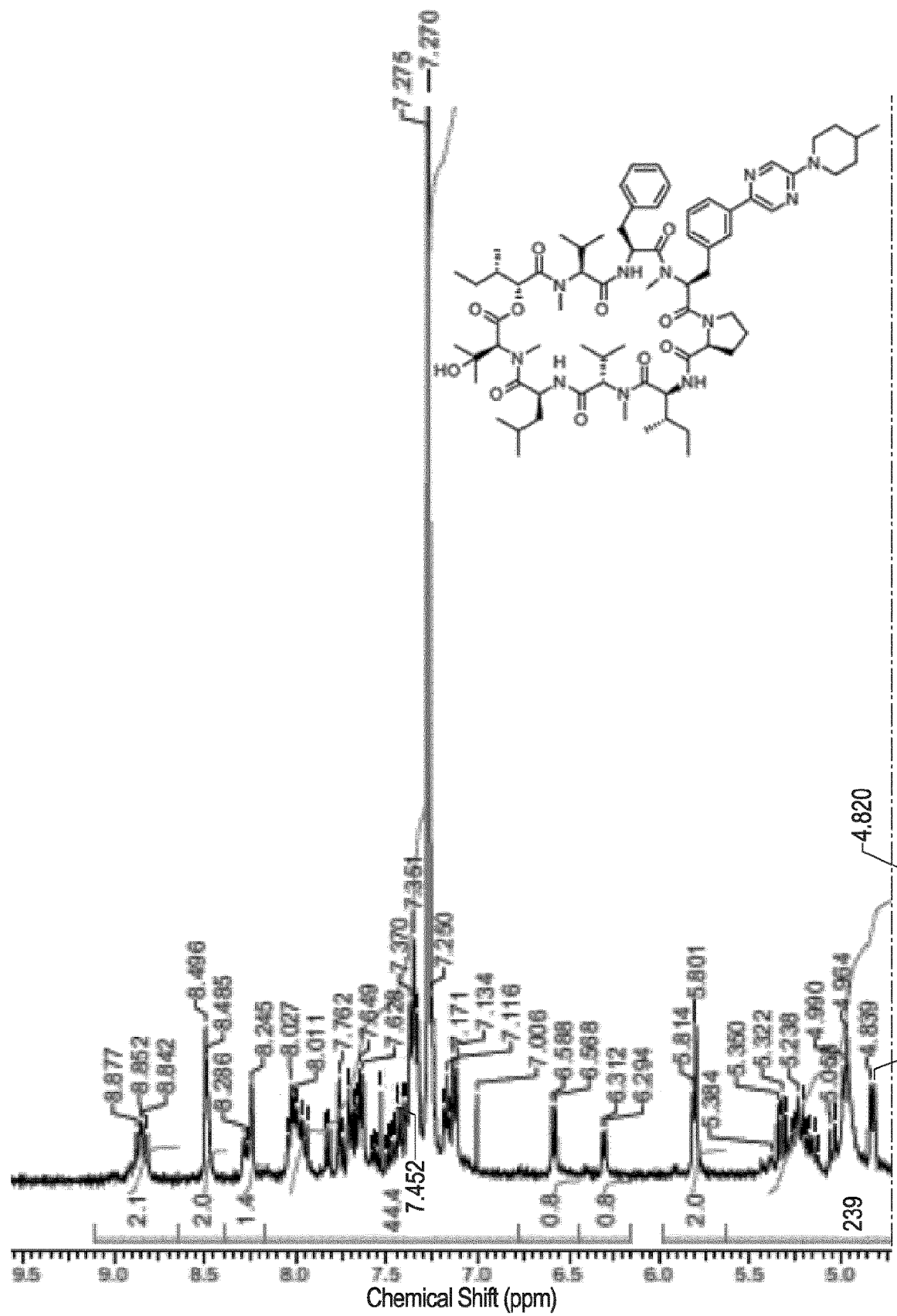
FIG. 11A and FIG. 11B presents a $^1$H NMR spectrum for Example 11.
Figure 11B:
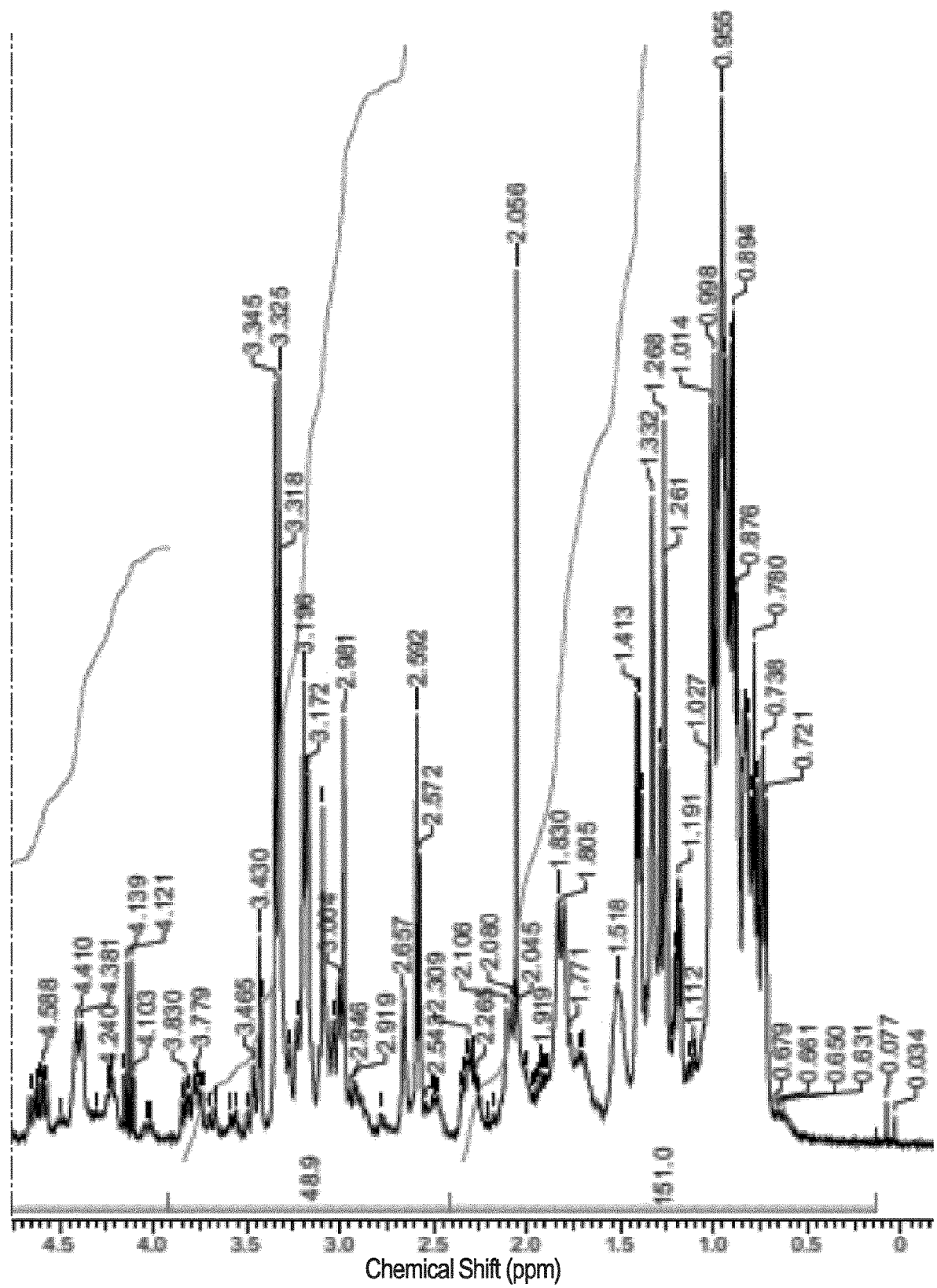
Figure 12A:
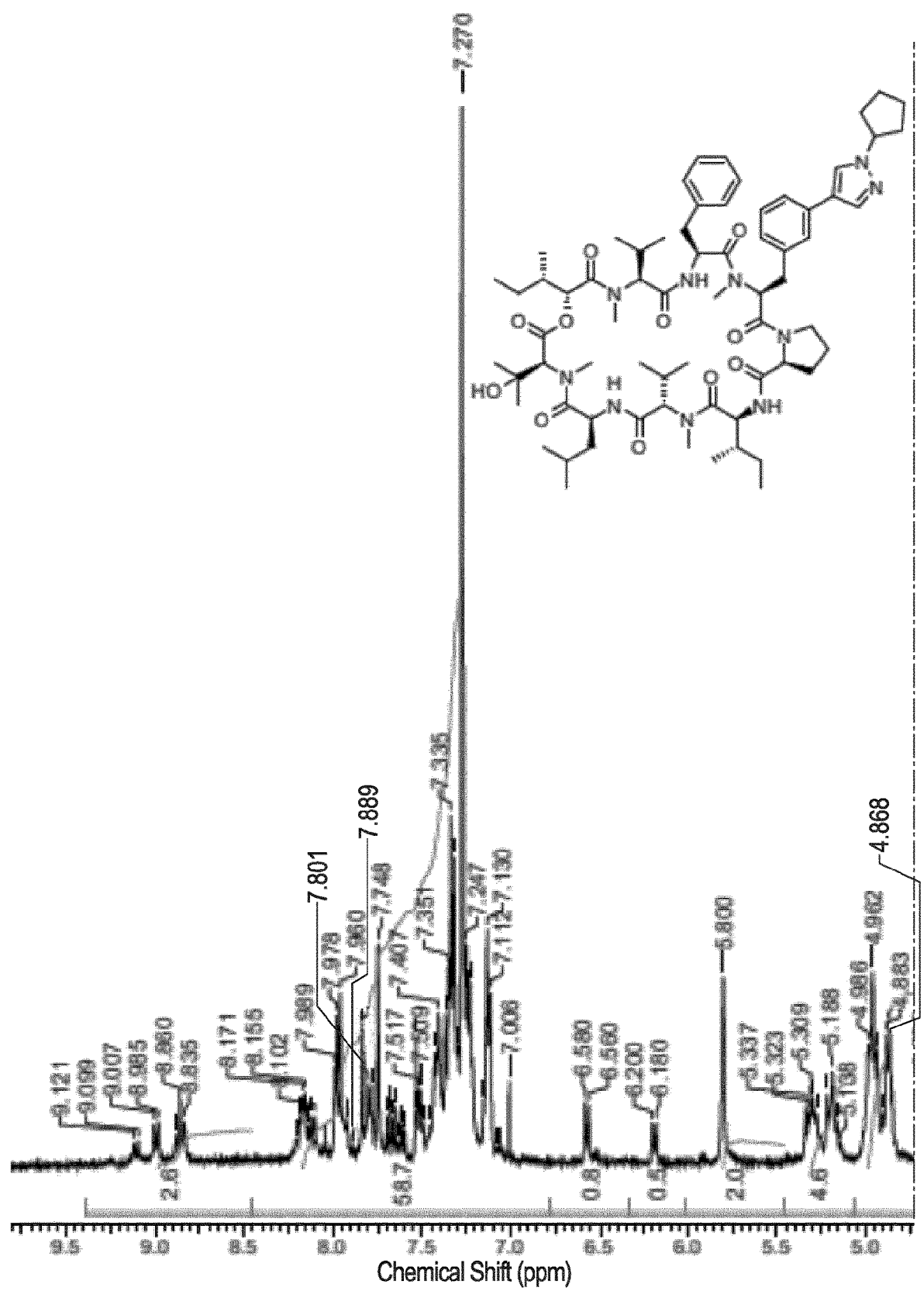
FIG. 12A and FIG. 12B presents a $^1$H NMR spectrum for Example 12.
Figure 12B:
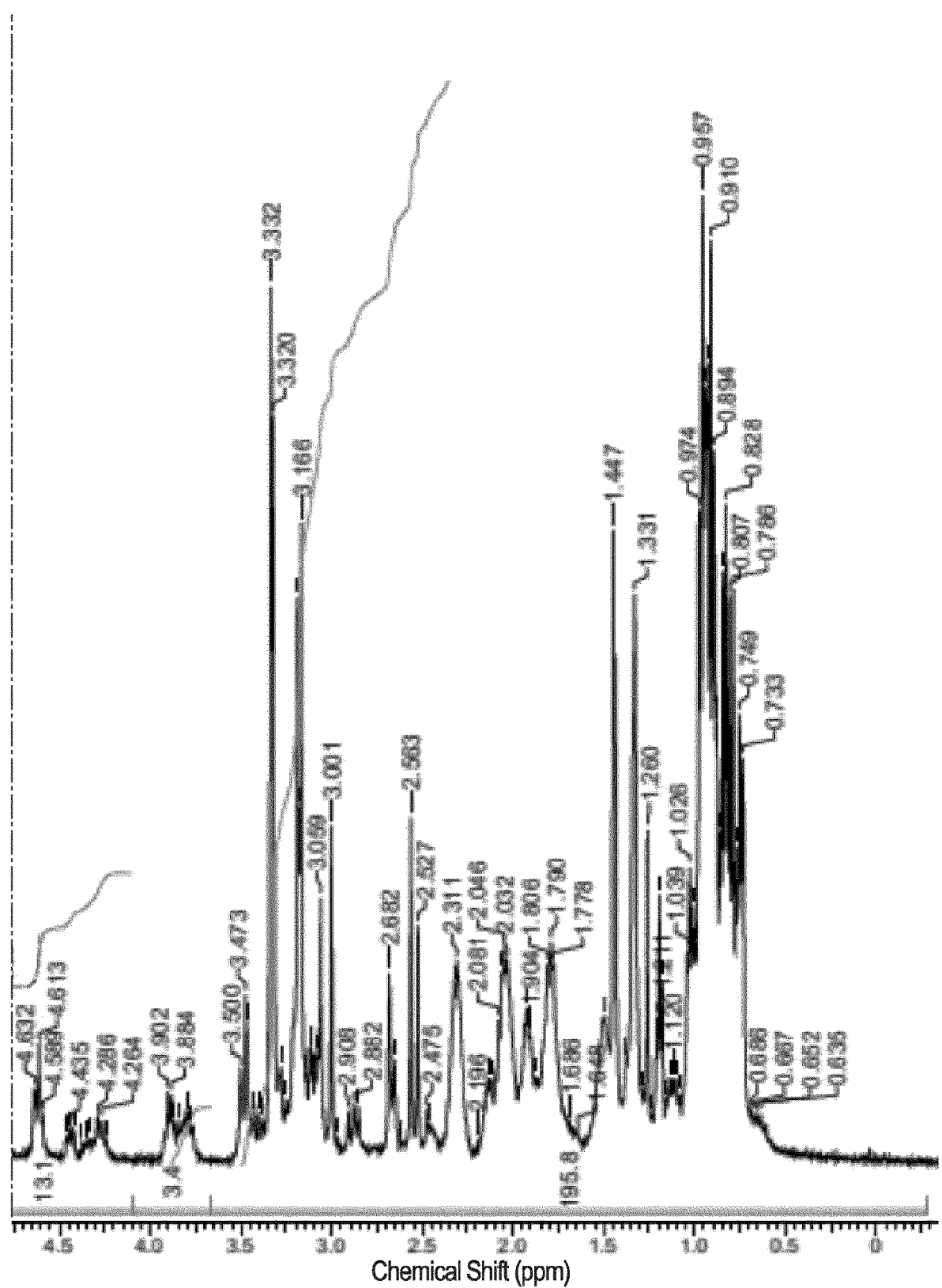
Figure 13A:
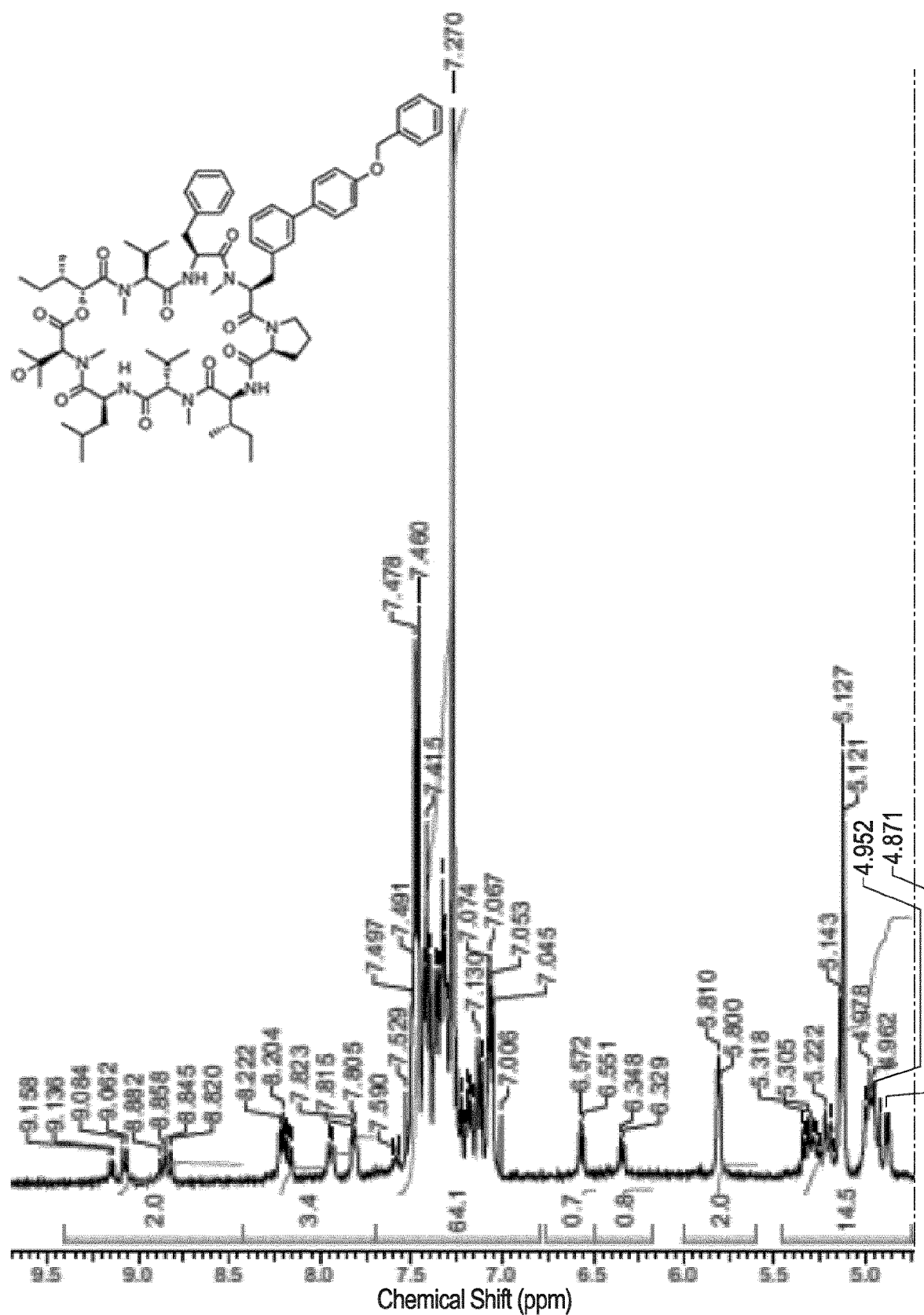
FIG. 13A and FIG. 13B presents a $^1$H NMR spectrum for Example 13.
Figure 13B:
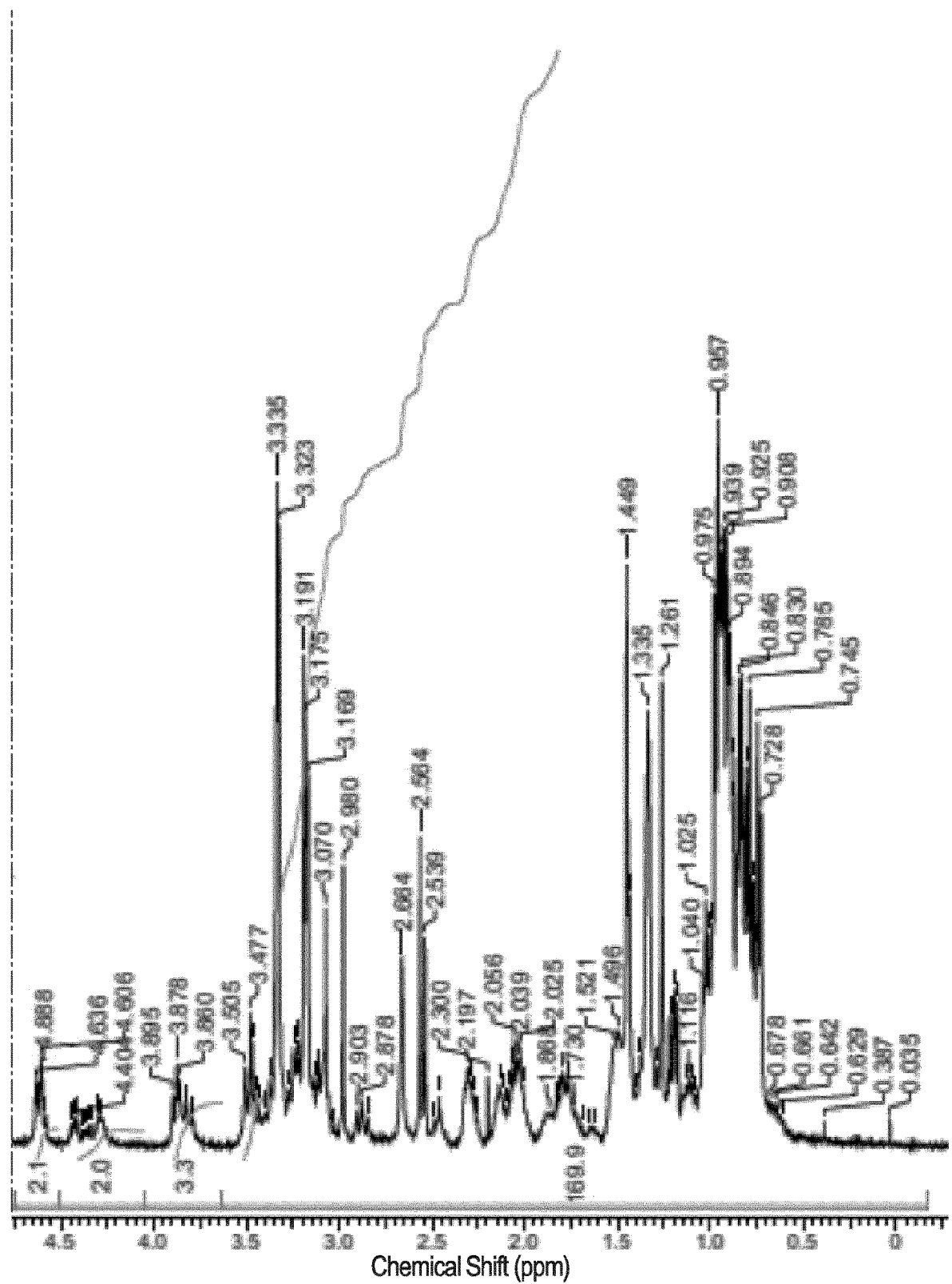
Figure 14A:
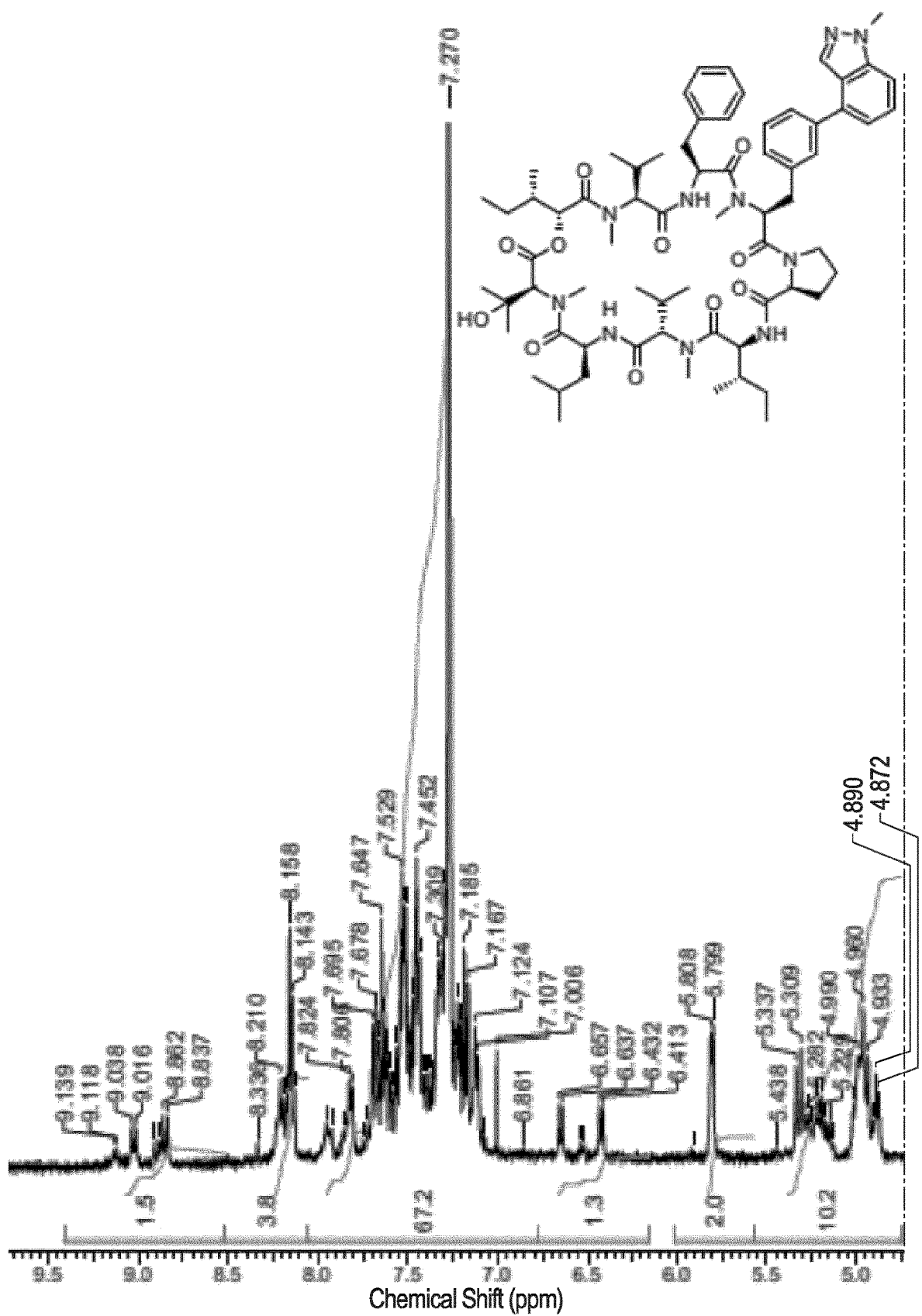
FIG. 14A and FIG. 14B presents a $^1$H NMR spectrum for Example 14.
Figure 14B:
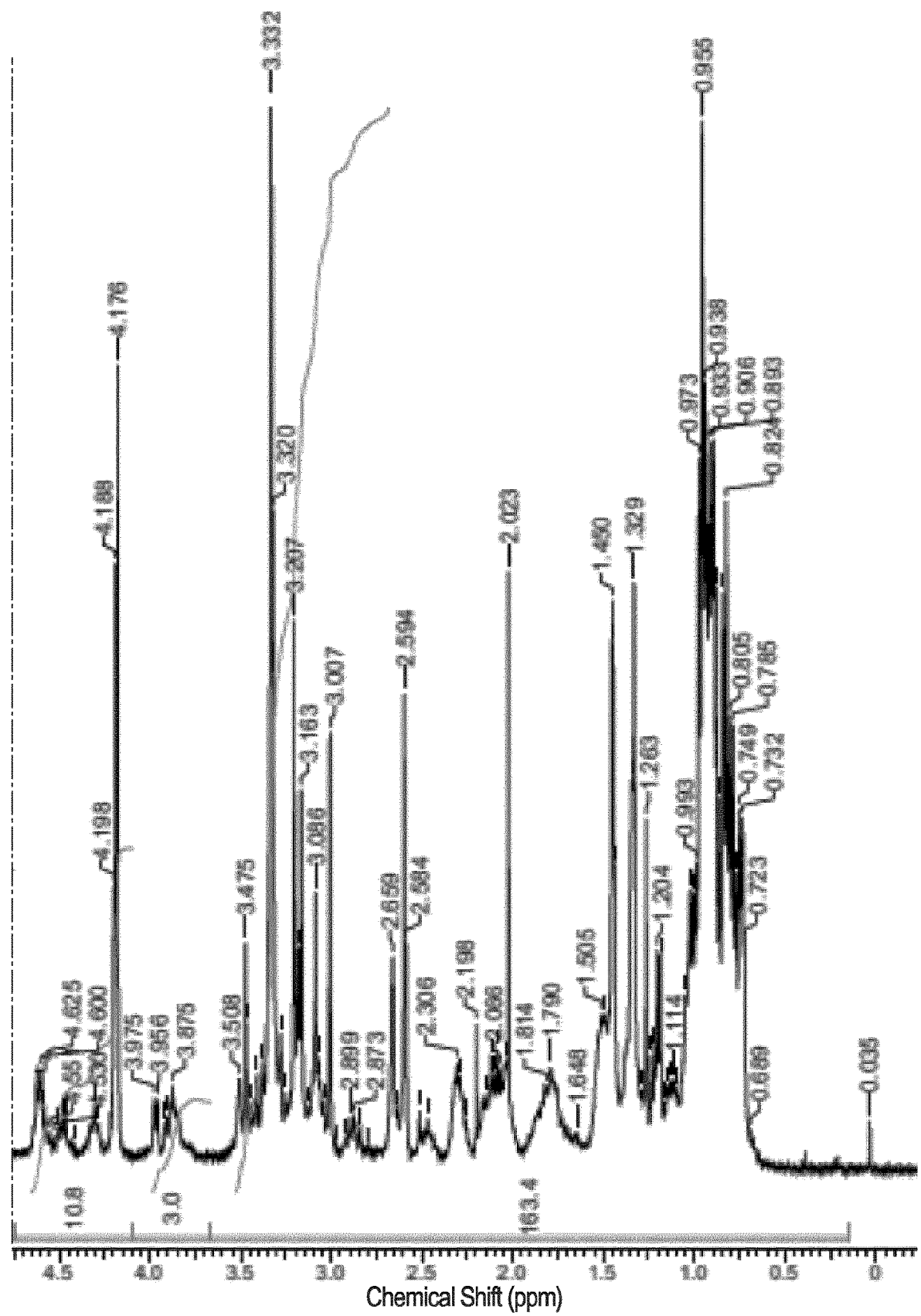
Figure 15A:
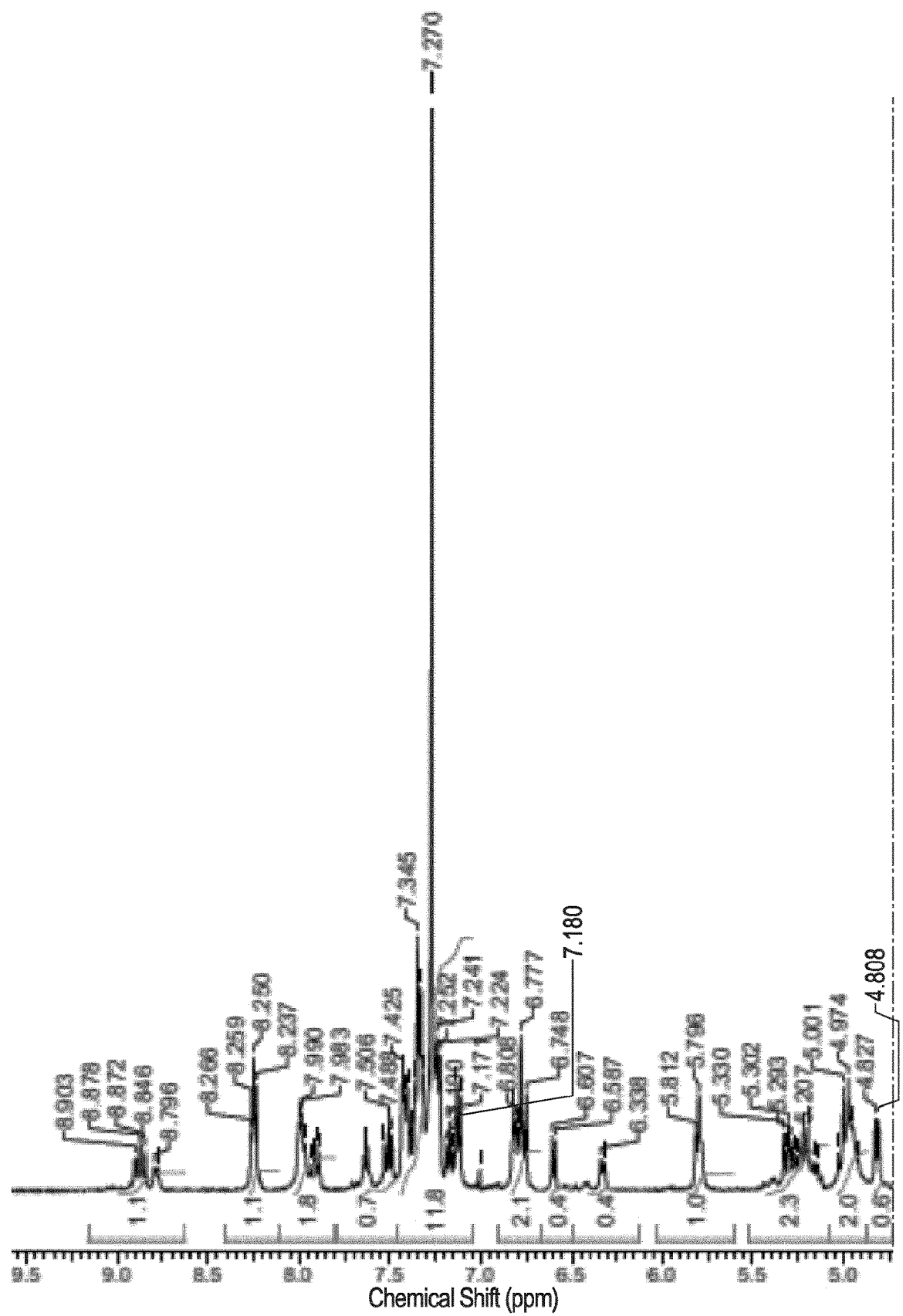
FIG. 15A and FIG. 15B presents a $^1$H NMR spectrum for Example 15.
Figure 15B:
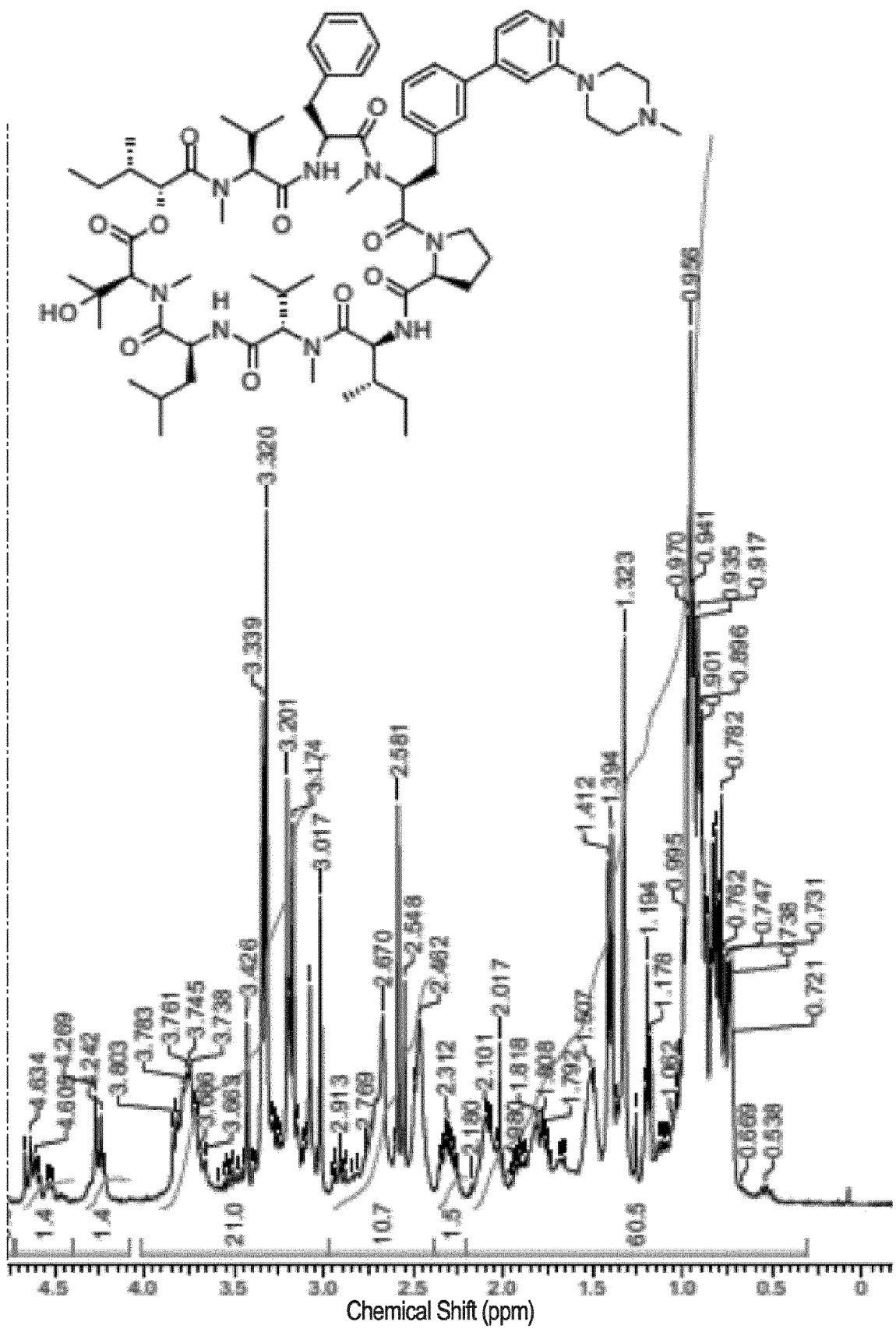
Figure 16A:
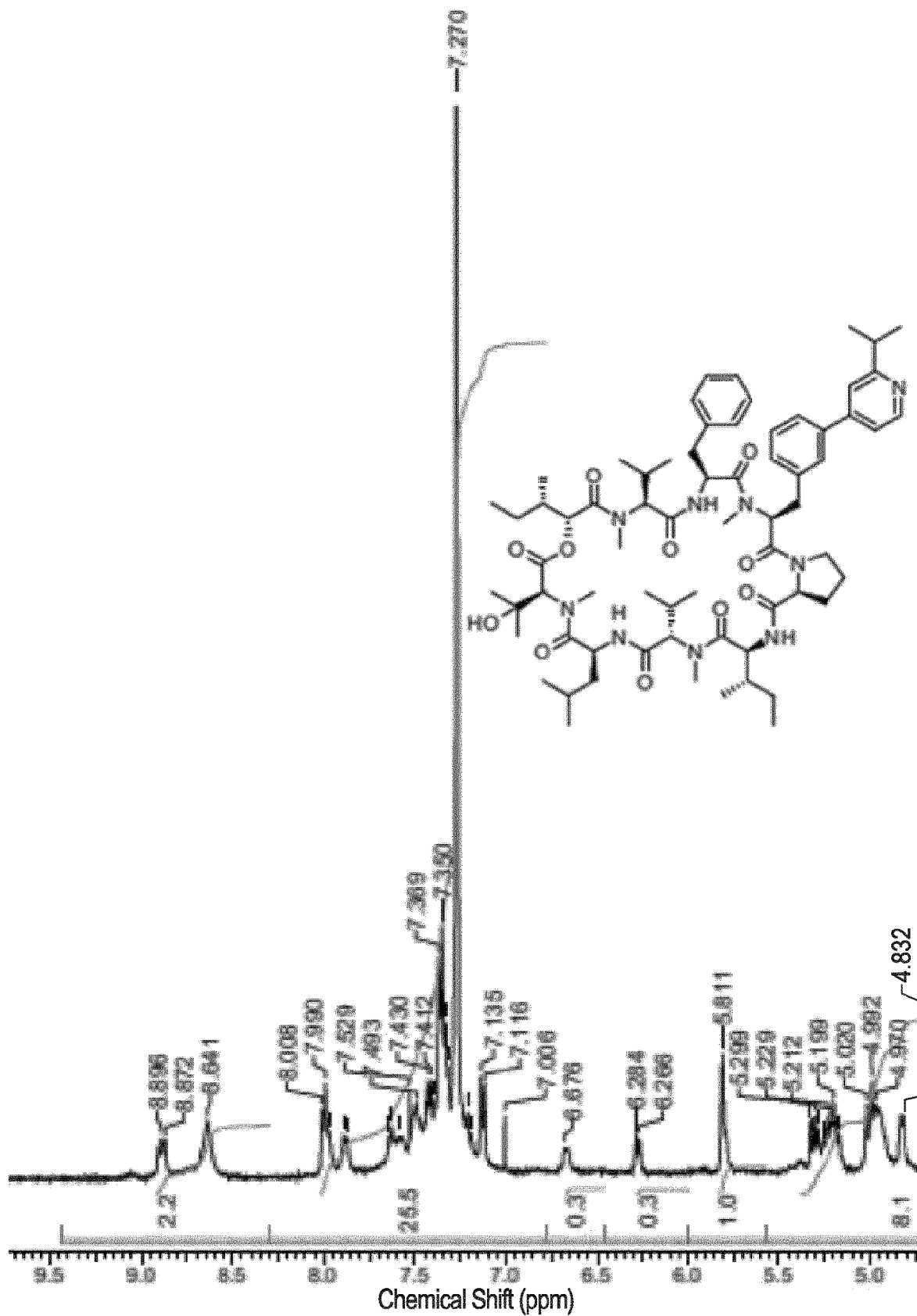
FIG. 16A and FIG. 16B presents a $^1$H NMR spectrum for Example 16.
Figure 16B:
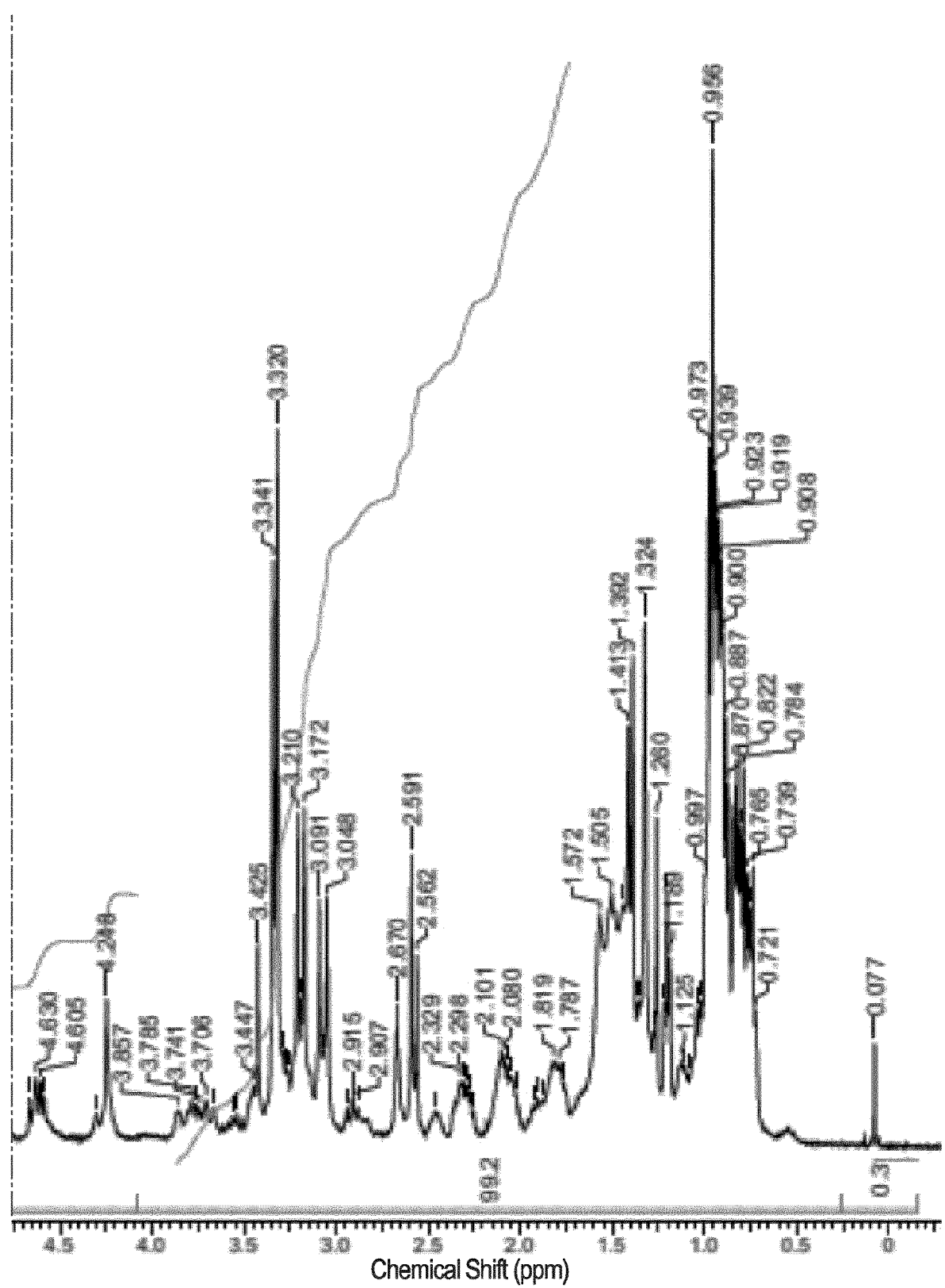
Figure 17A:
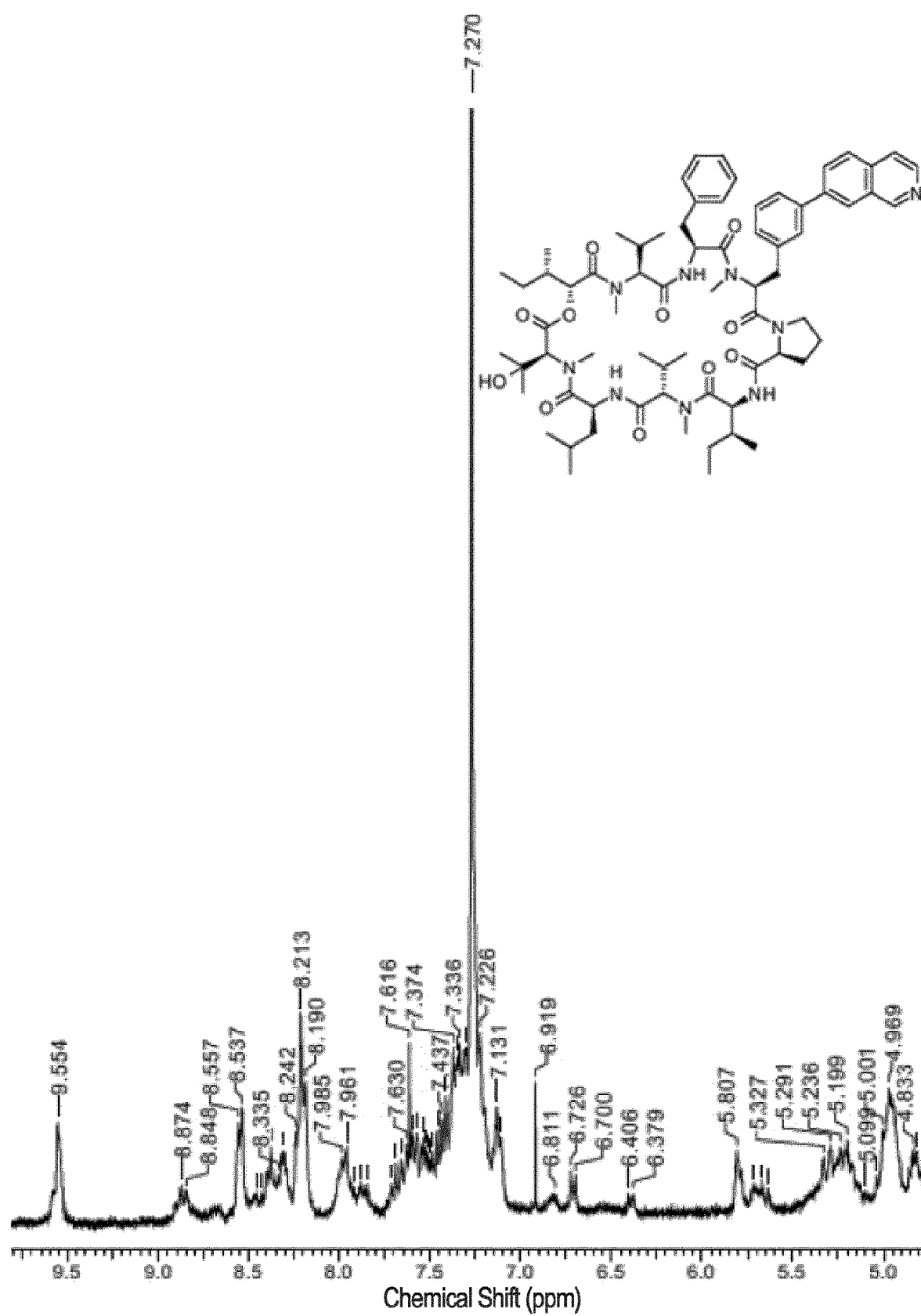
FIG. 17A and FIG. 17B presents a $^1$H NMR spectrum for Example 17.
Figure 17B:
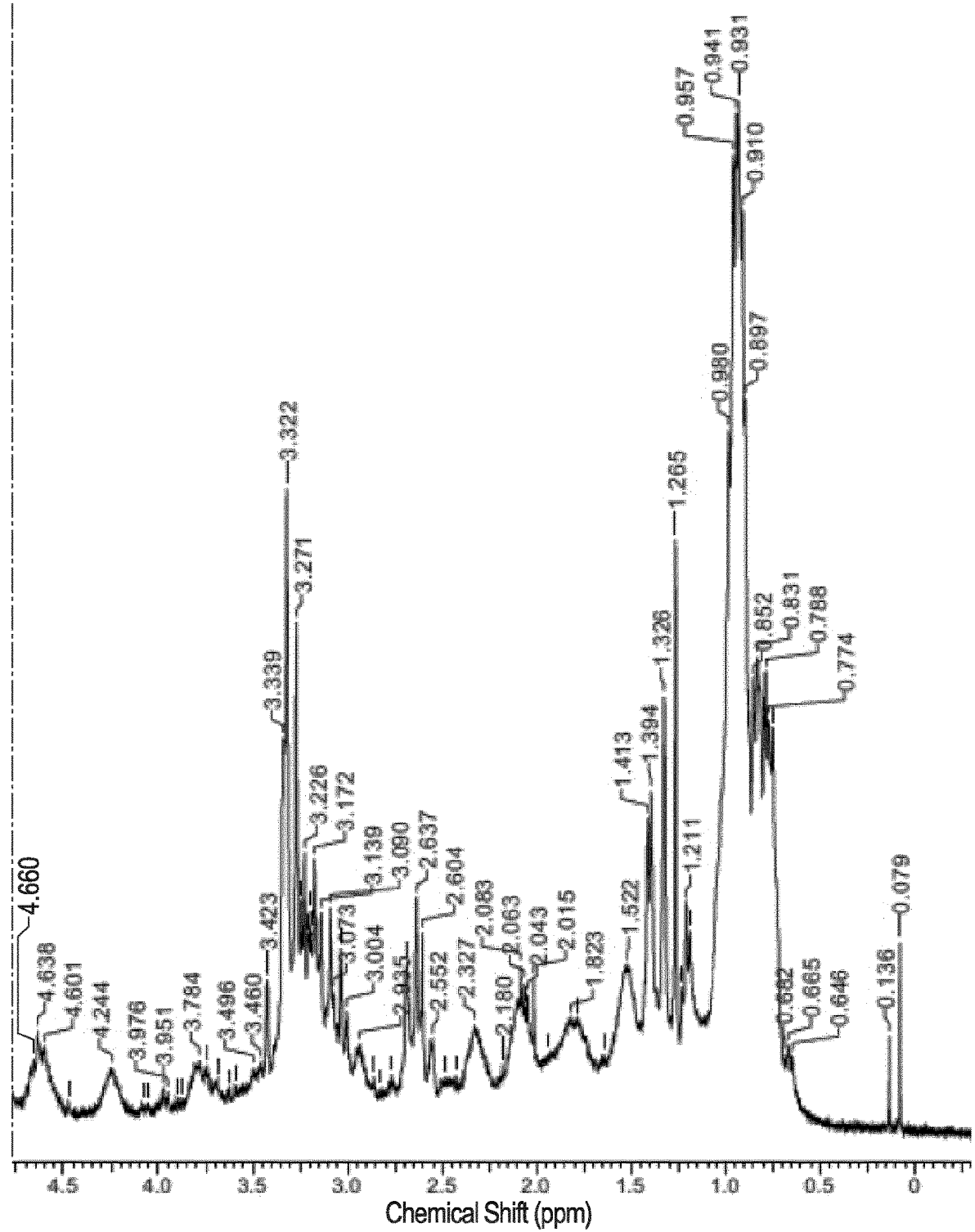
Figure 18A:
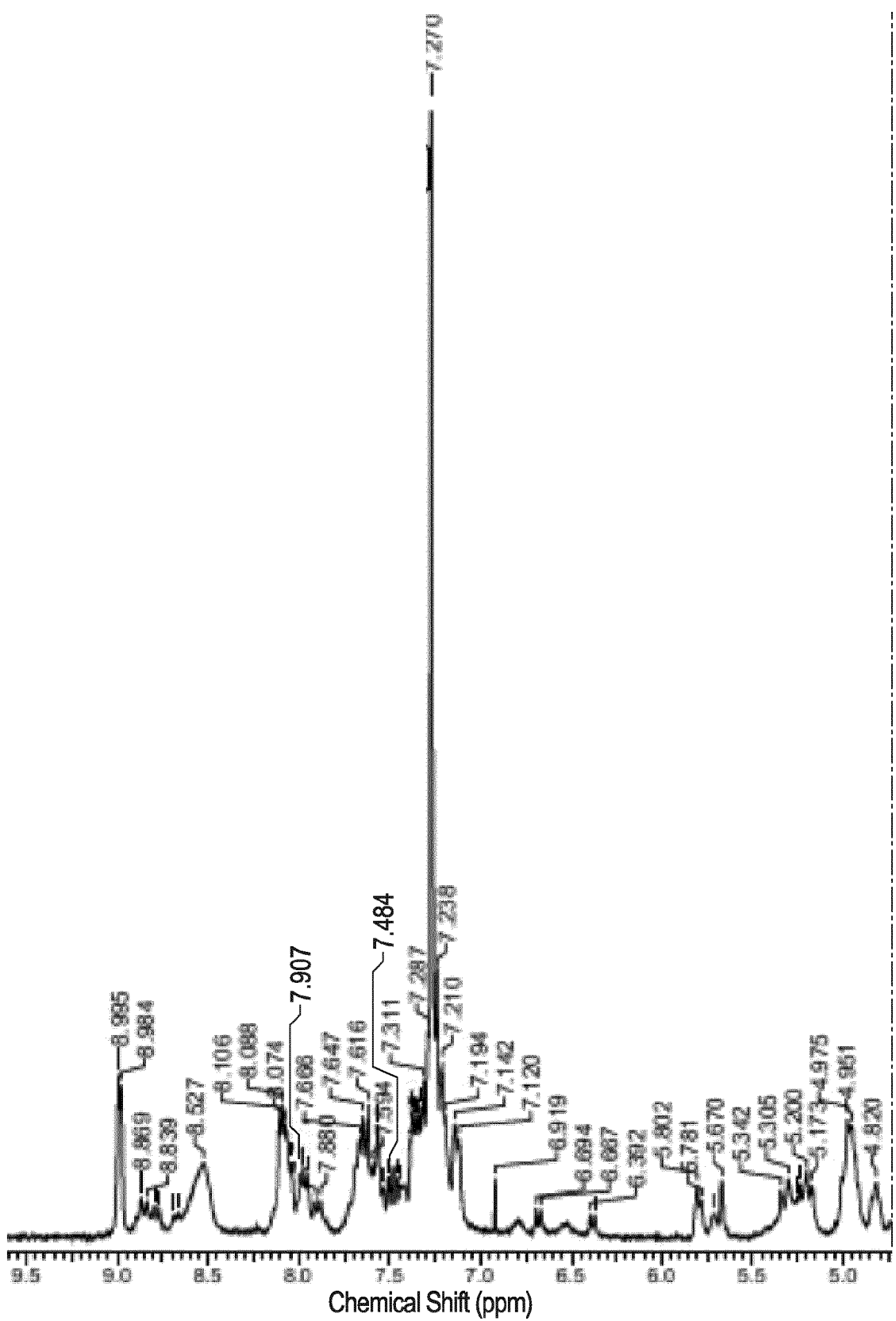
FIG. 18A and FIG. 18B presents a $^1$H NMR spectrum for Example 18.
Figure 18B:
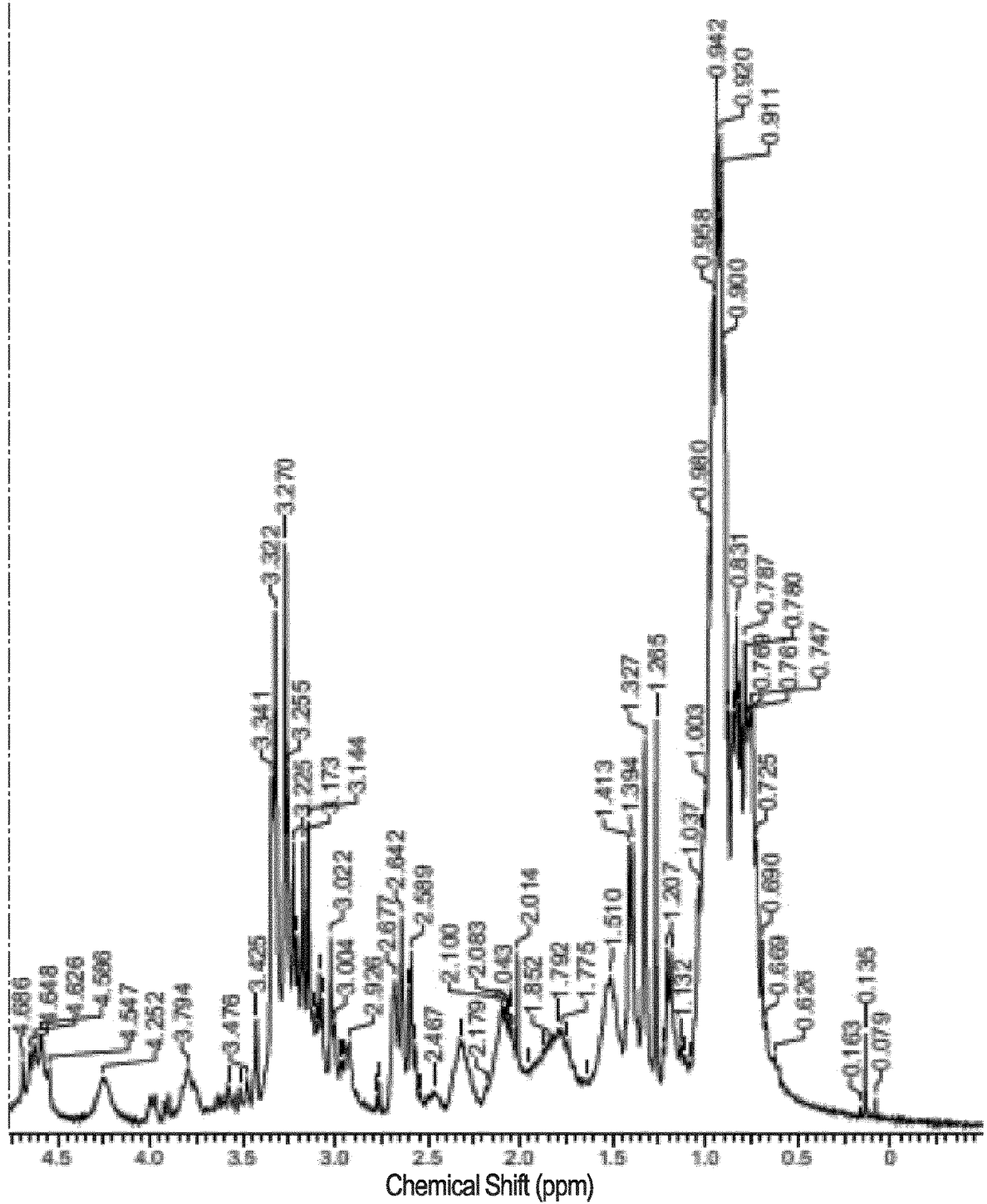
Figure 19A:
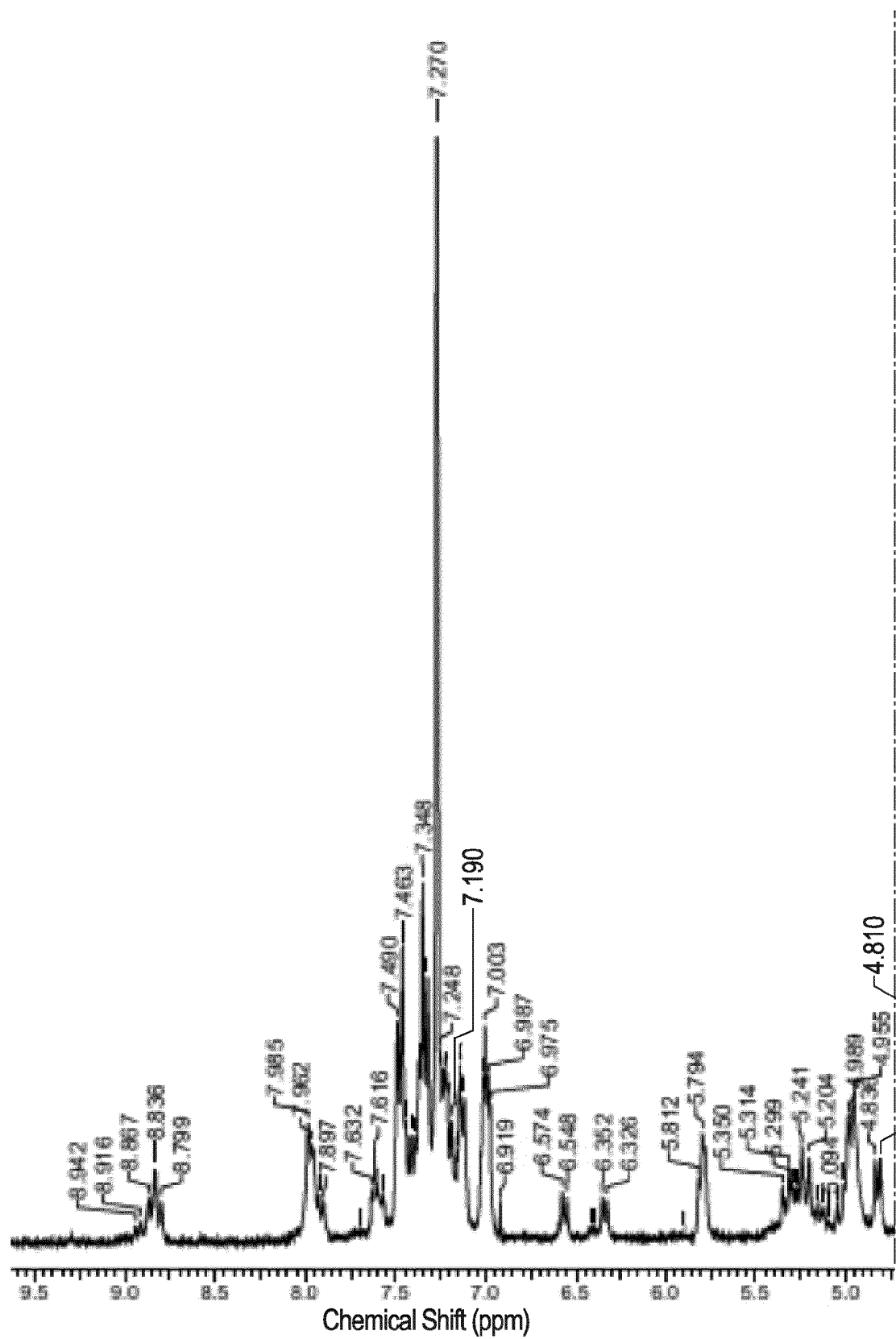
FIG. 19A and FIG. 19B presents a $^1$H NMR spectrum for Example 19.
Figure 19B:
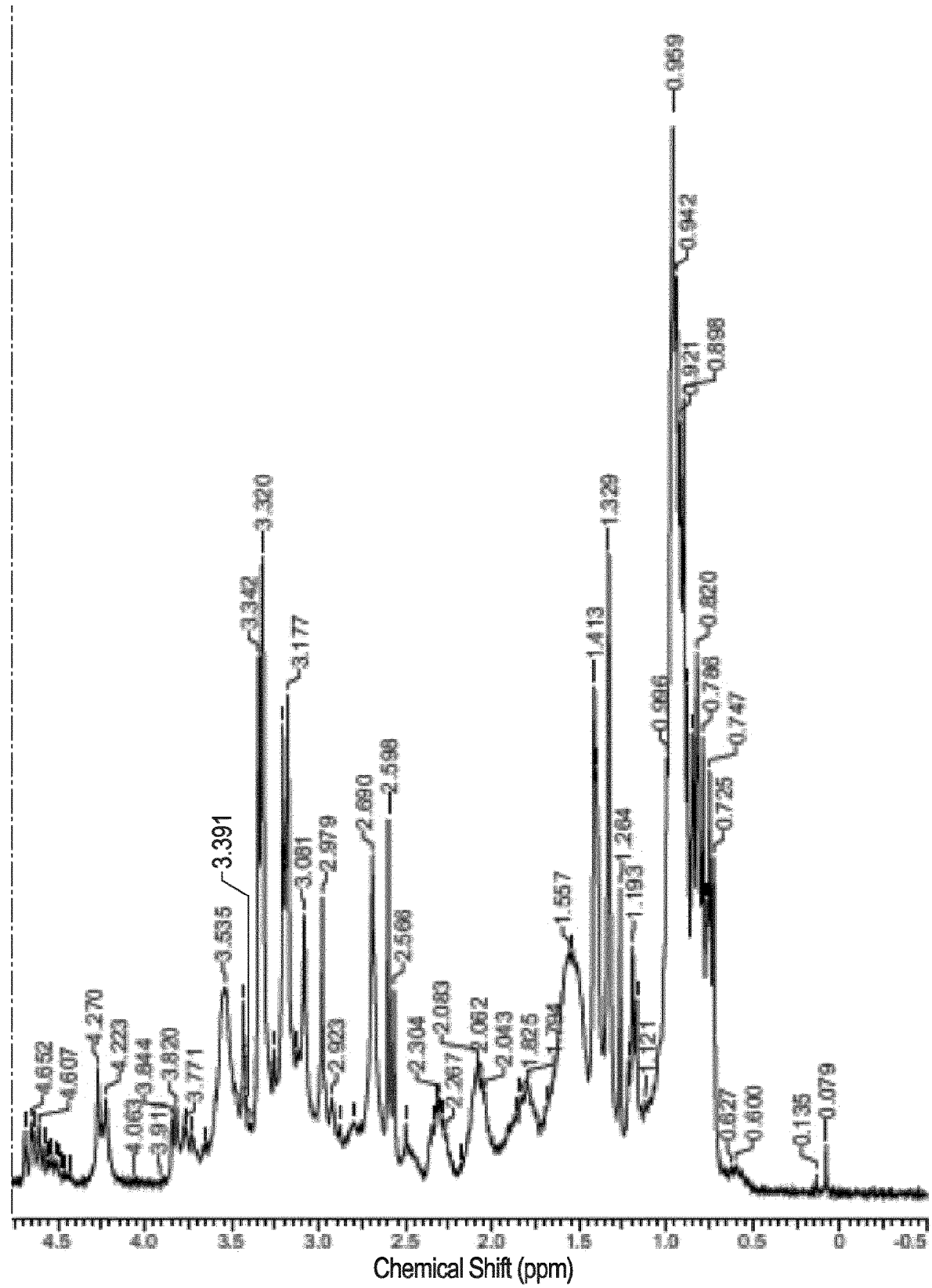
Figure 20A:
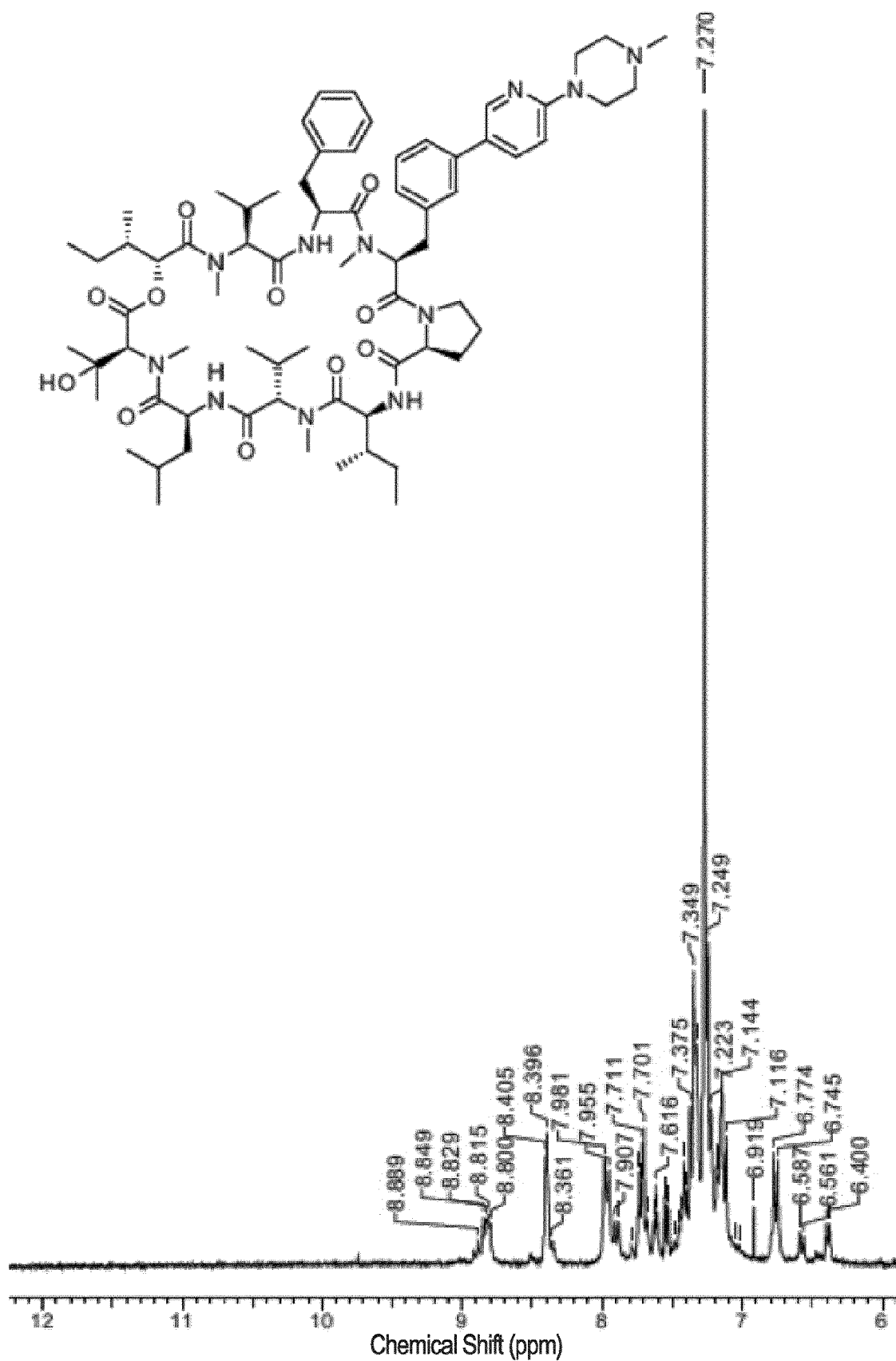
FIG. 20A and FIG. 20B presents a $^1$H NMR spectrum for Example 20.
Figure 20B:
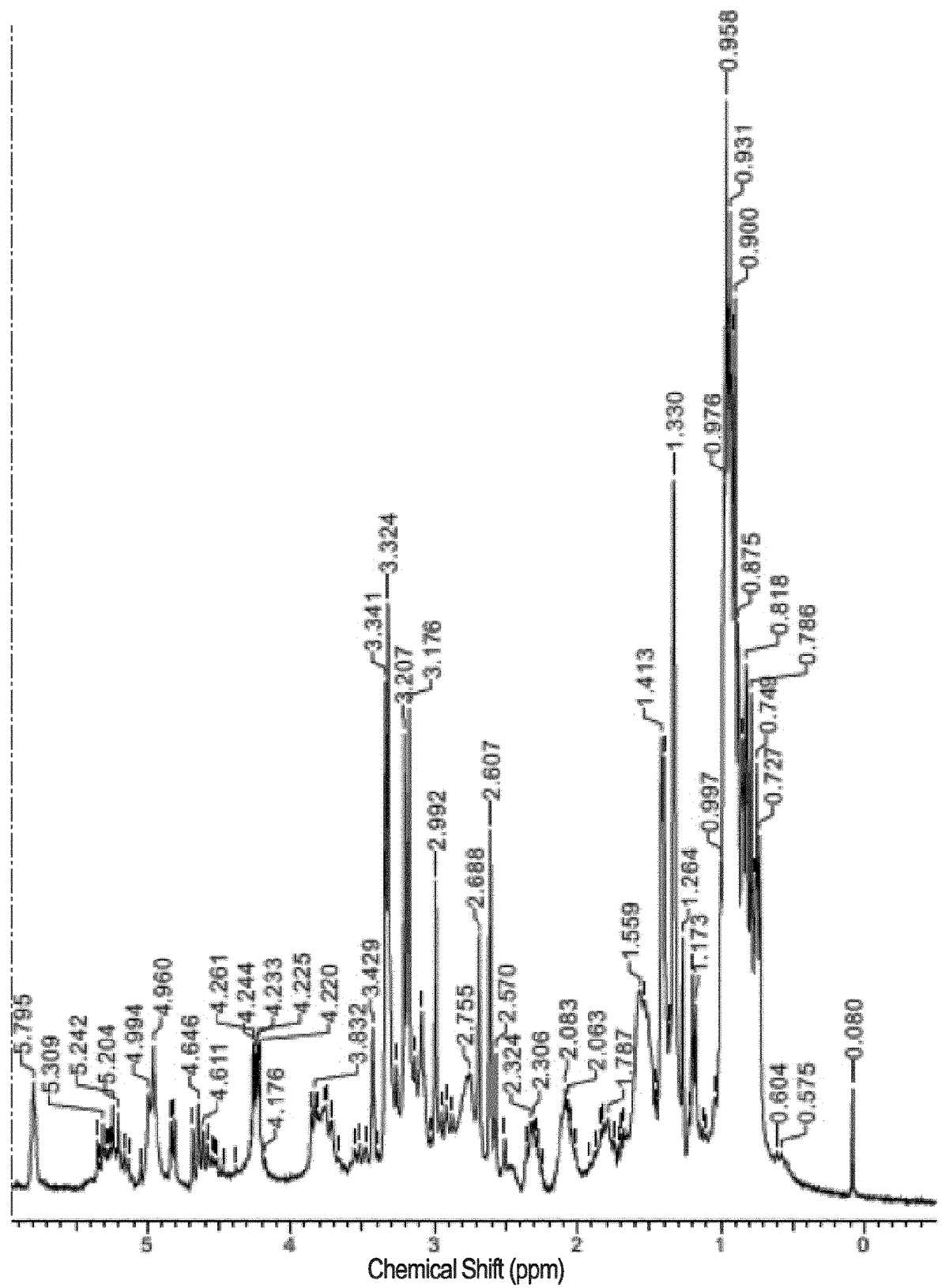
Figure 21A:
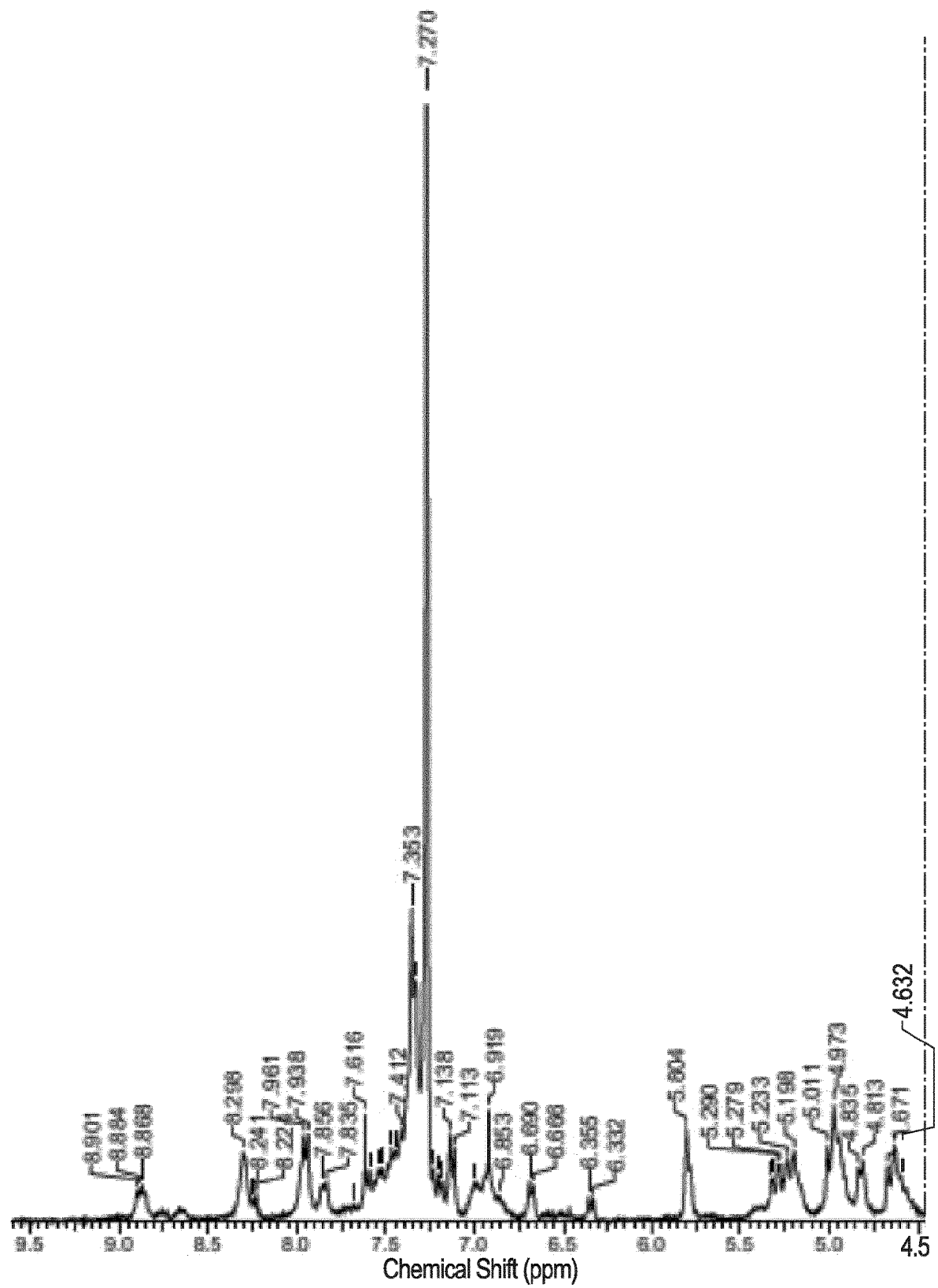
FIG. 21A and FIG. 21B presents a $^1$H NMR spectrum for Example 21.
Figure 21B:
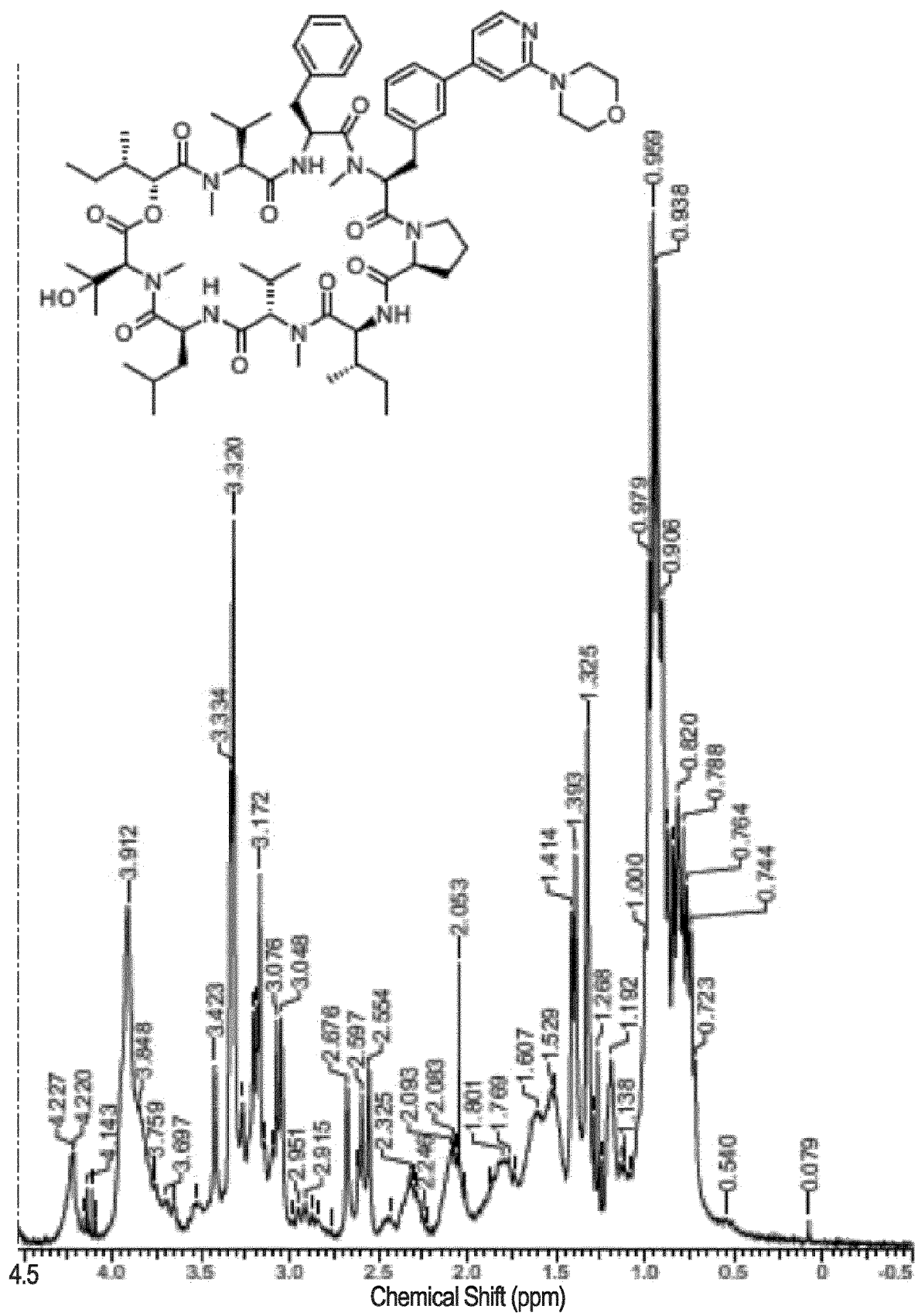
Figure 22A:
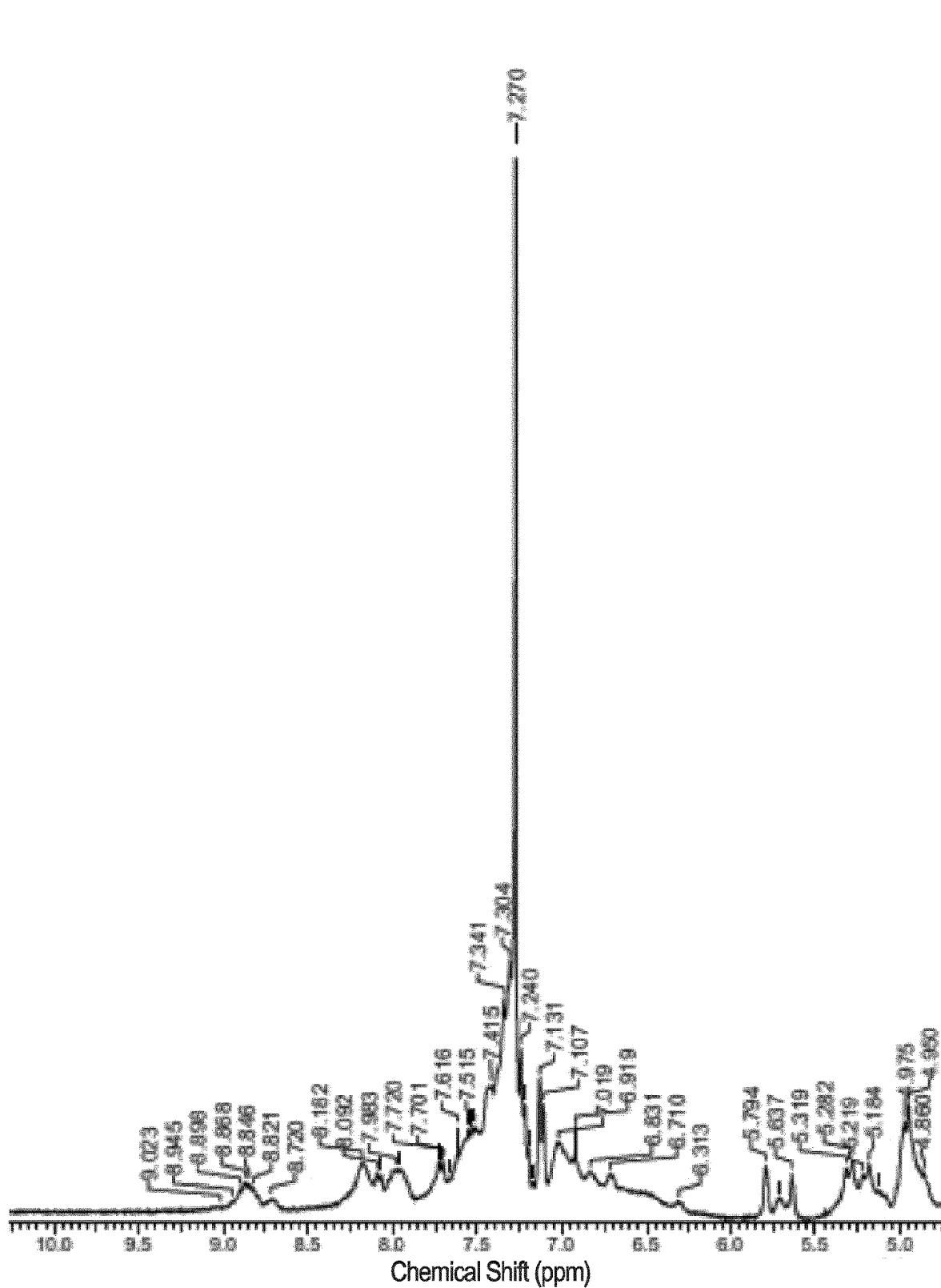
FIG. 22A and FIG. 22B presents a $^1$H NMR spectrum for Example 22.
Figure 22B:
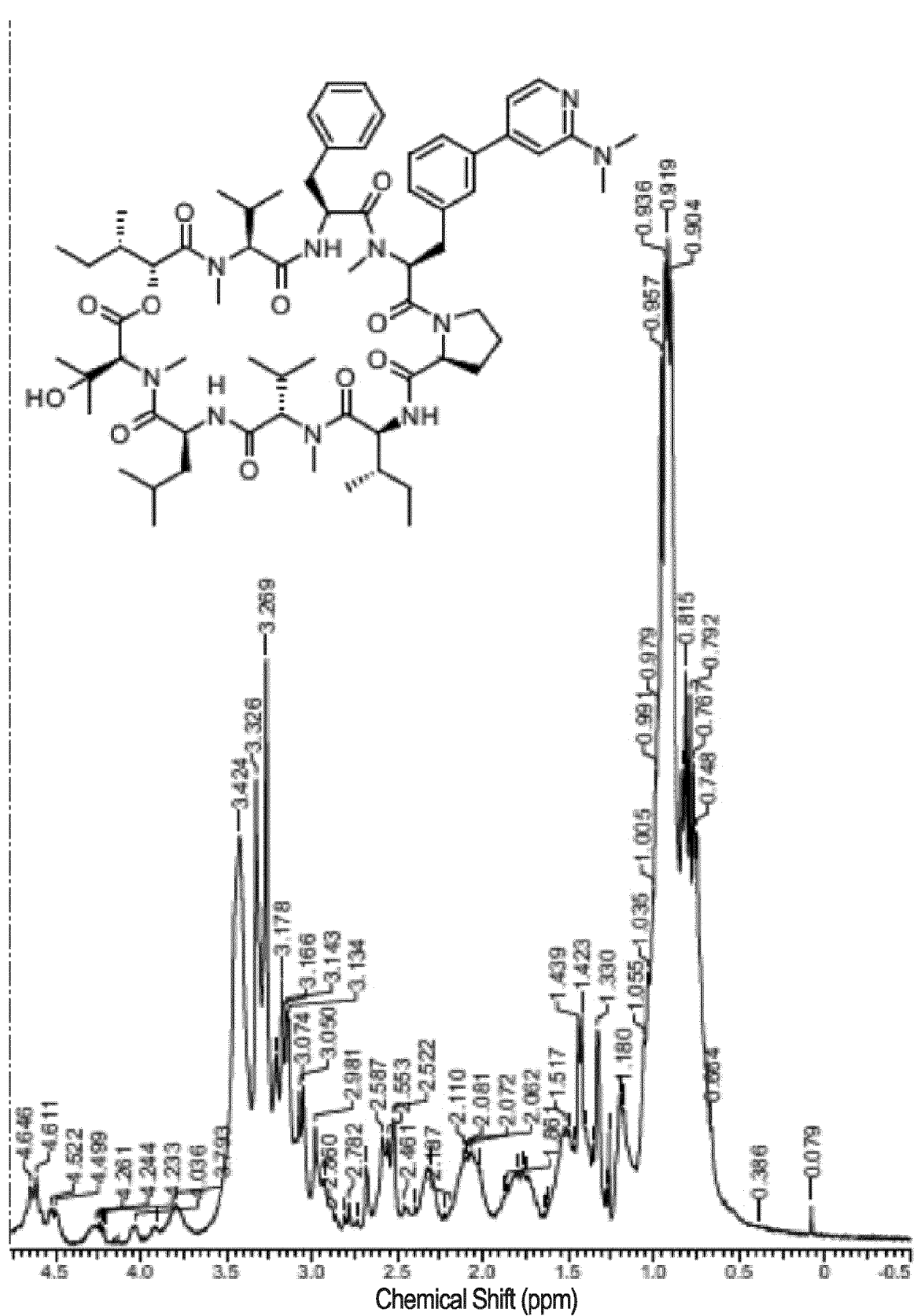
Figure 23A:
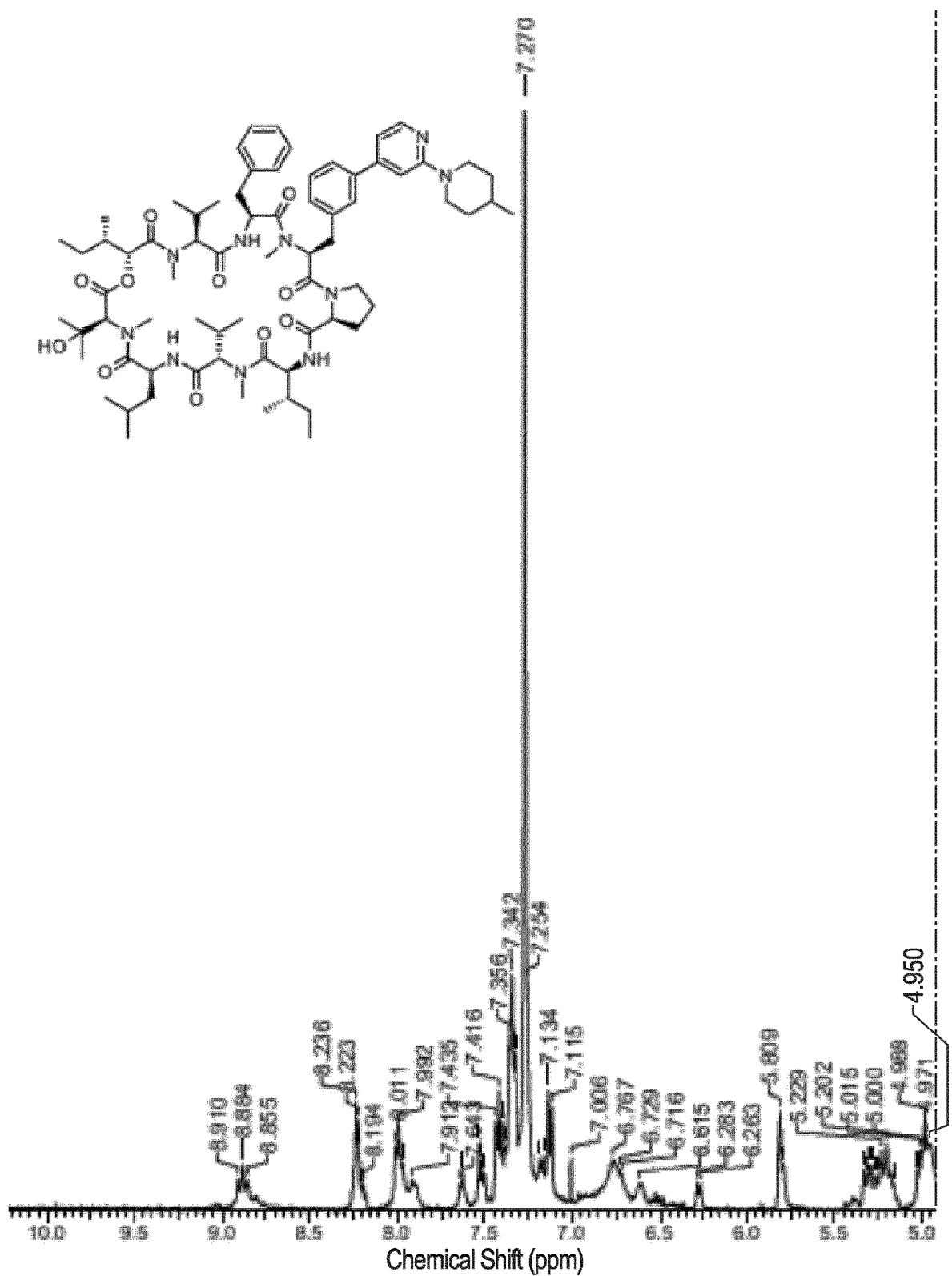
FIG. 23A and FIG. 23B presents a $^1$H NMR spectrum for Example 23.
Figure 23B:
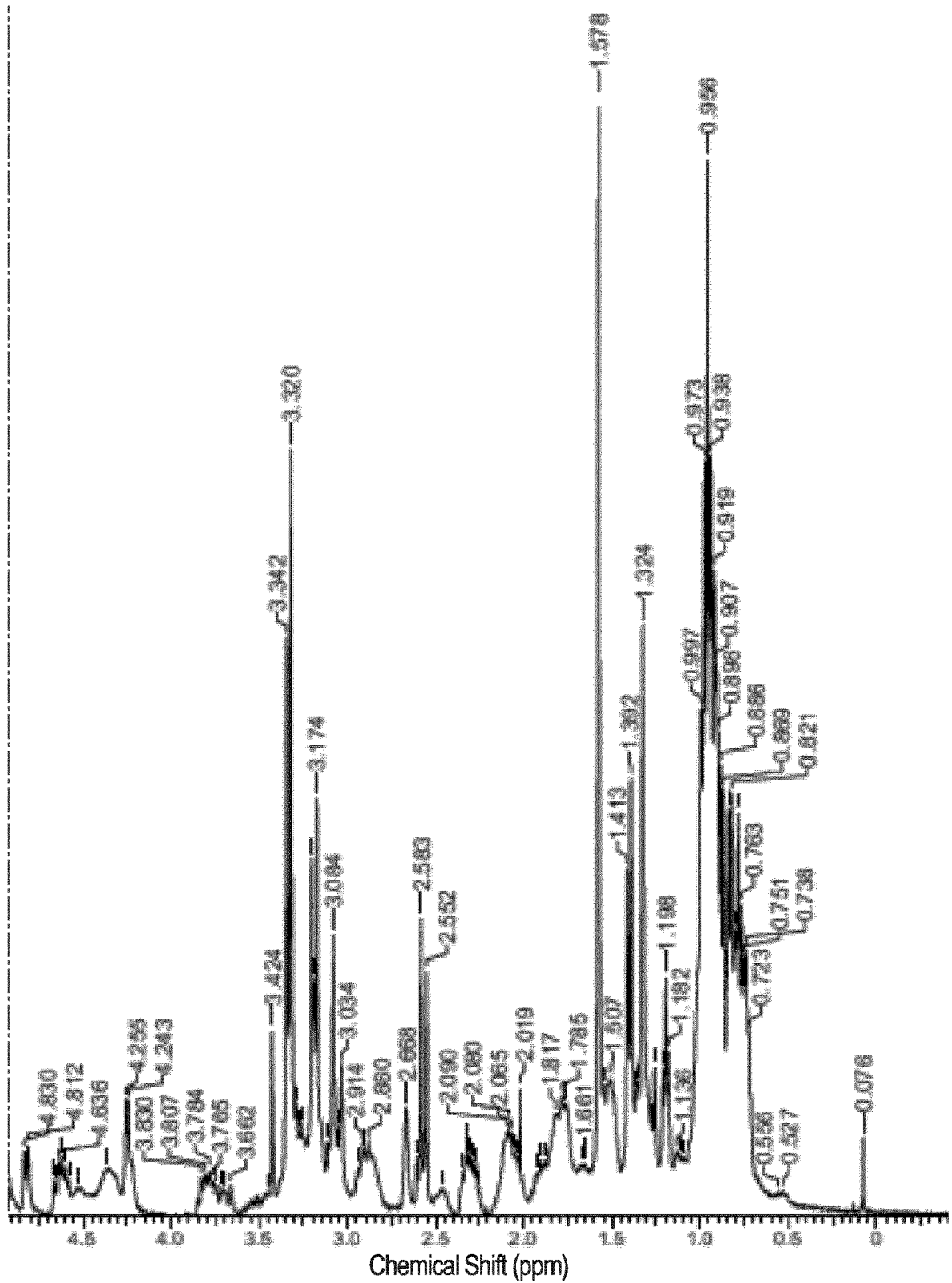
Figure 24A:
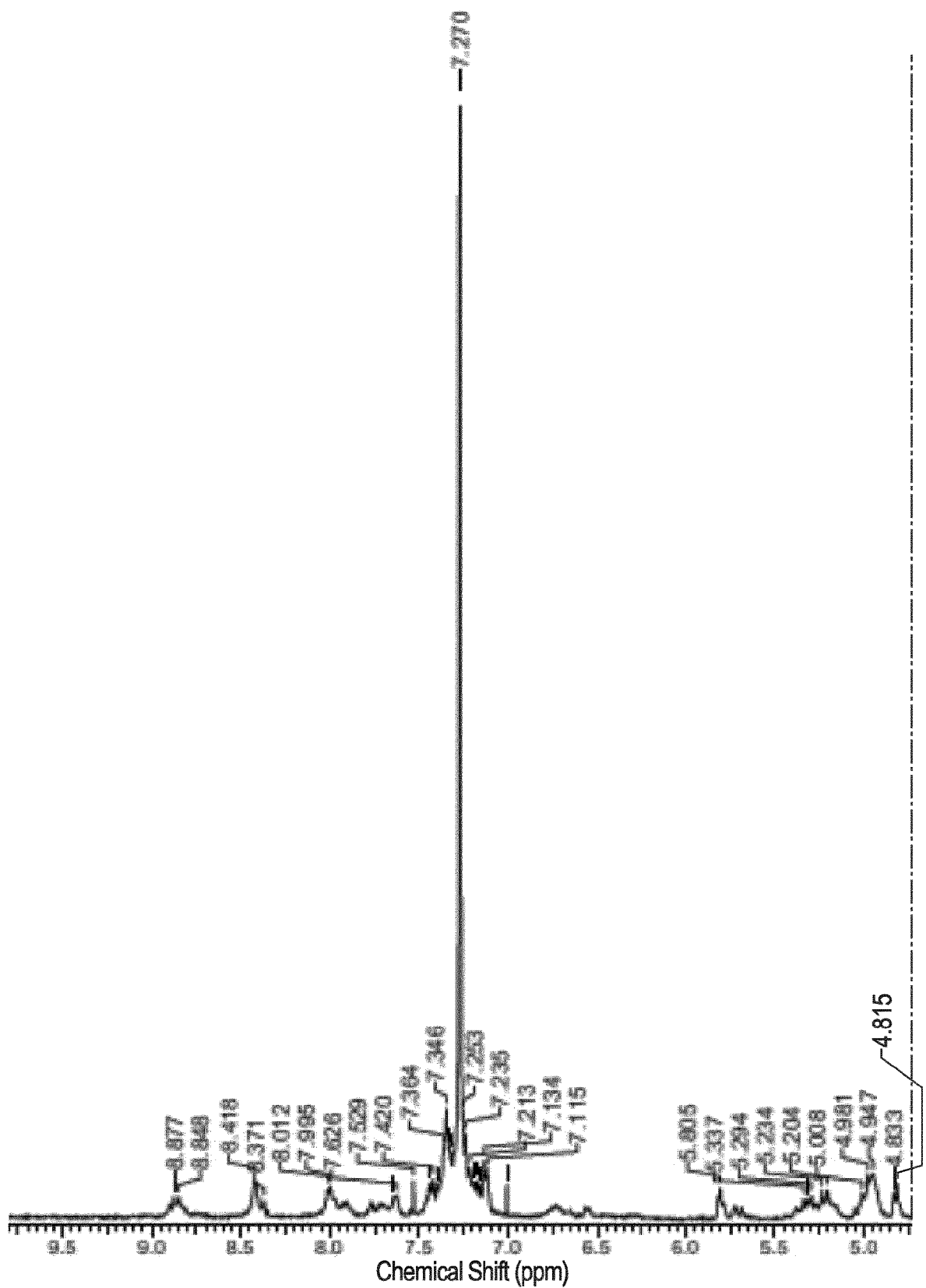
FIG. 24A and FIG. 24B presents a $^1$H NMR spectrum for Example 24.
Figure 24B:
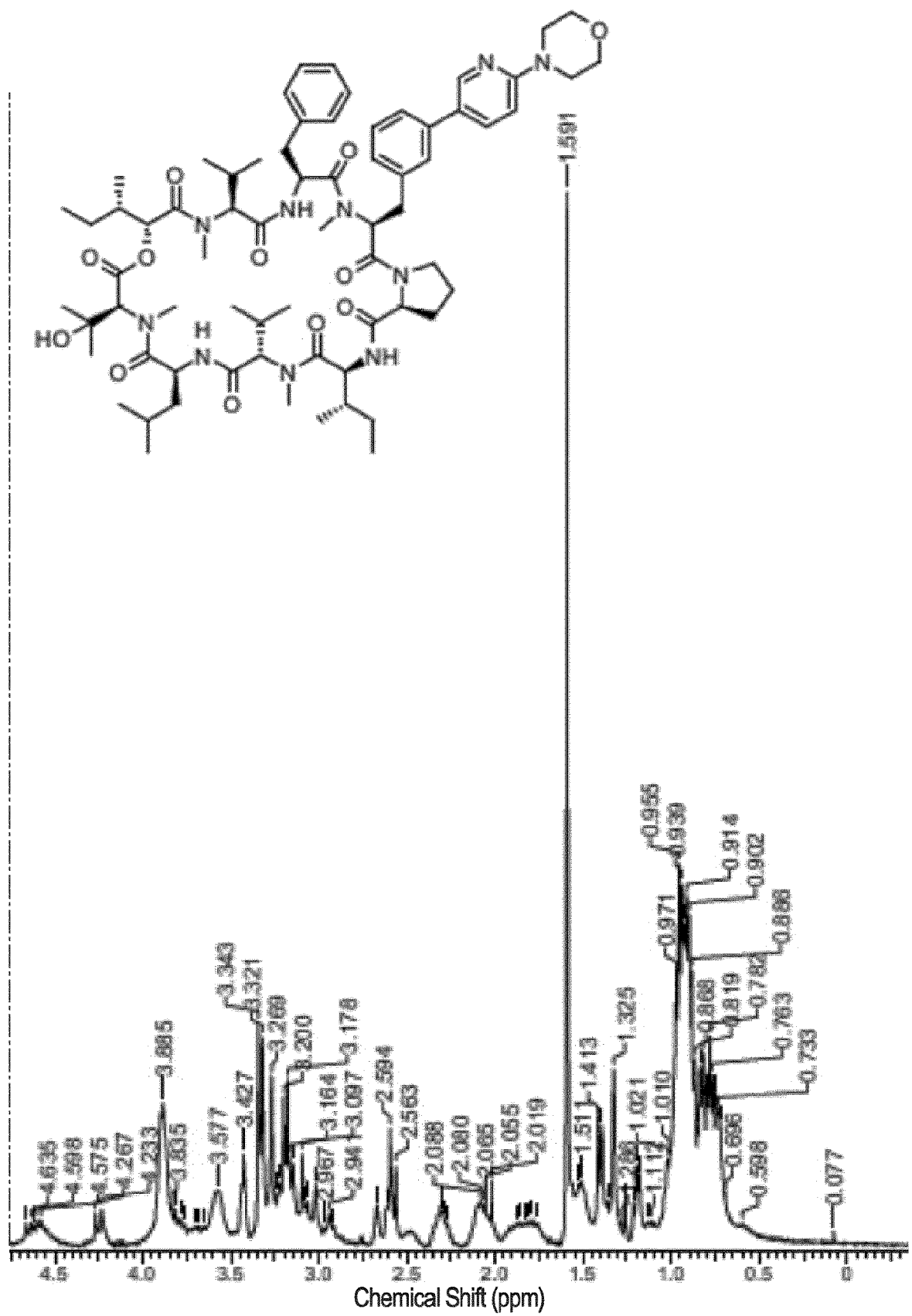
Figure 25A:
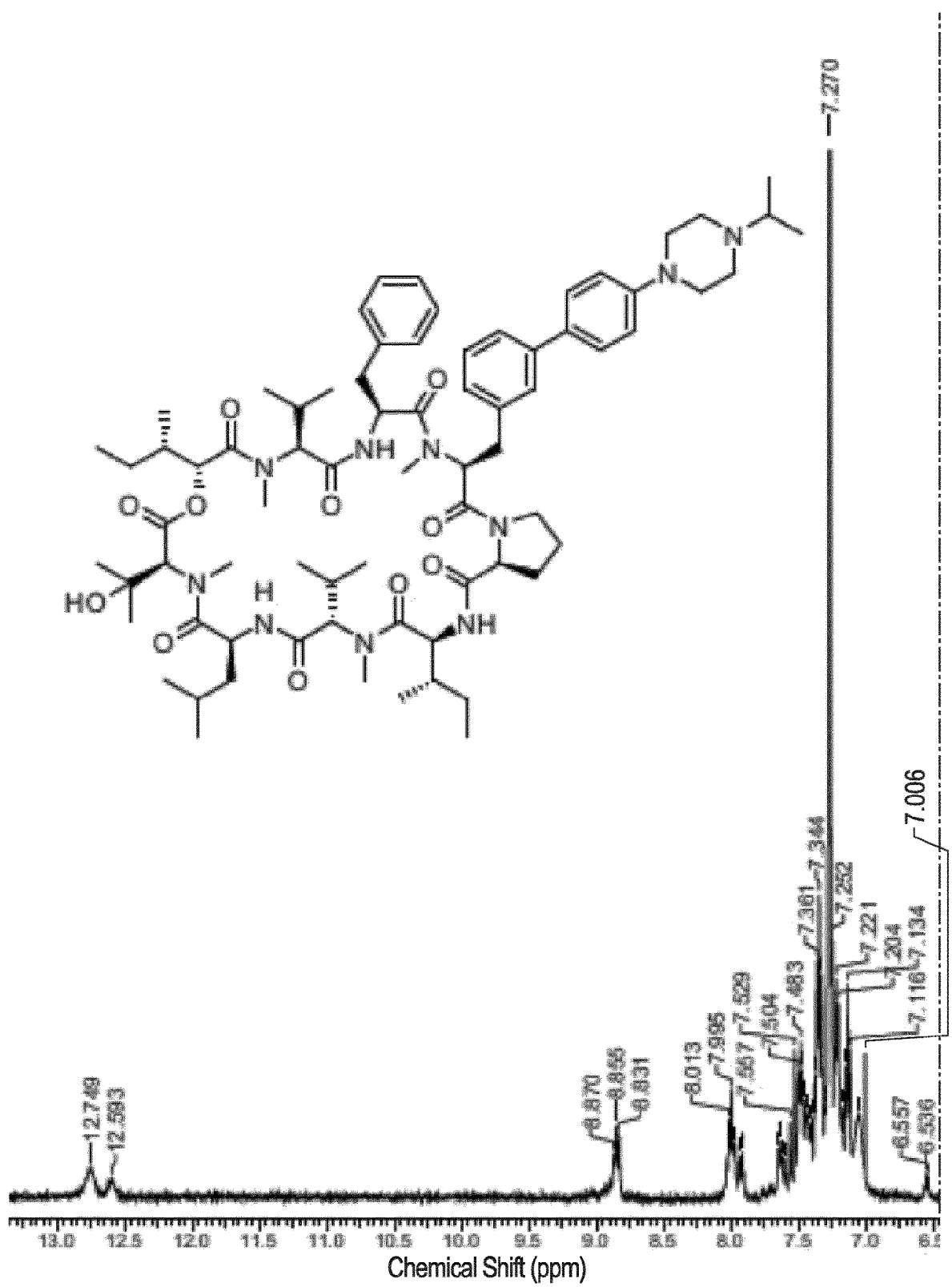
FIG. 25A and FIG. 25B presents a $^1$H NMR spectrum for Example 25.
Figure 25B:
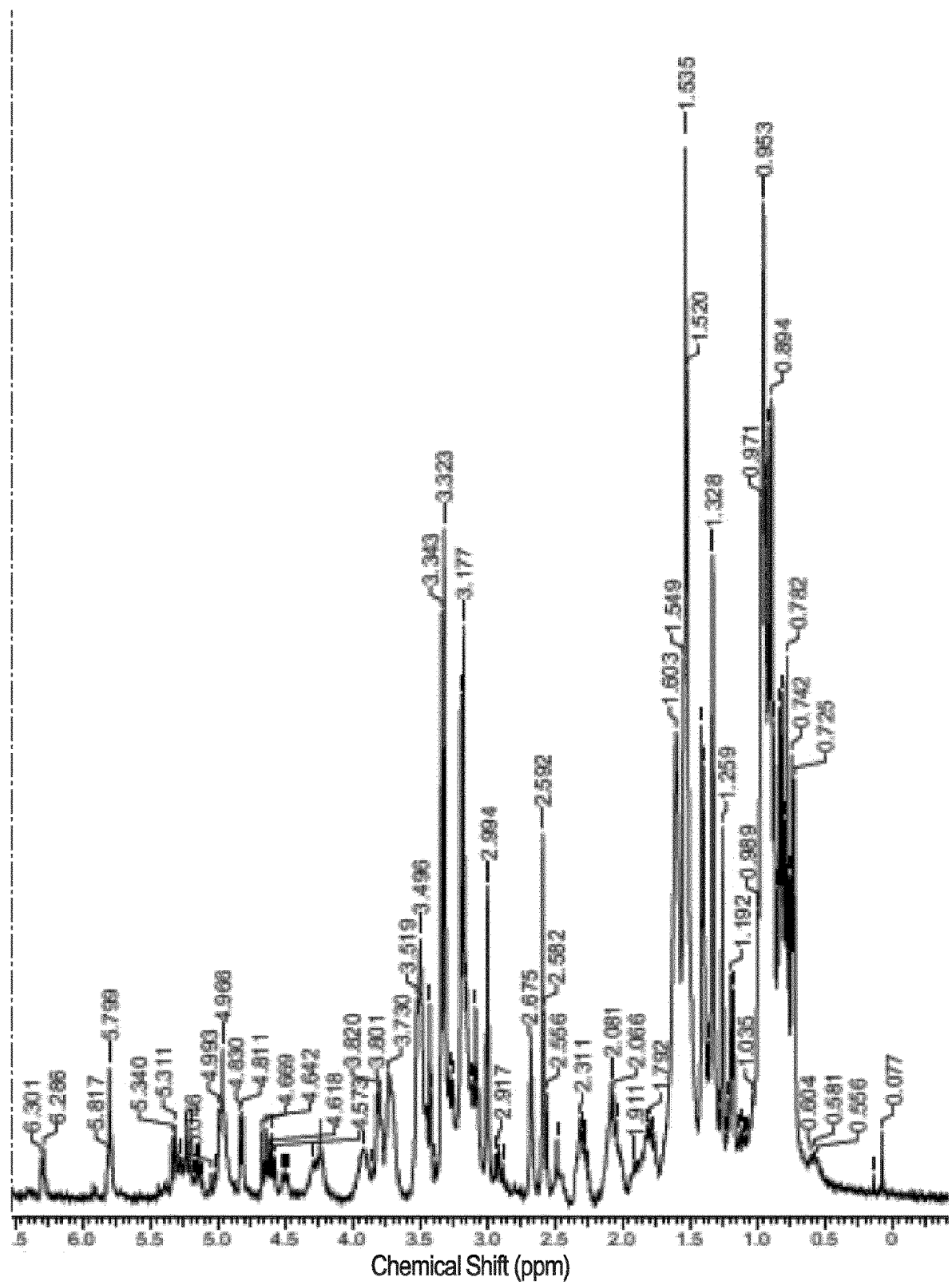
Figure 26A:
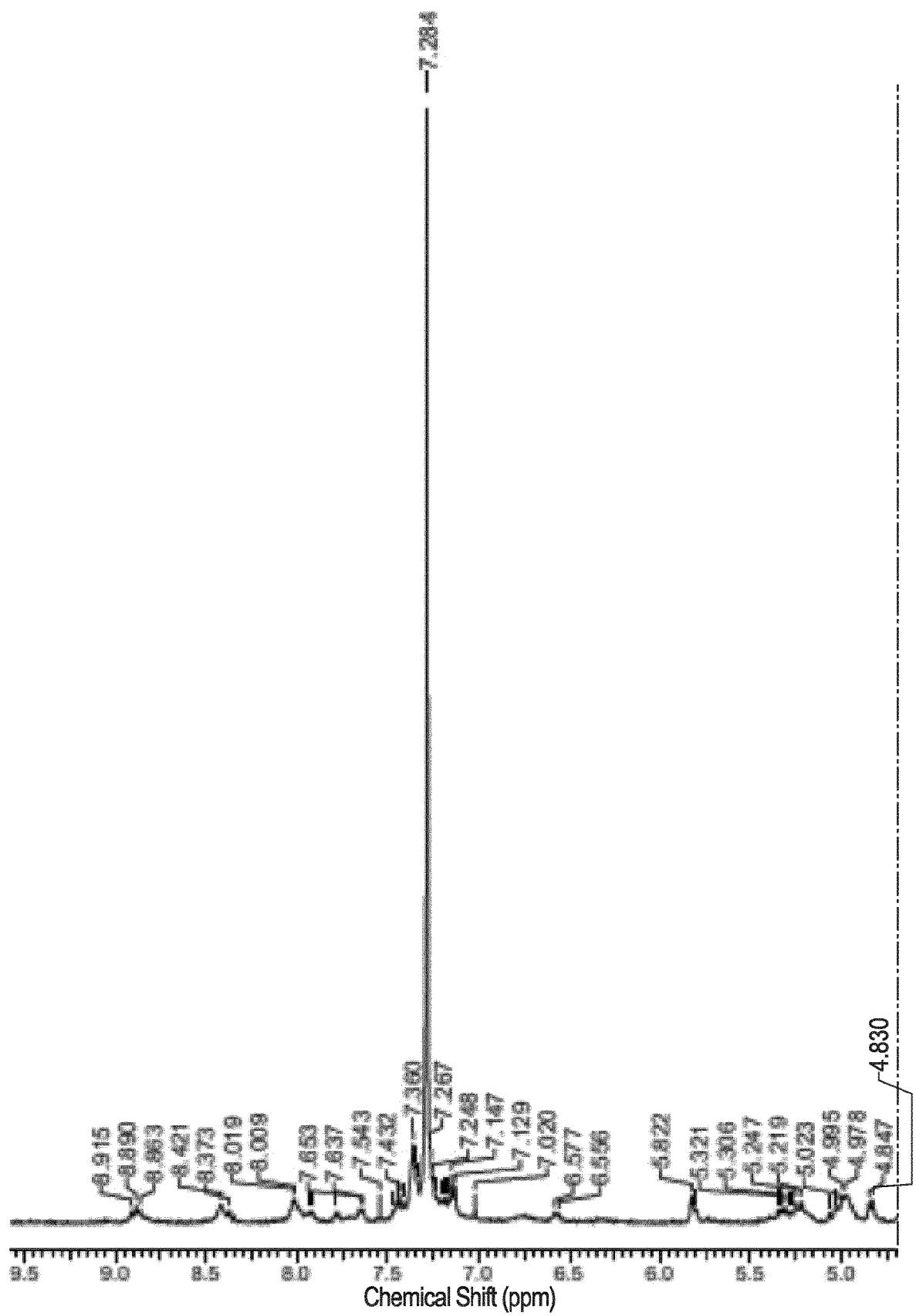
FIG. 26A and FIG. 26B presents a $^1$H NMR spectrum for Example 26.
Figure 26B:
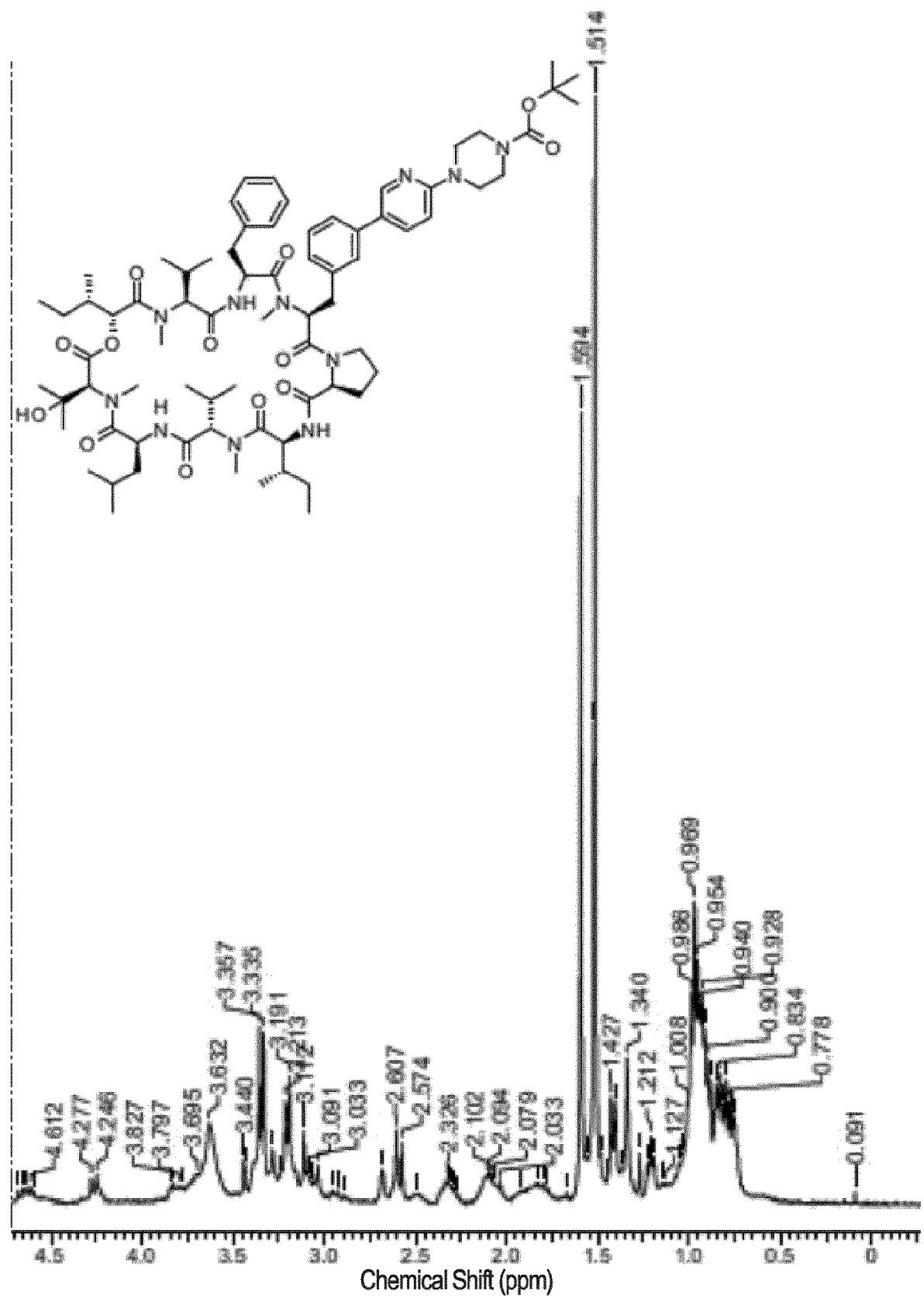
Figure 27A:
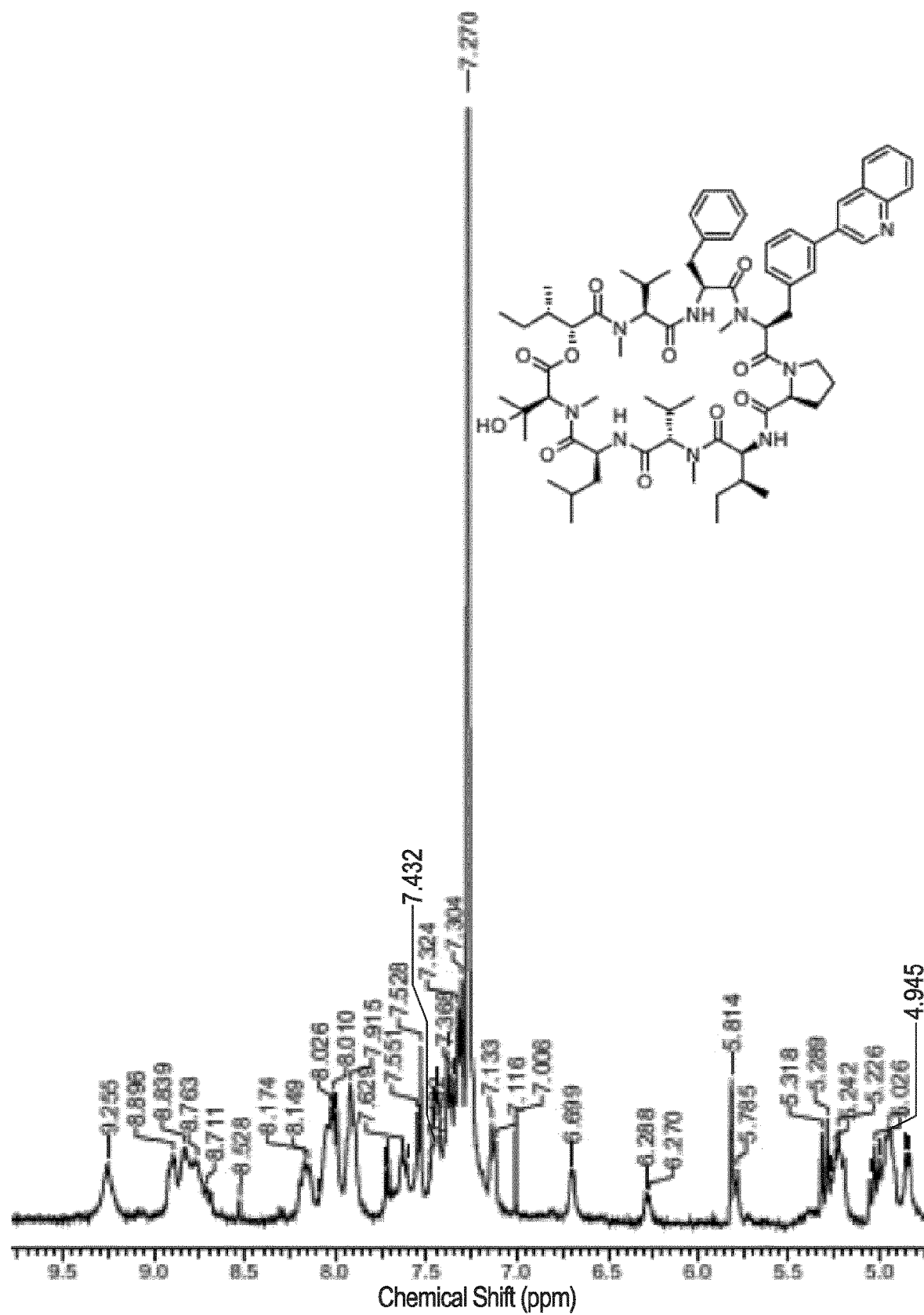
FIG. 27A and FIG. 27B presents a $^1$H NMR spectrum for Example 27.
Figure 27B:
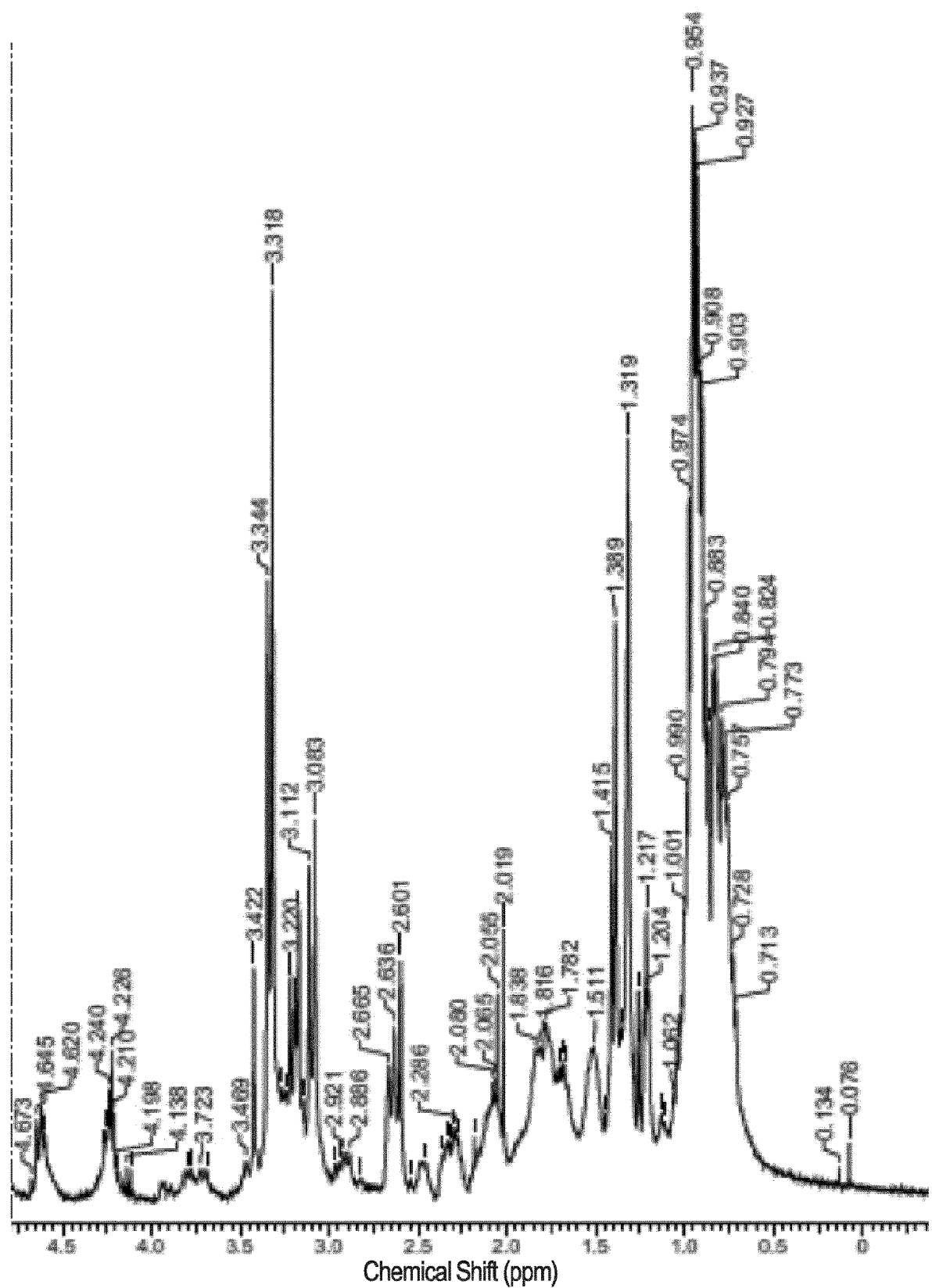
Figure 28A:
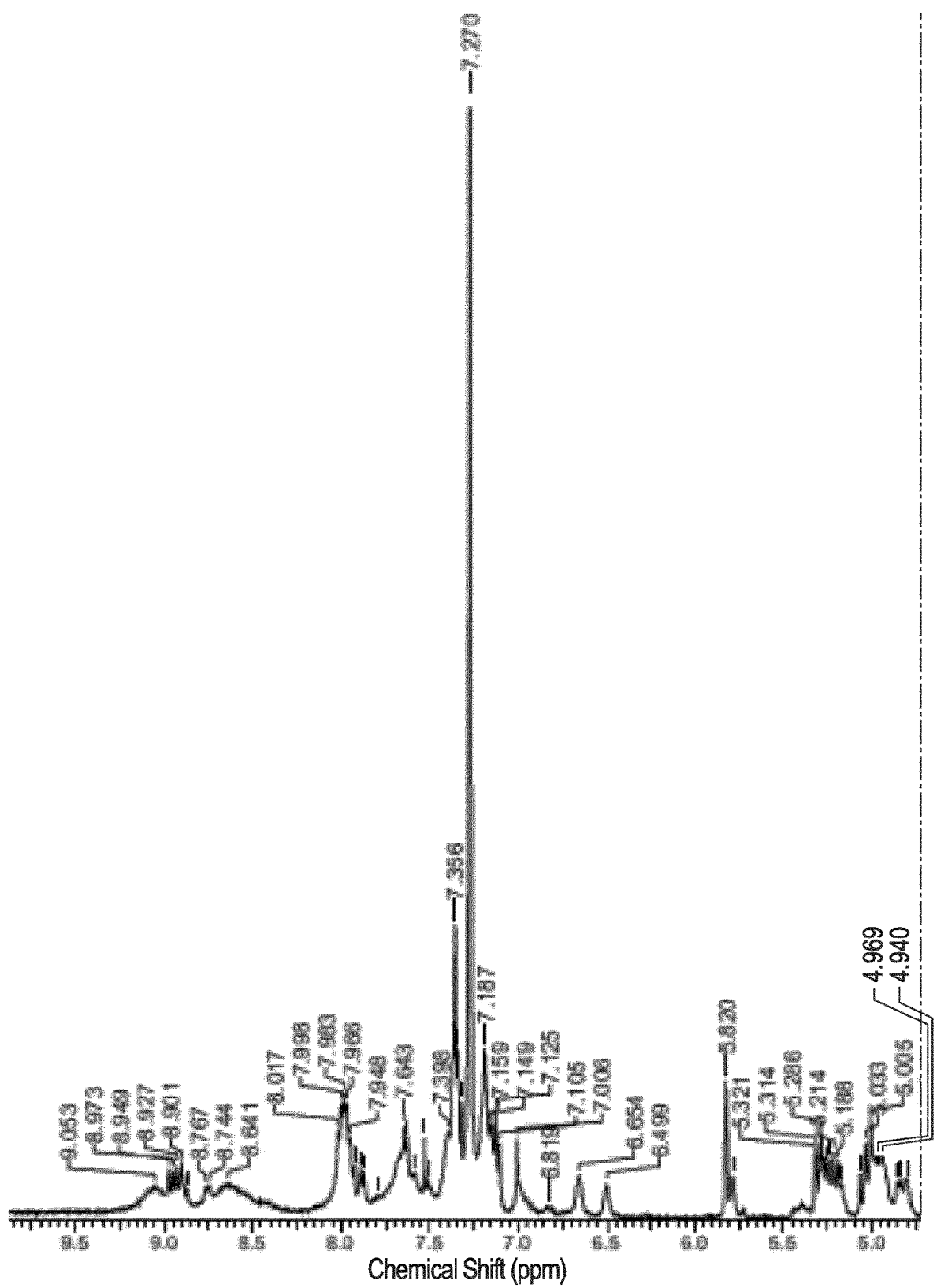
FIG. 28A and FIG. 28B presents a $^1$H NMR spectrum for Example 28.
Figure 28B:
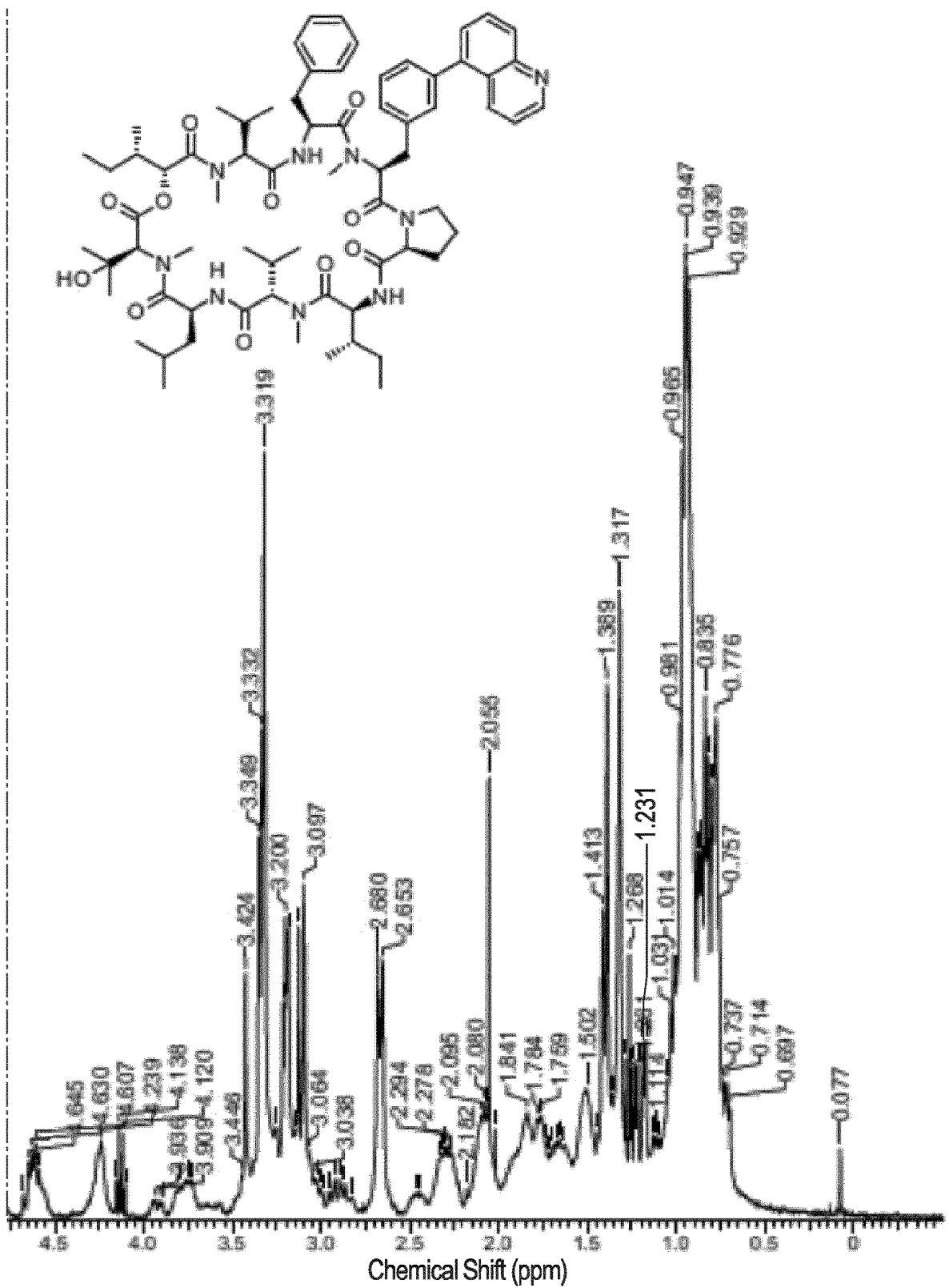
Figure 29A:
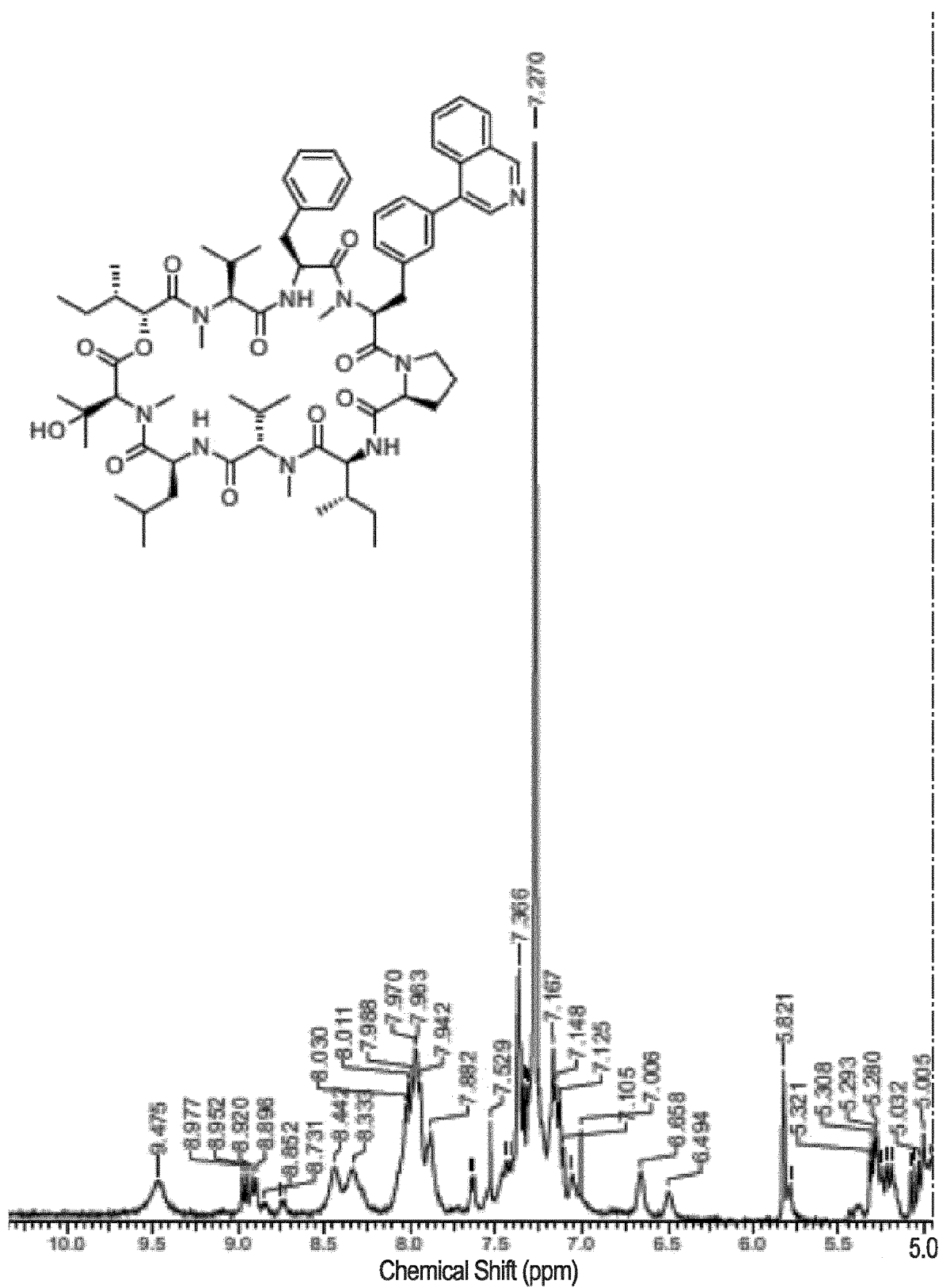
FIG. 29A and FIG. 29B presents a $^1$H NMR spectrum for Example 29.
Figure 29B:
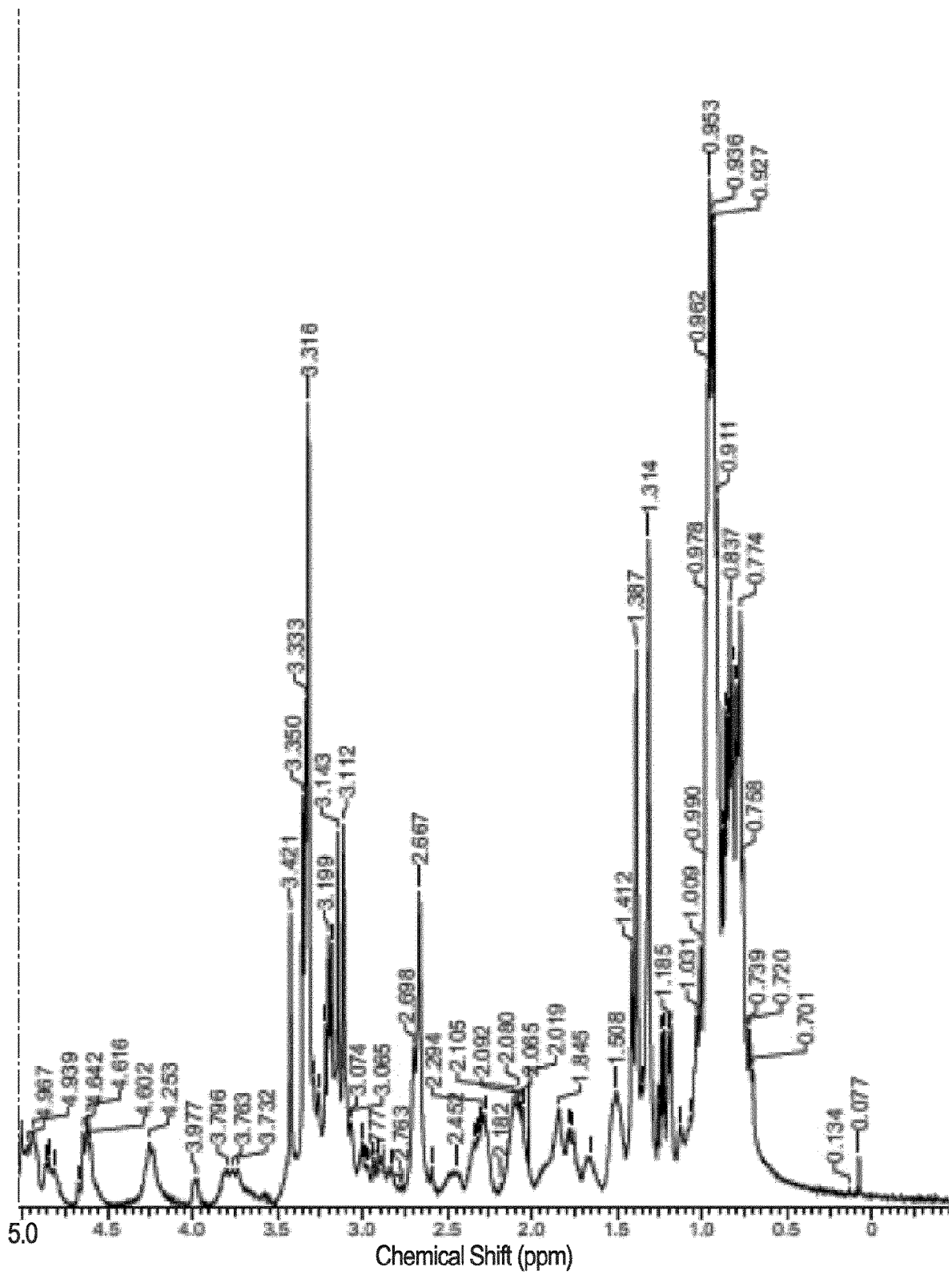
Figure 30A:
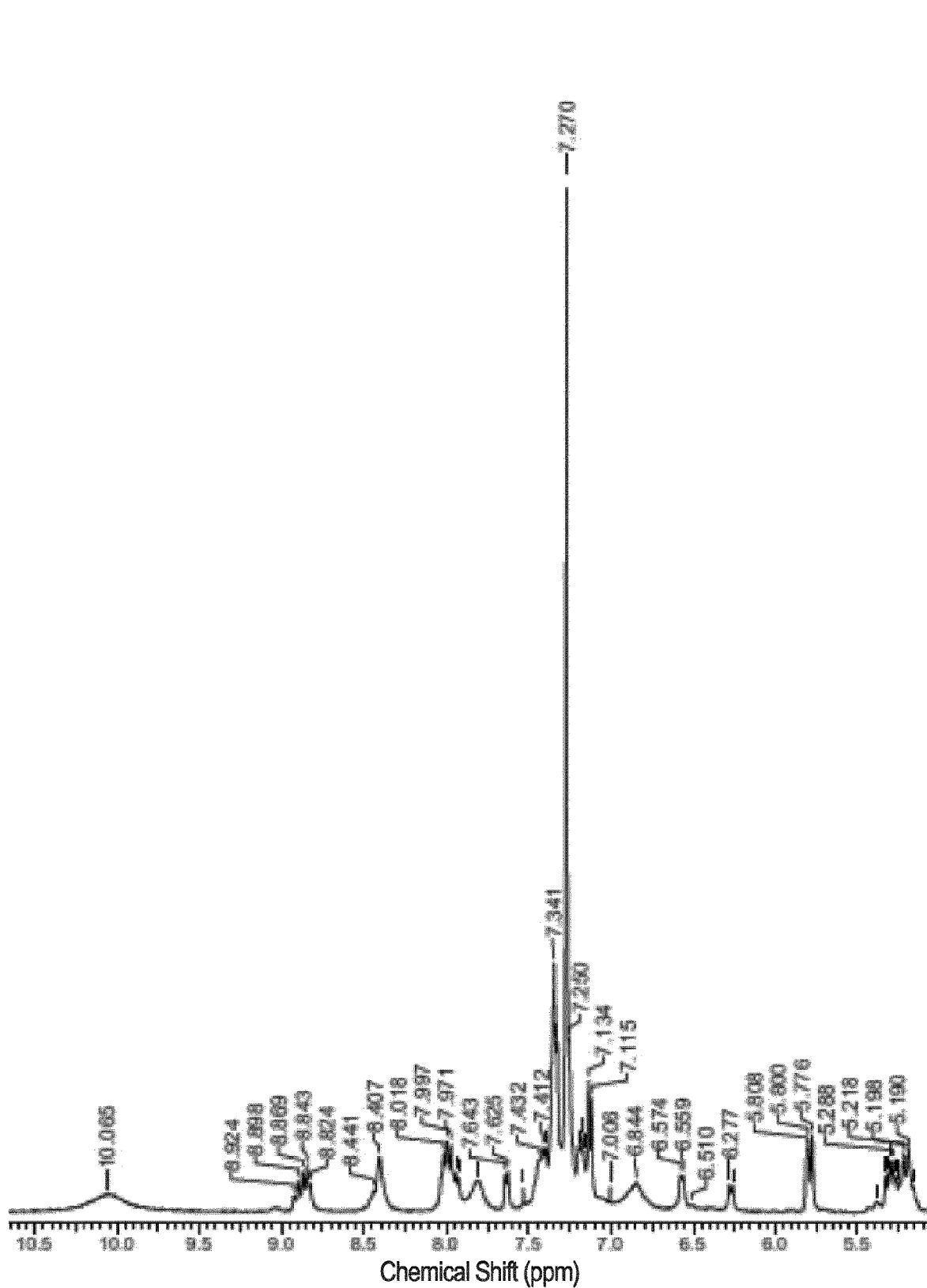
FIG. 30A and FIG. 30B presents a $^1$H NMR spectrum for Example 30.
Figure 30B:
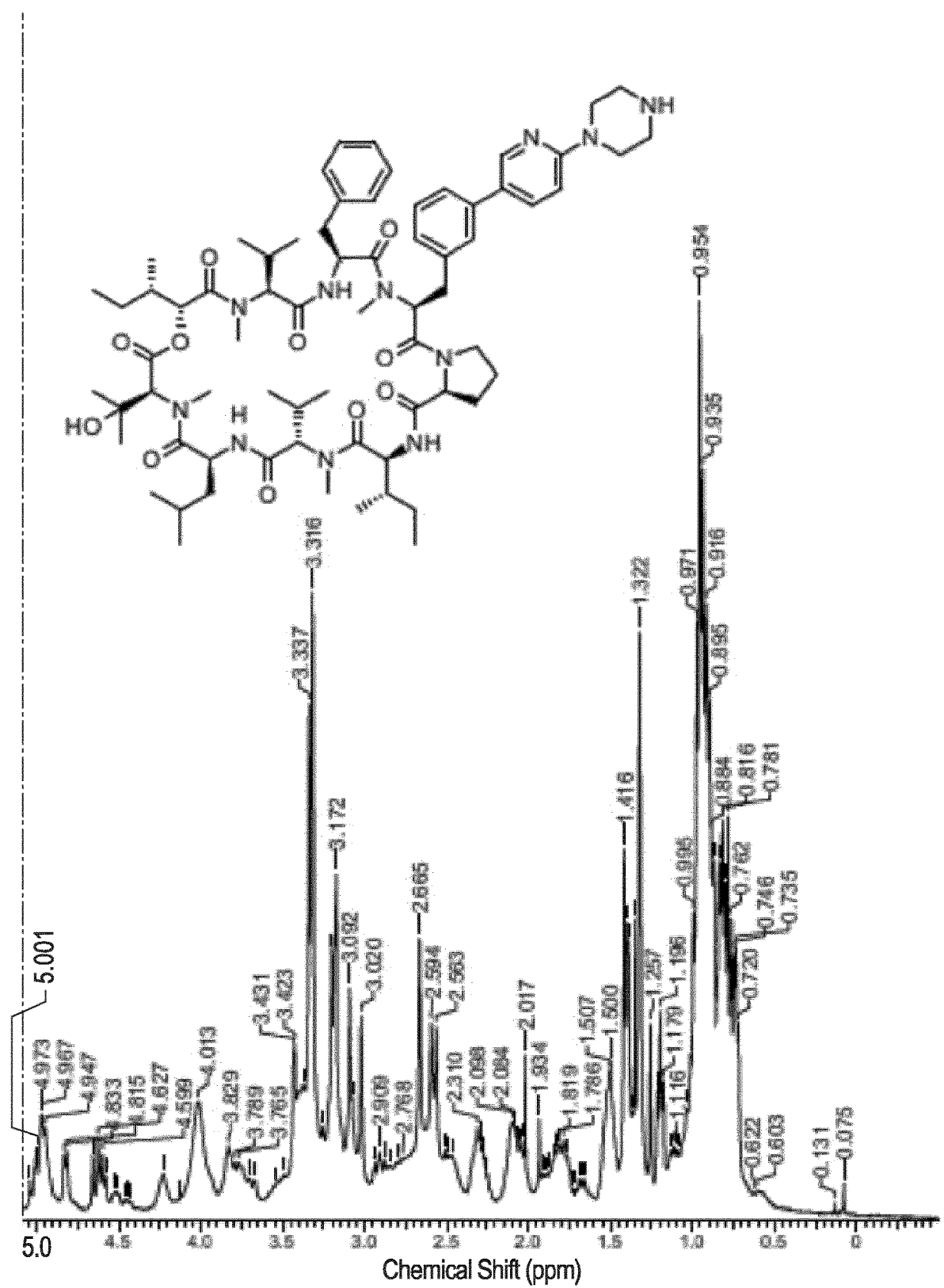
Figure 31A:
FIG. 31A and FIG. 31B presents a $^1$H NMR spectrum for Example 32.
Figure 31B:
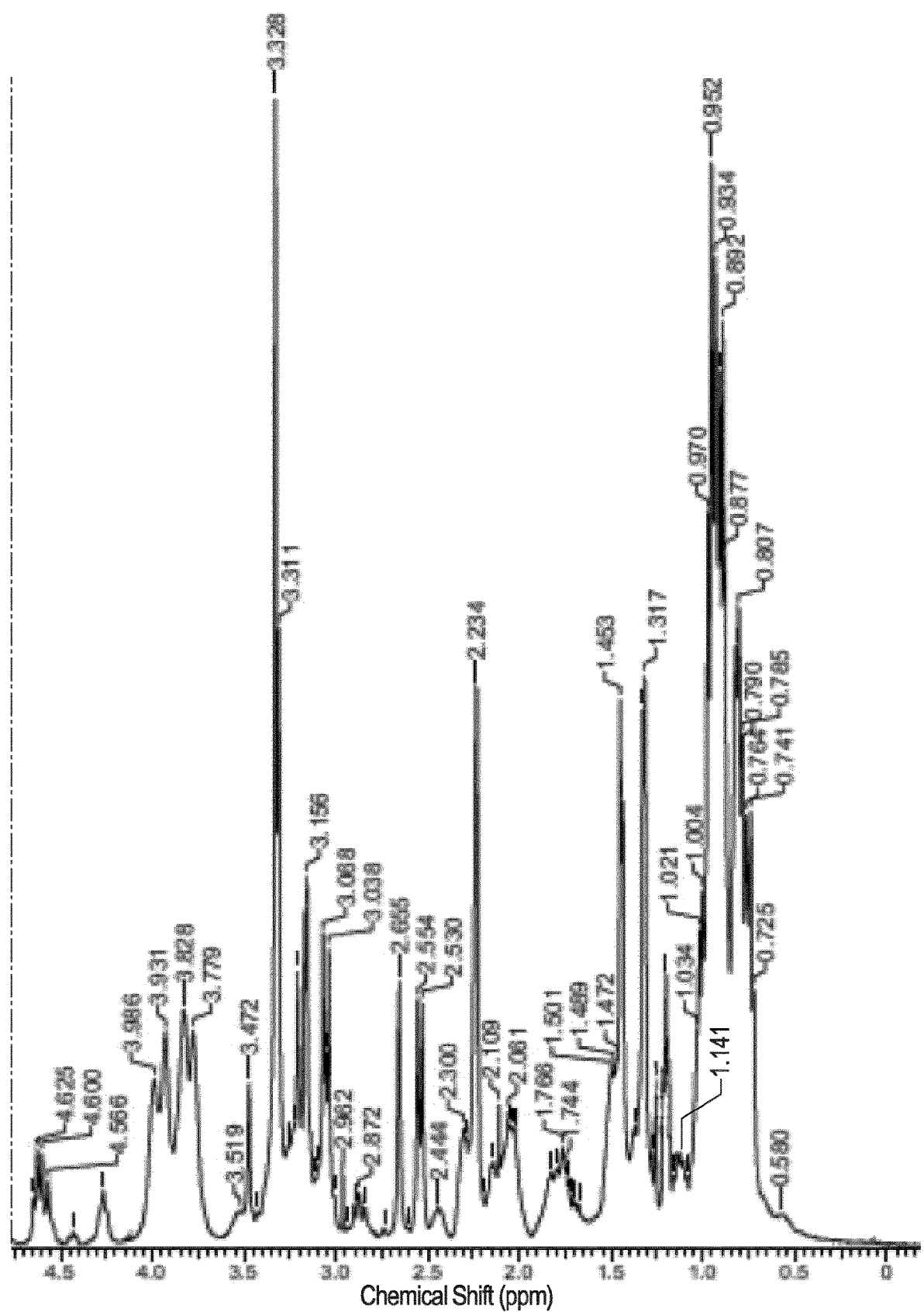
Figure 32A:
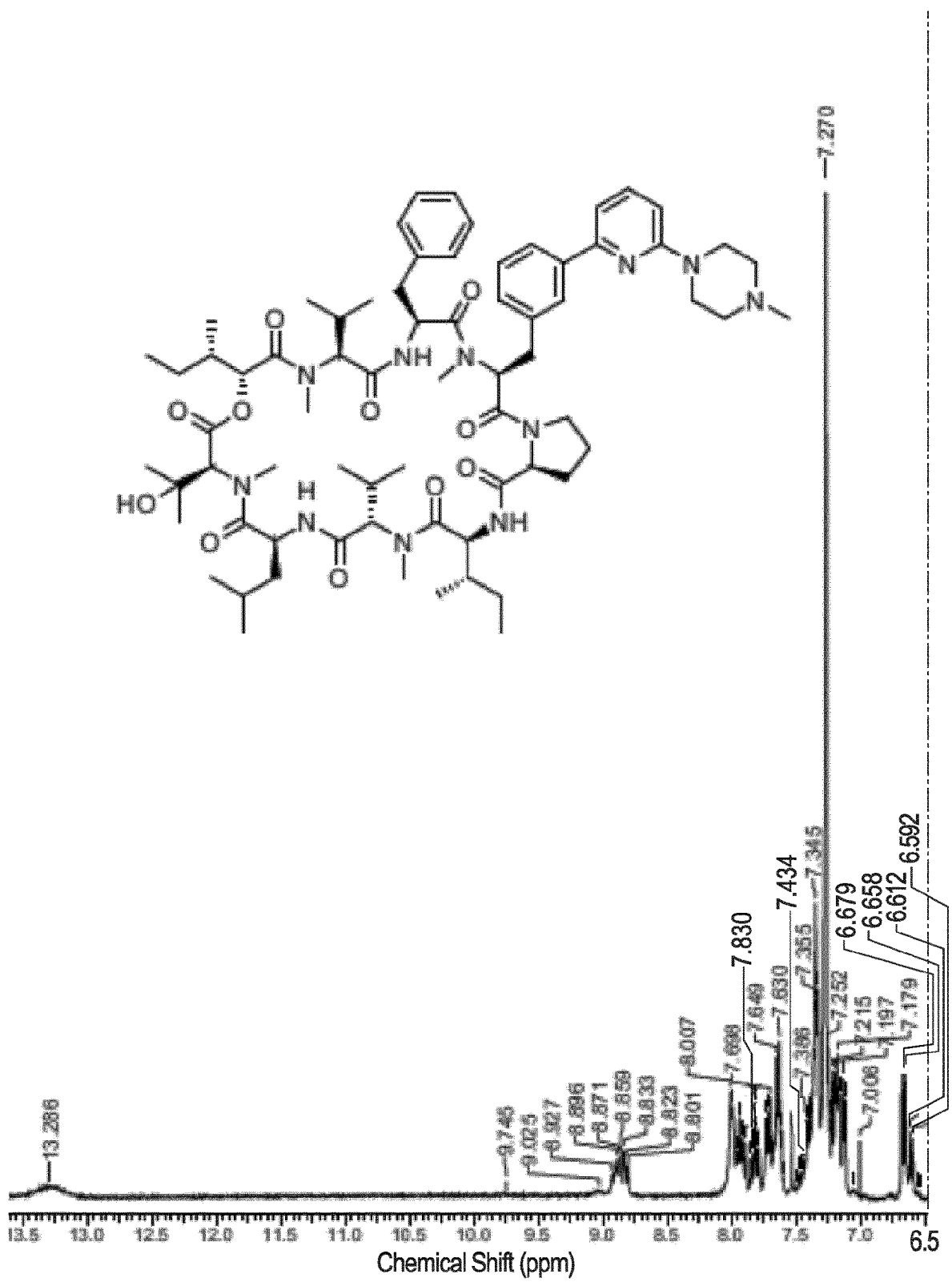
FIG. 32A and FIG. 32B presents a $^1$H NMR spectrum for Example 33.
Figure 32B:
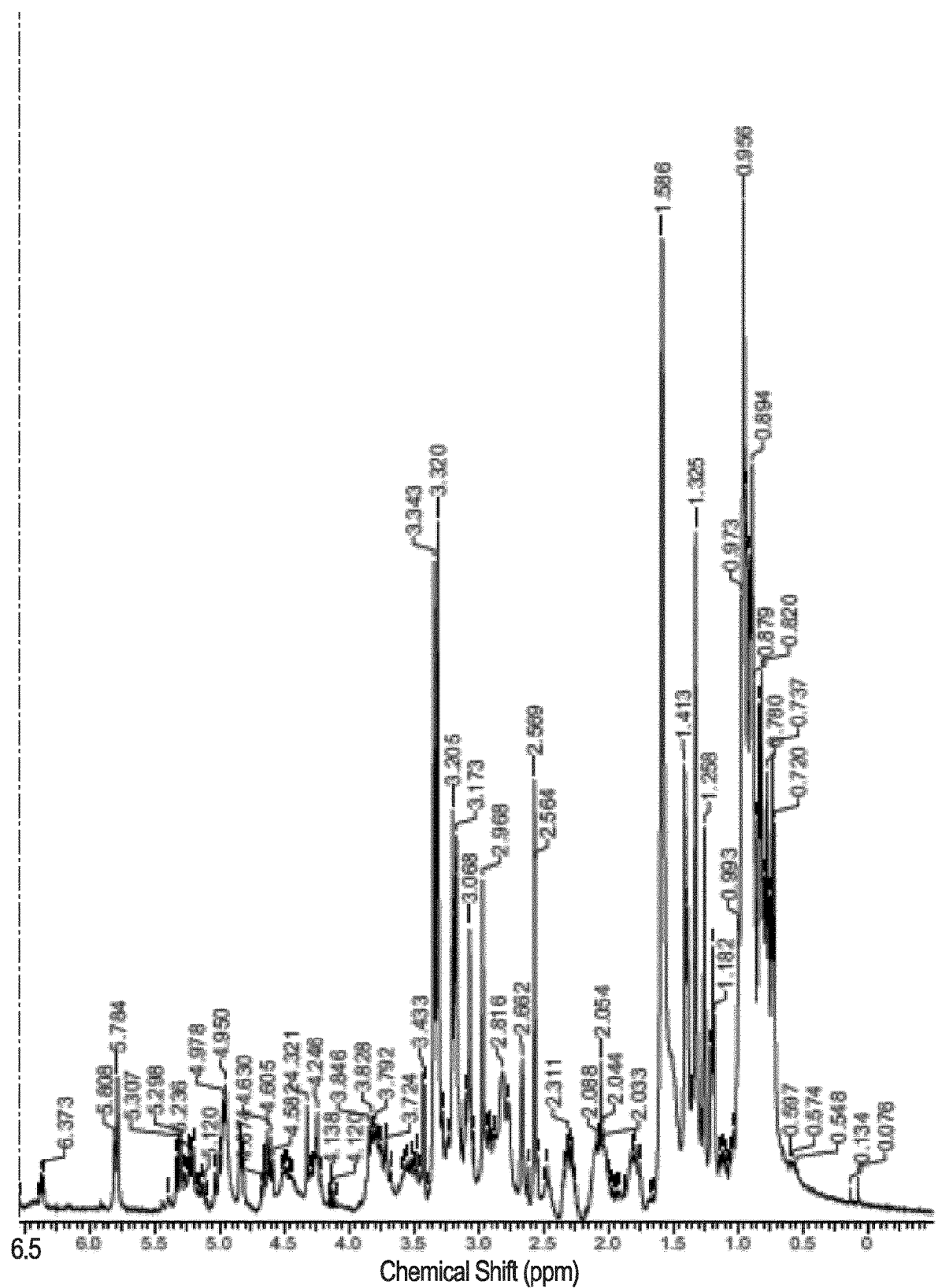
Figure 33:
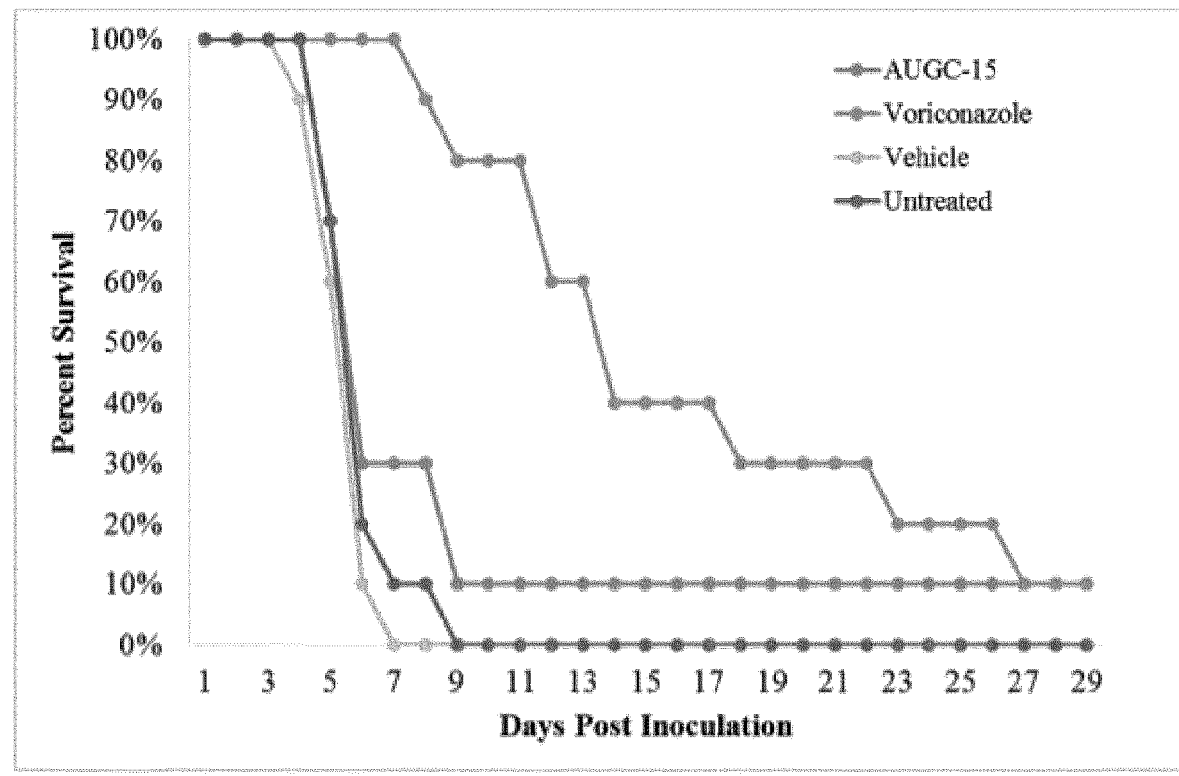
FIG. 33 presents a survival analysis for mice treated with selected antifungal compounds according to Example 36.
Figure 34:
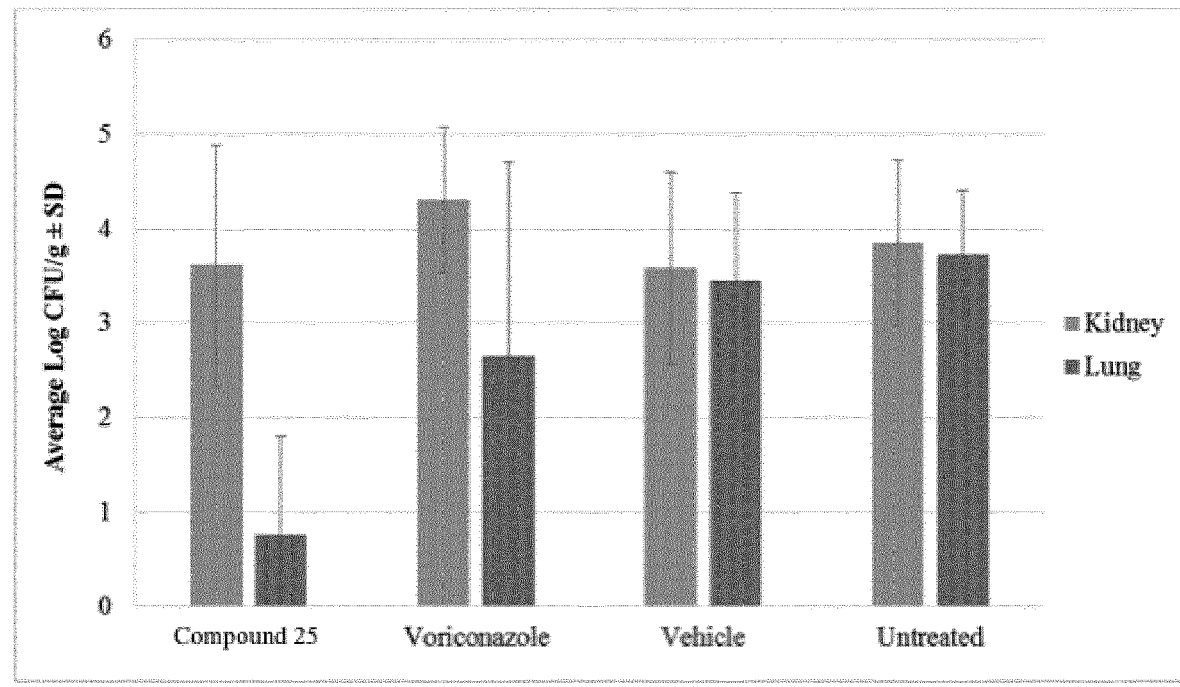
FIG. 34 presents a tissue fungal burden analysis for mice treated with selected antifungal compounds according to Example 36.

The present invention provides novel Aureobasidin A ("AbA") derivatives useful for treating fungal infections (mycoses).

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis" 4th Ed, Wuts, P. G. M. and Greene, T. W., Wiley-Interscience, New York: 2006.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic) alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocyclbalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl.

An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C (O)— when used internally, wherein $R^X$ and $R^Y$ can be hydrogen, aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic) amido, (heteroaralkyl)amido, (heteroaryl)amido, (heterocycloalkyl)alkylamido, arylamido, aralkylamido, (cycloalkyl) alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—, where $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C4-8 carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic ring of a benzofused bicyclic or tricyclic aryl);

nitro; carboxy; amido; acyl [e.g., (aliphatic)carbonyl; (cycloaliphatic)carbonyl; ((cycloaliphatic)aliphatic)carbonyl; (aralkyl)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl; ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a C$_{1-6}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydronaphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimadazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic", "alkyl", and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1] octyl, bicyclo[2.2.2]octyl, bicyclo[3.3.1]nonyl, bicyclo [3.3.2]decyl, 2-oxabicyclo[2.2.2]octyl, 1-azabicyclo[2.2.2] octyl, 3-azabicyclo[3.2.1]octyl, and 2,6-dioxa-tricyclo [3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$, wherein $R^X$ and $R^Y$ have been defined above and $R^Z$ can be aliphatic, aryl, aralphatic, heterocycloaliphatic, heteroaryl, or heteroaralphatic.

As used herein, a "carboxy" group refers to —COOH, —$COOR^X$, —OC(O)H, —OC(O)$R^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the groups —$CF_3$, —$CHF_2$, and —$CH_2F$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —O—$S(O)_2$—$NR^YR^Z$ wherein $R^Y$ and $R^Z$ have been defined above.

As used herein, a "sulfonamide" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Exemplary sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—S(O)—$R^X$ or —S(O)—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —$P(O)(R^P)_2$, wherein $R^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure $(R^X)_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). In some examples, a straight aliphatic chain has the structure —$[CH_2]_v$—, where v is 1-12. In some examples, a branched aliphatic chain is a straight aliphatic chain that is substituted with one or more aliphatic groups. A branched aliphatic chain has the structure —$[CQQ]_v$— where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R^1$, $R^{P1}$, $R^2$, $R^{P2}$, $R^3$, $R^4$, $R^5$, $R^6$, $R^{10}$, $R^{11}$, $R^{12}$, $R^{13}$, $R^{14}$, $R^{15}$, $R^{16}$, $R^A$, $R^B$, and other variables contained in Formula I-P1, I-P2, I, IA, IA-1, IB, or IB-1 described herein encompass specific groups, such as alkyl and aryl. Unless otherwise noted, each of the specific groups for the variables $R^1$, $R^{P1}$, $R^2$, $R^{P2}$, $R^3$, $R^4$, $R^5$, $R^6$, $R^{10}$, $R^{11}$, $R^{12}$, $R^{13}$, $R^{14}$, $R^{15}$, $R^{16}$, $R^A$, $R^B$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

As used herein, "alkylidene" refers to any of a class of divalent functional groups derived from an alkyl group by removal of two hydrogen atoms from the same carbon atom, the free valencies being part of a double bond ($R_2C=$).

In general, the term "substituted," whether preceded by the term "optionally" or not, refers to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

It is noted that the use of the descriptors "first", "second", "third", or the like is used to differentiate separate elements (e.g., solvents, reaction steps, processes, reagents, or the like) and may or may not refer to the relative order or relative chronology of the elements described.

II. Commonly Used Abbreviations

The following definitions describe terms and abbreviations used herein:
Ac acetyl
Bu butyl
Et ethyl
Ph phenyl
BOC tert-butyloxycarbonyl amine protecting group
Fmoc fluorenylmethyloxycarbonyl amine protecting group
Me methyl
THF tetrahydrofuran
DCM dichloromethane
$CH_2Cl_2$ dichloromethane
EtOAc ethyl acetate
$CH_3CN$ acetonitrile
EtOH ethanol
MeOH methanol
MTBE methyl tert-butyl ether
DMF N,N-dimethylformamide
DMA N,N-dimethylacetamide
DMSO dimethyl sulfoxide
HOAc acetic acid
TFA trifluoroacetic acid
$Et_3N$ triethylamine
DIPEA diisopropylethylamine
DIEA diisopropylethylamine
$K_2CO_3$ dipotassium carbonate
$Na_2CO_3$ disodium carbonate
NaOH sodium hydroxide
$K_3PO_4$ tripotassium phosphate
HPLC high performance liquid chromatography
hr or h hours
min minute
atm atmosphere
rt or RT room temperature
HCl hydrochloric acid
HBr hydrobromic acid
$H_2O$ water
NaOAc sodium acetate
$H_2SO_4$ sulfuric acid
$N_2$ nitrogen gas
$H_2$ hydrogen gas Br$_2$ bromine
n-BuLi n-butyl lithium
Pd(OAc)$_2$ palladium(II)acetate
PPh$_3$ triphenylphosphine
rpm revolutions per minute
Equiv. equivalents
Ts tosyl
IPA isopropyl alcohol As used herein, other abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference.

III. Novel ABA Derivatives

One aspect of the present invention provides novel Aureobasidin derivatives that are useful for the treatment of infections. These compounds are generally described by a compound of Formula I-P1:

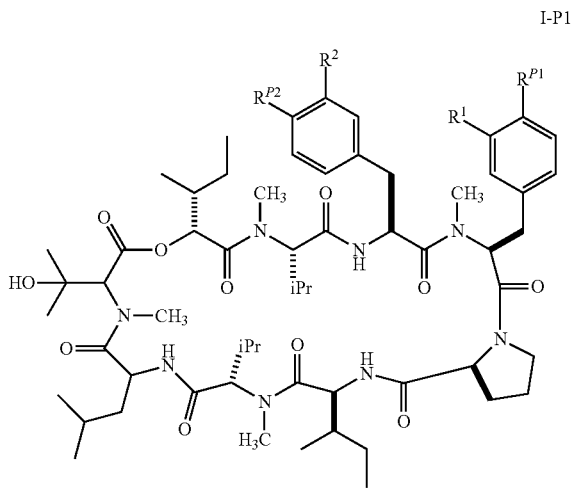

I-P1 or a pharmaceutically acceptable salt thereof, wherein

Each of $R^1$ and $R^{P1}$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^1$ and $R^{P1}$ are each independently and optionally substituted with x instances of $R^3$;

x is independently 1, 2, or 3;

Each $R^3$ is independently —$L^1$-$R^4$, wherein if $R^1$ is phenyl or a 5 to 6 membered monocyclic heteroaryl, at least one $R^3$ is other than —H;

Each $L^1$ is independently a bond or an optionally substituted branched or straight $C_{1-4}$ aliphatic chain, wherein up to two carbon atoms of $L^1$ are optionally and independently replaced by —NR$^A$—, —S—, —O—, —OC(O)—, —C(O)O—, —C(O)—, —C(O)C(O)—, —C(O)NR$^A$—, —NR$^A$C(O)—, —NR$^A$C(O)O—, —S(O)$_2$NR$^A$—, —NR$^A$S(O)$_2$—, —C(O)NR$^A$NR$^A$—, —NR$^A$C(O)NR$^A$—, —OC(O)NR$^A$—, —NR$^A$NR$^A$—, —NR$^A$S(O)$_2$NR$^A$—, —S(O)—, or —S(O)$_2$—;

Each $R^4$ is independently selected from $R^A$, halo, or —CF$_3$;

Each $R^A$ is independently selected from —H, or an optionally substituted group selected from a $C_{1-6}$ alkyl group, a 3 to 8 membered saturated, partially unsaturated, or fully unsaturated monocyclic ring having 0-3 heteroatoms independently selected from nitrogen, oxygen, or sulfur; an 8-12 membered saturated, partially unsaturated, or fully unsaturated bicyclic ring system having 0-5 heteroatoms independently selected from nitrogen, oxygen, or sulfur; or a 13 to 14 membered saturated, partially unsaturated, or fully unsaturated tricyclic ring system having 0 to 5 heteroatoms independently selected from N, O, or S, wherein each of the $C_{1-6}$ alkyl, the monocyclic ring, the bicycling ring system, or the tricyclic ring system is optionally substituted with up to 2 occurrences of $R^5$;

Each $R^5$ is independently —$L^2$-$R^6$;

Each $L^2$ is independently a bond or an optionally substituted branched or straight $C_{1-6}$ aliphatic chain, wherein up to two carbon atoms of $L^2$ are optionally and independently replaced by —NR$^B$—, —O—, —OC(O)—, —C(O)O—, —C(O)—, —C(O)C(O)—, —C(O)NR$^B$—, —NR$^B$C(O)—, or —NR$^B$C(O)O—; and Each $R^6$ is independently selected from $R^B$, halo, —CF$_3$, or Boc;

Each $R^B$ is independently selected from —H, $C_{1-3}$ alkyl, or phenyl;

Each of $R^2$ and $R^{P2}$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^2$ and $R^{P2}$ is independently and optionally substituted with x instances of $R^3$ Each $R^{P2}$ is $R^{P1}$, provided that i) at least one of $R^1$ and $R^{P1}$ is hydrogen;
ii) at least one of $R^2$ and $R^{P2}$ is hydrogen;
iii) at least one of $R^1$, $R^2$, $R^{P1}$, and $R^{P2}$ is not hydrogen;
iv) when $R^1$ is phenyl or pyridinyl, x is 1, and each of $R^2$, $R^{P1}$, and $R^{P2}$ is hydrogen, then $R^3$ is not chloro;
v) when $R^1$ is phenyl or pyridinyl, x is 1, and each of $R^2$, $R^{P1}$, and $R^{P2}$ is hydrogen, then $R^3$ is not unsubstituted phenyl;
vi) when $R^1$ is phenyl, x is 1, and each of $R^2$, $R^{P1}$, and $R^{P2}$ is hydrogen, then $R^3$ is not —N(H)C(O)CH$_3$ or —C(O)NH$_2$; and
vii) when $R^1$ is furyl or thiophenyl, x is 1, and each of $R^2$, $R^{P1}$, and $R^{P2}$ is hydrogen, then $R^3$ is not —CH$_3$.

In some embodiments, $R^2$ and $R^{P2}$ are both —H.

In some embodiments, one of $R^1$ and $R^{P1}$ is hydrogen and the other is phenyl substituted with x occurrences of $R^3$. In some of these embodiments, x is 1 and $R^3$ is selected from halo, an optionally substituted $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur, a 13 to 14 membered saturated, partially unsaturated, or fully unsaturated tricyclic ring system having 0 to 5 heteroatoms independently selected from N, O, or S, or —O—($C_{1-3}$ alkyl)-phenyl, wherein each $R^3$ is substituted with up to 2 occurrences of $R^5$ at any chemically feasible position. In other embodiments, $R^3$ is selected from halo, an unsubstituted $C_{1-6}$ alkyl group, a halo-substituted $C_{1-6}$ alkyl group, an optionally substituted 5 to 6 membered saturated, partially unsaturated, or fully unsaturated monocyclic ring having 0-3 heteroatoms independently selected from nitrogen, oxygen, or sulfur; or —O—(CH$_2$)$_{1-2}$ phenyl. And, in some embodiments, R$^3$ is selected from —Cl, —F, —I, —CH$_3$, —CF$_3$, —CH$_2$CH$_3$, or —CH$_2$CF$_3$.

In some embodiments, R$^3$ is selected from piperidine, piperazine, morpholine, pyrrolidine, imidazolidine, pyrrole, thiophene, furan, oxazole, pyridine, pyrimidine, or pyrazine, wherein R$^3$ is substituted with C$_{1-6}$ alkyl. In some of these embodiments, R$^3$ is selected from piperidine or piperazine, either of which is optionally substituted with C$_{1-6}$ alkyl. In other embodiments, R$^3$ is selected from

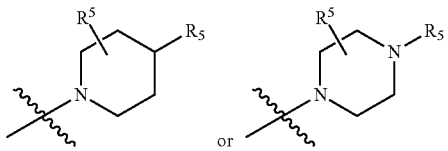

wherein each R$^5$ is independently —H or C$_{1-6}$ alkyl.

In some embodiments, R$^3$ is BOC. For example, x is 1 and R$^3$ is BOC.

In some embodiments, x is 2, and at least one occurrence of R$^3$ is halogen. For example, x is 2, and each R$^3$ is halogen.

In some embodiments, one of R$^1$ and R$^{P1}$ is hydrogen and the other is naphthyl substituted with x occurrences of R$^3$. For example, one of R$^1$ and R$^{P1}$ is hydrogen and the other is selected from

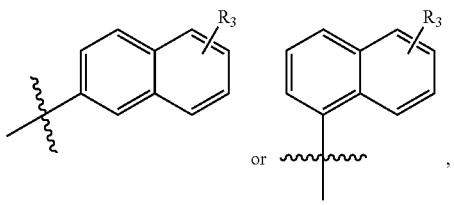

wherein R$^3$ is —H or C$_{1-6}$ alkyl.

In some embodiments, one of R$^1$ and R$^{P1}$ is hydrogen and the other is a 5 to 6 membered monocyclic heteroaryl having 1 to 3 nitrogen atoms, wherein the monocyclic heteroaryl is substituted with x occurrences of R$^3$. For example, one of R$^1$ and R$^{P1}$ is hydrogen and the other is selected from pyrazole, pyridine, pyrazine, or pyrimidine, and x is 1 or 2. In other examples, one of R$^1$ and R$^{P1}$ hydrogen and the other is

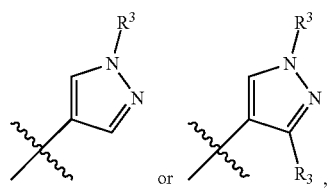

wherein R$^3$ is hydrogen, —CF$_3$, C$_{1-6}$ alkyl, or a 5 to 6 membered cycloaliphatic group. And, in some examples, each R$^3$ is independently selected from hydrogen, methyl, trifluoromethyl, ethyl, propyl, cyclopentyl, or cyclohexyl.

In some embodiments, one of R$^1$ and R$^{P1}$ is hydrogen and the other is selected from

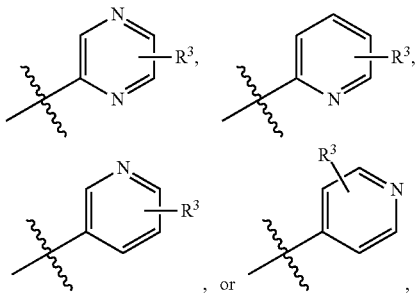

wherein each R$^3$ is hydrogen, a C$_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of the C$_{1-6}$ alkyl, the monocyclic ring, or the bicycling ring system is optionally substituted with up to 2 occurrences of R$^5$. For example, one of R$^1$ and R$^{P1}$ is hydrogen and the other is

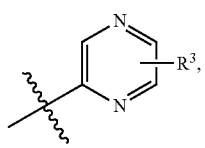

wherein R$^3$ is an optionally substituted 5 to 6 membered saturated, partially unsaturated, or fully unsaturated monocyclic ring having 0-2 heteroatoms independently selected from nitrogen or oxygen, and the other is hydrogen. In other examples, one of R$^1$ and R$^{P1}$ is hydrogen and the other is

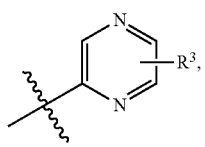

wherein R$^3$ is piperidine-1-yl optionally substituted with C$_{1-6}$ alkyl. And, in some examples, one of R$^1$ and R$^{P1}$ is hydrogen and the other is selected from

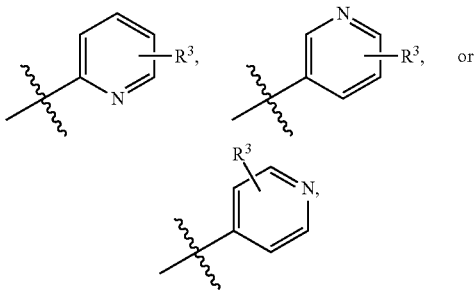

wherein each R$^3$ is —H, C$_{1-6}$ alkyl, or an optionally substituted 5 to 6 membered, saturated, or fully unsaturated monocyclic ring having 0-2 heteroatoms independently selected from nitrogen or oxygen, wherein the monocyclic ring is optionally substituted with up to 2 occurrences of $R^5$. In some examples, $R^3$ is selected from —H, $C_{1-4}$ alkyl,

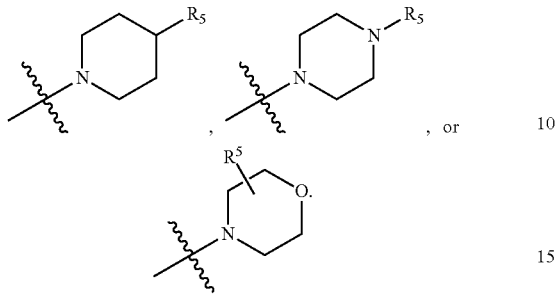

And, in other examples, each $R^5$ is independently selected from —H, $C_{1-4}$ alkyl, —N(CH$_3$)$_2$, —C(O)—CH$_3$, —C(O)—CH$_2$—CH$_3$, or —C(O)—O—C(CH$_3$)$_3$.

In some embodiments, one of $R^1$ and $R^{P1}$ is hydrogen and the other is a 9 to 10 membered bicyclic heteroaryl having 1 to 3 heteroatoms independently selected from N, O, or S, wherein the bicyclic heteroaryl is substituted with x occurrences of $R^3$.

In some embodiments, one of $R^1$ and $R^{P1}$ is hydrogen and the other is selected from

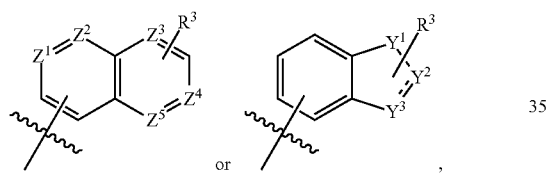

wherein

Each of $Z^1$, $Z^2$, $Z^3$, $Z^4$, and $Z^5$ is independently $CR^3$ or N, wherein at least one of $Z^1$, $Z^2$, $Z^3$, $Z^4$, and $Z^5$ is N;

Each of $Y^1$, $Y^2$, and $Y^3$ is independently CH, $CR^3$, N, $NR^3$, or O, wherein at least one of $Y^1$, $Y^2$, and $Y^3$ are N, $NR^3$, or O; and --- is a bond or absent, provided that i) No more than three of $Z^1$, $Z^2$, $Z^3$, $Z^4$, and $Z^5$ is N;

ii) $R^1$ is substituted with no more than three occurrences of $R^3$;

iii) If either of $Y^2$ or $Y^3$ is —O—, then --- is absent; and iv) If --- is bond, then $Y^2$ is N, CH, or $CR^3$, and $Y^3$ is N, CH, or $CR^3$.

In some embodiments, one of $R^1$ and $R^{P1}$ is hydrogen and the other is selected from

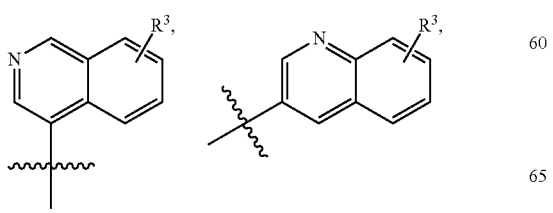

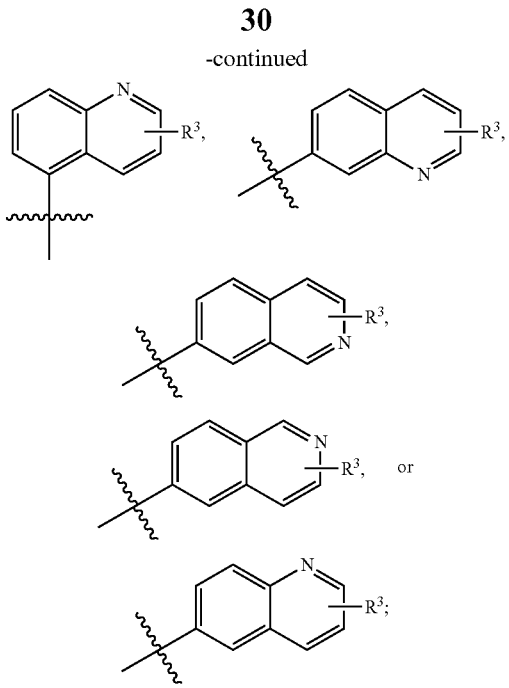

wherein $R^3$ is —H or $C_{1-6}$ alkyl.

In some embodiments, one of $R^1$ and $R^{P1}$ is hydrogen and the other is selected from

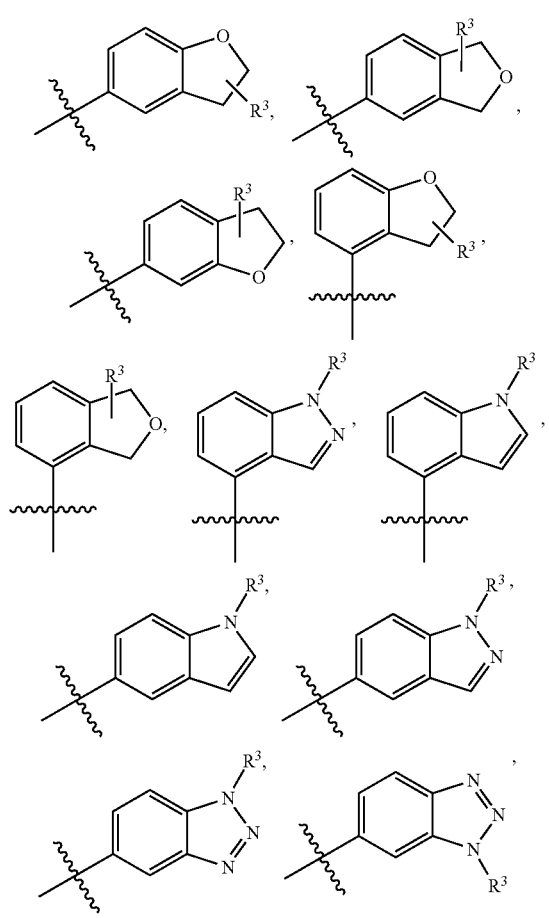

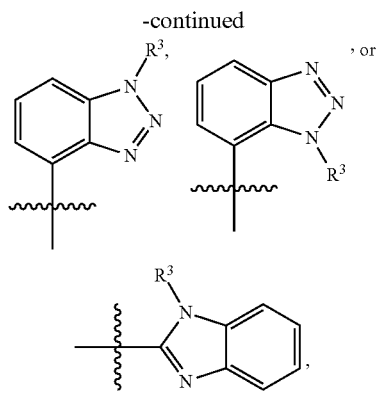

wherein $R^3$ is —H or $C_{1-6}$ alkyl.

In some embodiments, $R^1$ and $R^{P1}$ are both —H.

In some embodiments, one of $R^2$ and $R^{P2}$ is hydrogen and the other is phenyl substituted with x occurrences of $R^3$. For example, x is 1 and $R^3$ is selected from halo, an optionally substituted $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur, a 13 to 14 membered saturated, partially unsaturated, or fully unsaturated tricyclic ring system having 0 to 5 heteroatoms independently selected from N, O, or S, or —O—($C_{1-3}$ alkyl)-phenyl, wherein each $R^3$ is substituted with up to 2 occurrences of $R^5$ at any chemically feasible position. In other examples, $R^3$ is selected from halo, an unsubstituted $C_{1-6}$ alkyl group, a halo-substituted $C_{1-6}$ alkyl group, an optionally substituted 5 to 6 membered saturated, partially unsaturated, or fully unsaturated monocyclic ring having 0-3 heteroatoms independently selected from nitrogen, oxygen, or sulfur; or —O—($CH_2$)$_{1-2}$phenyl. And, in some examples, $R^3$ is selected from —Cl, —F, —I, —CH$_3$, —CF$_3$, —CH$_2$CH$_3$, or —CH$_2$CF$_3$.

In some embodiments, $R^3$ is selected from piperidine, piperazine, morpholine, pyrrolidine, imidazolidine, pyrrole, thiophene, furan, oxazole, pyridine, pyrimidine, or pyrazine, wherein $R^3$ is substituted with $C_{1-4}$ alkyl.

In some embodiments, $R^3$ is selected from piperidine or piperazine, either of which is optionally substituted with $C_{1-6}$ alkyl. For example, $R^3$ is selected from

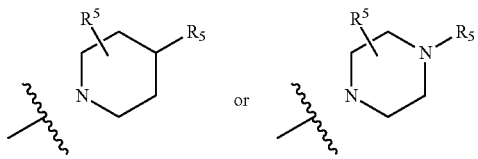

wherein each $R^5$ is independently —H or $C_{1-6}$ alkyl.

In some embodiments, $R^3$ is BOC.

In some embodiments, x is 2, and at least one occurrence of $R^3$ is halogen. For example, x is 2, and each $R^3$ is halogen.

In some embodiments, one of $R^2$ and $R^{P2}$ is hydrogen and the other is naphthyl substituted with x occurrences of $R^3$. For example, one of $R^2$ and $R^{P2}$ is hydrogen and the other is selected from

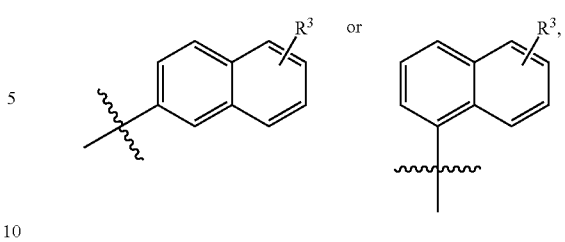

wherein $R^3$ is —H or $C_{1-6}$ alkyl.

In some embodiments, one of $R^2$ and $R^{P2}$ is hydrogen and the other is a 5 to 6 membered monocyclic heteroaryl having 1 to 3 nitrogen atoms, wherein the monocyclic heteroaryl is substituted with x occurrences of $R^3$.

In some embodiments, one of $R^2$ and $R^{P2}$ is hydrogen and the other is selected from pyrazole, pyridine, pyrazine, or pyrimidine, and x is 1 or 2. For example, one of $R^2$ and $R^{P2}$ hydrogen and the other is

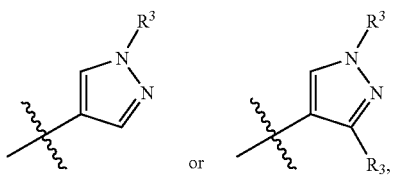

wherein $R^3$ is hydrogen, —CF$_3$, $C_{1-6}$ alkyl, or a 5 to 6 membered cycloaliphatic group. In other examples, each $R^3$ is independently selected from hydrogen, methyl, trifluoromethyl, ethyl, propyl, cyclopentyl, or cyclohexyl. In some examples, one of $R^2$ and $R^{P2}$ is hydrogen and the other is selected from

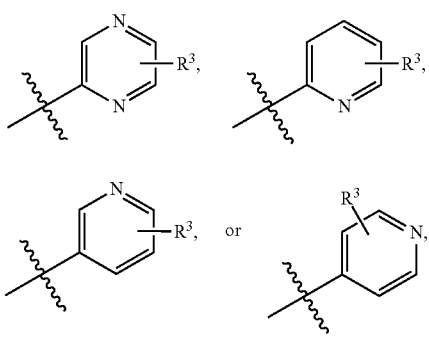

wherein each $R^3$ is hydrogen, a $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of the $C_{1-6}$ alkyl, the monocyclic ring, or the bicycling ring system is optionally substituted with up to 2 occurrences of $R^5$. In other examples, one of $R^2$ and $R^{P2}$ is hydrogen and the other is

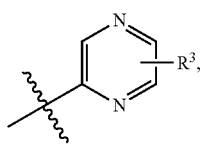

wherein R³ is an optionally substituted 5 to 6 membered saturated, partially unsaturated, or fully unsaturated monocyclic ring having 0-2 heteroatoms independently selected from nitrogen or oxygen, and the other is hydrogen. In some examples, one of R² and R^{P2} is hydrogen and the other is

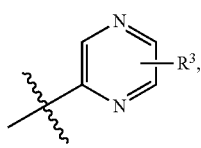

wherein R³ is piperidine-1-yl optionally substituted with $C_{1-6}$ alkyl. In some examples, one of R² and R^{P2} is hydrogen and the other is selected from

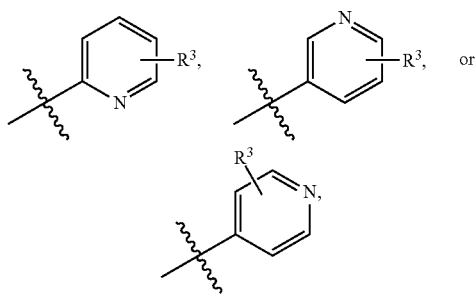

wherein each R³ is —H, $C_{1-6}$ alkyl, or an optionally substituted 5 to 6 membered, saturated, or fully unsaturated monocyclic ring having 0-2 heteroatoms independently selected from nitrogen or oxygen, wherein the monocyclic ring is optionally substituted with up to 2 occurrences of R⁵.

In some embodiments, R³ is selected from —H, $C_{1-4}$ alkyl,

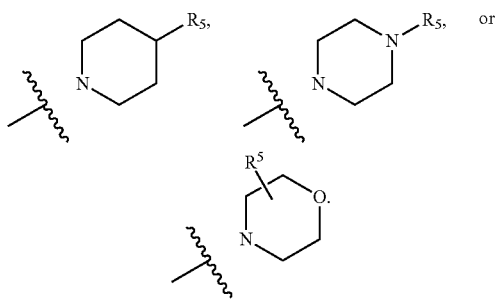

In some embodiments, each R⁵ is independently selected from —H, $C_{1-4}$ alkyl, —N(CH₃)₂, —C(O)—CH₃, —C(O)—CH₂—CH₃, or —C(O)—O—C(CH₃)₃.

In some embodiments, one of R² and R^{P2} is hydrogen and the other is a 9 to 10 membered bicyclic heteroaryl having 1 to 3 heteroatoms independently selected from N, O, or S, wherein the bicyclic heteroaryl is substituted with x occurrences of R³.

In some embodiments, one of R² and R^{P2} is hydrogen and the other is selected from

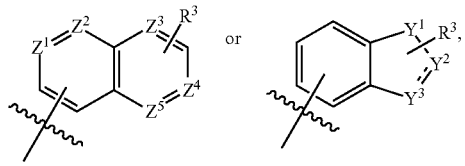

wherein

Each of Z¹, Z², Z³, Z⁴, and Z⁵ is independently CR³ or N, wherein at least one of Z¹, Z², Z³, Z⁴, and Z⁵ is N;

Each of Y¹, Y², and Y³ is independently CH, CR³, N, NR³, or O, wherein at least one of Y¹, Y², and Y³ are N, NR³, or O; and --- is a bond or absent, provided that i) No more than three of Z¹, Z², Z³, Z⁴, and Z⁵ is N;

ii) R¹ is substituted with no more than three occurrences of R³;

iii) If either of Y² or Y³ is —O—, then --- is absent; and iv) If --- is bond, then Y² is N, CH, or CR³, and Y³ is N, CH, or CR³.

In some embodiments, one of R² and R^{P2} is hydrogen and the other is selected from

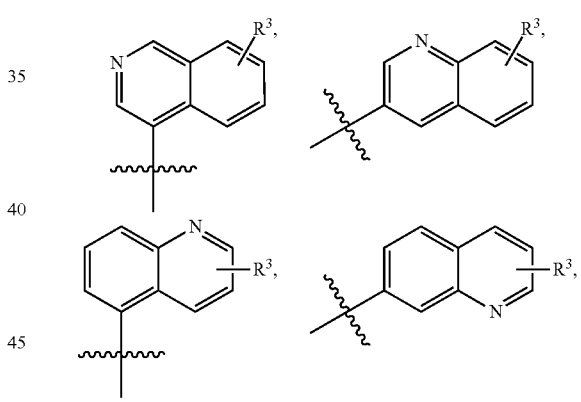

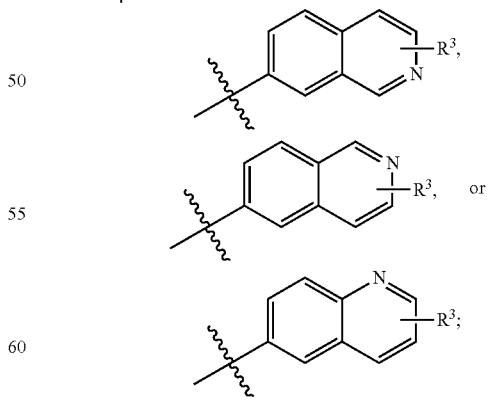

wherein R³ is —H or $C_{1-6}$ alkyl.

In some embodiments, one of R² and R^{P2} is hydrogen and the other is selected from

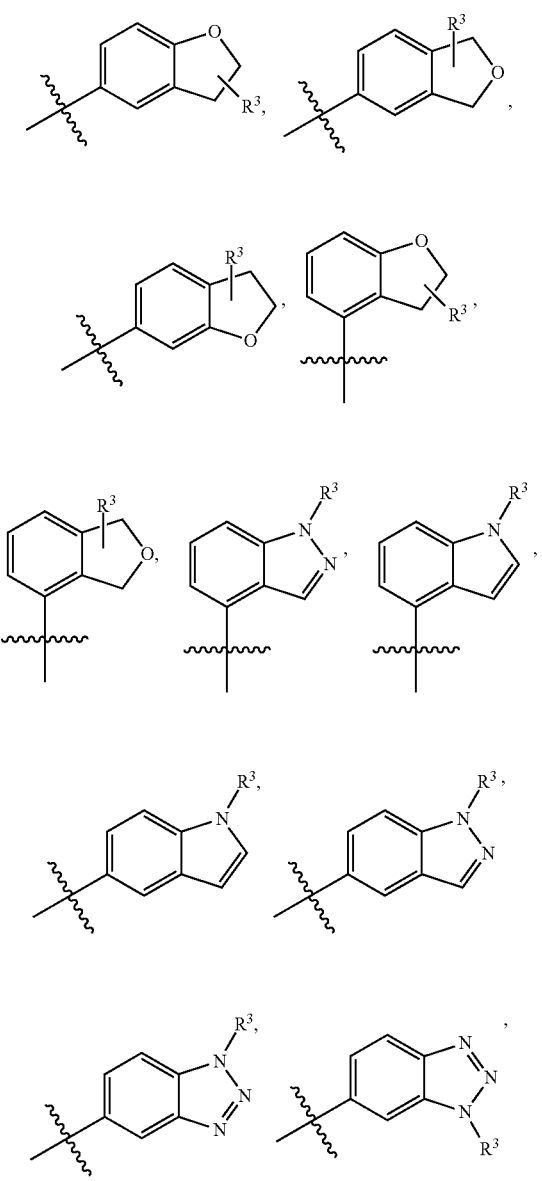
wherein R³ is —H or C₁₋₆ alkyl.
In some aspects, the compound of Formula I-P1 is selected from
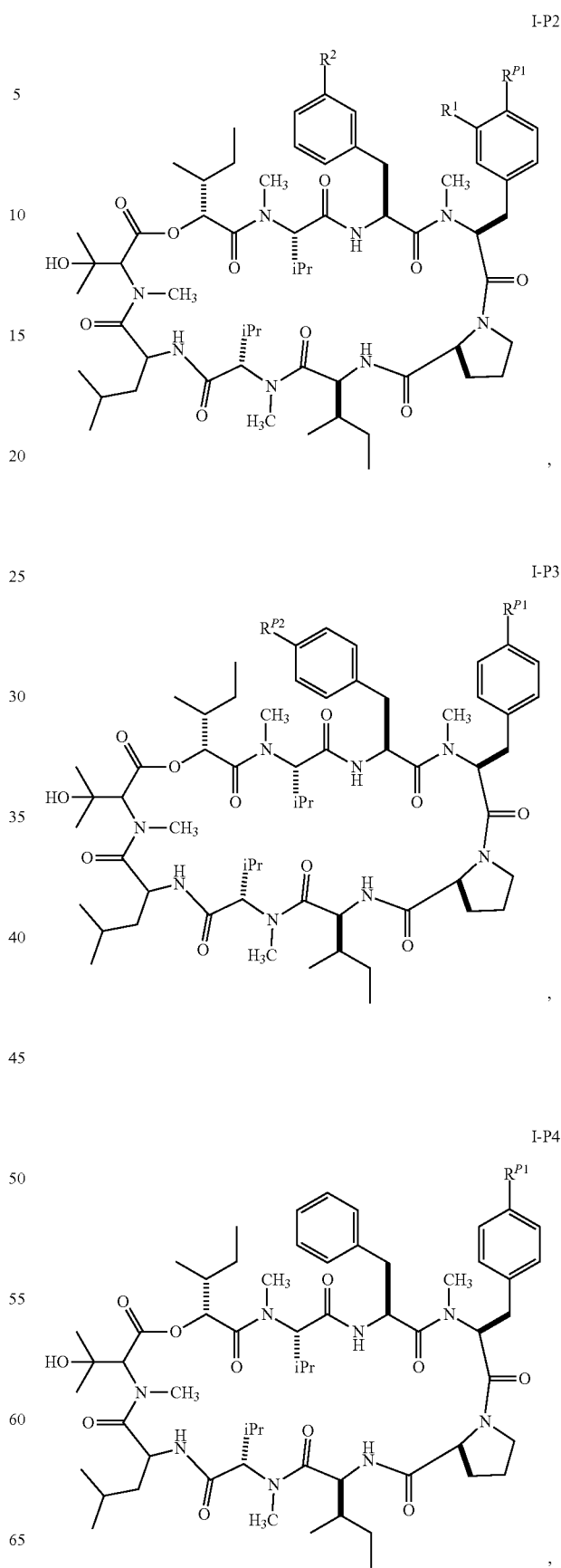

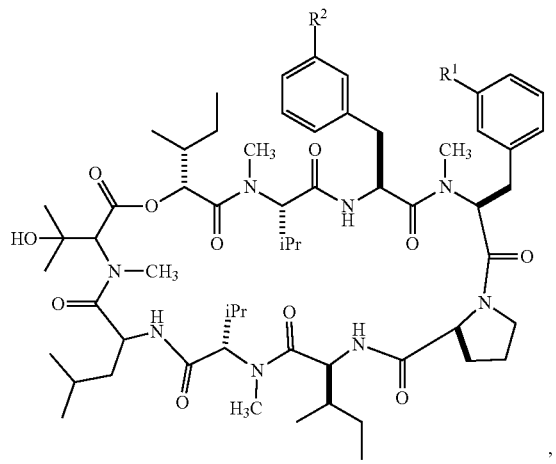

, or

I-A

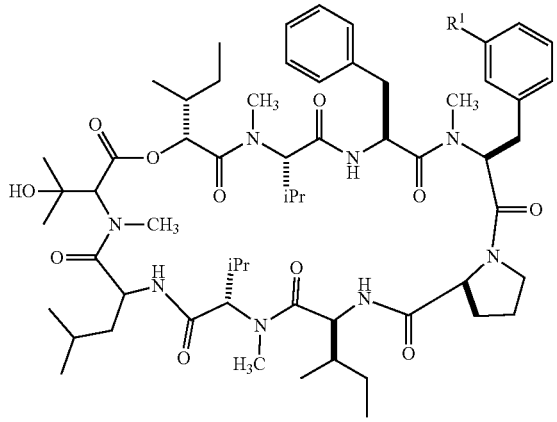

, wherein each of the groups $R^1$, $R^{P1}$, $R^2$, and $R^{P2}$ are as defined herein.

In another aspect, the present invention provides a compound of Formula I:

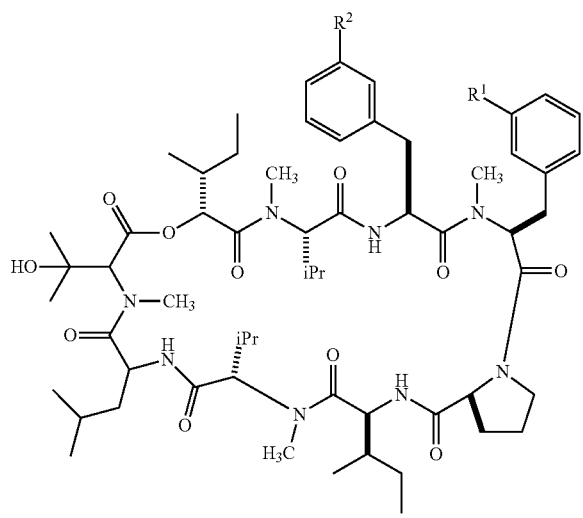

I or a pharmaceutically acceptable salt thereof, wherein $R^1$ is phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^1$ is substituted with x instances of $R^3$;

x is 1, 2, or 3;

each $R^3$ is independently —$L^1$-$R^4$, wherein if $R^1$ is phenyl or a 5 to 6 membered monocyclic heteroaryl, at least one $R^3$ is other than —H;

each $L^1$ is independently a bond or an optionally substituted branched or straight $C_{1-4}$ aliphatic chain, wherein up to two carbon atoms of $L^1$ are optionally and independently replaced by —$NR^A$—, —S—, —O—, —OC(O)—, —C(O)O—, —C(O)—, —C(O)C(O)—, —C(O)$NR^A$—, —$NR^A$C(O)—, —$NR^A$C(O)O—, —S(O)$_2$$NR^A$—, —$NR^A$S(O)$_2$—, —C(O)$NR^A$$NR^A$—, —$NR^A$C(O)$NR^A$—, —OC(O)$NR^A$—, —$NR^A$$NR^A$—, —$NR^A$S(O)$_2$$NR^A$—, —S(O)—, or —S(O)$_2$—;

each $R^4$ is independently selected from $R^A$, halo, or —$CF_3$;

each $R^A$ is independently selected from —H, or an optionally substituted group selected from a $C_{1-6}$ alkyl group, a 3 to 8 membered saturated, partially unsaturated, or fully unsaturated monocyclic ring having 0-3 heteroatoms independently selected from nitrogen, oxygen, or sulfur; an 8-12 membered saturated, partially unsaturated, or fully unsaturated bicyclic ring system having 0-5 heteroatoms independently selected from nitrogen, oxygen, or sulfur; or a 13 to 14 membered saturated, partially unsaturated, or fully unsaturated tricyclic ring system having 0 to 5 heteroatoms independently selected from N, O, or S, wherein each of the $C_{1-6}$ alkyl, the monocyclic ring, the bicycling ring system, or the tricyclic ring system is optionally substituted with up to 2 occurrences of $R^5$;

each $R^5$ is independently —$L^2$-$R^6$;

each $L^2$ is independently a bond or an optionally substituted branched or straight $C_{1-6}$ aliphatic chain, wherein up to two carbon atoms of $L^2$ are optionally and independently replaced by —$NR^B$—, —O—, —OC(O)—, —C(O)O—, —C(O)—, —C(O)C(O)—, —C(O)$NR^B$—, —$NR^B$C(O)—, or —$NR^B$C(O)O—; and each $R^6$ is independently selected from $R^B$, halo, —$CF_3$, or Boc;

each $R^B$ is independently selected from —H, $C_{1-3}$ alkyl, or phenyl; and $R^2$ is —H or $R^1$, provided that i) when $R^1$ is phenyl or pyridinyl, and x is 1, then $R^3$ is not chloro;

ii) when $R^1$ is phenyl or pyridinyl, and x is 1, then $R^3$ is not unsubstituted phenyl;

iii) when $R^1$ is phenyl, and x is 1, then $R^3$ is not —N(H)C(O)$CH_3$ or —C(O)$NH_2$; and iv) when $R^1$ is furyl or thiophenyl, and x is 1, then $R^3$ is not —$CH_3$.

In some embodiments, $R^2$ is —H.

In other embodiments, $R^1$ is phenyl substituted with x occurrences of $R^3$.

In some embodiments, x is 1 and $R^3$ is selected from halo, an optionally substituted $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur, a 13 to 14 membered saturated, partially unsaturated, or fully unsaturated tricyclic ring system having 0 to 5 heteroatoms independently selected from N, O, or S, or —O—($C_{1-3}$ alkyl)-phenyl, wherein each $R^3$ is substituted with up to 2 occurrences of $R^5$ at any chemically feasible position.

In further embodiments, $R^3$ is selected from halo, an unsubstituted $C_{1-6}$ alkyl group, a halo-substituted $C_{1-6}$ alkyl group, an optionally substituted 5 to 6 membered saturated, partially unsaturated, or fully unsaturated monocyclic ring having 0-3 heteroatoms independently selected from nitrogen, oxygen, or sulfur; or —O—$(CH_2)_{1-2}$ phenyl. In other embodiments, $R^3$ is selected from —Cl, —F, —I, —$CH_3$, —$CF_3$, —$CH_2CH_3$, or —$CH_2CF_3$. In other embodiments, $R^3$ is selected from piperidine, piperazine, morpholine, pyrrolidine, imidazolidine, pyrrole, thiophene, furan, oxazole, pyridine, pyrimidine, or pyrazine, wherein $R^3$ is substituted with $C_{1-6}$ alkyl. In some embodiments, $R^3$ is selected from piperidine or piperazine, either of which is optionally substituted with $C_{1-6}$ alkyl. In other embodiments $R^3$ is selected from

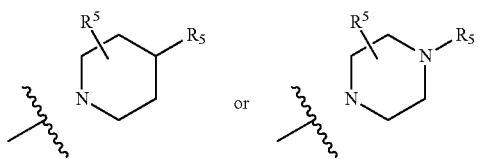

wherein each $R^5$ is independently —H or $C_{1-6}$ alkyl. In other embodiments, $R^3$ is BOC.

In other embodiments, x is 2, and at least one occurrence of $R^3$ is halogen. In further embodiments, x is 2, and each $R^3$ is halogen.

In some embodiments, $R^1$ is naphthyl substituted with x occurrences of $R^3$. In some embodiments, $R^1$ is selected from

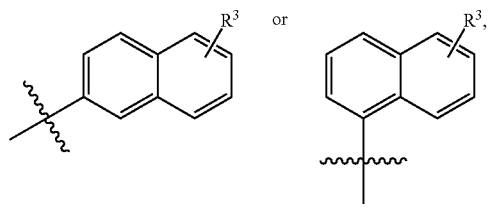

wherein $R^3$ is —H or $C_{1-6}$ alkyl.

In other embodiments, $R^1$ is a 5 to 6 membered monocyclic heteroaryl having 1 to 3 nitrogen atoms, wherein the monocyclic heteroaryl is substituted with x occurrences of $R^3$. In some embodiments, $R^1$ is selected from pyrazole, pyridine, pyrazine, or pyrimidine, and x is 1 or 2. In further embodiments, $R^1$ is

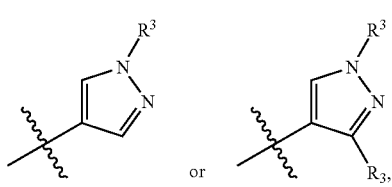

and $R^3$ is hydrogen, —$CF_3$, $C_{1-6}$ alkyl, or a 5 to 6 membered cycloaliphatic group. In some embodiments, $R^1$ is

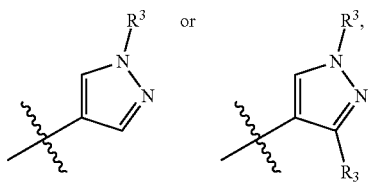

and each $R^3$ is independently selected from hydrogen, methyl, trifluoromethyl, ethyl, propyl, cyclopentyl, or cyclohexyl.

In other embodiments, $R^1$ is

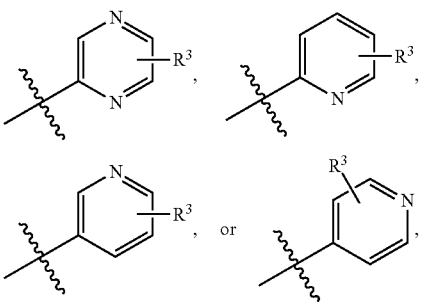

wherein each $R^3$ is hydrogen, a $C_{1-6}$ alkyl group, an optionally substituted 3 to 8 membered saturated, partially unsaturated, or fully unsaturated monocyclic ring having 0-3 heteroatoms independently selected from nitrogen, oxygen, or sulfur; or an 8-12 membered saturated, partially unsaturated, or fully unsaturated bicyclic ring system having 0-5 heteroatoms independently selected from nitrogen, oxygen, or sulfur; wherein each of the $C_{1-6}$ alkyl, the monocyclic ring, or the bicycling ring system is optionally substituted with up to 2 occurrences of $R^5$.

In some embodiments, $R^1$ is

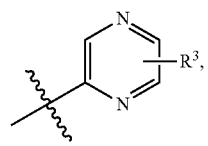

and $R^3$ is an optionally substituted 5 to 6 membered saturated, partially unsaturated, or fully unsaturated monocyclic ring having 0-2 heteroatoms independently selected from nitrogen or oxygen.

In other embodiments, $R^1$ is

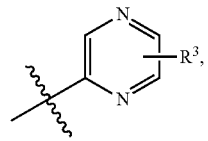

and $R^3$ is piperidine-1-yl optionally substituted with $C_{1-6}$ alkyl.

In some embodiments R¹ is selected from

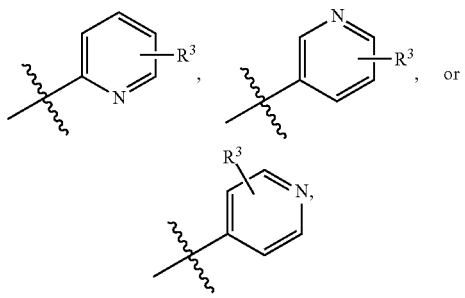

and each R³ is —H, $C_{1-6}$ alkyl, or an optionally substituted 5 to 6 membered, saturated, or fully unsaturated monocyclic ring having 0-2 heteroatoms independently selected from nitrogen or oxygen, wherein the monocyclic ring is optionally substituted with up to 2 occurrences of R⁵. In other embodiments, R³ is selected from —H, $C_{1-4}$ alkyl,

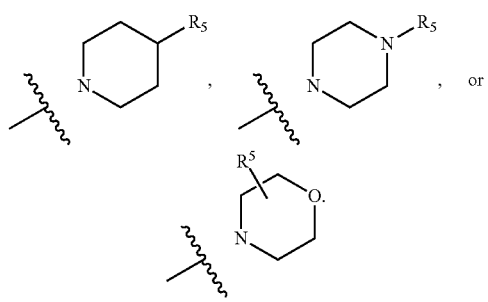

In some embodiments, each R⁵ is independently selected from —H, $C_{1-4}$ alkyl, —N(CH₃)₂, —C(O)—CH₃, —C(O)—CH₂—CH₃, or —C(O)—O—C(CH₃)₃.

In some embodiments, R¹ is a 9 to 10 membered bicyclic heteroaryl having 1 to 3 heteroatoms independently selected from N, O, or S, wherein the bicyclic heteroaryl is substituted with x occurrences of R³. In other embodiments, R¹ is selected from

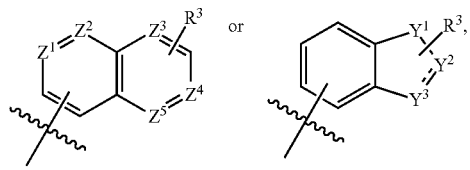

wherein
each of Z¹, Z², Z³, Z⁴, and Z⁵ is independently CR³ or N, wherein at least one of Z¹, Z², Z³, Z⁴, and Z⁵ is N;
each of Y¹, Y², and Y³ is independently CH, CR³, N, NR³, or O, wherein at least one of Y¹, Y², and Y³ are N, NR³, or O; and
--- is a bond or absent, provided that
a) no more than three of Z¹, Z², Z³, Z⁴, and Z⁵ is N;
b) R¹ is substituted with no more than three occurrences of R³;
c) if either of Y² or Y³ is —O—, then --- is absent; and
d) if --- is bond, then Y² is N, CH, or CR³, and Y³ is N, CH, or CR³.

In further embodiments, R¹ is selected from

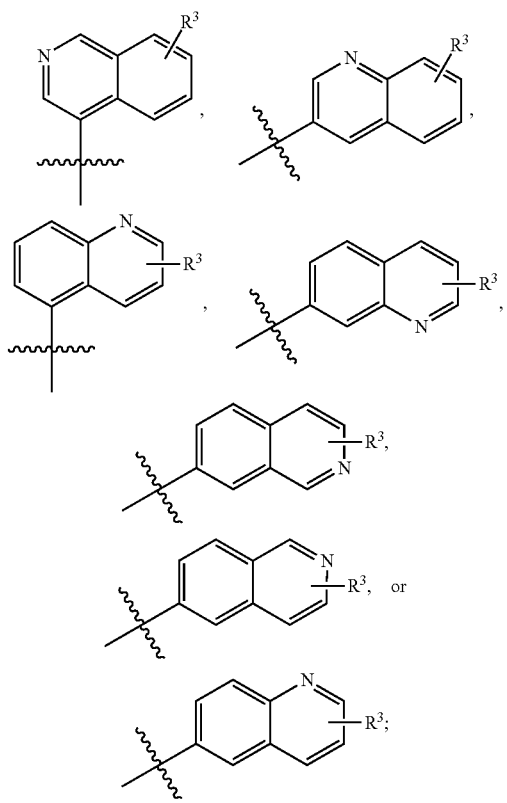

and R³ is —H or $C_{1-6}$ alkyl.

In other embodiments, R¹ is selected from

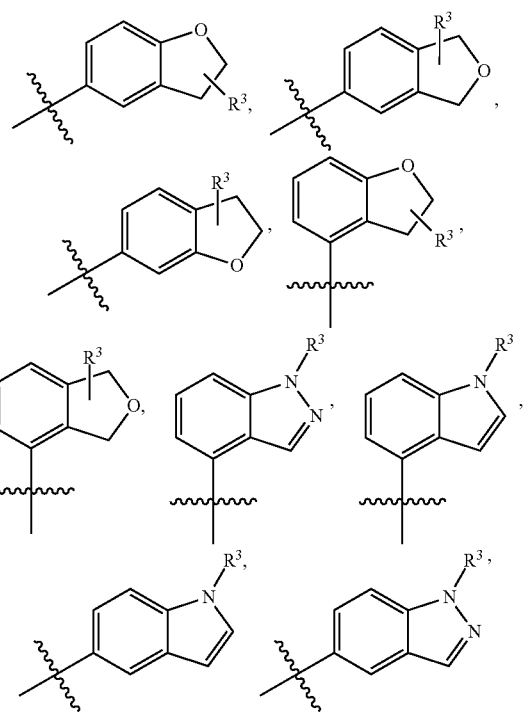

-continued

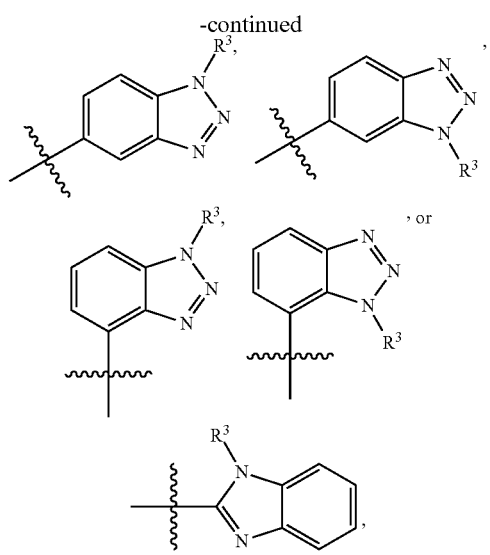

wherein $R^3$ is —H or $C_{1-6}$ alkyl.

Another aspect of the invention provides for a compound of Formula I-A:

I-A

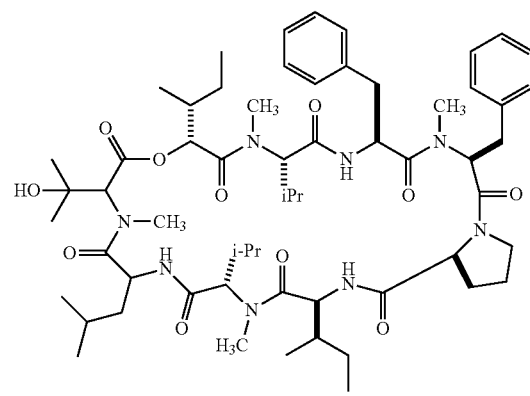

or a pharmaceutically acceptable salt thereof, wherein $R^1$ is

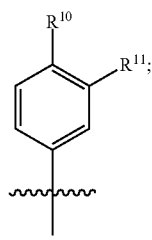

each of $R^{10}$ and $R^{11}$ is independently selected from —H, —Cl, —F, —$C_{1-6}$ alkyl, —O($C_{1-3}$ alkyl)-phenyl, —BOC, or a 5 to 8 membered saturated, partially unsaturated, or fully unsaturated monocyclic ring having 0-3 heteroatoms independently selected from N, O, or S, wherein the $C_{1-6}$ alkyl or the monocyclic ring is substituted with 0-3 of $R^{13}$; or $R^{10}$, $R^{11}$, and the carbon atoms to which they are attached form a 5 to 6 membered saturated, partially unsaturated, or fully unsaturated monocyclic ring having 0 to 3 heteroatoms independently selected from N, O, or S, wherein the monocyclic ring is substituted with 0-2 of $R^{13}$; and each $R^{13}$ is independently halo or $C_{1-3}$ alkyl, provided that:

when $R^{10}$ is —H, then $R^{11}$ is not —H.

In some embodiments, the compound of Formula I-A is a compound of Formula I-A1:

I-A1

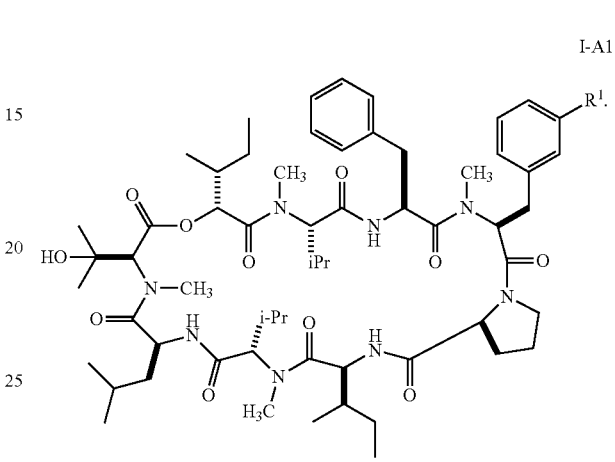

In one aspect, the present invention provides a compound of formula I-A1 where $R^1$ is

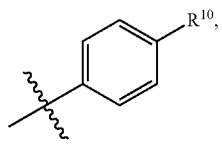

and $R^{10}$ is selected from the group consisting of —F, —$CF_3$,

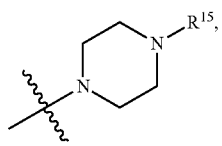

—BOC, or —O—($C_{1-3}$ alkyl)-phenyl, wherein $R^{15}$ is —H, or —$C_{1-3}$ alkyl.

In another embodiment, a compound of formula I-A1 is provided where $R^1$ is

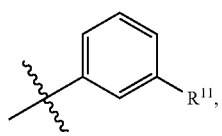

and $R^{11}$ is selected from —F, —$CF_3$,

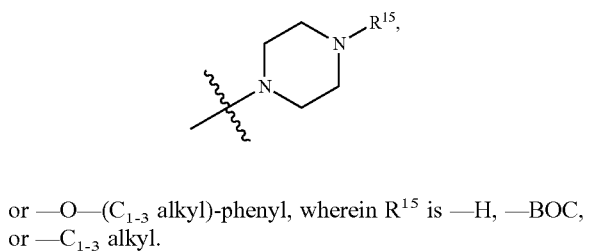

or —O—(C$_{1-3}$ alkyl)-phenyl, wherein R$^{15}$ is —H, —BOC, or —C$_{1-3}$ alkyl.

In another embodiment, a compound of formula I-A1 is provided where R$^1$ is selected from the group consisting of

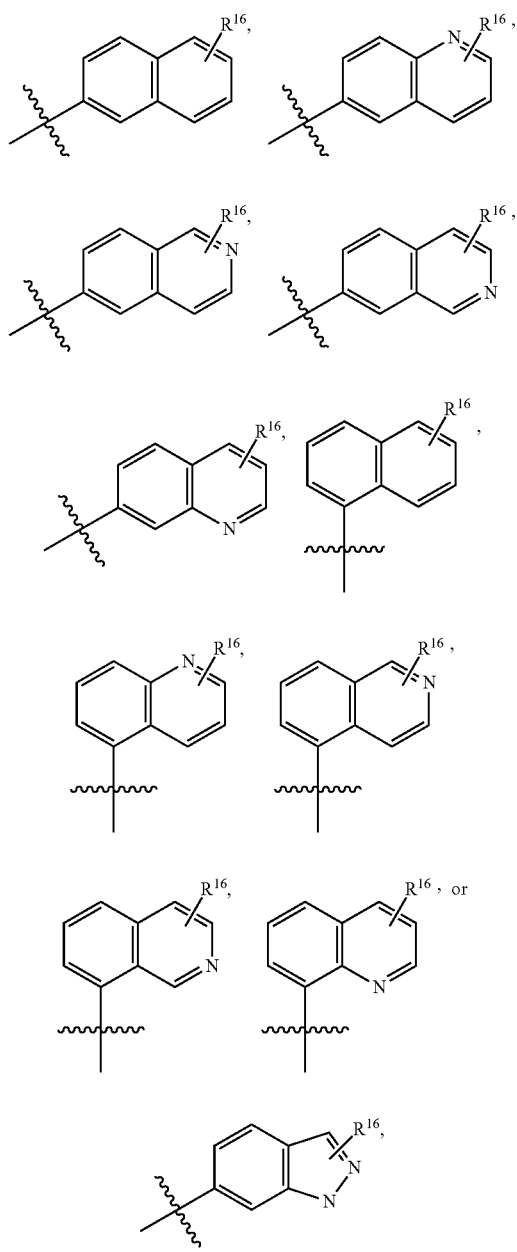

wherein R$^{16}$ is —H or —C$_{1-3}$ alkyl.

Another aspect of the invention provides a compound of Formula I-B:

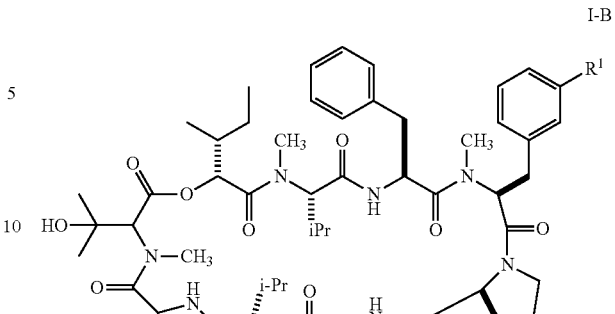

I-B or a pharmaceutically acceptable salt thereof, wherein R$^1$ is

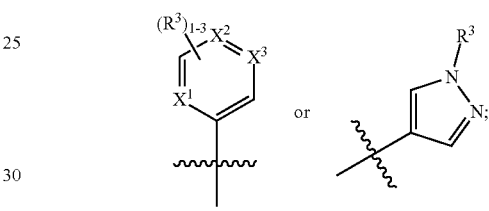

each of X$^1$, X$^2$, and X$^3$ is independently CH, CR$^3$ or N, wherein R$^1$ is substituted with 1 to 3 occurrences of R$^3$;

each R$^3$ is independently selected from —H, —N(C$_{1-4}$ alkyl)$_2$, C$_{1-6}$ alkyl, or a 5 to 8 membered saturated, partially unsaturated, or fully unsaturated monocyclic ring having 0-3 heteroatoms independently selected from N, O, or S, wherein the C$_{1-4}$ alkyl, the C$_{1-4}$ alkyl or the monocyclic ring is substituted with 0-2 of R$^5$; or two occurrences of R$^3$ taken together with the carbon atoms to which they are attached form a 5 to 6 membered saturated, partially unsaturated, or fully unsaturated monocyclic ring having 0-3 heteroatoms independently selected from N, O, or S, wherein the monocyclic ring is substituted with 0-2 of R$^5$;

Each R$^5$ is independently —L$^2$-R$^6$;

each L$^2$ is independently a bond or an optionally substituted branched or straight C$_{1-6}$ aliphatic chain, wherein up to two carbon atoms of L$^2$ are optionally and independently replaced by —NR$^B$—, —O—, —OC(O)—, —C(O)O—, —C(O)—, —C(O)C(O)—, —C(O)NR$^B$—, —NR$^B$C(O)—, or —NR$^B$C(O)O—;

each R$^6$ is independently selected from R$^B$, halo, —CF$_3$, or —BOC; and each R$^B$ is independently selected from —H, C$_{1-3}$ alkyl, or phenyl, provided that a) when X$^2$ is N, then X$^3$ is CH or CR$^3$; and
b) when X$^3$ is N, then X$^2$ is CH or CR$^3$.

In another aspect of the invention, the compound of Formula I-B is a compound of Formula I-B1:

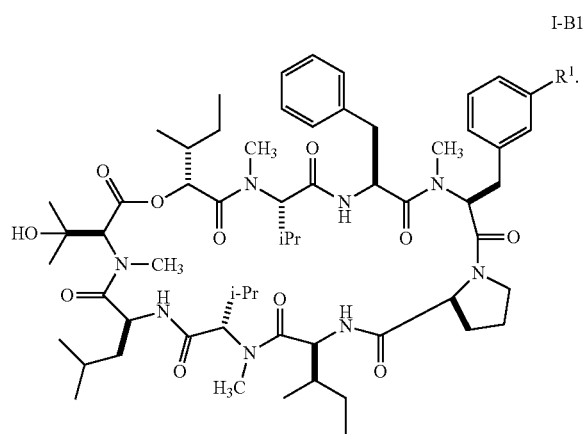

In some embodiments, a compound of Formula I-B1 is described where $R^1$ is selected from

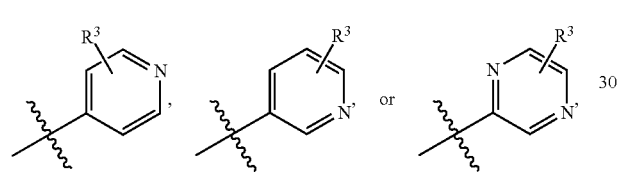

wherein $R^3$ is selected from —N(C$_{1-4}$ alkyl)$_2$, —C$_{1-6}$ alkyl, phenyl, piperazinyl, piperidinyl, or morpholinyl, wherein any of the C$_{1-4}$ alkyl, C$_{1-6}$ alkyl, phenyl, piperazinyl, piperidinyl, or morpholinyl is optionally substituted up to two occurrences of $R^5$; and each $R^5$ is independently selected from halo, —CF$_3$, C$_{1-6}$ alkyl, or —C(O)—O—(C$_{1-6}$ alkyl).

In another embodiment, a compound of Formula I-B1 is described where $R^1$ is selected from

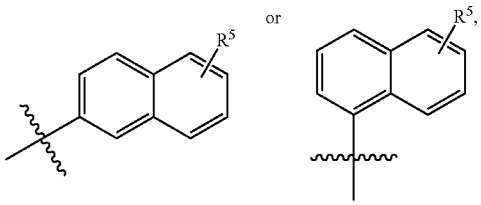

wherein $R^5$ is —H or —C$_{1-4}$ alkyl.

In some embodiments, a compound of Formula I-B1 is described wherein $R^1$ is

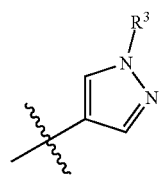

and $R^3$ is C$_{3-7}$ cycloaliphatic.

In another aspect of the invention, a compound is described, wherein the compound is selected from a compound listed in Table 1 below.

TABLE 1

Examples of Aba derivatives of the present invention.

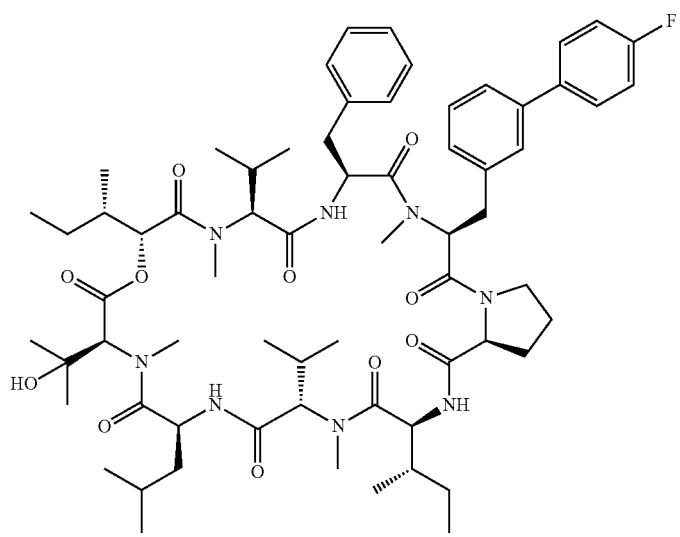 [SMILES: CC[C@H](C)[C@@H]1NC(=O)[C@@H]2CCCN2C(=O)[C@H](Cc2cccc(-c3ccc(F)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]

1

TABLE 1-continued
Examples of Aba derivatives of the present invention.
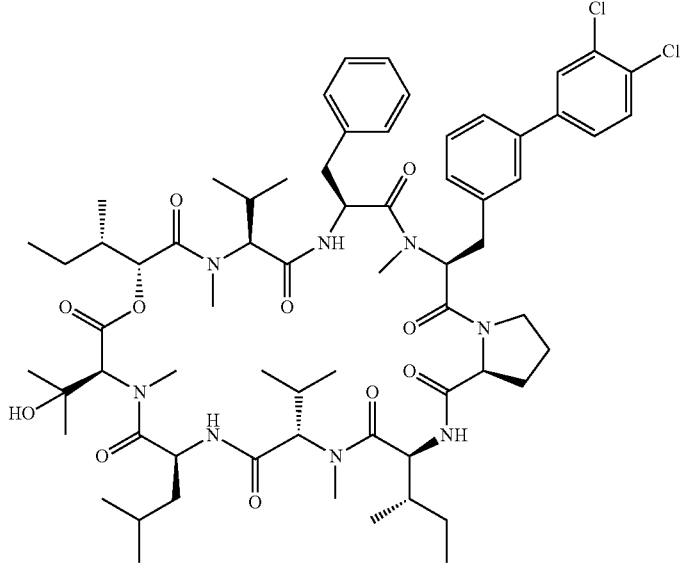 [SMILES: CC[C@H](C)[C@@H]1NC(=O)[C@@H]2CCCN2C(=O)[C@H](Cc2cccc(-c3ccc(Cl)c(Cl)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
2
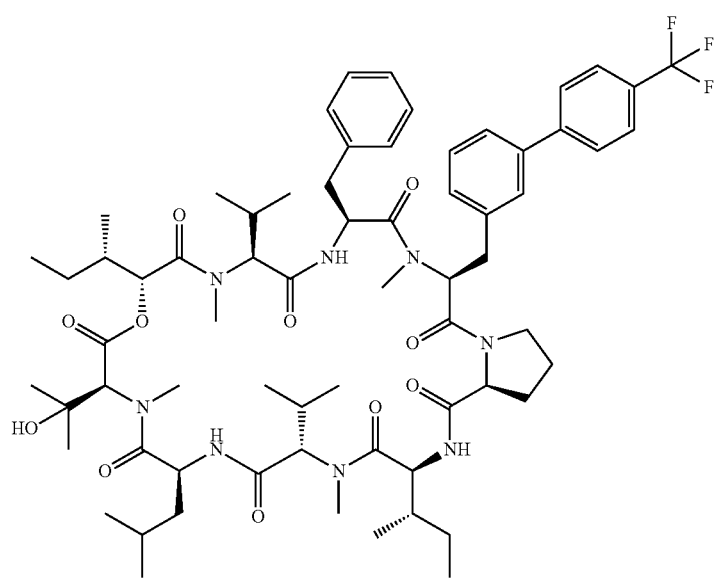 [SMILES: CC[C@H](C)[C@@H]1NC(=O)[C@@H]2CCCN2C(=O)[C@H](Cc2cccc(-c3ccc(C(F)(F)F)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
3

TABLE 1-continued
Examples of Aba derivatives of the present invention.
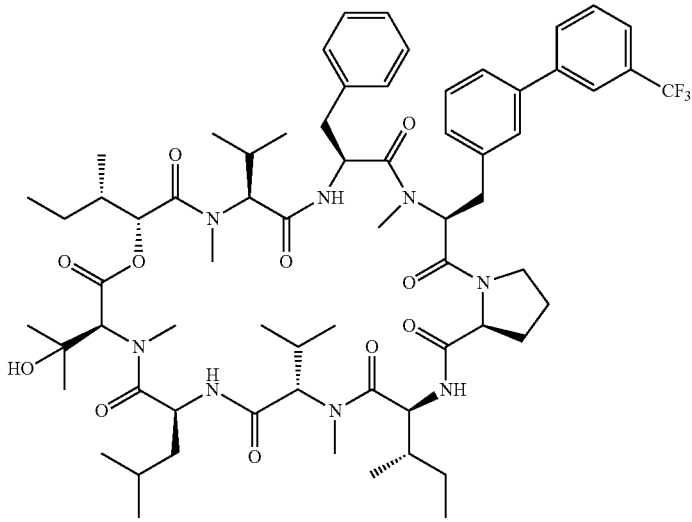 [SMILES: CC[C@H](C)[C@@H]1NC(=O)[C@@H]2CCCN2C(=O)[C@H](Cc2cccc(-c3cccc(C(F)(F)F)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
4
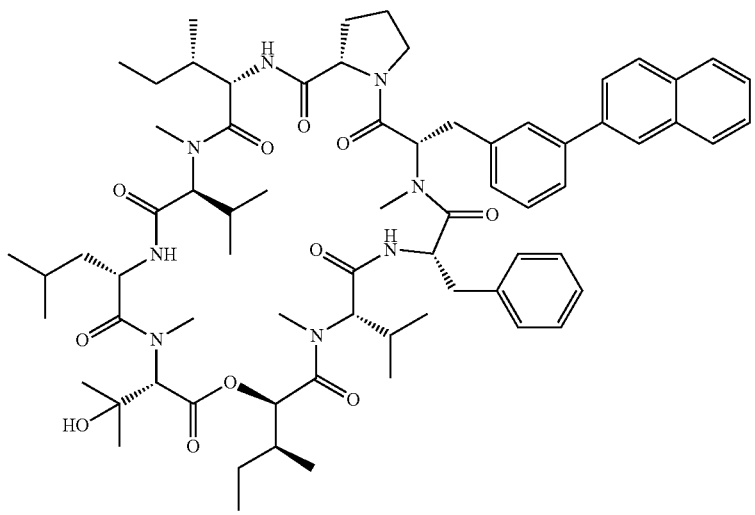 [SMILES: CC[C@H](C)[C@@H]1NC(=O)[C@@H]2CCCN2C(=O)[C@H](Cc2cccc(-c3ccc4ccccc4c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
5
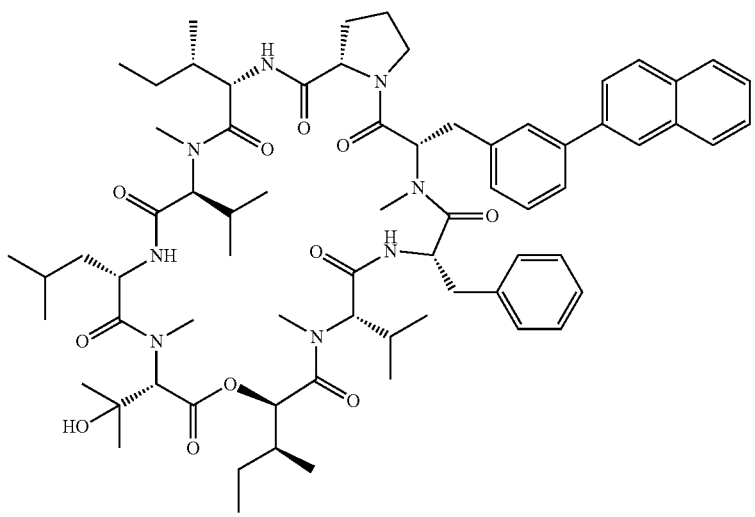 [SMILES: CC[C@H](C)[C@@H]1NC(=O)[C@@H]2CCCN2C(=O)[C@H](Cc2cccc(-c3ccc4ccccc4c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
6

TABLE 1-continued
Examples of Aba derivatives of the present invention.
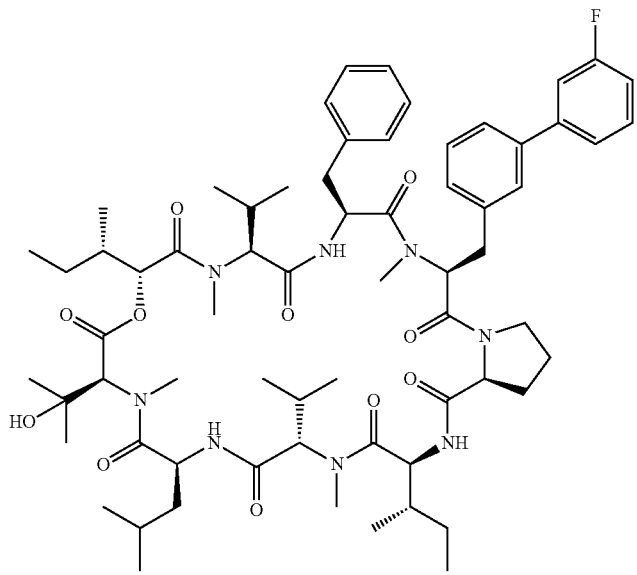 [SMILES: CC[C@H](C)[C@@H]1NC(=O)[C@@H]2CCCN2C(=O)[C@H](Cc2cccc(-c3cccc(F)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
7
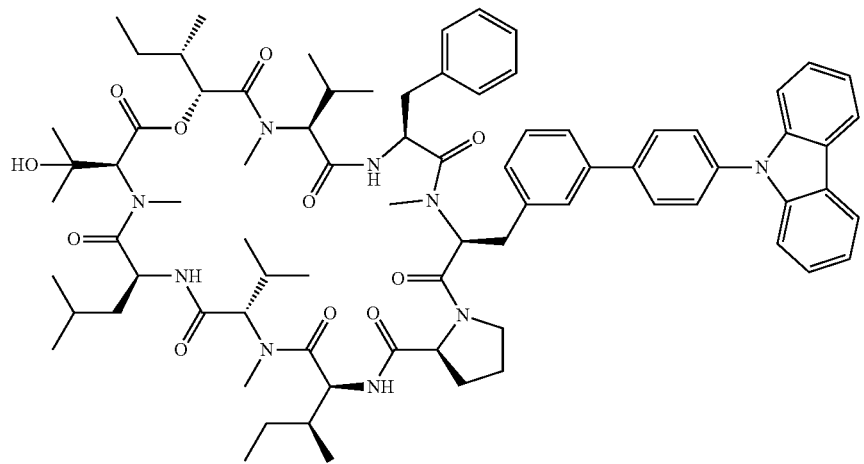 [SMILES: CC[C@H](C)[C@@H]1NC(=O)[C@@H]2CCCN2C(=O)[C@H](Cc2cccc(-c3ccc(-n4c5ccccc5c5ccccc54)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
8
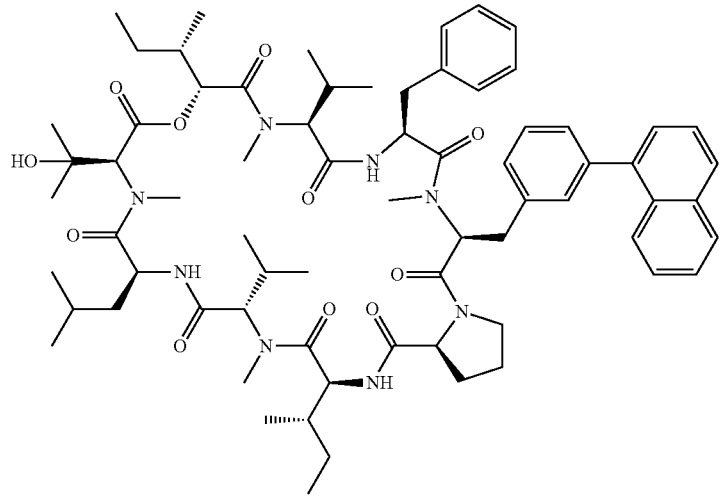 [SMILES: CC[C@H](C)[C@@H]1NC(=O)[C@@H]2CCCN2C(=O)[C@H](Cc2cccc(-c3cccc4ccccc34)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
9

TABLE 1-continued
Examples of Aba derivatives of the present invention.
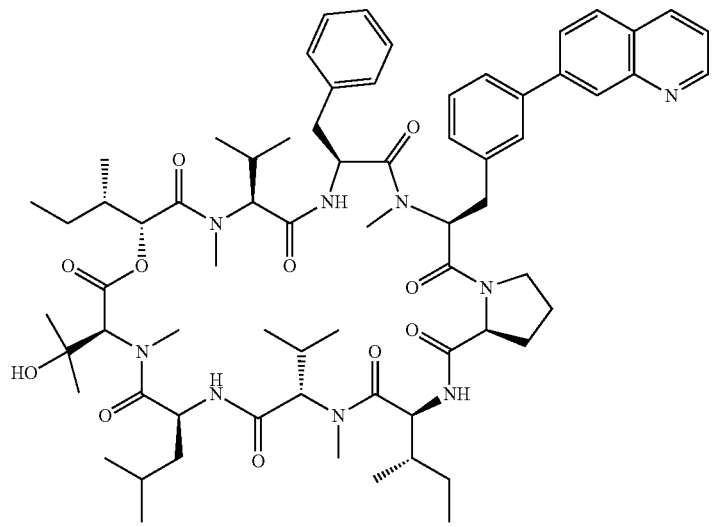 [SMILES: CC[C@H](C)[C@@H]1NC(=O)[C@@H]2CCCN2C(=O)[C@H](Cc2cccc(-c3ccc4cccnc4c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
10
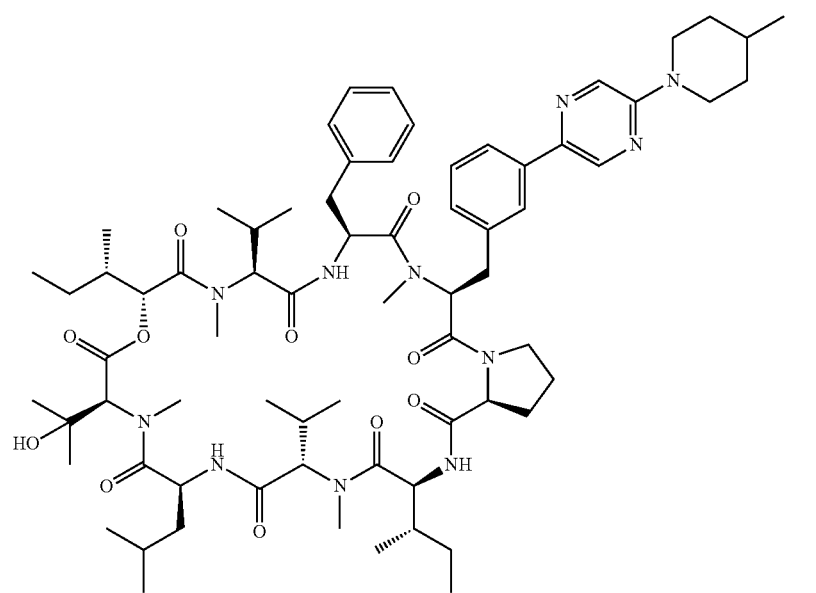 [SMILES: CC[C@H](C)[C@@H]1NC(=O)[C@@H]2CCCN2C(=O)[C@H](Cc2cccc(-c3cnc(N4CCC(C)CC4)cn3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
11

TABLE 1-continued
Examples of Aba derivatives of the present invention.
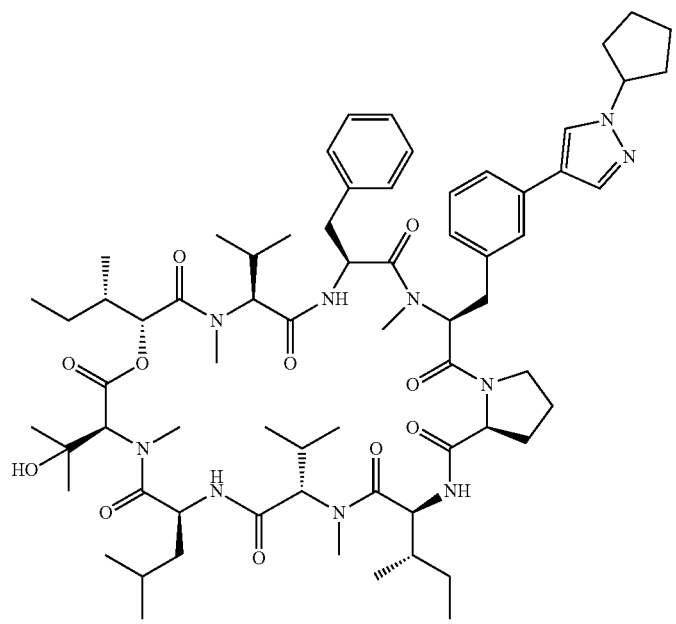 [SMILES: CC[C@H](C)[C@@H]1NC(=O)[C@@H]2CCCN2C(=O)[C@H](Cc2cccc(-c3cnn(C4CCCC4)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
12
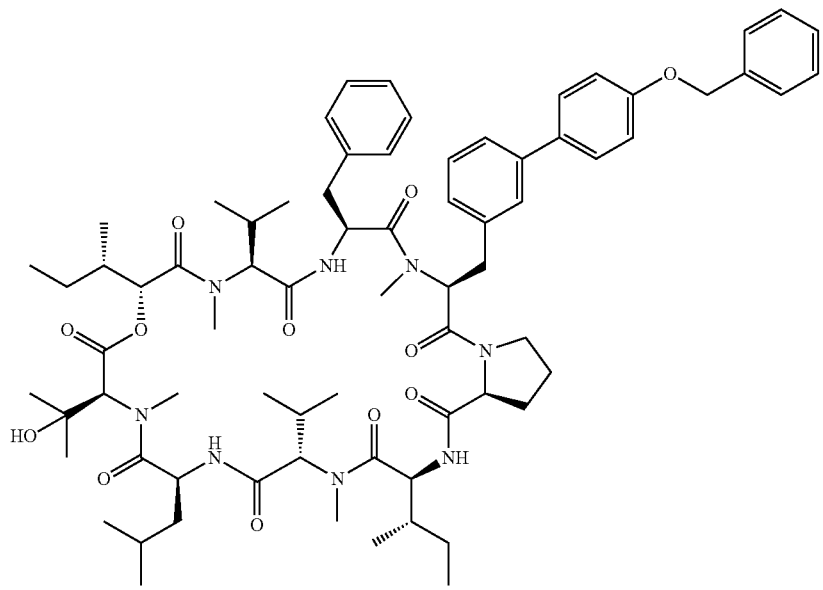 [SMILES: CC[C@H](C)[C@@H]1NC(=O)[C@@H]2CCCN2C(=O)[C@H](Cc2cccc(-c3ccc(OCc4ccccc4)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
13

TABLE 1-continued
Examples of Aba derivatives of the present invention.
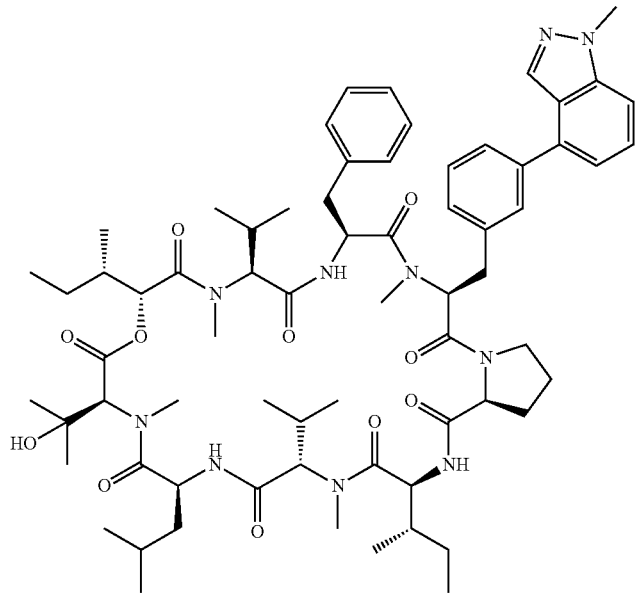 [SMILES: CC[C@H](C)[C@@H]1NC(=O)[C@@H]2CCCN2C(=O)[C@H](Cc2cccc(-c3cccc4c3cnn4C)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
14
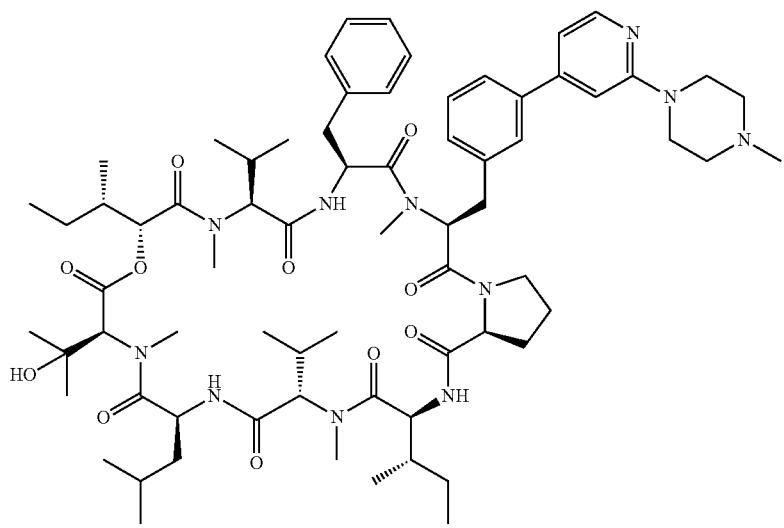 [SMILES: CC[C@H](C)[C@@H]1NC(=O)[C@@H]2CCCN2C(=O)[C@H](Cc2cccc(-c3ccnc(N4CCN(C)CC4)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
15

TABLE 1-continued
Examples of Aba derivatives of the present invention.
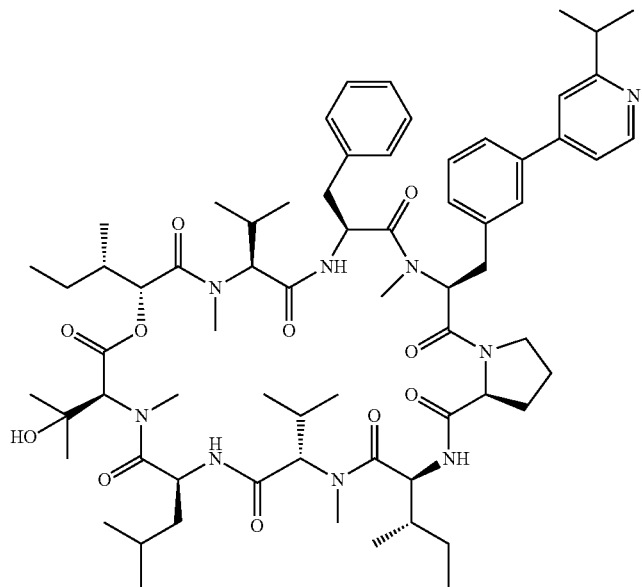 [SMILES: CC[C@H](C)[C@@H]1NC(=O)[C@@H]2CCCN2C(=O)[C@H](Cc2cccc(-c3ccnc(C(C)C)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
16
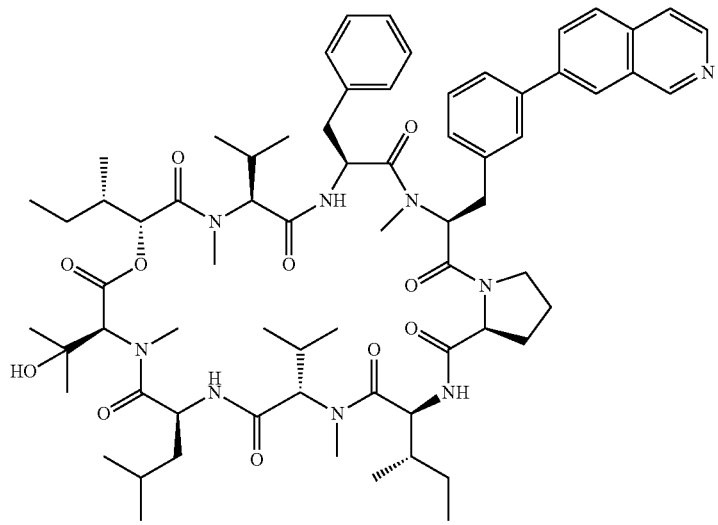 [SMILES: CC[C@H](C)[C@@H]1NC(=O)[C@@H]2CCCN2C(=O)[C@H](Cc2cccc(-c3ccc4ccncc4c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
17

TABLE 1-continued
Examples of Aba derivatives of the present invention.
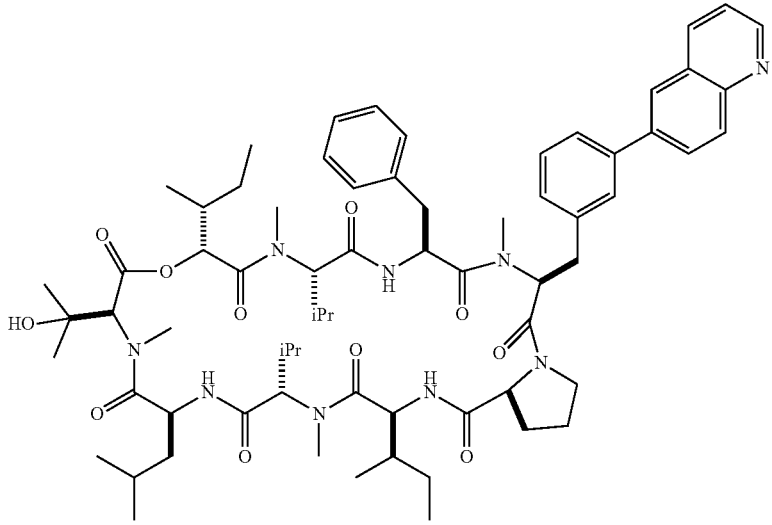 [SMILES: CCC(C)[C@@H]1NC(=O)[C@@H]2CCCN2C(=O)[C@H](Cc2cccc(-c3ccc4ncccc4c3)c2)N(C)C(=O)[C@H](Cc2ccccc2)NC(=O)[C@H](C(C)C)N(C)C(=O)[C@@H](C(C)CC)OC(=O)[C@H](C(C)(C)O)N(C)C(=O)[C@H](CC(C)C)NC(=O)[C@H](C(C)C)N(C)C1=O]
18
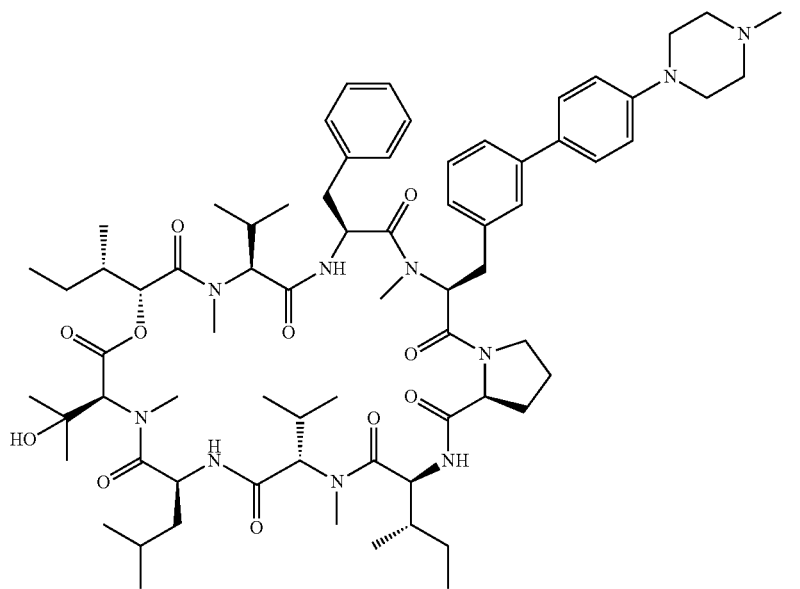 [SMILES: CC[C@H](C)[C@@H]1NC(=O)[C@@H]2CCCN2C(=O)[C@H](Cc2cccc(-c3ccc(N4CCN(C)CC4)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
19

TABLE 1-continued
Examples of Aba derivatives of the present invention.
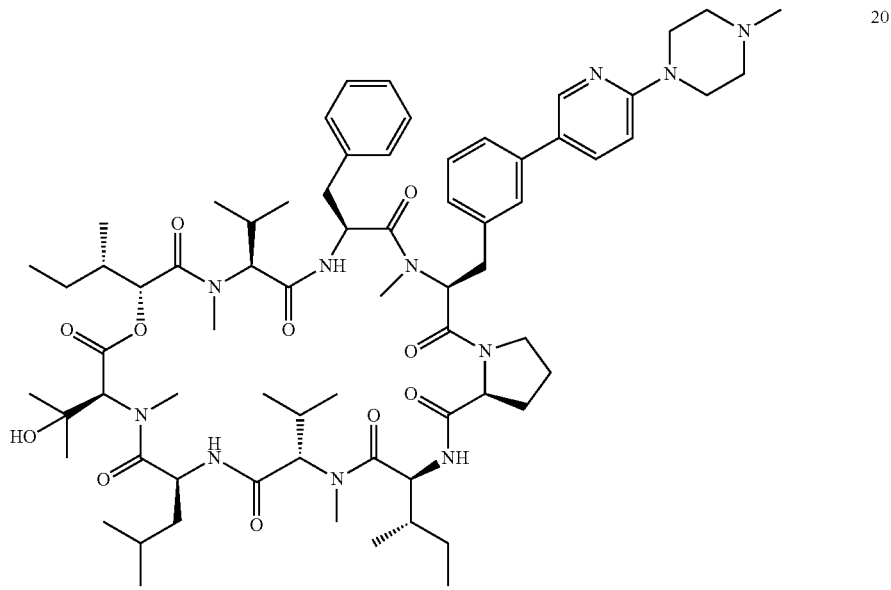
20
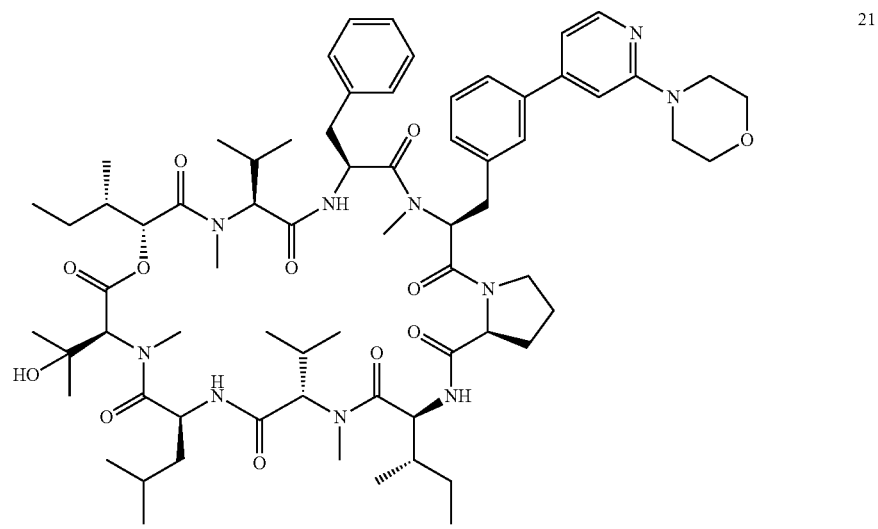
21
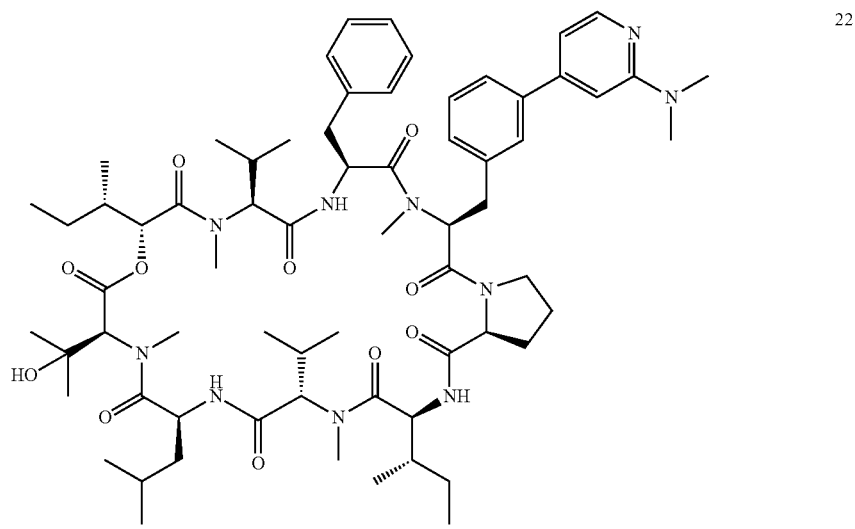
22

TABLE 1-continued
Examples of Aba derivatives of the present invention.
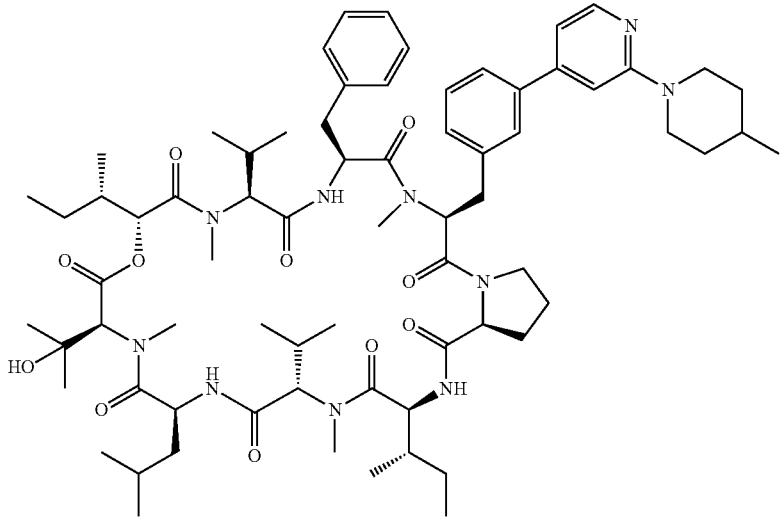 [SMILES: CC[C@H](C)[C@@H]1NC(=O)[C@@H]2CCCN2C(=O)[C@H](Cc2cccc(-c3ccnc(N4CCC(C)CC4)c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
23
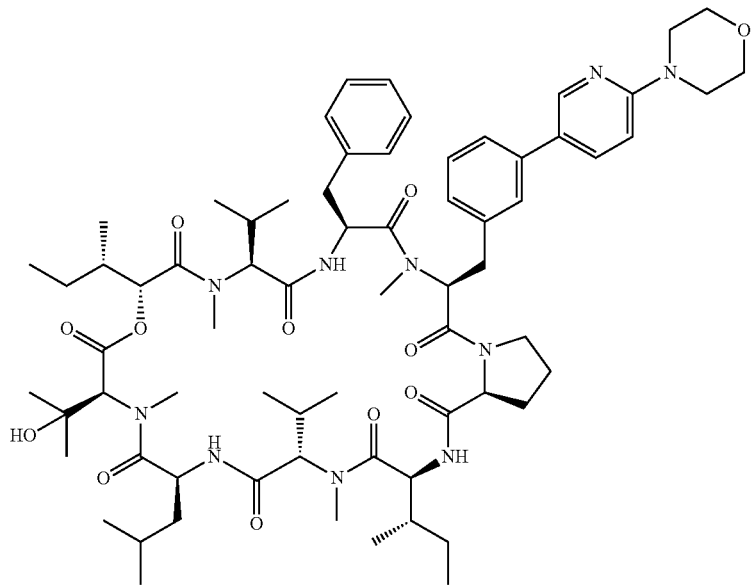 [SMILES: CC[C@H](C)[C@@H]1NC(=O)[C@@H]2CCCN2C(=O)[C@H](Cc2cccc(-c3ccc(N4CCOCC4)nc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
24

TABLE 1-continued
Examples of Aba derivatives of the present invention.
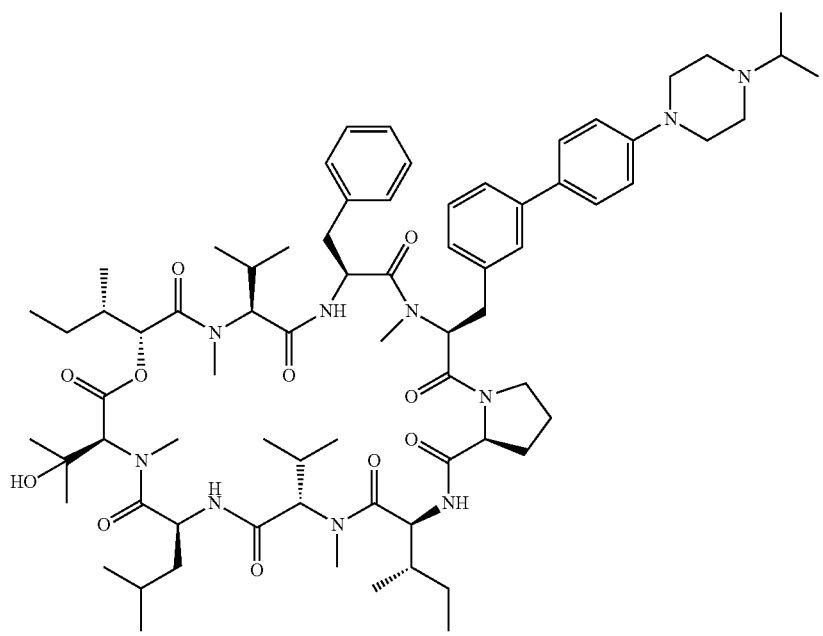 [SMILES: CC[C@H](C)[C@@H]1NC(=O)[C@@H]2CCCN2C(=O)[C@H](Cc2cccc(-c3ccc(N4CCN(C(C)C)CC4)cc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
25
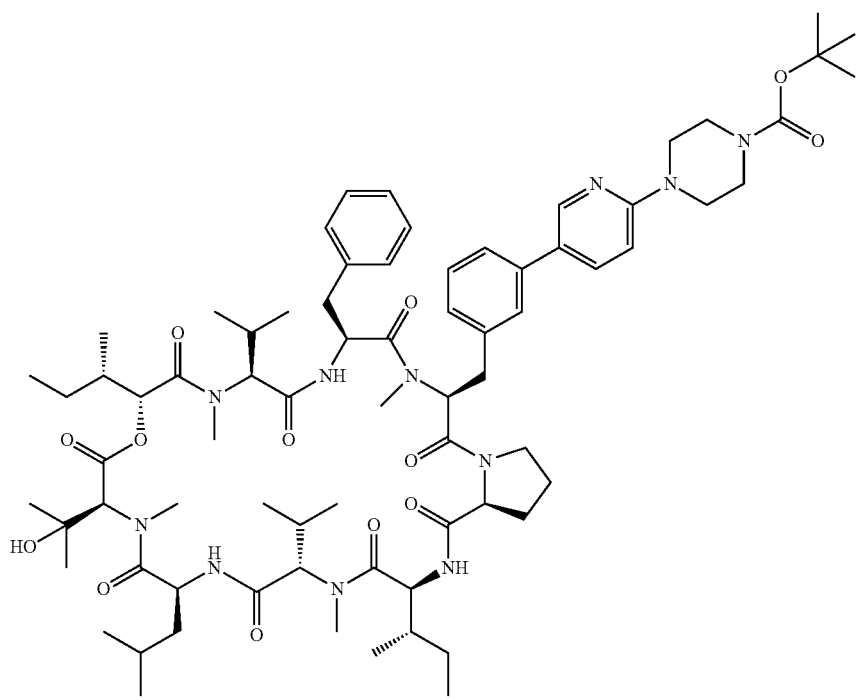 [SMILES: CC[C@H](C)[C@@H]1NC(=O)[C@@H]2CCCN2C(=O)[C@H](Cc2cccc(-c3ccc(N4CCN(C(=O)OC(C)(C)C)CC4)nc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
26

TABLE 1-continued
Examples of Aba derivatives of the present invention.
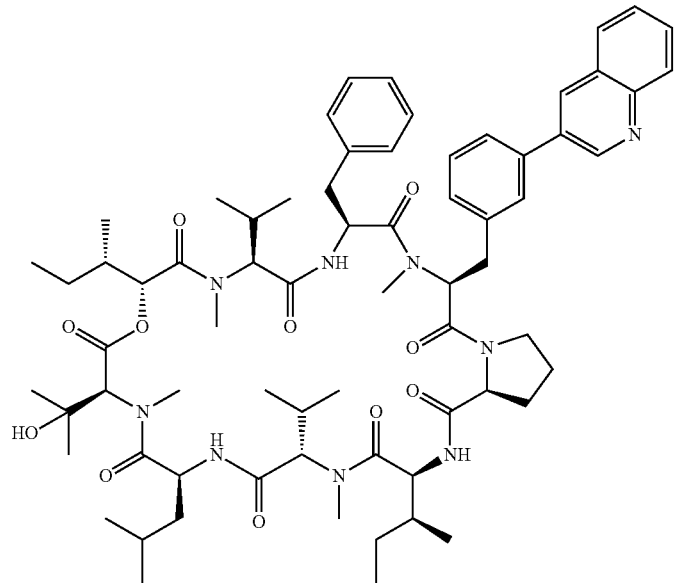 [SMILES: CC[C@H](C)[C@@H]1NC(=O)[C@@H]2CCCN2C(=O)[C@H](Cc2cccc(-c3cnc4ccccc4c3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
27
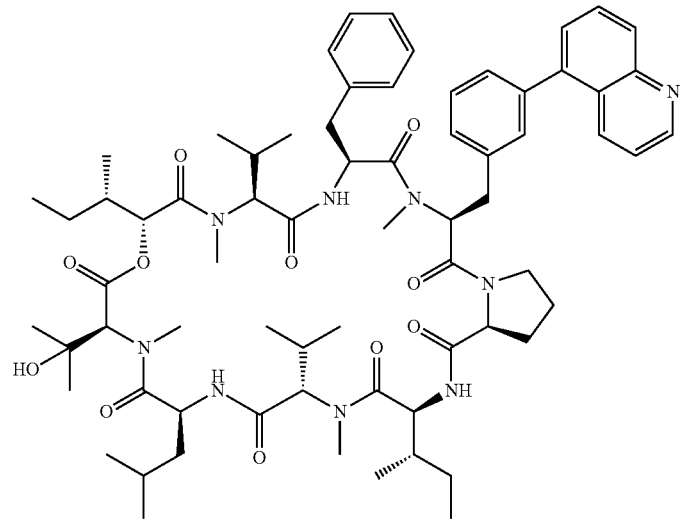 [SMILES: CC[C@H](C)[C@@H]1NC(=O)[C@@H]2CCCN2C(=O)[C@H](Cc2cccc(-c3cccc4ncccc34)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
28

TABLE 1-continued
Examples of Aba derivatives of the present invention.
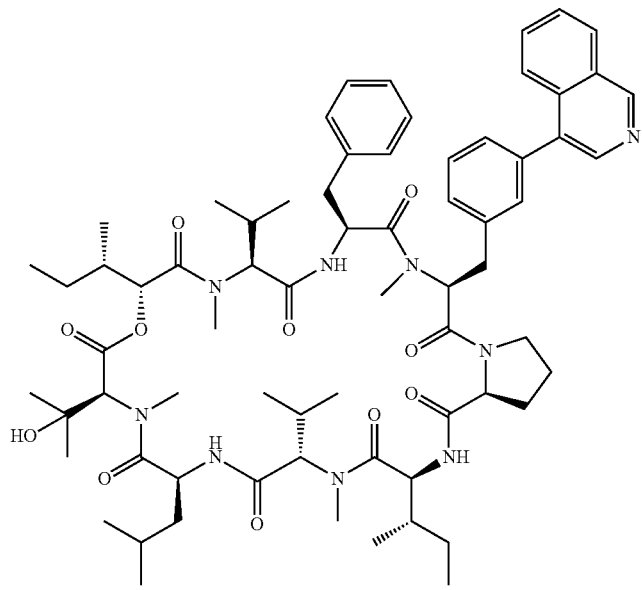 [SMILES: CC[C@H](C)[C@@H]1NC(=O)[C@@H]2CCCN2C(=O)[C@H](Cc2cccc(-c3cncc4ccccc34)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
29
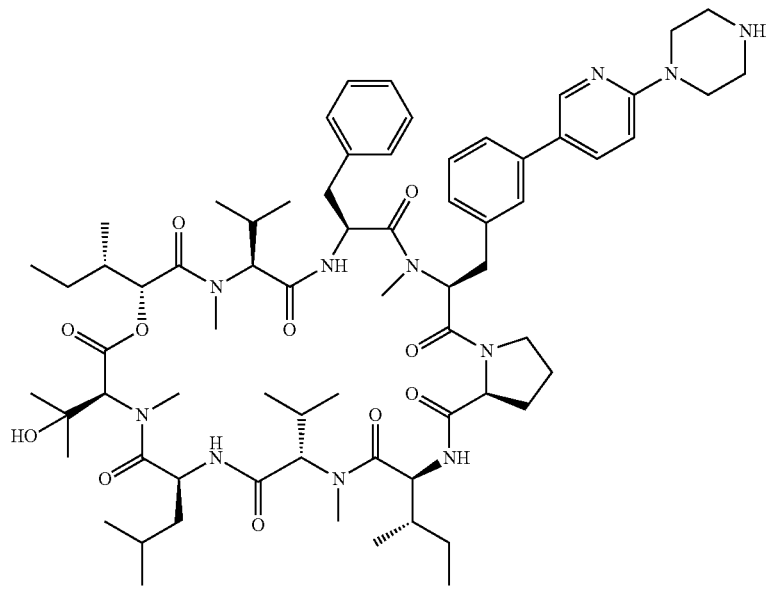 [SMILES: CC[C@H](C)[C@@H]1NC(=O)[C@@H]2CCCN2C(=O)[C@H](Cc2cccc(-c3ccc(N4CCNCC4)nc3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]
30

TABLE 1-continued
Examples of Aba derivatives of the present invention.
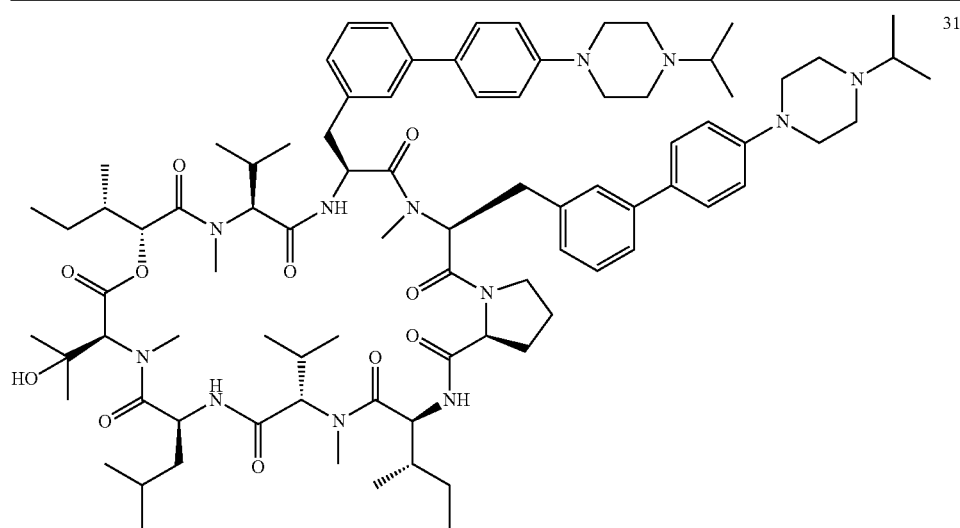
31
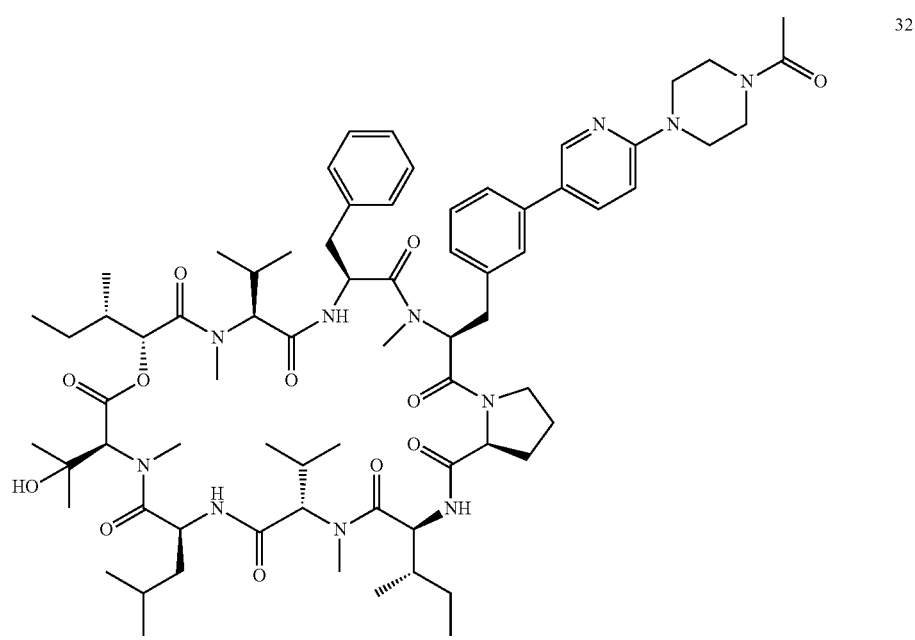
32

TABLE 1-continued

Examples of Aba derivatives of the present invention.

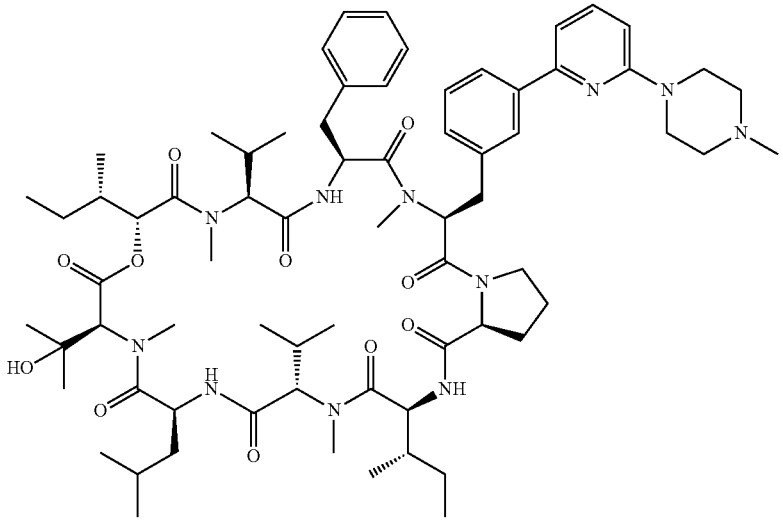 [SMILES: CC[C@H](C)[C@@H]1NC(=O)[C@@H]2CCCN2C(=O)[C@H](Cc2cccc(-c3cccc(N4CCN(C)CC4)n3)c2)N(C)C(=O)[C@H](Cc2ccccc2)NC(=O)[C@H](C(C)C)N(C)C(=O)[C@@H]([C@@H](C)CC)OC(=O)[C@H](C(C)(C)O)N(C)C(=O)[C@H](CC(C)C)NC(=O)[C@H](C(C)C)N(C)C1=O]

33

In another aspect of the invention, a pharmaceutical composition comprising a compound of any one of the compounds disclosed herein, and a pharmaceutically acceptable carrier, vehicle, or adjuvant.

In another aspect of the invention a method of treating a fungal infection in a patient is described, comprising administering an effective amount of a compound according to any one of the compounds disclosed herein or a pharmaceutical composition as disclosed herein. In some instances the fungal infection is an infection caused by fungi selected from *Aspergillus, Candida, Cryptococcus, Coccidiodes, Issatchenkia, Saccharomyces, Emericella,* or *Trichophyton*.

In another aspect of the invention, a method of reducing the number of fungi in a biological sample is described, comprising administering an effective amount of a compound disclosed herein or a pharmaceutical composition disclosed herein. In further embodiments the compounds disclosed herein are used in a method of reducing the number of fungi in a biological sample, where the fungi is selected from *Aspergillus, Candida, Cryptococcus, Coccidiodes, Issatchenkia, Saccharomyces, Emericella, Coccidiodes,* or *Trichophyton*.

IV. Uses, Formulations, and Administration

In yet another aspect, the present invention provides a method of treating infection comprising administering one or more novel compounds, as described above, or a pharmaceutical composition comprising one or more of these novel compounds, preferably to a mammal, in need thereof.

According to yet another embodiment, the present invention provides a method of treating or reducing the severity of infection.

Another aspect of the invention relates to treating infection in a biological sample or a patient (e.g., in vitro or in vivo), which method comprises administering to the patient, or contacting said biological sample with a pharmaceutical composition comprising a novel compound as described above. The term "biological sample", as used herein, includes, without limitation, cell cultures or extracts thereat biopsied material obtained from a mammal or extracts thereof; and blood, saliva, urine, feces, semen, tears, or other body fluids or extracts thereof.

A. Pharmaceutical Compositions

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion (e.g., spray dry dispersion) or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

According to the invention an "effective amount" of the compound or pharmaceutically acceptable composition is that amount effective for treating or lessening the severity of infection (e.g., fungal infection).

The pharmaceutical compositions, according to the present invention, may be administered using any amount and any route of administration effective for treating or lessening the severity of an infection.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, and more specifically a human.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the compounds of the invention may be administered orally or parenterally at dosage levels of between 10 mg/kg and about 120 mg/kg.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes: Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121, each of which is incorporated by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

V. Methods of Synthesizing ABA Derivatives

Compounds described herein are generally synthesized according to the reaction scheme set forth in U.S. Pat. No. 8,906,848, which is herein incorporated by reference in its entirety. For example, the compounds of the present invention are generally synthesized according to the following reactions schemes:

83

Scheme 1

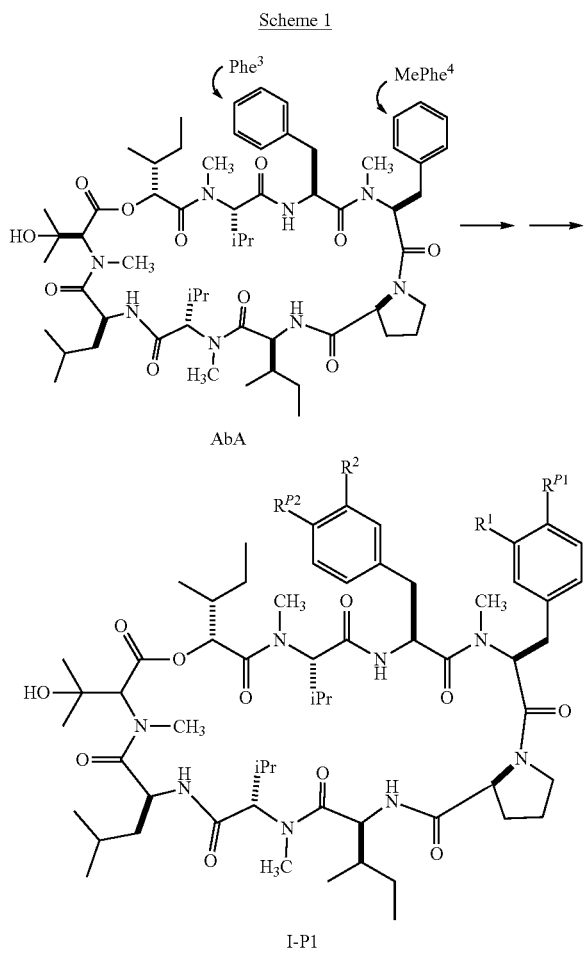

AbA

I-P1

84

In Scheme 1, AbA undergoes sequential borylation, halogenation, and optional cross-coupling reactions to generate compounds of Formula I-P1 that are substituted at the meta or para positions (in approximately a 2:1 ratio of meta to para isomers) of the phenyl moieties on Phe³ and/or MePhe⁴.

In order that the invention described herein may be more fully understood, the following examples are set forth. It should be understood that these examples are for illustrative purposes only and are not to be construed as limiting this invention in any manner.

VI. Examples

Example 1: Analytical Chemistry

The products from the chemical syntheses described in Examples 2-34 were characterized without further purification or separation of positional isomers using the methods described below.

HPLC Analysis:

HPLC analysis was performed using an Agilent 1100 HPLC with a Zorbax Eclipse XDB-C18 50×4.6 mm 1.8 micron column. Two solvents were used: Solvent A was water (0.1% TFA); and Solvent B was acetonitrile (0.07% TFA). The gradient was 5 min. 95% solvent A to 95% solvent B; 1 min hold; 1 min recycle; 30 sec. hold. UV Detection was performed at 210 nm and 254 nm with no reference. Native AbA was used as an internal standard for this chromatography.

Mass Spectrometry:

Mass spectrometry analyses were performed using a Waters ZQ mass spectrometer using electrospray ionization, 750-2000 amu, sample injected directly through the sample loop, without going through an HPLC column.

ESI-MS was performed for the synthetic products (AbA derivatives) of Examples 2-34.

Table 2 provides the analytical results of the HPLC and mass spectrometry analyses of the synthetic products (AbA derivatives) of Examples 2-34.

TABLE 2

| HPLC and mass spectometry data for AbA derivatives of the present invention. | | | |
|---|---|---|---|
| Compound No. | HPLC | HPLC AbA (Internal Std.) | Mass Spec |
| 1 | Retention time: 6.04 min 100% Area at 254 and 99.0% Area at 210 nm | Retention time: 3.40 Min 100% Area at 254 and 99.1% Area at 210 nm | MS (ESI+) for $C_{66}H_{95}FN_8O_{11}$ m/z 1196.0 $(M + H)^+$. MS (ESI+) for $C_{66}H_{95}FN_8O_{11}$ m/z 1217.9 $(M + Na)^+$. |
| 2 | Retention time: 6.72 min 99.1% Area at 254 and 99.5% Area at 210 nm. | Retention time: 4.41 min 98.9% Area at 254 and 99.4% Area at 210 nm. | MS (ESI+) for $C_{66}H_{94}Cl_2N_8O_{11}$ m/z 1246.0 $(M + H)^+$. MS (ESI+) for $C_{66}H_{94}Cl_2N_8O_{11}$ m/z 1267.8 $(M + Na)^+$. |
| 3 | Retention time: 6.25 min 98.2% Area at 254 and 99.0% Area at 210 nm. | Retention time: 3.82 min 100% Area at 254 and 100% Area at 210 nm. | MS (ESI+) for $C_{67}H_{95}F_3N_8O_{11}$ m/z 1246.1 $(M + H)^+$. MS (ESI+) for $C_{67}H_{95}F_3N_8O_{11}$ m/z 1265.6 $(M + Na)^+$. |
| 4 | Retention time: 6.24 min 98.0% Area at 254 and 99.3% Area at 210 nm. | Retention time: 3.80 min 98.6% Area at 254 and 99.3% Area at 210 nm. | MS (ESI+) for $C_{67}H_{95}F_3N_8O_{11}$ m/z 1245.9 $(M + H)^+$. MS (ESI+) for $C_{67}H_{95}F_3N_8O_{11}$ m/z 1267.9 $(M + Na)^+$. |

TABLE 2-continued

HPLC and mass spectometry data for AbA derivatives of the present invention.

| Compound No. | HPLC | HPLC AbA (Internal Std.) | Mass Spec |
|---|---|---|---|
| 5 | Retention time: 6.45 min 97.24% Area at 254 and 97.0% Area at 210 nm. | Retention time: 4.122 min 97.5% Area at 254 and 96.3% Area at 210 nm. | MS (ESI+) for $C_{70}H_{98}N_8O_{11}$ m/z 1228.0 $(M + H)^+$. MS (ESI+) for $C_{70}H_{98}N_8O_{11}$ m/z 1249.9 $(M + Na)^+$. |
| 6 | Retention time: 4.69 min; ca. 8% minor isomer at 4.87 min 98.0% Area at 254 and 98.7% Area at 210 nm. | Retention time: 1.64 min; ca. 8% minor isomer at 1.79 min 98.2% Area at 254 and 98.8% Area at 210 nm. | MS (ESI+) for $C_{69}H_{97}N_9O_{11}$ m/z 1229.1 $(M + H)^+$. |
| 7 | Retention time: 6.06 min 99.4% Area at 254 and 98.5% Area at 210 nm. | Retention time: 3.44 min 98.5% Area at 254 and 98.0% Area at 210 nm. | MS (ESI+) for $C_{66}H_{95}FN_8O_{11}$ m/z 1196.0 $(M + H)^+$. |
| 8 | Retention time: 6.90 min; ca. 9% isomer at 6.72 min 98.3% Area at 254 and 98.2% Area at 210 nm. | Retention time: 5.45 min; ca. 11% isomer at 5.11 min 98.6% Area at 254 and 98.4% Area at 210 nm. | MS (ESI+) for $C_{78}H_{103}N_9O_{11}$ m/z 1343.0 $(M + H)^+$. |
| 9 | Retention time: 6.43 (54%) and 6.51 min (45%) 98.6% Area at 254 and 99.2% Area at 210 nm. | Retention time: 4.09 (56%) and 4.21 min (43%) 98.8% Area at 254 and 99.0% Area at 210 nm. | MS (ESI+) for $C_{70}H_{98}N_8O_{11}$ m/z 1228.0 $(M + H)^+$. |
| 10 | Retention time: 4.78 min 93.7% Area at 254 and 93.4% Area at 210 nm. | Retention time: 1.73 min 94.5% Area at 254 and 94.7% Area at 210 nm. | MS (ESI+) for $C_{69}H_{97}N_9O_{11}$ m/z 1229.1 $(M + H)^+$. |
| 11 | Retention time: 6.46 min 89.1% Area at 254 and 94.5% Area at 210 nm. | Retention time: 4.07 min 88.3% Area at 254 and 93.3% Area at 210 nm. | MS (ESI+) for $C_{70}H_{105}N_{11}O_{11}$ m/z 1277.2 $(M + H)^+$. |
| 12 | Retention time: 5.88 min 97.3% Area at 254 and 95.3% Area at 210 nm. | Retention time: 3.07 min 97.9% Area at 254 and 92.9% Area at 210 nm. | MS (ESI+) for $C_{68}H_{102}N_{10}O_{11}$ m/z 1236.0 $(M + H)^+$. |
| 13 | Retention time: 6.35 min 99.1% Area at 254 and 99.4% Area at 210 nm. | Retention time: 4.01 min 99.2% Area at 254 and 99.4% Area at 210 nm. | MS (ESI+) for $C_{73}H_{102}N_8O_{12}$ m/z 1284.1 $(M + H)^+$. MS (ESI+) for $C_{73}H_{102}N_8O_{12}$ m/z 1306.1 $(M + Na)^+$. |
| 14 | Retention time: 5.83 min 89.5% Area at 254 and 94.6% Area at 210 nm. | Retention time: 2.97 min 91.8% Area at 254 and 95.8% Area at 210 nm. | MS (ESI+) for $C_{68}H_{98}N_{10}O_{11}$ m/z 1232.1 $(M + H)^+$. |
| 15 | Retention time: 4.23 min 91.6% Area at 254 and 90.4% Area at 210 nm. | Retention time: 1.37 min 99.4% Area at 254 and 99.3% Area at 210 nm. | MS (ESI+) for $C_{70}H_{105}N_{11}O_{11}$ m/z 1277.2 $(M + H)^+$. MS (ESI+) for $C_{70}H_{105}N_{11}O_{11}$ m/z 1299.2 $(M + Na)^+$. |
| 16 | Retention time: 4.76 min 97.4% Area at 254 and 96.8% Area at 210 nm. | Retention time: 1.69 min 97.7% Area at 254 and 96.9% Area at 210 nm. | MS (ESI+) for $C_{68}H_{101}N_9O_{11}$ m/z 1221.2 $(M + H)^+$. MS (ESI+) for $C_{68}H_{101}N_9O_{11}$ m/z 1243.2 $(M + Na)^+$. |
| 17 | Retention time: 4.64 and 4.76 min 98.6% Area at 254 and 99.3% Area at 210 nm. | Retention time: 1.60 and 1.69 min 98.5% Area at 254 and 98.5% Area at 210 nm. | MS (ESI+) for $C_{69}H_{97}N_9O_{11}$ m/z 1229.1 $(M + H)^+$. |

TABLE 2-continued

HPLC and mass spectometry data for AbA derivatives of the present invention.

| Compound No. | HPLC | HPLC AbA (Internal Std.) | Mass Spec |
|---|---|---|---|
| 18 | Retention time: 4.66 and 4.79 min 97.1% Area at 254 and 98.6% Area at 210 nm. | Retention time: 1.64 and 1.73 min 98.0% Area at 254 and 98.3% Area at 210 nm. | MS (ESI+) for $C_{69}H_{97}N_9O_{11}$ m/z 1229.1 $(M + H)^+$. |
| 19 | Retention time: 4.739 min 98.9% Area at 254 and 99.3% Area at 210 nm. | Retention time: 1.668 min 98.9% Area at 254 and 99.2% Area at 210 nm. | MS (ESI+) for $C_{71}H_{106}N_{10}O_{11}$ m/z 1276.7 $(M + H)^+$. |
| 20 | Retention time: 4.37 min 97.2% Area at 254 and 94.4% Area at 210 nm. | Retention time: 1.43 min 98.4% Area at 254 and 95.9% Area at 210 nm. | MS (ESI+) for $C_{70}H_{105}N_{11}O_{11}$ m/z 1277.1 $(M + H)^+$. MS (ESI+) for m/z 1299.1 $(M + Na)^+$. |
| 21 | Retention time: 4.635 min 95.2% Area at 254 and 92.8% Area at 210 nm. | Retention time: 1.585 min 94.7% Area at 254 and 92.7% Area at 210 nm. | MS (ESI+) for $C_{69}H_{102}N_{10}O_{12}$ m/z 1264.1 $(M + H)^+$. |
| 22 | Retention time: 4.617 and 4.722 min 98.4% Area at 254 and 97.8% Area at 210 nm. | Retention time: 1.584 and 1.654 min 98.4% Area at 254 and 98.1% Area at 210 nm. | MS (ESI+) for $C_{67}H_{100}N_{10}O_{11}$ m/z 1222.0 $(M + H)^+$. |
| 23 | Retention time: 5.005 min 96.0% Area at 254 and 96.1% Area at 210 nm. | Retention time: 1.919 min 95.6% Area at 254 and 97.0% Area at 210 nm. | MS (ESI+) for $C_{71}H_{106}N_{10}O_{11}$ m/z 1276.2 $(M + H)^+$. |
| 24 | Retention time: 4.660 min 95.7% Area at 254 and 96.1% Area at 210 nm. | Retention time: 1.617 min 96.3% Area at 254 and 96.4% Area at 210 nm. | MS (ESI+) for $C_{69}H_{102}N_{10}O_{12}$ m/z 1264.2 $(M + H)^+$. |
| 25 | Retention time: 4.902 min 90.6% Area at 254 and 98.2% Area at 210 nm. | Retention time: 1.813 min 97.5% Area at 254 and 99.5% Area at 210 nm. | MS (ESI+) for $C_{73}H_{110}N_{10}O_{11}$ m/z 1304.3 $(M + H)^+$. |
| 26 | Retention time: 5.000 min 95.1% Area at 254 and 96.8% Area at 210 nm. | Retention time: 1.878 min 95.5% Area at 254 and 95.3% Area at 210 nm. | MS (ESI+) for $C_{74}H_{111}N_{11}O_{13}$ m/z 1363.2 $(M + H)^+$. |
| 27 | Retention time: 4.908 min 94.5% Area at 254 and 93.1% Area at 210 nm. | Retention time: 1.775 min 95.2% Area at 254 and 93.9% Area at 210 nm. | MS (ESI+) for $C_{69}H_{97}N_9O_{11}$ m/z 1229.2 $(M + H)^+$. |
| 28 | Retention time: 4.787 min 94.5% Area at 254 and 94.6% Area at 210 nm. | Retention time: 1.716 min 96.3% Area at 254 and 96.5% Area at 210 nm. | MS (ESI+) for $C_{69}H_{97}N_9O_{11}$ m/z 1229.2 $(M + H)^+$. |
| 29 | Retention time: 4.770 min 92.7% Area at 254 and 93.4% Area at 210 nm. | Retention time: 1.699 min 91.8% Area at 254 and 95.9% Area at 210 nm. | MS (ESI+) for $C_{69}H_{97}N_9O_{11}$ m/z 1229.2 $(M + H)^+$. |
| 30 | Retention time: 4.30 min 98.1% Area at 254 and 97.8% Area at 210 nm. | — | MS (ESI+) for $C_{69}H_{103}N_{11}O_{11}$ m/z 1263.3 $(M + H)^+$. |
| 31 | Retention time: 4.30 min 94.5% Area at 254 and 92.5% Area at 210 nm. | — | MS (ESI+) for $C_{82}H_{120}N_{12}O_{11}$ m/z 753.7 $(M + 2H)^{+2}$. MS (ESI−) for $C_{82}H_{120}N_{12}O_{11}$ m/z 752.3 $(M − 2H)^{−2}$. |

TABLE 2-continued

HPLC and mass spectometry data for AbA derivatives of the present invention.

| Compound No. | HPLC | HPLC AbA (Internal Std.) | Mass Spec |
|---|---|---|---|
| 32 | Retention time: 4.57 min 95.3% Area at 254 and 95.1% Area at 210 nm. | — | MS (ESI+) for $C_{71}H_{105}N_{11}O_{12}$ m/z 1305.3 $(M + H)^+$. |
| 33 | Retention time: 4.78 min 99.4% Area at 254 and 99.3% Area at 210 nm. | — | MS (ESI+) for $C_{70}H_{105}N_{11}O_{11}$ m/z 1277.3 $(M + H)^+$. |

NMR:

$^1$H NMR analysis was performed using a Bruker Avance 400 MHz instrument. All sample analyses were performed in CDCl$_3$. $^1$H NMR spectra for the synthetic products (AbA derivatives) of Examples 2-34 are provided in FIGS. 1-33.

Synthesis of Compound Nos. 1-33

Scheme 2 presents the synthetic route employed for synthesizing Compound Nos. 1-33 in Table 1.

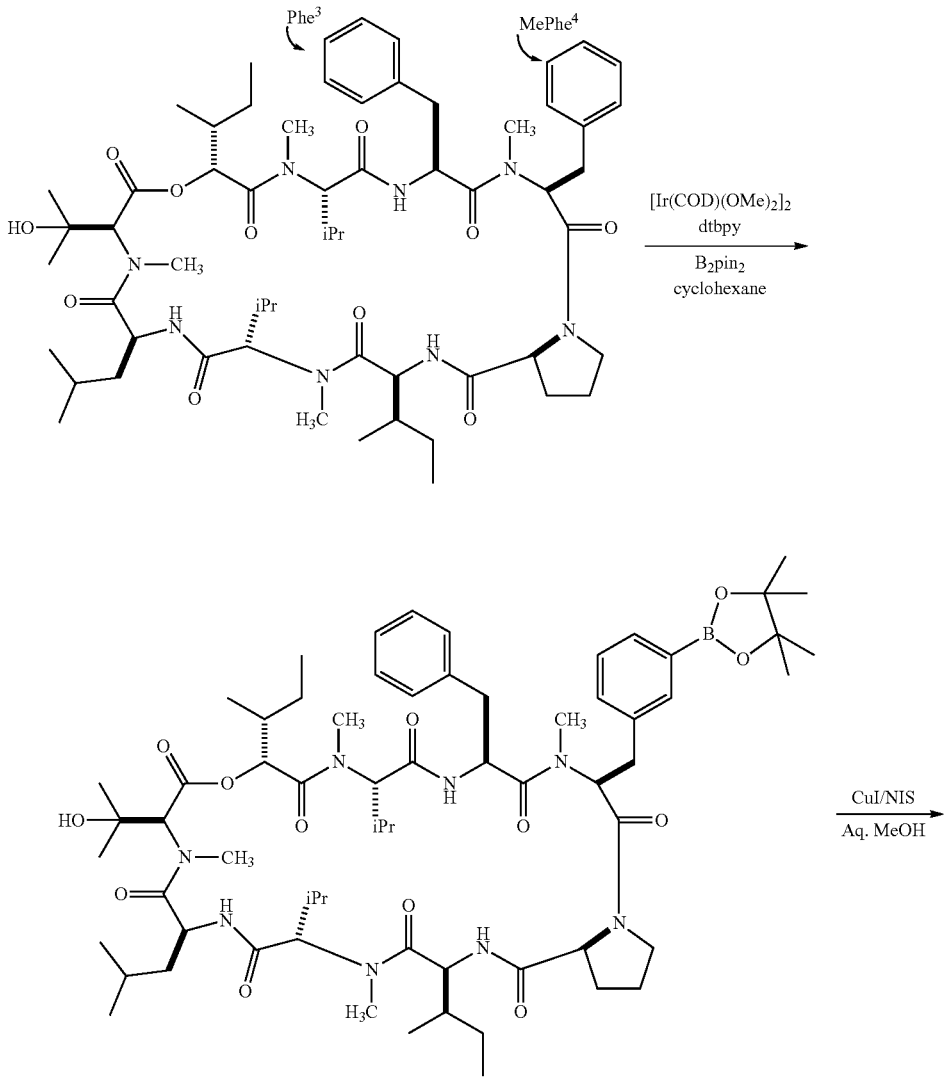

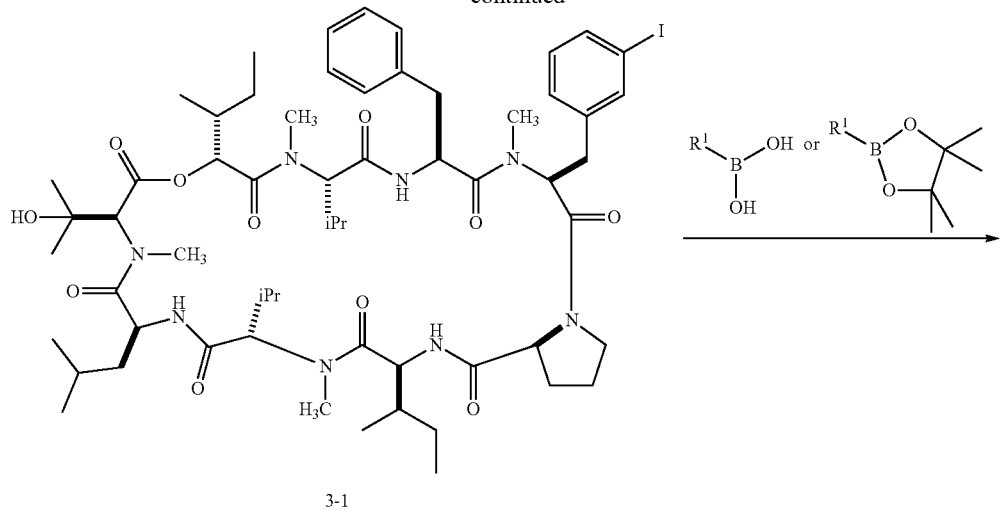

3-1

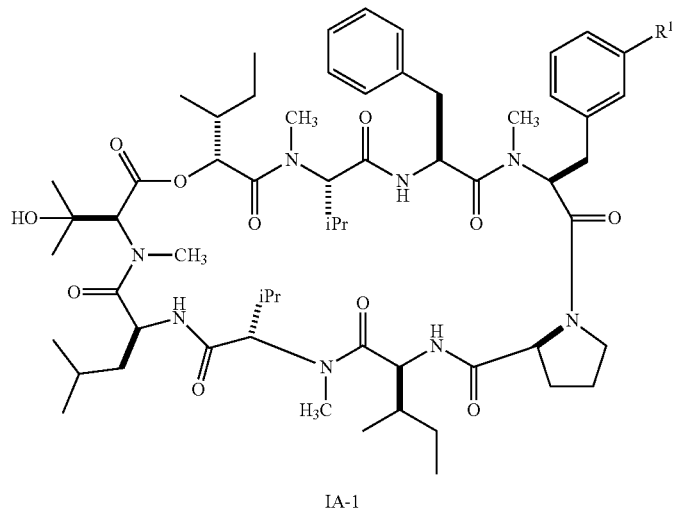

IA-1

Method A:

AbA iodide (3-1) (75 to 100 mg), tetrakis (triphenylphosphine)palladium(0) (0.2 equiv.), coupling reagent as boronic acid or pinacol ester (2 to 6 equiv.), and cesium carbonate (3 to 6 equiv.) were combined in a 10 mL Schlenk apparatus. The apparatus was evacuated and filled with dry nitrogen three times. Toluene (2 mL) and 0.6M ethanol in water (0.25 mL) were added. The resulting mixture was sparged with dry nitrogen for one minute and then heated to 80° C. with rapid stirring and the reaction was monitored by HPLC analysis. Once the reaction was complete, the mixture was cooled, and partitioned between toluene and/or ethyl acetate and water. The layers were separated, and the organic layer was washed with brine, dried with sodium sulfate, filtered through Magnesol filtration media, and the solvent was removed in vacuo. The residue was purified by reverse-phase chromatography (C18 silica gel, 95% water with 0.1% v/v TFA to 95% acetonitrile with 0.07% v/v TFA) to give the desired products.

Method B:

Method A was used, substituting [1,1'-Bis(diphenylphosphino)ferrocene]dichloropalladium(II) (1:1) for tetrakis (triphenylphosphine)palladium(0).

Method C:

Method A was used, substituting [1,1'-Bis(diphenylphosphino)ferrocene]dichloropalladium(II) (1:1) for tetrakis (triphenylphosphine)palladium(0), potassium carbonate for cesium carbonate, and 1,4-dioxane with 10% water was substituted for the toluene and aqueous ethanol.

Example 2: Compound No. 1
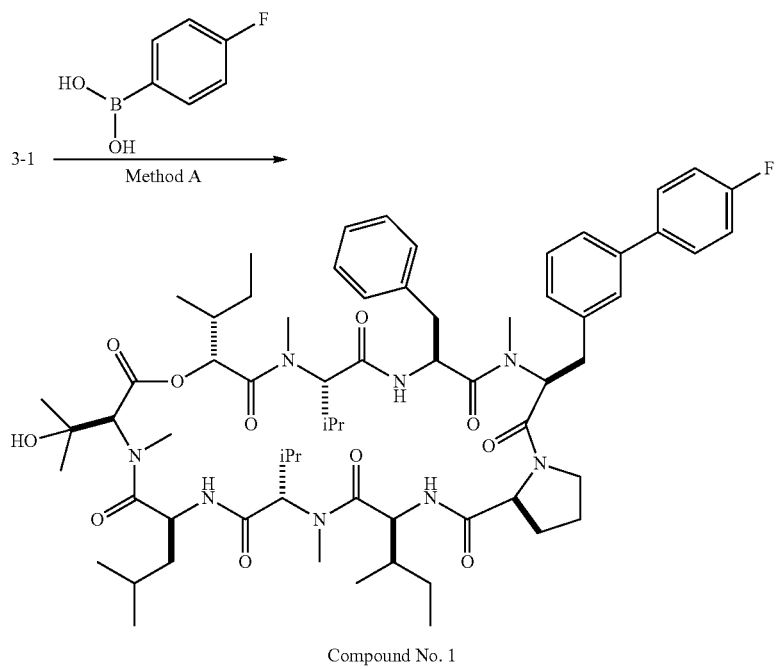
Compound No. 1
Using Method A, compound 3-1 (101 mg) was coupled with 4-fluorophenylboronic acid (3.6 equiv.) using tetrakis(triphenylphosphine)palladium(0) (15% mol), cesium carbonate (3.0 equiv.), toluene (2 mL), and 0.6 M ethanol in water (0.3 mL) to give Compound No. 1.
Example 3: Compound No. 2
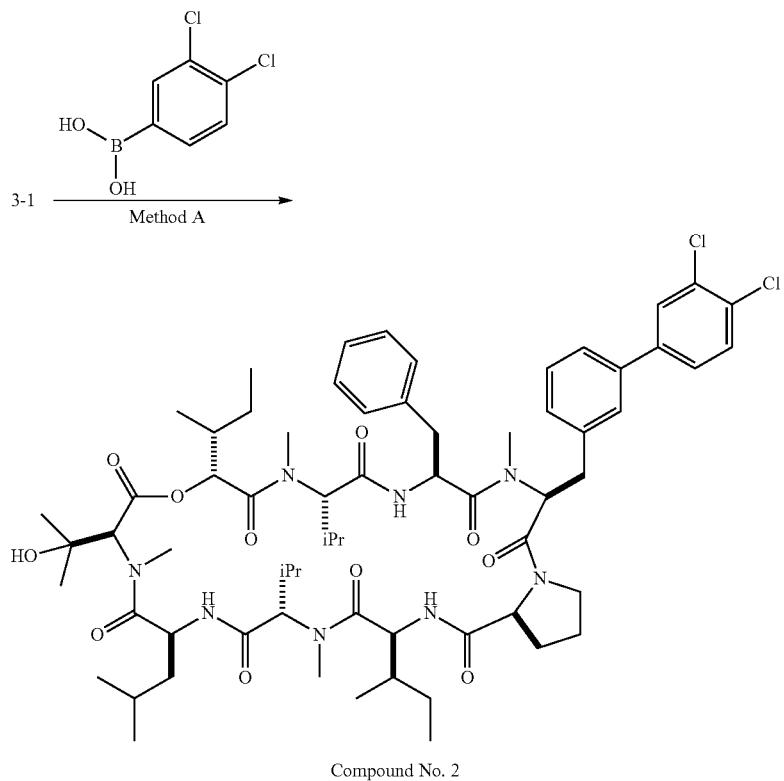
Compound No. 2

Using Method A, compound 3-1 (79 mg) was coupled with 3,4-dichlorophenylboronic acid (3.5 equiv.) using tetrakis (triphenylphosphine)palladium(0) (14% mol), cesium carbonate (3.0 equiv.), toluene (2 mL), and 0.6M ethanol in water (0.3 mL) to give Compound No. 2 in 45% yield.

Example 4: Compound No. 3

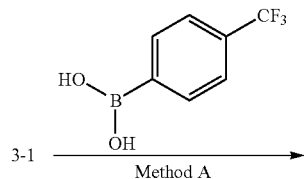

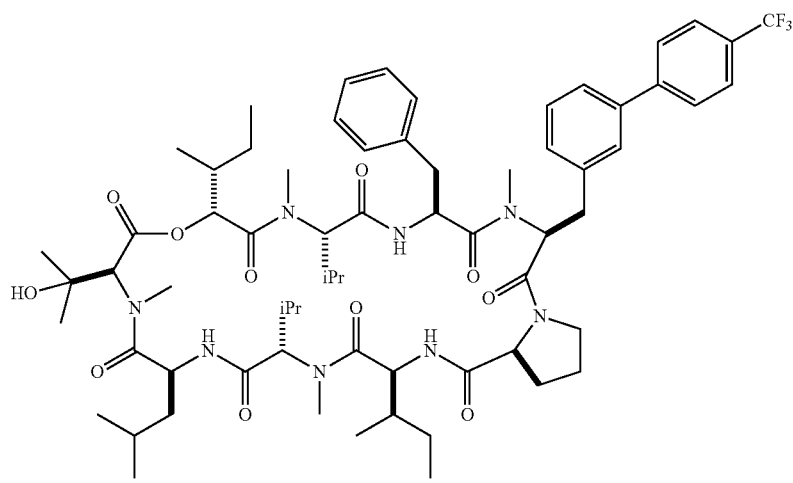

Compound No. 3

Using Method A, compound 3-1 (79 mg) was coupled with 4-trifluoromethylphenylboronic acid (3.7 equiv.) using tetrakis (triphenylphosphine)palladium(0) (16% mol), cesium carbonate (3.0 equiv.), toluene (2 mL), and 0.6M ethanol in water (0.3 mL) to give Compound No. 3 in 44% yield.

Example 5: Compound No. 4

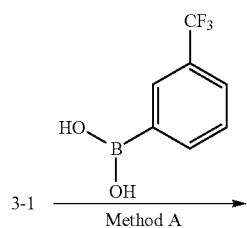

-continued

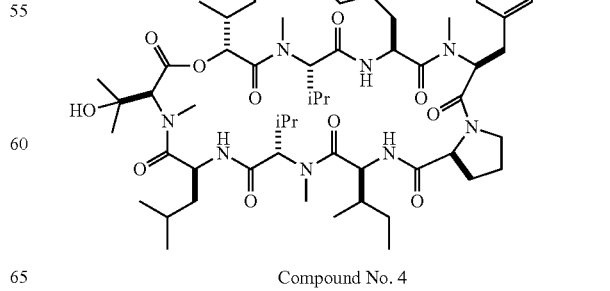

Compound No. 4

Using Method A, compound 3-1 (76 mg) was coupled with 3-(trifluoromethyl)phenylboronic acid (3.7 equiv.) using tetrakis (triphenylphosphine)palladium(0) (18% mol), cesium carbonate (3.0 equiv.), toluene (2 mL), and 0.6M ethanol in water (0.3 mL) to give Compound No. 4 in 24% yield.

Example 6: Compound No. 5

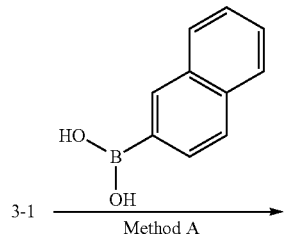

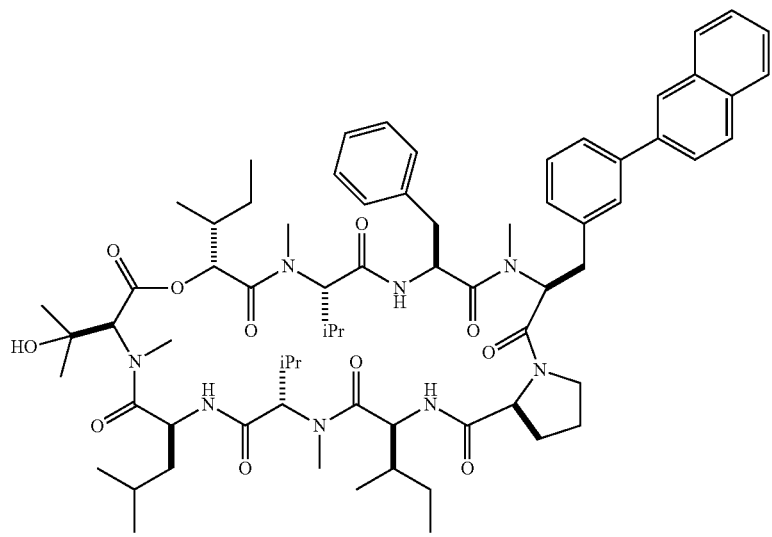

Compound No. 5

Using Method A, compound 3-1 (77 mg) was coupled with 2-naphthylboronic acid (3.5 equiv.) using tetrakis (triphenylphosphine)palladium(0) (17% mol), cesium carbonate (3.0 equiv.), toluene (2 mL), and 0.6M ethanol in water (0.3 mL) to give Compound No. 5 in 61% yield.

Example 7: Compound No. 6

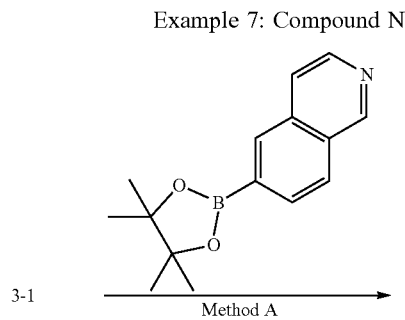

-continued

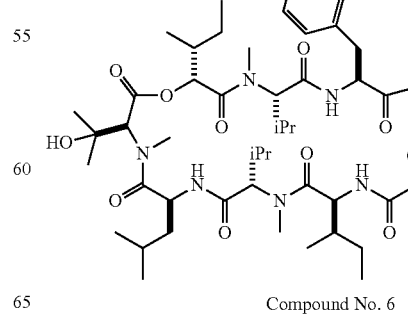

Compound No. 6

Using Method A, compound 3-1 (101 mg) was coupled with 6-isoquinolineboronic acid pinacol ester (4 equiv.) using tetrakis (triphenylphosphine)palladium(0) (18% mol), cesium carbonate (4 equiv.), toluene (2 mL), and 0.6M ethanol in water (0.3 mL) to give Compound No. 6 in 32% yield.

Example 8: Compound No. 7

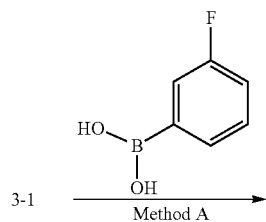

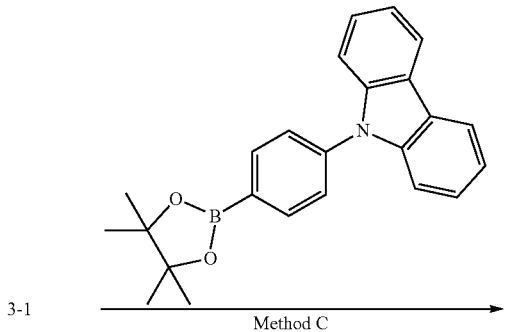

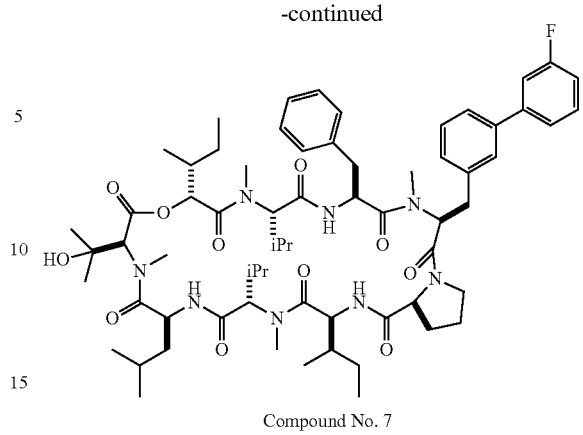

Compound No. 7

Using Method A, compound 3-1 (77 mg) was coupled with 3-fluorophenylboronic acid (4.1 equiv.) using tetrakis (triphenylphosphine)palladium(0) (14% mol), cesium carbonate (6.0 equiv.), toluene (2 mL), and 0.6M ethanol in water (0.3 mL) to give Compound No. 7 in 59% yield.

Example 9: Compound No. 8

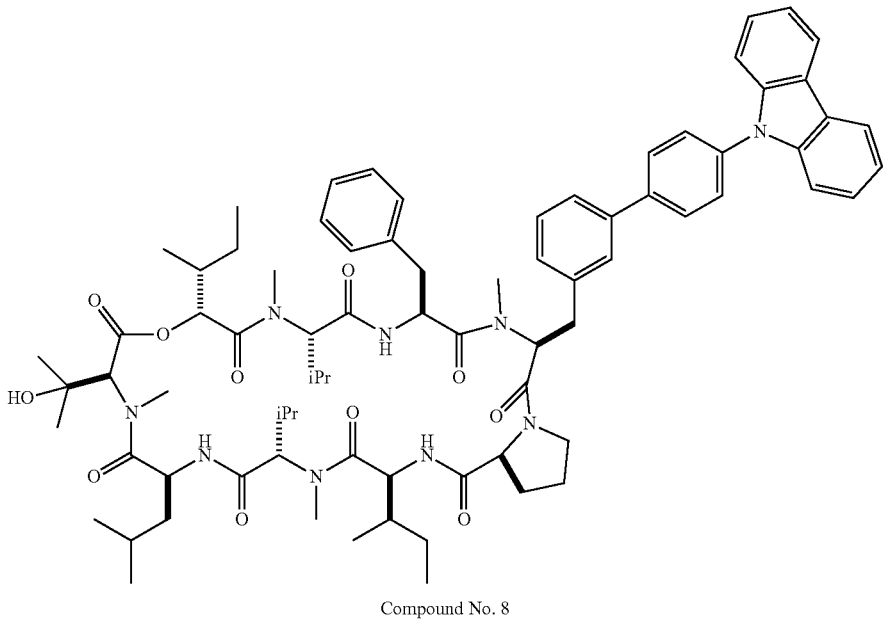

Compound No. 8

Using Method C, compound 3-1 (108 mg) was coupled with 4-(9H-carbazole)phenylboronic acid pinacol ester (4 equiv.) using [1,1′-bis(diphenylphosphino)ferrocene]dichloropalladium(II) (1:1) (13% mol), potassium carbonate (3 equiv.), and 1,4-dioxane with 10% water (1.3 mL) to give Compound No. 8 in 64% yield.

Example 10: Compound No. 9

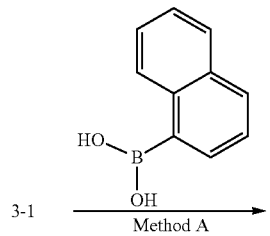

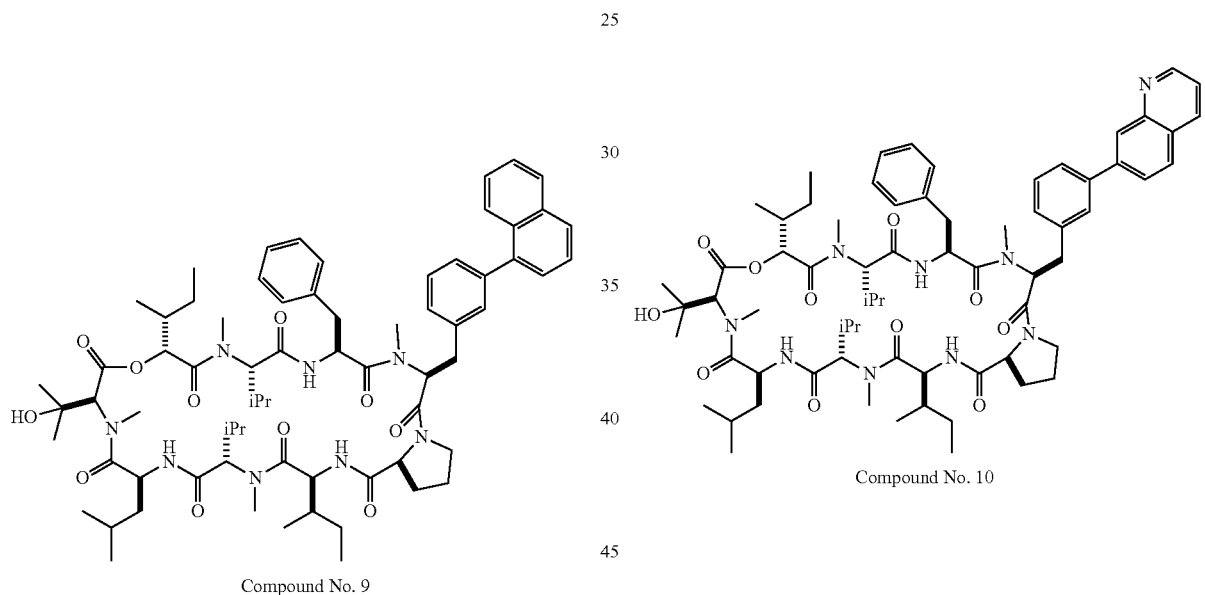

Compound No. 9

Using Method A, compound 3-1 (78 mg) was coupled with 1-naphthylboronic acid (4 equiv.) using tetrakis (triphenylphosphine)palladium(0) (19% mol), cesium carbonate (3.0 equiv.), toluene (2 mL), and 0.6M ethanol in water (0.3 mL) to give Compound No. 9 in 26% yield.

Example 11: Compound No. 10

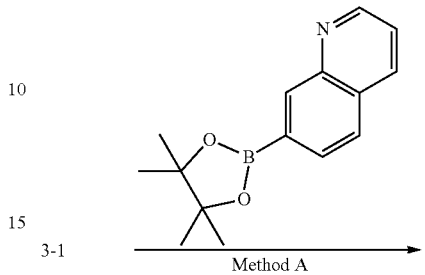

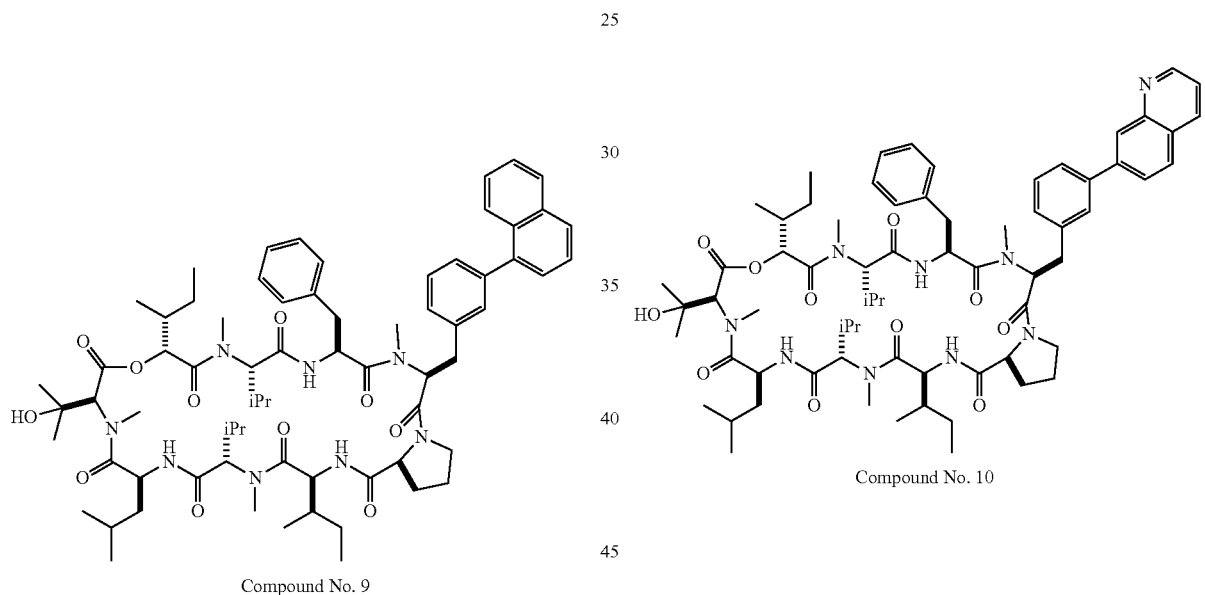

Compound No. 10

Using Method A, compound 3-1 (83 mg) was coupled with 7-quinolineboronic acid pinacol ester (5 equiv.) using tetrakis (triphenylphosphine)palladium(0) (19% mol), cesium carbonate (4 equiv.), toluene (2 mL), and 0.6M ethanol in water (0.3 mL) to give Compound No. 10 in 39% yield.

Example 12: Compound No. 11

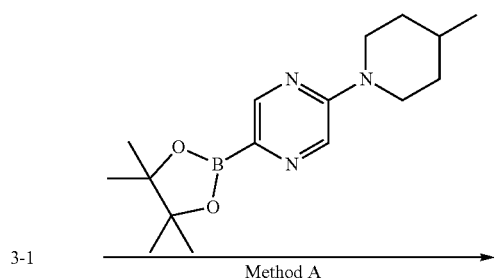

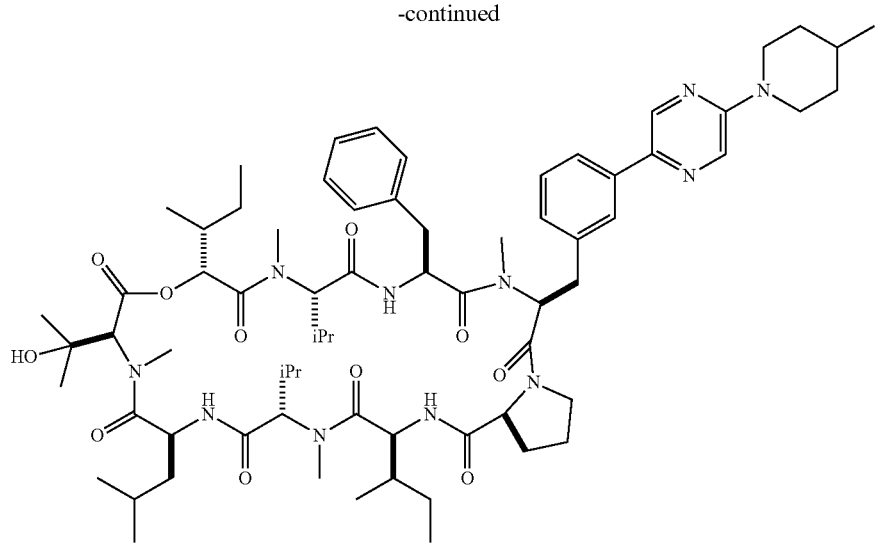

Compound No. 11

Using Method A, compound 3-1 (81 mg) was coupled with 2-(4-methylpiperidin-1-yl)pyrazineboronic acid pinacol ester (4 equiv.) using tetrakis (triphenylphosphine)palladium(0) (13% mol), cesium carbonate (4 equiv.), toluene (2 mL), and 0.6M ethanol in water (0.3 mL) to give Compound No. 11 in 58% yield.

Example 13: Compound No. 12

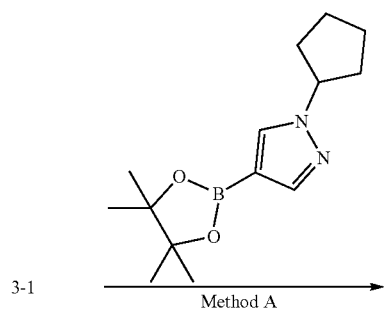

3-1 →  Method A

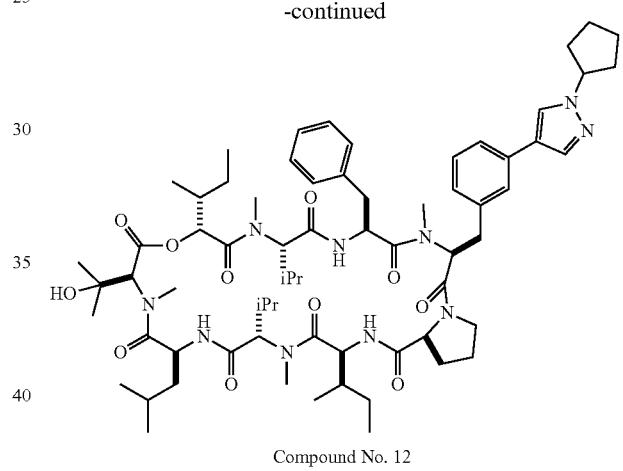

Compound No. 12

Using Method A, compound 3-1 (81 mg) was coupled with 4-(1-cyclopentyl)pyrazoleboronic acid pinacol ester (5 equiv.) using tetrakis (triphenylphosphine)palladium(0) (13% mol), cesium carbonate (4 equiv.), toluene (2 mL), and 0.6M ethanol in water (0.3 mL) to give Compound No. 12 in 57% yield.

Example 14: Compound No. 13

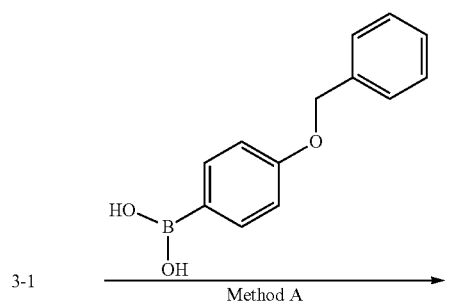

3-1 →  Method A

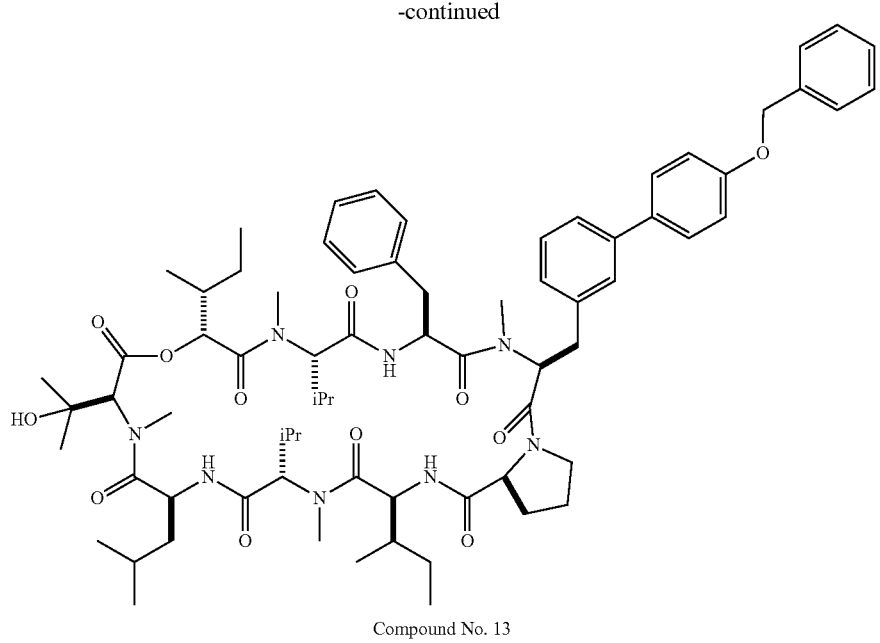

Compound No. 13

Using Method A, compound 3-1 (77 mg) was coupled with [4-(benzyloxy)phenyl]boronic acid (4 equiv.) using tetrakis (triphenylphosphine)palladium(0) (14% mol), cesium carbonate (3 equiv.), toluene (1.5 mL), and 0.6M ethanol in water (0.25 mL) to give Compound No. 13 in 78% yield.

Example 15: Compound No. 14

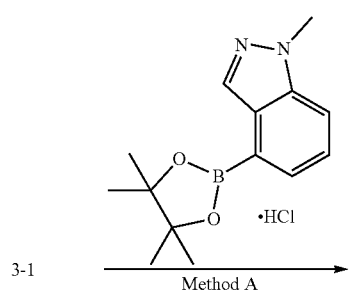

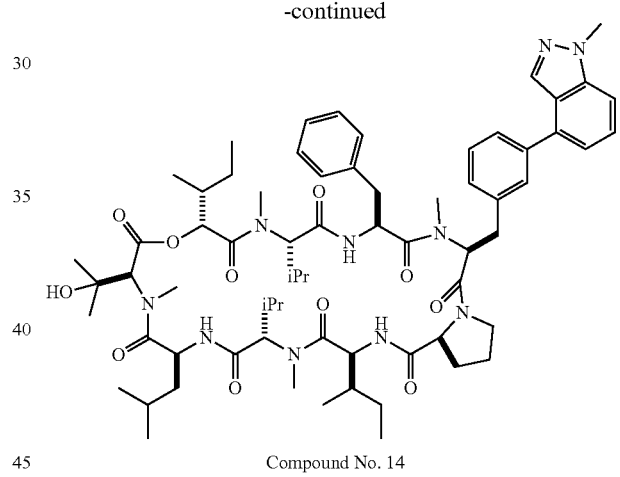

Compound No. 14

Using Method A, compound 3-1 (77 mg) was coupled with 4-(1-methyl-1H-indazole) hydrochloride boronic acid pinacol ester (4 equiv.) using tetrakis (triphenylphosphine) palladium(0) (14% mol), cesium carbonate (6 equiv.), toluene (2 mL), and 0.6M ethanol in water (0.3 mL) to give Compound No. 14 in 38% yield.

Example 16: Compound No. 15

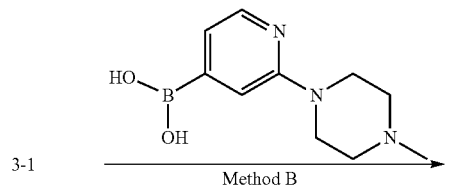

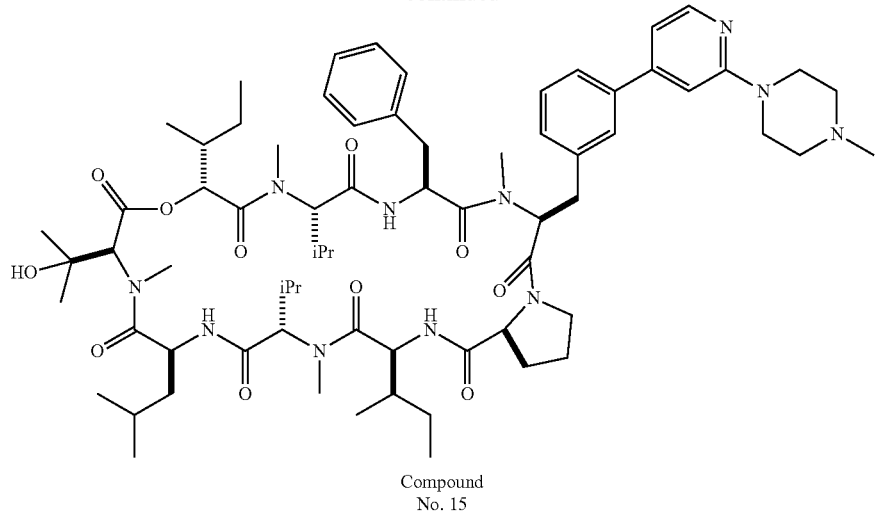

Compound No. 15

Using Method B, compound 3-1 (97.1 mg) was coupled with [2-(4-methylpiperazin-1-yl-pyridin-4-yl]boronic acid (4.6 equiv.) using Pd(dppf)Cl$_2$.CH$_2$Cl$_2$ (21% mol), cesium carbonate (5.5 equiv.), toluene (2.0 mL), and 0.6M ethanol in water (0.323 mL) to give Compound No. 15 in 31% yield.

Example 17: Compound No. 16

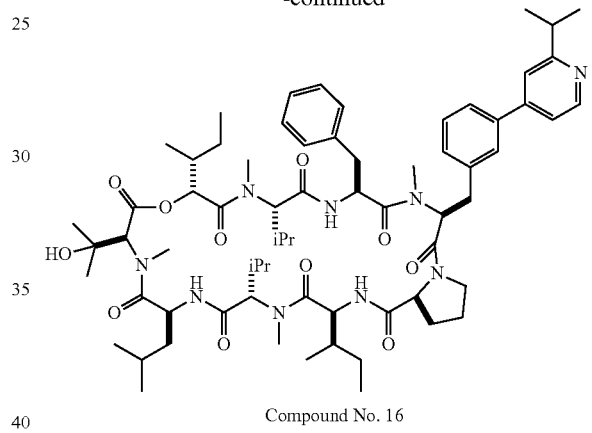

Compound No. 16

Using Method A, compound 3-1 (78 mg) was coupled with 4-(2-isopropyl)pyridineboronic acid pinacol ester (6 equiv.) using tetrakis (triphenylphosphine)palladium(0) (17% mol), cesium carbonate (4 equiv.), toluene (2 mL), and 0.6M ethanol in water (0.3 mL) to give Compound No. 16 in 39% yield.

Example 18: Compound No. 17

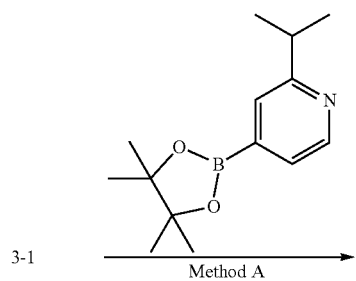

3-1 Method A

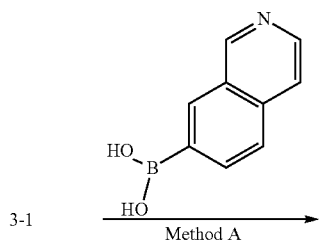

3-1 Method A

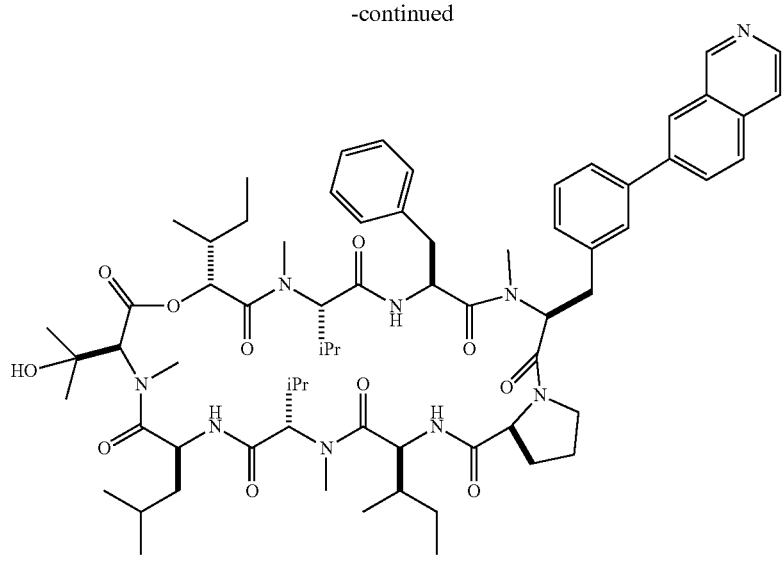

Compound No. 17

Using Method A, compound 3-1 (82 mg) was coupled with 7-isoquinolineboronic acid (4.5 equiv.) using tetrakis(triphenylphosphine)palladium(0) (17% mol), cesium carbonate (4.5 equiv.), toluene (2 mL), and 0.6M ethanol in water (0.3 mL) to give Compound No. 17 in 35% yield.

Example 19: Compound No. 18

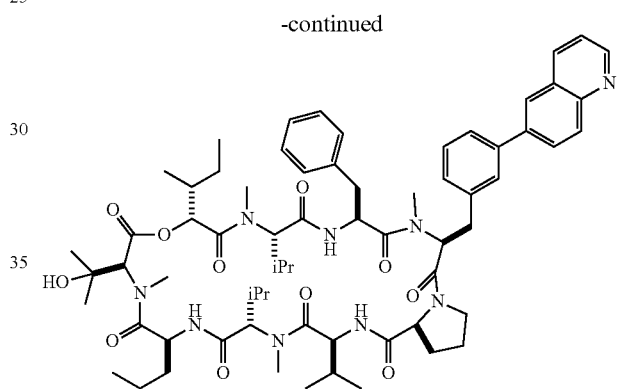

Compound No. 18

Using Method A, compound 3-1 (82 mg) was coupled with 6-quinolineboronic acid (4.5 equiv.) using tetrakis(triphenylphosphine)palladium(0) (16% mol), cesium carbonate (4.5 equiv.), toluene (2 mL), and 0.6M ethanol in water (0.3 mL) to give Compound No. 18 in 38% yield.

Example 20: Compound No. 19

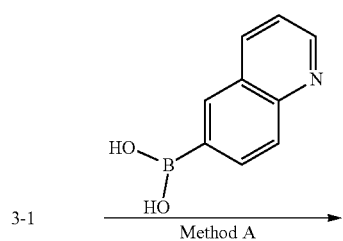

3-1 → Method A

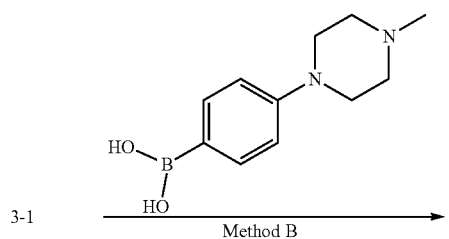

3-1 → Method B

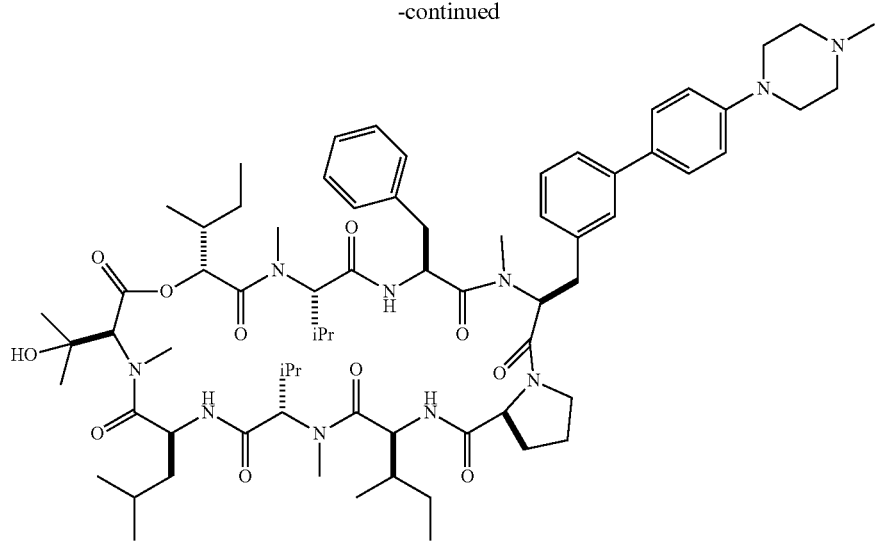
Compound No. 19
Using Method B, compound 3-1 (97 mg) was coupled with 4-(4-methylpiperizin-1-yl)phenylboronic acid (4 equiv.) using [1,1'-Bis(diphenylphosphino)ferrocene]dichloropalladium(II) (1:1) (22% mol), cesium carbonate (5 equiv.), toluene (2 mL), and 0.6M ethanol in water (0.3 mL) to give Compound No. 19 in 46% yield.
Example 21: Compound No. 20
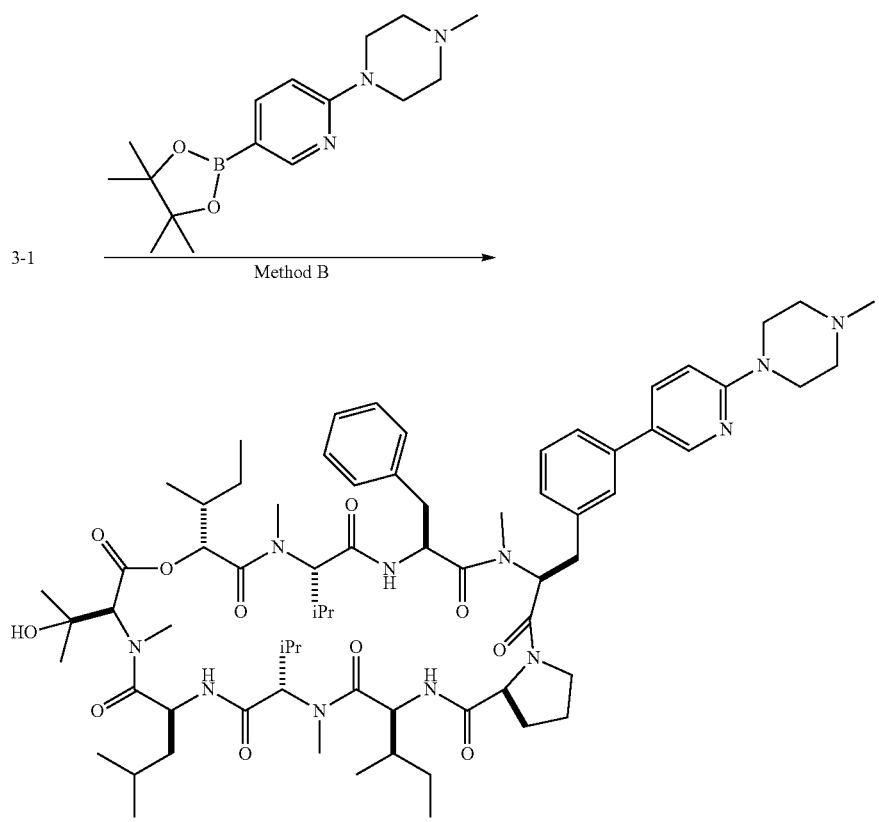
Compound No. 20

Using Method B, compound 3-1 (104 mg) was coupled with 5-[2-(4-methylpiperazin-1-yl)]pyridineboronic acid pinacol ester (4 equiv.) using [1,1'-Bis(diphenylphosphino)ferrocene] dichloropalladium(II) (1:1) (17% mol), cesium carbonate (5 equiv.), toluene (2 mL), and 0.6M ethanol in water (0.3 mL) to give Compound No. 20 in 31% yield.

Example 22: Compound No. 21

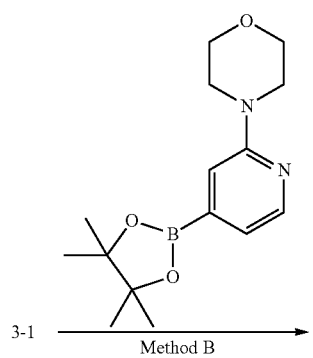

equiv.) using [1,1'-Bis(diphenylphosphino)ferrocene] dichloropalladium(II) (1:1) (17% mol), cesium carbonate (5 equiv.), toluene (2 mL), and 0.6M ethanol in water (0.3 mL) to give Compound No. 21 in 47% yield.

Example 23: Compound No. 22

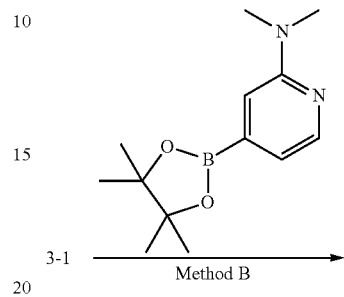

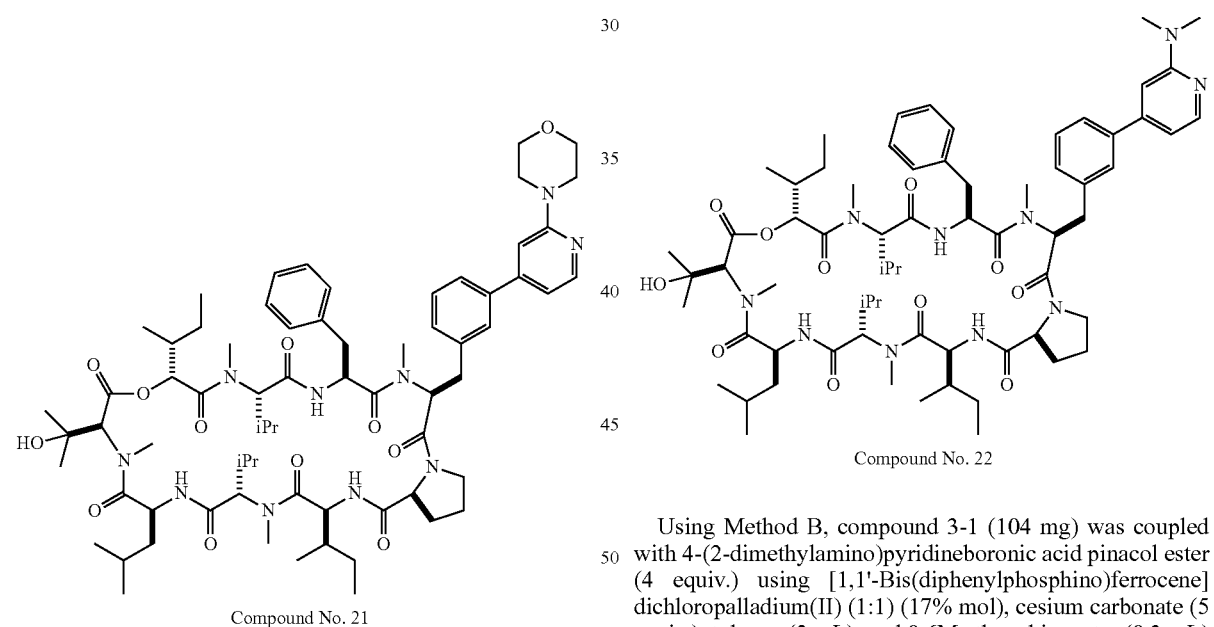

Compound No. 21

Compound No. 22

Using Method B, compound 3-1 (104 mg) was coupled with 4-(2-morpholino)pyridineboronic acid pinacol ester (4

Using Method B, compound 3-1 (104 mg) was coupled with 4-(2-dimethylamino)pyridineboronic acid pinacol ester (4 equiv.) using [1,1'-Bis(diphenylphosphino)ferrocene] dichloropalladium(II) (1:1) (17% mol), cesium carbonate (5 equiv.), toluene (2 mL), and 0.6M ethanol in water (0.3 mL) to give Compound No. 22 in 74% yield.

Example 24: Compound No. 23

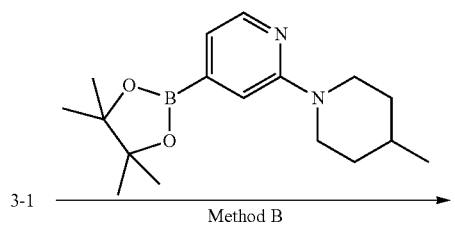

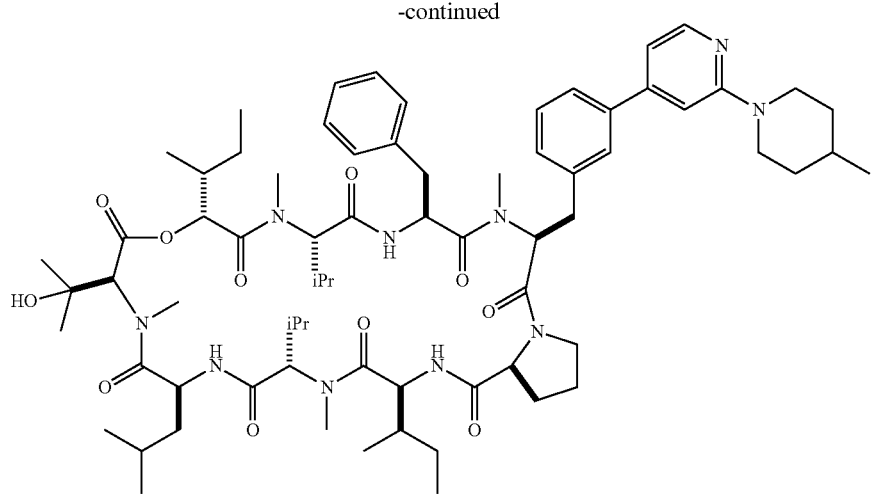
Compound No. 23
Using Method B, compound 3-1 (104 mg) was coupled with 4-[2-(4-methylpiperidin-1-yl)]-pyridine boronic acid pinacol ester (4.0 equiv.) using Pd(dppf)Cl$_2$.CH$_2$Cl$_2$ (17% mol), cesium carbonate (5.0 equiv.), toluene (2 mL), and 0.6M ethanol in water (0.31 mL) to give Compound No. 23 in 53% yield.
Example 25: Compound No. 24
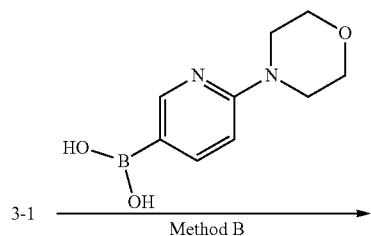
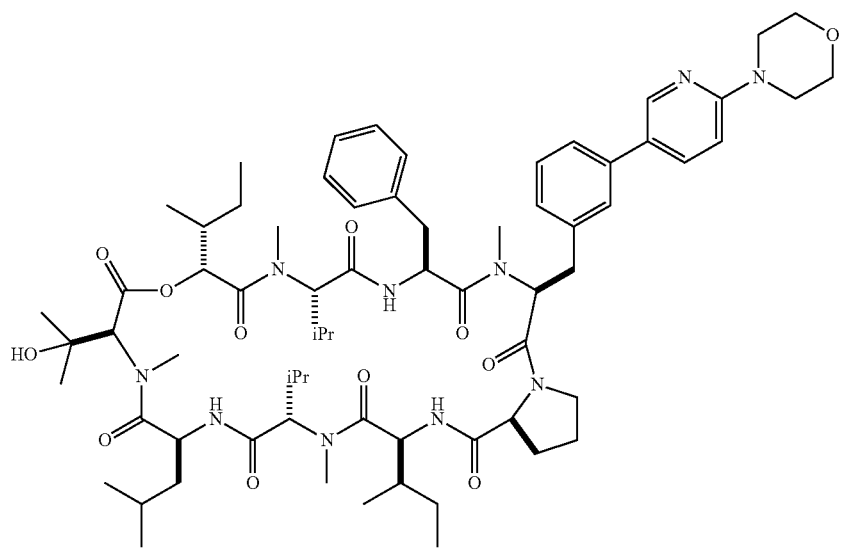
Compound No. 24

Using Method B, compound 3-1 (104 mg) was coupled with 5-(2-morpholino)pyridylboronic acid (4.0 equiv.) using Pd(dppf)Cl$_2$.CH$_2$Cl$_2$ (17% mol), cesium carbonate (5.0 equiv.), toluene (2 mL), and 0.6M ethanol in water (0.31 mL) to give Compound No. 24 in 45% yield.

Example 26: Compound No. 25

Using Method B, compound 3-1 (104 mg) was coupled with 4-(4-isopropylpiperizinyl)phenylboronic acid pinacol ester (4.0 equiv.) using Pd(dppf)Cl$_2$.CH$_2$Cl$_2$ (17% mol), cesium carbonate (5.0 equiv.), toluene (2 mL), and 0.6M ethanol in water (0.31 mL) to give Compound No. 25 in 28% yield.

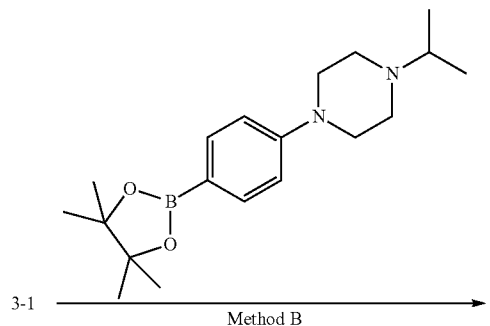

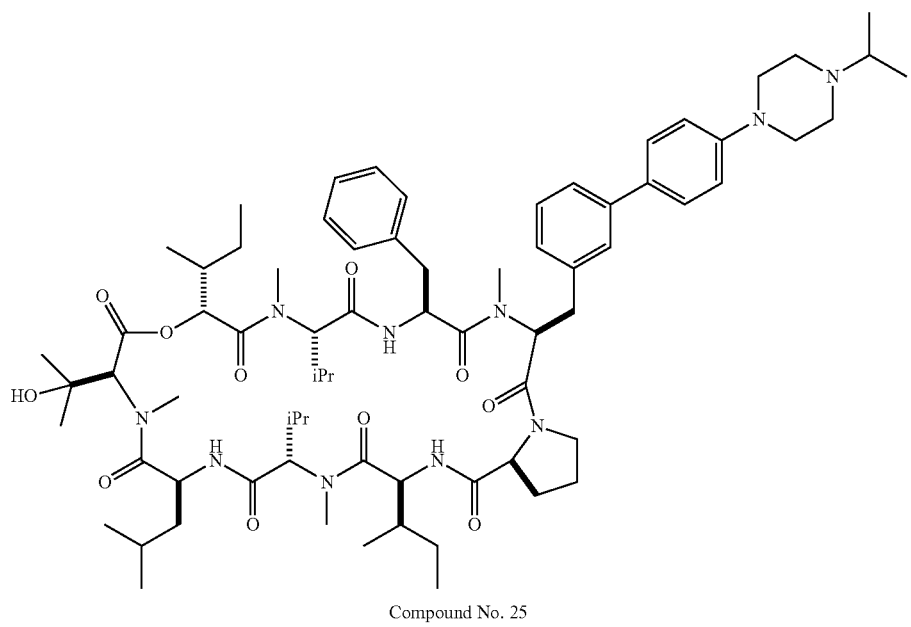

Compound No. 25

Example 27: Compound No. 26

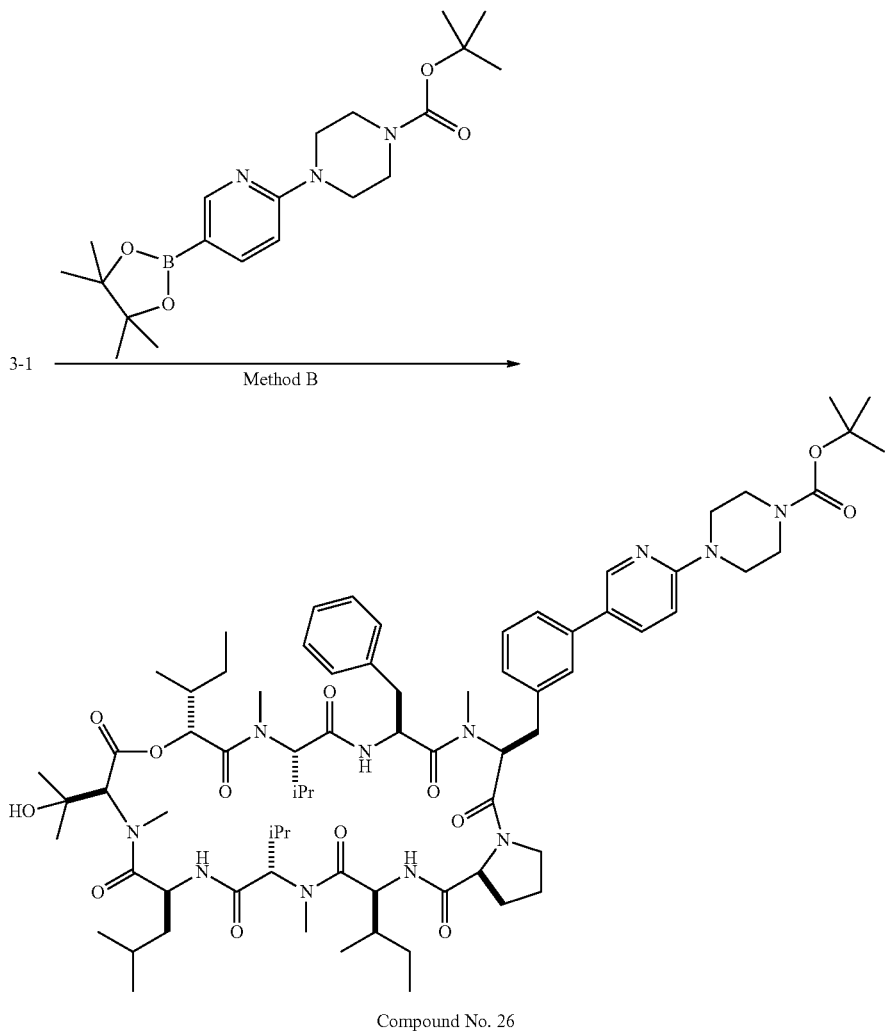

Compound No. 26

Using Method B, compound 3-1 (104 mg) was coupled with 5-[2-(4-Boc-piperizin-1yl)]pyridine boronic acid (4.0 equiv.) using Pd(dppf)Cl$_2$.CH$_2$Cl$_2$ (17% mol), cesium carbonate (5.0 equiv.), toluene (2 mL), and 0.6M ethanol in water (0.31 mL) to give Compound No. 26 in 41% yield.

Example 28: Compound No. 27

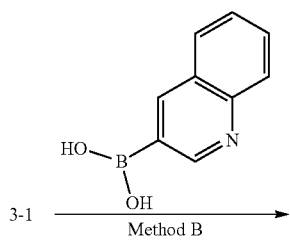

-continued

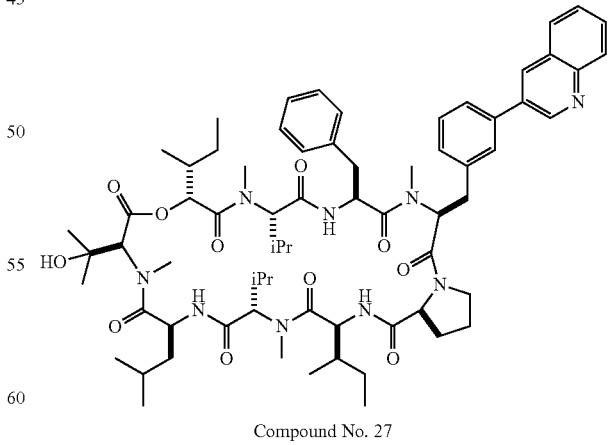

Compound No. 27

Using Method B, compound 3-1 (85 mg) was coupled with 3-quinoline boronic acid (4.5 equiv.) using Pd(dppf)Cl$_2$.CH$_2$Cl$_2$ (21% mol), cesium carbonate (4.0 equiv.), toluene (1.5 mL), and 0.6M ethanol in water (0.25 mL) to give Compound No. 27 in 55% yield.

Example 29: Compound No. 28

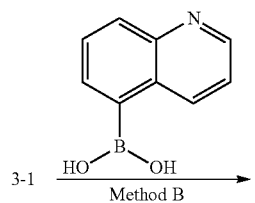

3-1 —Method B→

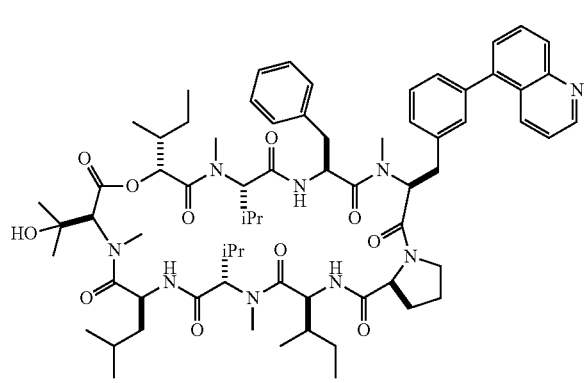

Compound No. 28

Using Method B, compound 3-1 (83 mg) was coupled with 5-quinoline boronic acid (4.5 equiv.) using Pd(dppf)Cl$_2$.CH$_2$Cl$_2$ (22% mol), cesium carbonate (4.5 equiv.), toluene (1.5 mL), and 0.6M ethanol in water (0.25 mL) to give Compound No. 28 in 53% yield.

Example 30: Compound No. 29

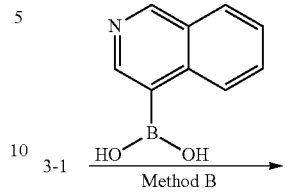

3-1 —Method B→

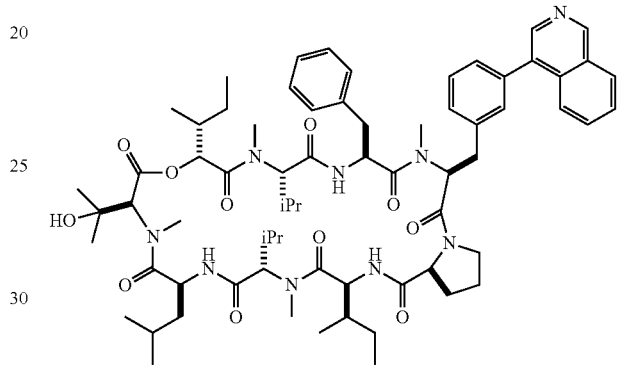

Compound No. 29

Using Method B, compound 3-1 (82 mg) was coupled with 4-isoquinoline boronic acid (5.0 equiv.) using Pd(dppf)Cl$_2$.CH$_2$Cl$_2$ (25% mol), cesium carbonate (4.7 equiv.), toluene (1.5 mL), and 0.6M ethanol in water (0.25 mL) to give Compound No. 29 in 63% yield.

Example 31: Compound No. 30

Compound No. 26 —TFA/CH$_2$Cl$_2$→

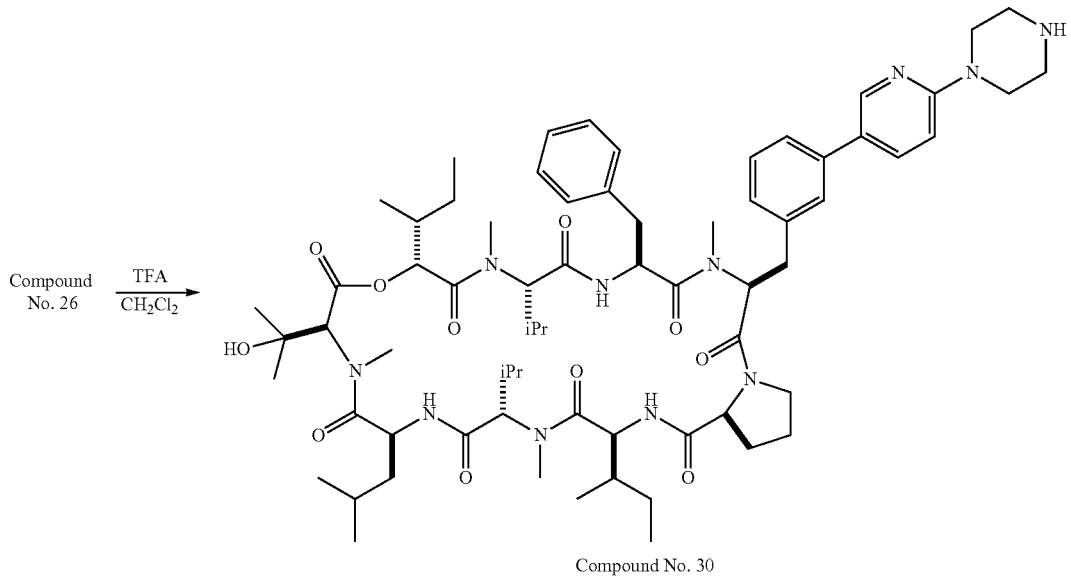

Compound No. 30

Compound No. 26 (163.7 mg) was dissolved in dichloromethane (2.0 mL), and trifluoroacetic acid (0.40 mL) was added. The reaction was lightly capped, stirred, and monitored by HPLC. When the reaction was complete, the reaction mixture was poured onto 2 mL saturated sodium bicarbonate, and 2 mL ethyl acetate was added. The layers were separated, and the aqueous layer was extracted with ethyl acetate (2×10 mL). The organics were combined, washed with brine, dried over magnesium sulfate, filtered and concentrated in vacuo to provide Compound No. 30 (78%).

Example 32: Compound No. 31

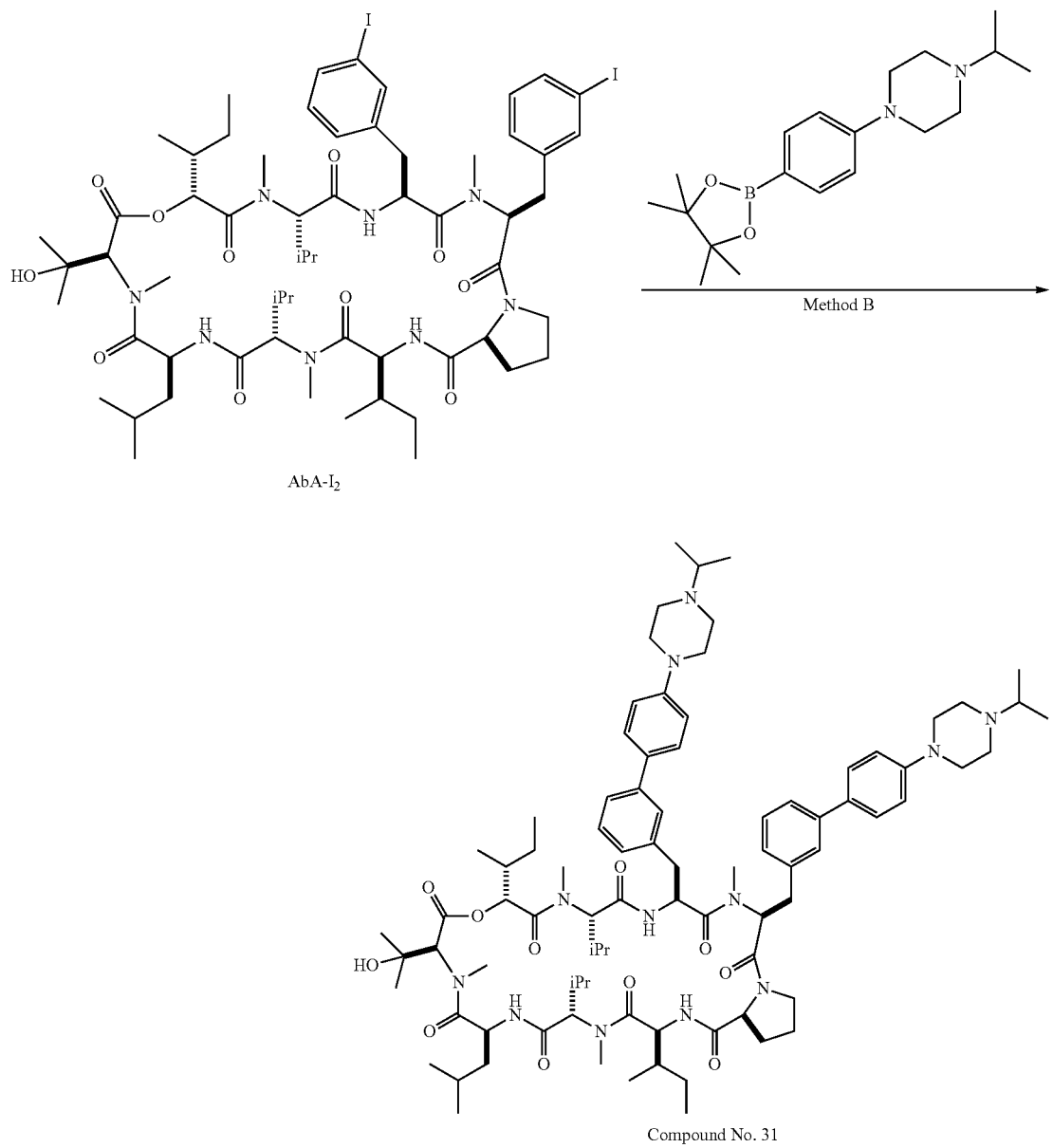

Using Method B, ABA-I$_2$ (117 mg) was coupled with 4-(4-isopropylpiperizinyl)phenylboronic acid (5.4 equiv.) using Pd(dppf)Cl$_2$.CH$_2$Cl$_2$ (13% mol), cesium carbonate (4.7 equiv.), toluene (2.0 mL), and 0.6M ethanol in water (0.33 mL) to give Compound No. 31 in 8% yield.

Example 33: Compound No. 32

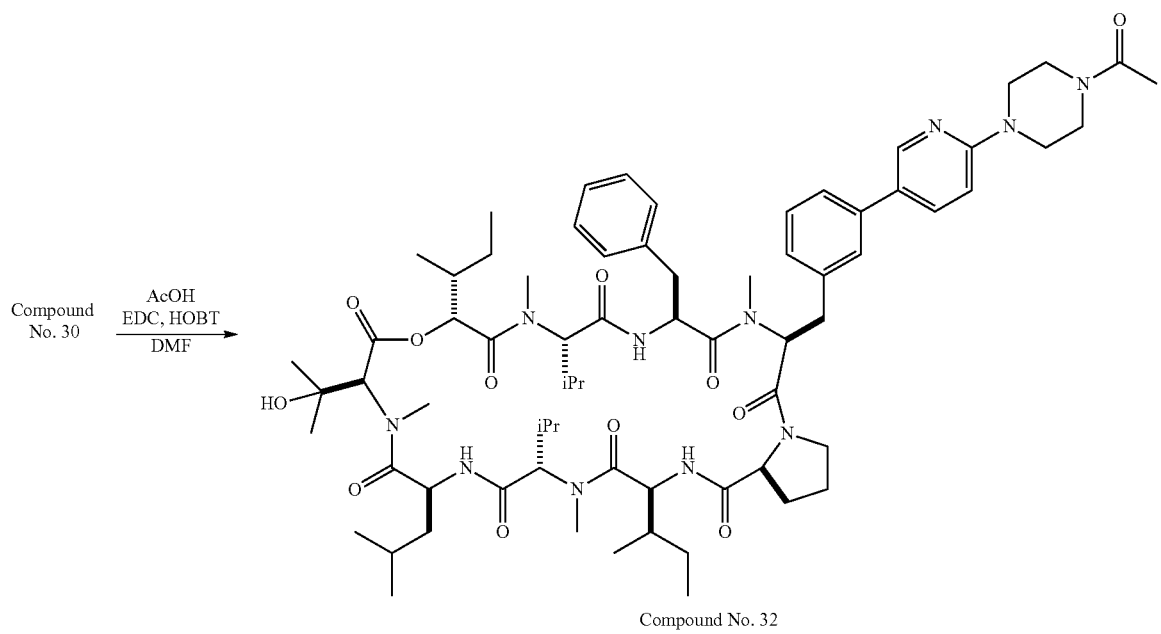

Compound No. 32

Compound No. 30 (93.9 mg), EDC (1.16 equiv.), and HOBT.H$_2$O (1.21 equiv.) were dissolved in N,N-dimethylformamide (1.0 mL) with sonication. Acetic acid (1.2 equiv) was added, and the clear, light yellow solution was stirred at room temperature for ca. 3.5 h. Another portion of acetic acid (6.0 equiv), HOBT.H$_2$O (4.83 equiv), and EDC (5.0 equiv) was added, and the reaction was monitored by HPLC. Once complete, the reaction was concentrated, and chromatographed (Reverse-phase chromatography, 40-100% ACN (0.07% v/v TFA) in water (0.1% v/v TFA)). Like fractions were combined, basified with aq. sodium bicarbonate, and extracted with ethyl acetate. The combined organics were dried over magnesium sulfate, filtered, and concentrated in vacuo to give Compound No. 32 in 92% yield.

Example 34: Compound No. 33

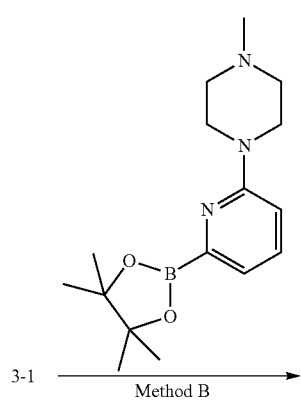

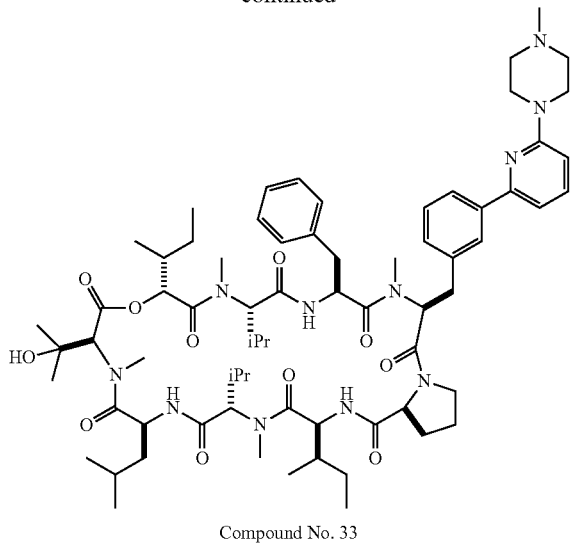

Compound No. 33

Using Method B, compound 3-1 (103 mg) was coupled with 6-[2-(4-methylpiperizin-1-yl)]-pyridine boronic acid pinacol ester (4.0 equiv.) using Pd(dppf)Cl$_2$.CH$_2$Cl$_2$ (11% mol), cesium carbonate (5.0 equiv.), toluene (2.0 mL), and 0.6M ethanol in water (0.33 mL) to give Compound No. 33 in 23% yield.

Example 35: Antifungal Activity of AbA Derivatives

The products from the chemical syntheses described in Examples 2-34 were assayed for antibiotic activity against several strains of fungi, without further purification or separation of positional isomers, using an in vitro assay that employed amphotericin B as a negative control without further purification or separation of positional isomers using the methods described below.

Materials and Methods

Test Compounds

Aureobasidin and test compounds (i.e., AbA derivatives of the present invention) were received from Kalexsyn, Inc. (Kalamazoo, Mich.) as powder and were stored at 4° C. until the day of assay. Negative control amphotericin was obtained from Sigma Aldrich and stored under like conditions. The test compound concentration range in the minimum inhibitory concentration (MIC) assay was 0.002-64 µg/mL as shown in Table 3. Ethanol (95%) was used as a solvent and diluent for all AbA compounds. Amphotericin B was tested from 0.06-64 µg/mL. Amphotericin B (Sigma Aldrich; St. Louis, Mo.; Cat No. A9528-100MG, Lot No. 120M4087) was dissolved and diluted with dimethylsulfoxide (DMSO; Sigma Aldrich; St. Louis, Mo.; Cat No. 472301 Lot No. SHBD2072V).

The solvents were added to the test agents and the stock solutions stood for approximately 1 hr at room temperature prior to use to auto sterilize. Stock solutions were prepared at 40× the desired top concentration in the test plate.

TABLE 3

Test compound concentration range used in MIC assay.

| Test/Control Agents | Solvent/Diluent | Conc. Of Stock Solution (µg/mL) | Test Range (µg/mL) |
| --- | --- | --- | --- |
| Compound 1 | 95% EtOH | 2560 | 0.002-64 |
| Compound 2 | 95% EtOH | 2560 | 0.002-64 |
| Compound 3 | 95% EtOH | 2560 | 0.002-64 |
| Compound 4 | 95% EtOH | 2560 | 0.002-64 |
| Compound 5 | 95% EtOH | 2560 | 0.002-64 |
| Compound 6 | 95% EtOH | 2560 | 0.002-64 |
| Compound 7 | 95% EtOH | 2560 | 0.002-64 |
| Compound 8 | 95% EtOH | 2560 | 0.002-64 |
| Compound 9 | 95% EtOH | 2560 | 0.002-64 |
| Compound 10 | 95% EtOH | 2560 | 0.002-64 |
| Compound 11 | 95% EtOH | 2560 | 0.002-64 |
| Compound 12 | 95% EtOH | 2560 | 0.002-64 |
| Compound 13 | 95% EtOH | 2560 | 0.002-64 |
| Compound 14 | 95% EtOH | 2560 | 0.002-64 |
| Compound 15 | 95% EtOH | 2560 | 0.002-64 |
| Compound 16 | 95% EtOH | 2560 | 0.002-64 |
| Compound 17 | 95% EtOH | 2560 | 0.002-64 |
| Compound 18 | 95% EtOH | 2560 | 0.002-64 |
| Compound 19 | 95% EtOH | 2560 | 0.002-32 |
| Compound 20 | 95% EtOH | 2560 | 0.002-64 |
| Compound 21 | 95% EtOH | 2560 | 0.002-64 |
| Compound 22 | 95% EtOH | 2560 | 0.002-64 |
| Compound 23 | 95% EtOH | 2560 | 0.002-64 |
| Compound 24 | 95% EtOH | 2560 | 0.002-64 |
| Compound 25 | 95% EtOH | 2560 | 0.002-64 |
| Compound 26 | 95% EtOH | 2560 | 0.002-64 |
| Compound 27 | 95% EtOH | 2560 | 0.002-64 |
| Compound 28 | 95% EtOH | 2560 | 0.002-64 |
| Compound 29 | 95% EtOH | 2560 | 0.002-64 |
| Compound 30 | 95% EtOH | 2560 | 0.002-64 |
| Compound 31 | 95% EtOH | 2560 | 0.002-64 |
| Compound 32 | 95% EtOH | 2560 | 0.002-64 |
| Compound 33 | 95% EtOH | 2560 | 0.002-64 |
| Compound 34 | 95% EtOH | 2560 | 0.002-64 |
| Compound 35 | 95% EtOH | 2560 | 0.002-64 |
| Aureobasidin | 95% EtOH | 2560 | 0.002-64 |
| Amphotericin B | 100% DMSO | 2560 | 0.002-64 |

All of the test isolates were originally received from either the American Type Culture Collection (ATCC), clinical labs, or directly from Aureogen Biosciences. Organisms stored by Micromyx were cultured on agar medium appropriate to each organism. Colonies were picked by swab from the isolation plates and put into suspension in appropriate broth containing cryoprotectant. The suspensions were aliquoted into cryogenic vials and maintained at −80° C.

Prior to testing, Candida isolates were streaked from the frozen vials on Sabouraud dextrose agar. The yeast isolates were incubated for 48 hours at 35° C. before use. The fungal isolates were obtained from enumerated fungal stocks previously prepared at Micromyx and stored in phosphate buffered saline at 4° C.

Test Media. The medium employed for the MIC assay was RPMI-1640 medium from HyClone Laboratories (Logan, Utah; Lot No. AYB60287A). The medium was prepared according to Clinical and Laboratory Standards Institute (CLSI) guidelines (1, 2), and modified to include 0.002% Tween-80. Candida parapsilosis ATCC 22019 (MMX 2323) and Aspergillus fumigatus ATCC MYA-3626 (MMX 5280) were also tested without Tween-80 to provide data for the quality control of amphotericin B in accordance with CLSI (3) and to assess the effect of Tween-80 on the activity of the test agents.

Test Procedure. The MIC assay method followed the procedure described by CLSI (1, 2) and employed automated liquid handlers to conduct serial dilutions and liquid transfers. Automated liquid handlers included the Multidrop 384 (Labsystems, Helsinki, Finland), Biomek 2000 and Biomek FX (Beckman Coulter, Fullerton Calif.). The wells in columns 2-12 in standard 96-well microdilution plates (Costar 3795) were filled with 150 µl of the appropriate diluent (95% EtOH for investigational compounds, 100% DMSO for amphotericin B). These assay plates would become the 'mother plates' from which the assay 'daughter plates' would be prepared. The drugs (300 µL at 40× the desired top concentration in the test plates) were dispensed into the appropriate well in Column 1 of the mother plates. The Biomek 2000 was used to make two-fold serial dilutions through Column 11 in the "mother plate". The wells of Column 12 contained no drug and served as the organism growth control wells.

The daughter plates were loaded with 185 µL per well on the Multidrop 384 with RPMI plus 0.002% Tween-80 or RPMI containing no Tween-80 for the testing of the two QC isolates. The daughter plates were prepared on the Biomek FX instrument which transferred 5 µL of drug solution from each well of a mother plate to each corresponding well of each daughter plate in a single step.

A standardized inoculum of each organism was prepared per CLSI methods (1, 2). For the Candida isolates, colonies were picked from the streak plate and a suspension was prepared in RPMI to equal a 0.5 McFarland standard. This suspension was diluted 1:100 in RPMI resulting in a final concentration of approximately 0.5-2.5×10$^3$ CFU/mL. For the *Aspergillus* isolates, based on the previously determined spore count (CFU/mL), the suspension was diluted in RPMI such that after inoculation a final concentration of approximately 0.2-2.5×104 CFU/mL was achieved. The inoculum for each organism was dispensed into sterile reservoirs divided by length (Beckman Coulter), and the Biomek 2000 was used to inoculate the plates. Daughter plates were placed on the Biomek 2000 work surface reversed so that inoculation took place from low to high drug concentration. The Biomek 2000 delivered 10 µL of standardized inoculum into each well. Thus, the wells of the daughter plates ultimately contained 185 µL of broth, 5 µL of drug solution, and 10 µL of inoculum.

Plates were stacked 3 high, covered with a lid on the top plate, placed into plastic bags, and incubated at 35° C. The *Candida* isolates were read after 24 hr incubation and again at 48 hr. The *Aspergillus* plates were incubated for 48 hr before reading.

The microplates were viewed from the bottom using a plate viewer. For each mother plate, an un-inoculated solubility control plate was observed for evidence of drug precipitation. The MIC was read and recorded as the lowest concentration of drug that inhibited visible growth of the organism. MECs were read where the growth shifted to a small, rounded, compact hyphal form as compared to the hyphal growth seen in the growth control well.

Compound precipitation was noted for all test compounds when tested with and without Tween-80. Distinct precipitation was noted at high concentrations for the tested compounds. However, lack of solubility at these high concentrations did not affect the ability to read the MIC/MEC endpoints.

Minimum inhibitory concentration (MIC) and minimum effective concentration (MEC) values for all test drugs are shown in Tables 4-13.

TABLE 4

MIC values for selected fungi for compounds 1-9.

| | MIC (µg/mL) | | | |
|---|---|---|---|---|
| Cmpd. No. | C. albicans MMX 2000 ATCC 10231 | C. parapsilosis MMX 2323 ATCC 22019 | C. parapsilosis MMX 2323 ATCC 22019 Without Tween-80 | C. neoformans MMX 0634 ATCC 90112 |
| 1 | 0.015 | 0.12 | 1 | 0.12 |
| 2 | 0.12 | 0.5 | 2 | 0.12 |
| 3 | 0.12 | 0.5 | 2 | 0.12 |
| 4 | 0.12 | 0.5 | 2 | 0.25 |
| 5 | 0.12 | 0.5 | 2 | 0.12 |
| 6 | 0.015 | 0.12 | 1 | 0.12 |
| 7 | 0.015 | 0.12 | 1 | 0.12 |
| 8 | >64 | >64 | >64 | >64 |
| 9 | 0.12 | 0.25 | 1 | 0.12 |
| Aureobasidin A | ≤0.002 | 0.008 | 0.25 | 0.06 |
| Amphotericin B | ≤0.06 | ≤0.06 | 0.25 (0.25-1)[1] | ≤0.06 |

[1]CLSI QC Range shown in parenthesis

TABLE 5

MIC and MEC values for selected fungi for compounds 1-9.

| | MIC/MEC (µg/mL) | | | | | | |
|---|---|---|---|---|---|---|---|
| Cmpd. No. | A. flavus MMX 5948 | A. fumigatus MMX MYA- 3626 | A. fumigatus MMX 5280 MYA- 3626 Without Tween-80 | A. fumigatus MMX 6781 MYA- 4609 | A. fumigatus MMX 6782 ATCC 13073 | A. fumigatus MMX 5944 | A. niger MMX 0624 ATCC 16888 |
| 1 | >64/1 | >64/0.5 | >64/2 | >64/0.5 | >64/0.5 | >64/0.5 | 0.25/0.25 |
| 2 | 1/0.5 | >64/0.5 | >64/8 | >64/0.5 | >64/0.25 | >64/0.5 | 0.5/0.5 |
| 3 | >64/>64 | >64/>64 | >64/>64 | >64/>64 | >64/>64 | >64/>64 | 1/1 |
| 4 | >64/>64 | >64/>64 | >64/>64 | >64/>64 | >64/1 | >64/1 | 0.5/0.5 |
| 5 | 1/0.5 | >64/0.5 | >64/4 | >64/0.5 | >64/0.5 | >64/0.5 | 0.5/0.5 |
| 6 | 0.25/0.12 | >64/1 | >64/2 | >64/1 | 1/0.25 | 1/0.5 | 0.12/0.12 |
| 7 | >64/>64 | >64/2 | >64/64 | >64/1 | >64/0.5 | >64/0.5 | 0.25/0.25 |
| 8 | >64/>64 | >64/>64 | >64/>64 | >64/>64 | >64/>64 | >64/>64 | >64/>64 |
| 9 | >64/>64 | >64/>64 | >64/>64 | >64/1 | >64/1 | >64/>64 | 0.25/0.25 |
| Aureobasidin | >64/>64 | >64/>64 | >64/>64 | >64/>64 | >64/2 | >64/2 | >64/>64 |
| Amphotericin B | 0.25 | 0.5 | 0.5 (0.5-4)[1] | 0.25 | 0.12 | 0.25 | 0.12 |

[1]CLSI QC Range shown in parenthesis

TABLE 6

MIC values for selected fungi for compounds 10-16, and 6.

| | MIC (μg/mL) | | | |
|---|---|---|---|---|
| Cmpd. No. | C. albicans MMX 2000 ATCC 10231 | C. parapsilosis MMX 2323 ATCC 22019 | C. parapsilosis MMX 2323 ATCC 22019 Without Tween-80 | C. neoformans MMX 0634 ATCC 90112 |
| 10 | 0.03 | 0.12 | 1 | 0.12 |
| 11 | 0.06 | 0.25 | 1 | 0.25 |
| 12 | 0.03 | 0.12 | 1 | 0.5 |
| 13 | 0.5 | >64 | >64 | 0.5 |
| 14 | 0.03 | 0.12 | 1 | 0.5 |
| 15 | 0.015 | 0.03 | 0.5 | 0.06 |
| 16 | 0.03 | 0.12 | 1 | 0.12 |
| 6 | 0.06 | 0.12 | 1 | 0.12 |
| Amph. B | 0.12 | 0.25 | 0.5 (0.25-1)[1] | 0.12 |

[1]CLSI QC Range shown in parenthesis

TABLE 7

MIC and MEC values for selected fungi for compounds 10-16, and 6.

| | MIC/MEC (μg/mL) | | | | | | | |
|---|---|---|---|---|---|---|---|---|
| Cmpd. No. | A. flavus MMX 5948 | A. fumigatus from Aureogen | A. fumigatus MMX 5280 MYA-3626 | A. fumigatus MMX 5280 MYA-3626 Without Tween-80 | A. fumigatus MMX 6781 MYA-4609 | A. fumigatus MMX 6782 ATCC 13073 | A. fumigatus MMX 5944 | A. niger MMX 0624 ATCC 16888 |
| 10 | 1/0.5 | 1/0.25 | 1/0.25 | 2/1 | 1/0.25 | 1/0.25 | 0.5/0.12 | 0.06/0.06 |
| 11 | >64/1 | >64/2 | >64/8 | >64/4 | 64/8 | >64/0.5 | >64/2 | 0.5/0.5 |
| 12 | >64/>64 | >64/>64 | >64/>64 | >64/>64 | >64/>64 | >64/>64 | >64/>64 | >64/>64 |
| 13 | >64/1 | >64/>64 | >64/>64 | >64/>64 | >64/>64 | >64/1 | >64/1 | 8/2 |
| 14 | >64/>64 | >64/1 | >64/0.5 | >64/2 | >64/1 | >64/0.25 | 8/1 | 0.12/0.12 |
| 15 | 0.25/0.12 | 0.25/0.06 | 0.25/0.12 | 1/1 | 0.25/0.12 | 0.5/0.12 | 0.5/0.06 | 0.03/0.03 |
| 16 | 1/0.5 | >64/2 | >64/2 | >64/2 | >64/2 | >64/1 | >64/2 | 0.5/0.5 |
| 6 | 0.5/0.12 | 1/0.5 | >64/1 | >64/2 | >64/1 | >64/0.5 | 1/0.5 | 0.06/0.06 |
| Amph. B | 0.5 | 2 | 2 | 2 (0.5-4)[1] | 1 | 1 | 2 | 0.25 |

[1]CLSI QC Range shown in parenthesis

TABLE 8

MIC values for selected fungi for compounds 15, 18-22, 17, and 23-29.

| | MIC (μg/mL) | | | |
|---|---|---|---|---|
| Cmpd. No. | C. albicans MMX 2000 ATCC 10231 | C. parapsilosis MMX 2323 ATCC 22019 | C. parapsilosis MMX 2323 ATCC 22019 Without Tween-80 | C. neoformans MMX 0634 ATCC 90112 |
| 15 | 0.004 | 0.015 | 0.5 | 0.03 |
| 18 | 0.03 | 0.12 | 1 | 0.25 |
| 19 | 0.015 | 0.03 | 1 | 0.03 |
| 20 | 0.008 | 0.03 | 1 | 0.03 |
| 21 | 0.015 | 0.06 | 1 | 0.25 |
| 22 | 0.03 | 0.06 | 1 | 0.25 |
| 17 | 0.015 | 0.06 | 1 | 0.25 |
| 23 | 0.06 | 0.12 | 1 | 0.25 |
| 24 | 0.03 | 0.12 | 1 | 0.5 |
| 25 | 0.015 | 0.03 | 1 | 0.015 |
| 26 | 0.12 | 1 | 2 | 0.25 |
| 27 | 0.015 | 0.12 | 1 | 0.12 |
| 28 | 0.015 | 0.06 | 0.5 | 0.06 |
| 29 | 0.008 | 0.06 | 1 | 0.06 |
| Amphotericin B | ≤0.06 | ≤0.06 | ≤0.06 (0.25-1)[1] | ≤0.06 |

[1]CLSI QC Range shown in parenthesis

TABLE 9

MIC and MEC values for selected fungi for compounds 15, 18-22, 17, and 23-29.

| | MIC/MEC (μg/mL) | | | | | | | |
|---|---|---|---|---|---|---|---|---|
| Cmpd. No. | A. flavus MMX 5948 | A. fumigatus from Aureogen | A. fumigatus MMX 5280 MYA-3626 | A. fumigatus MMX 5280 MYA-3626 Without Tween-80 | A. fumigatus MMX 6781 MYA-4609 | A. fumigatus MMX 6782 ATCC 13073 | A. fumigatus MMX 5944 | A. niger MMX 0624 ATCC 16888 |
| 15 | 0.25/0.03 | 0.25/0.12 | 0.5/0.12 | 2/1 | 0.5/0.12 | 0.25/0.03 | 0.25/0.06 | 0.015/0.008 |
| 18 | 0.5/0.25 | >64/>64 | >64/>64 | >64/>64 | >64/>64 | >64/5.64 | >64/>64 | 0.25/0.06 |
| 19 | 0.015/0.008 | 0.25/0.06 | 0.25/0.06 | 1/0.5 | 0.12/0.06 | 0.12/0.03 | 0.06/0.015 | 0.015/0.008 |
| 20 | 0.015/0.008 | 0.12/0.03 | 0.25/0.06 | 1/0.5 | 0.12/0.06 | 0.12/0.03 | 0.12/0.015 | 0.015/0.008 |
| 21 | >64/0.25 | >64/>64 | >64/>64 | >64/>64 | >64/>64 | >64/>64 | >64/>64 | 0.25/0.06 |
| 22 | >64/>64 | >64/>64 | >64/>64 | >64/>64 | >64/>64 | >64/>64 | >64/>64 | 0.5/0.25 |
| 17 | 0.5/0.12 | >64/>64 | >64/>64 | >64/>64 | >64/>64 | >64/>64 | >64/>64 | 0.12/0.06 |
| 23 | >64/>64 | >64/>64 | >64/>64 | >64/>64 | >64/>64 | >64/>64 | >64/>64 | 0.25/0.12 |
| 24 | 0.5/0.25 | >64/>64 | >64/>64 | >64/>64 | >64/>64 | >64/>64 | >64/>64 | 0.25/0.25 |
| 25 | 0.008/0.008 | 0.12/0.06 | 0.12/0.03 | 1/1 | 0.12/0.03 | 0.06/0.015 | 0.06/0.015 | 0.015/0.015 |
| 26 | >64/>64 | >64/>64 | >64/>64 | >64/>64 | >64/>64 | >64/>64 | >64/>64 | 2/2 |
| 27 | 0.5/0.12 | >64/>64 | >64/>64 | >64/>64 | >64/>64 | >64/>64 | >64/>64 | 0.06/0.06 |
| 28 | >64/>64 | >64/>64 | >64/>64 | >64/>64 | >64/>64 | >64/>64 | >64/>64 | 0.12/0.12 |
| 29 | >64/>64 | >64/>64 | >64/>64 | >64/>64 | >64/>64 | >64/5.64 | >64/>64 | 0.12/0.12 |
| Amph. B | ≤0.06 | 0.25 | 0.25 | 0.5 (0.5-4)[1] | 0.25 | 0.12 | 0.25 | 0.12 |

[1]CLSI QC Range shown in parenthesis

TABLE 10

MIC values for selected fungi for compounds 19, 20, 25, and 30-33.

| | MIC (μg/mL) | | | | |
|---|---|---|---|---|---|
| Cmpd. No. | C. albicans MMX 2000 ATCC 10231 | C. albicans MMX 2000 ATCC 10231 Without Tween-80 | C. parapsilosis MMX 2323 ATCC 22019 | C. parapsilosis MMX 2323 ATCC 22019 Without Tween-80 | C. neoformans MMX 0634 ATCC 90112[2] |
| 19 | 0.008 | 0.5 | 0.06 | 2 | 0.06 |
| 20 | 0.004 | 0.5 | 0.03 | 2 | 0.12 |
| 25 | 0.008 | 1 | 0.06 | 1 | 0.06 |
| 30 | 0.015 | 0.5 | 0.06 | 2 | 0.25 |
| 31 | 0.06 | 1 | 0.5 | 2 | 1 |
| 32 | 0.03 | 2 | 0.25 | 2 | 2 |
| 33 | 0.004 | 0.5 | 0.03 | 0.5 | 0.06 |
| Amph. B | ≤0.06 | ≤0.06 | ≤0.06 | ≤0.06 (0.25-1)[1] | ≤0.06 |

[1]CLSI QC Range shown in parenthesis
[2]72 hour

TABLE 11

MIC and MEC values for selected fungi for compounds 19, 20, 25, and 30-33.

| | MIC/MEC (μg/mL) | | | | | | | |
|---|---|---|---|---|---|---|---|---|
| Cmpd. No. | A. flavus MMX 5948 | A. fumigatus from Aureogen | A. fumigatus MMX 5280 MYA-3626 | A. fumigatus MMX 5280 MYA-3626 Without Tween-80 | A. fumigatus MMX 6781 MYA-4609 | A. fumigatus MMX 6782 ATCC 13073 | A. fumigatus MMX 5944 | A. niger MMX 0624 ATCC 16888 |
| 19 | 0.03/0.015 | 0.25/0.03 | 0.5/0.06 | 2/1 | 0.12/0.06 | 0.12/0.03 | 0.06/0.015 | 0.015/0.008 |
| 20 | 0.015/0.008 | 0.12/0.06 | 0.25/0.03 | 2/1 | 0.12/0.06 | 0.12/0.03 | 0.06/0.03 | 0.015/0.008 |
| 25 | 0.03/0.015 | 0.12/0.06 | 0.12/0.03 | 1/0.5 | 0.12/0.03 | 0.06/0.015 | 0.06/0.015 | 0.015/0.008 |
| 30 | 0.5/0.12 | 1/0.5 | 2/1 | 2/1 | 2/1 | 2/0.5 | 1/0.5 | 0.5/0.5 |
| 31 | 0.5/0.12 | 0.5/0.25 | 2/0.5 | 1/1 | 2/1 | 2/1 | 1/0.5 | 1/0.5 |

TABLE 11-continued

MIC and MEC values for selected fungi for compounds 19, 20, 25, and 30-33.

| | MIC/MEC (µg/mL) | | | | | | | |
|---|---|---|---|---|---|---|---|---|
| Cmpd. No. | A. flavus MMX 5948 | A. fumigatus from Aureogen | A. fumigatus MMX 5280 MYA-3626 | A. fumigatus MMX 5280 MYA-3626 Without Tween-80 | A. fumigatus MMX 6781 MYA-4609 | A. fumigatus MMX 6782 ATCC 13073 | A. fumigatus MMX 5944 | A. niger MMX 0624 ATCC 16888 |
| 32 | 1/0.25 | >64/>64 | >64/2 | >64/>64 | >64/>64 | >64/>64 | >64/1 | 1/0.5 |
| 33 | 0.5/0.12 | 0.06/0.06 | 0.25/0.015 | 1/0.5 | 0.12/0.03 | 0.12/0.06 | 0.5/0.5 | 0.03/0.03 |
| Amph. B | ≤0.06 | ≤0.06 | ≤0.06 | ≤0.06 (0.5-4)[1] | ≤0.06 | ≤0.06 | ≤0.06 | ≤0.06 |

[1] CLSI QC Range shown in parenthesis
[2] 72 hour

TABLE 12

MIC values for selected fungi for compounds 19, 20, 25, and 30-33.

| | MIC (µg/mL) | | | | |
|---|---|---|---|---|---|
| Cmpd. No. | C. albicans MMX 2000 ATCC 10231 | C. albicans MMX 2000 ATCC 10231 Without Tween-80 | C. parapsilosis MMX 2323 ATCC 22019 | C. parapsilosis MMX 2323 ATCC 22019 Without Tween-80 | C. neoformans MMX 0634 ATCC 90112[2] |
| 19 | 0.008 | 0.5 | 0.06 | 2 | 0.06 |
| 20 | 0.004 | 0.5 | 0.03 | 2 | 0.12 |
| 25 | 0.008 | 1 | 0.06 | 1 | 0.06 |
| 30 | 0.015 | 0.5 | 0.06 | 2 | 0.25 |
| 31 | 0.06 | 1 | 0.5 | 2 | 1 |
| 32 | 0.03 | 2 | 0.25 | 2 | 2 |
| 33 | 0.004 | 0.5 | 0.03 | 0.5 | 0.06 |
| Amph. B | ≤0.06 | ≤0.06 | ≤0.06 | ≤0.06 (0.25-1)[1] | ≤0.06 |

[1] CLSI QC Range shown in parenthesis
[2] 72 hour

TABLE 13

MIC and MEC values for selected fungi for compounds 19, 20, 25, and 30-33.

| | MIC/MEC (µg/mL) | | | | | | | |
|---|---|---|---|---|---|---|---|---|
| Cmpd. No. | A. flavus MMX 5948 | A. fumigatus from Aureogen | A. fumigatus MMX 5280 ATCC MYA-3626 | A. fumigatus MMX 5280 ATCC MYA-3626 Without Tween-80 | A. fumigatus MMX 6781 ATCC MYA-4609 | A. fumigatus MMX 6782 ATCC 13073 | A. fumigatus MMX 5944 | A. niger MMX 0624 ATCC 16888 |
| 19 | 0.03/0.015 | 0.25/0.03 | 0.5/0.06 | 2/1 | 0.12/0.06 | 0.12/0.03 | 0.06/0.015 | 0.015/0.008 |
| 20 | 0.015/0.008 | 0.12/0.06 | 0.25/0.03 | 2/1 | 0.12/0.06 | 0.12/0.03 | 0.06/0.03 | 0.015/0.008 |
| 25 | 0.03/0.015 | 0.12/0.06 | 0.12/0.03 | 1/0.5 | 0.12/0.03 | 0.06/0.015 | 0.06/0.015 | 0.015/0.008 |
| 30 | 0.5/0.12 | 1/0.5 | 2/1 | 2/1 | 2/1 | 2/0.5 | 1/0.5 | 0.5/0.5 |
| 31 | 0.5/0.12 | 0.5/0.25 | 2/0.5 | 2/1 | 2/1 | 2/1 | 1/0.5 | 1/0.5 |
| 32 | 1/0.25 | >64/>64 | >64/2 | >64/>64 | >64/>64 | >64/>64 | >64/1 | 1/0.5 |
| 33 | 0.5/0.12 | 0.06/0.06 | 0.25/0.015 | 1/0.5 | 0.12/0.03 | 0.12/0.06 | 0.5/0.5 | 0.03/0.03 |
| Amph. B | ≤0.06 | ≤0.06 | ≤0.06 | ≤0.06 (0.5-4)[1] | ≤0.06 | ≤0.06 | ≤0.06 | ≤0.06 |

[1] CLSI QC Range shown in parenthesis

Additionally, following the MIC assay procedure described above, Compound No. 25 possessed a MIC of 0.15 μg/ml in *Coccidiodes immitus.*

Example 36: Antifungal Efficacy of Compound No. 25 in an Immunocompromised Murine Model of Disseminated Aspergillosis This study was aimed at evaluating the efficacy of Compound No. 25 against hematogenously disseminated aspergillosis in an immunosuppressed murine model. Compound No. 25 was prepared as described in Example 26 without further purificiation or separation of positional isomers and A request was made to the Animal Resource Center (ARC) at Case Western Reserve University to order the required number of female CD-1 mice (Charles River Laboratories, Willmington, Mass.) with a body weight of ~20 g. Animals were allowed to acclimate for a minimum of 5 days prior to use. Environmental controls for the animal room were set to maintain a temperature of 16 to 22° C., a relative humidity of 30-70%, and a 12:12 light-dark cycle.

Preparation of Standard Inoculum a. Organism

A clinical isolate of *Aspergillus fumigatus* MRL #21865 was obtained from the Culture Collection of CWRU Center for Medical Mycology. The minimum inhibitory concentration (MIC) of Compound 25 against this strain was assessed prior to initiation of this in vivo study to confirm the activity of the test compound. Endpoints for the MIC evaluation were read at 50 and 100% inhibition at 24 and 48 hours. From the frozen stock, the cells were sub-cultured on Potato Dextrose Agar (PDA) plates. Cells were harvested using sterile saline with 0.05% Tween 80, centrifuged, and washed three times with normal saline (0.85% NaCl). A challenge inoculum of $1\times10^7$ was prepared using a hemacytometer.

b. Supplies and Equipment

| | |
|---|---|
| Hemacytometer | Vortex |
| Sterile conical tubes | Centrifuge |
| Serological pipettes | Gloves |
| Disposable syringes | Cell counter |
| Adjustable volume pipettes | Culture plates |
| Microscope | Shaking water bath | c. Reagents and Media

Sterile normal saline (0.85%)

Chloramphenicol (0.05 g/L of agar medium)

Potato Dextrose Agar (Difco Laboratories)

d. Verification of Inoculum Count

To check the inoculum count, ten-fold dilutions of *A. fumigatus* working conidial suspension were plated onto PDA media. The plates were incubated at 37° C. for 2-4 days and the colony counts determined.

Immunosuppression

Mice received cyclophosphamide, 200 mg/kg administered intravenously 3 days prior to challenge. On the day of the challenge, blood was collected from one mouse from each group for a white blood cell count to verify immunosuppression.

Infection

Each mouse was inoculated with $1\times10^7$ conidia in 0.1 ml of normal saline (via the tail vein). Animals were considered infected after successful IV dosing of the inoculum and inoculum confirmation. The efficacy of the treatment and control groups was assessed using tissue fungal burden and survival as indicators, using 5 mice per group (selected randomly) for fungal burden and 10 mice per group for survival.

Treatment Groups

Infected mice were randomized into the following groups (5 for tissue fungal burden, and 10 for survival per group); Compound No. 25 (200 mg/kg), voriconazole, vehicle, and untreated control groups.

Schedule of Treatment

Beginning two hours post inoculation, animals were treated orally. Compound 25 was administered once a day for a period of seven days, while voriconazole 30 mg/kg was administered twice daily for seven days.

Tissue Fungal Burden

Mice were sacrificed one day after the last day of treatment; then kidneys and lungs were removed aseptically and weighed. Tissues were homogenized and serially diluted in phosphate buffered saline. The homogenates were cultured for 2-4 days on PDA plates to determine the colony forming units (CFU); tissue fungal burden was expressed as CFUs/gram of tissue. Data from this experiment are provided in FIG. 34.

Survival Analysis

Infected mice were monitored and any signs of illness (i.e. lethargy, weight loss, general failure to thrive), or mortality was recorded twice daily for 28 days post inoculation. An average weight for each treatment group was recorded daily. Moribund animals that fail to take food/drink were euthanized. Data from this experiment are provided in FIG. 33.

Statistical Analysis

For analyses, the average log 10 CFU±the standard deviation was calculated from the obtained data and compared between different treatment groups. The Oneway ANOVA with a Bonferroni post-hoc test was employed in determining significance. Differences in survival will be compared using the Kaplan-Meier test. All statistical analysis was performed using SPSS for Windows, version 22.0 (Chicago, Ill.). A P-value of less than 0.05 was considered statistically significant.

Example 37: Antifungal Activity of Positional Isomers of Compound X

Compound X

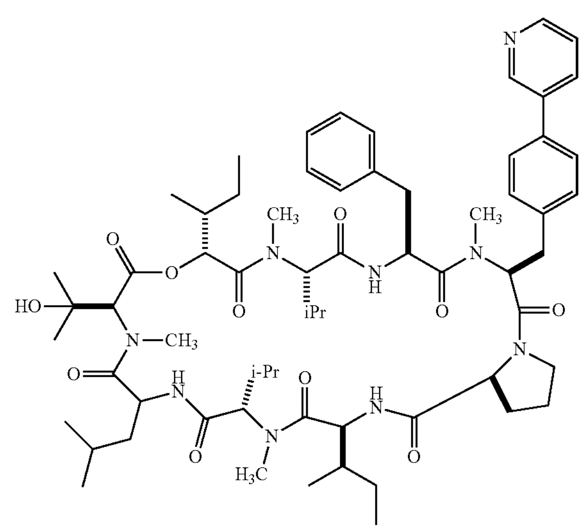

Para-substituted Isomer

139

-continued

Compound X

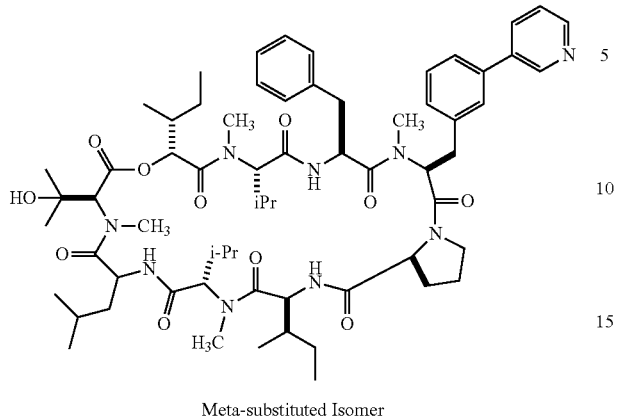

Meta-substituted Isomer

Figure 35:
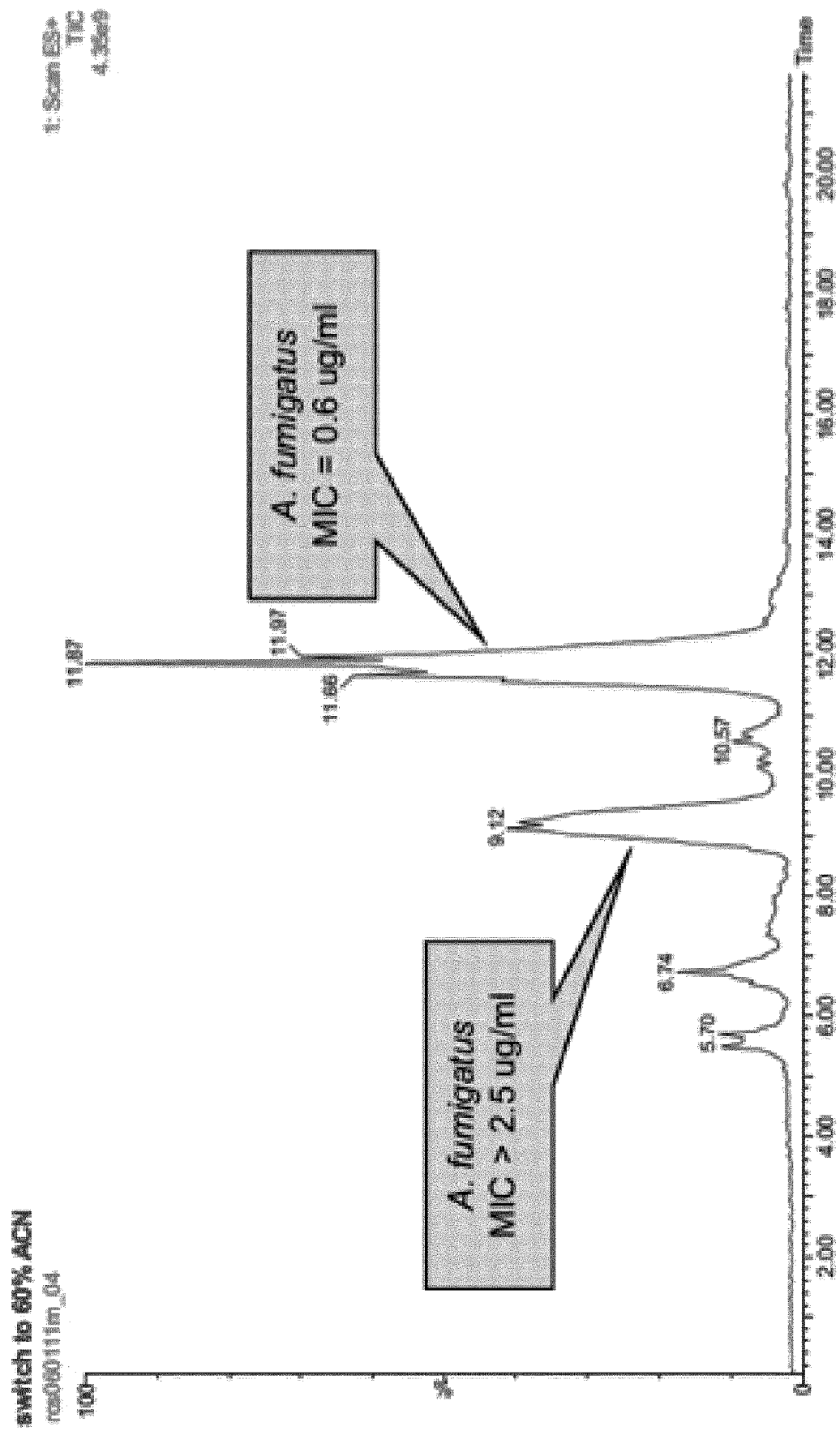
FIG. 35 presents the HPLC chromatograph of Compound X and MIC values for its meta and para positional isomers according to Example 37.

Referring to FIG. 35, preparative separation of the Compound X isomers was done on a Waters XBridge BEH130 PREP C18 5 μm 19×150 mm column. The column was run isocratically in 55% ACN (containing 0.1% formic acid) at room temperature (23 degree C.) using boxcar (several sequential) injections. The flow rate was 8.5 ml/min.

Each of the separated positional isomers was assayed, as described in Example 35 for antifungal activity in *A. fumigates*. The para substituted positional isomer of Compound X had a MIC of >2.5 μg/ml while the meta-substituted positional isomer of Compound X had a MIC of 0.6 μg/ml.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of Formula I-P2:

I-P2

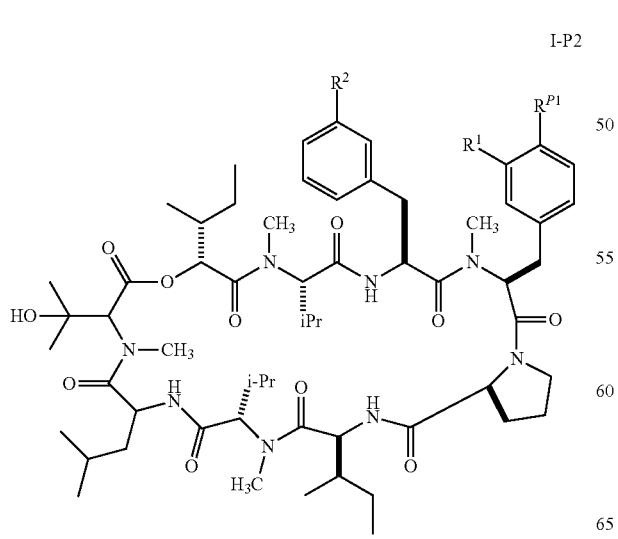

or a pharmaceutically acceptable salt thereof, wherein
R$^1$ is phenyl, naphthyl, a 5 to 6 membered monocyclic heteroaryl with 1 to 3 nitrogen atoms, or a 9-12

140 or a pharmaceutically acceptable salt thereof, wherein
each of R$^1$ and R$^{P1}$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein the phenyl, naphthyl, 5 to 6 membered monocyclic heteroaryl, and 9-12 membered bicyclic heteroaryl are each independently substituted with x instances of R$^3$;
x is independently 1, 2, or 3;
each R$^3$ is independently

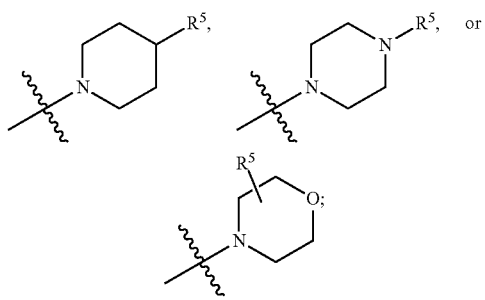

each R$^5$ is independently selected from the group consisting of —H, C$_{1-4}$ alkyl, —N(CH$_3$)$_2$, —C(O)—CH$_3$, —C(O)—CH$_2$—CH$_3$, and —C(O)—O—C(CH$_3$)$_3$;
R$^2$ is independently selected from hydrogen, phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein R$^2$ is optionally substituted with x instances of R$^3$;
provided that
at least one of R$^1$, R$^2$, and R$^{P1}$ is not hydrogen.
2. The compound of claim 1, wherein the compound of Formula I-P2 is a compound of Formula I:

I

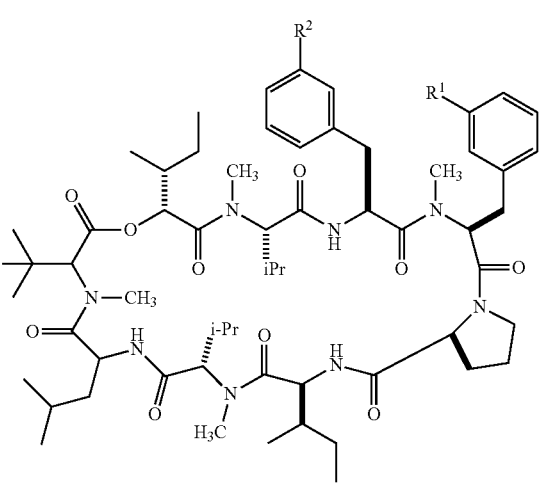

or a pharmaceutically acceptable salt thereof, wherein
R$^1$ is phenyl, naphthyl, a 5 to 6 membered monocyclic heteroaryl with 1 to 3 nitrogen atoms, or a 9-12 membered bicyclic heteroaryl having 1-5 heteroatoms independently selected from nitrogen, oxygen, or sulfur, wherein $R^1$ is substituted with x instances of $R^3$;

x is 1, 2, or 3; and $R^2$ is —H or $R^1$.

3. The compound of claim 2, wherein $R^2$ is —H.

4. The compound of claim 2, wherein $R^1$ is phenyl substituted with x occurrences of $R^3$, wherein x is 1.

5. The compound of claim 4, wherein $R^3$ is

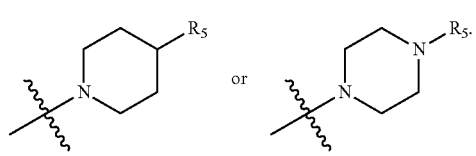

6. The compound of claim 5, wherein each $R^5$ is independently —H or $C_{1-4}$ alkyl.

7. The compound of claim 2, wherein x is 2.

8. The compound of claim 2, wherein $R^1$ is naphthyl substituted with x occurrences of $R^3$, wherein x is 1.

9. The compound of claim 8, wherein $R^1$ is selected from

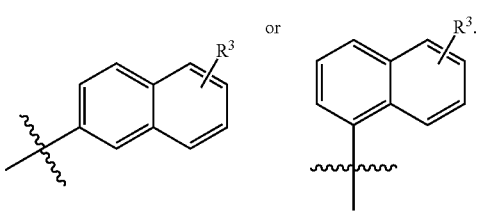

10. The compound of claim 2, wherein $R^1$ is a 5 to 6 membered monocyclic heteroaryl having 1 to 3 nitrogen atoms, wherein the monocyclic heteroaryl is substituted with x occurrences of $R^3$, wherein x is 1, 2, or 3.

11. The compound of claim 10, wherein $R^1$ is selected from pyrazole, pyridine, pyrazine, or pyrimidine, and x is 1 or 2.

12. The compound of claim 11, wherein $R^1$ is

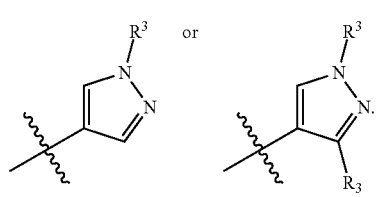

13. The compound of claim 10, wherein $R^1$ is

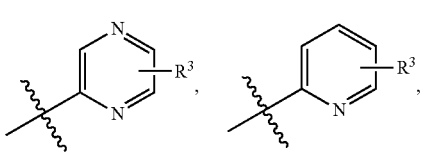

-continued

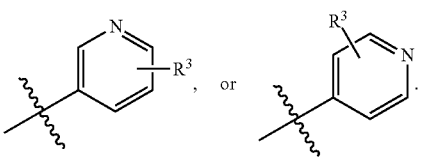

14. The compound of claim 13, wherein $R^1$ is

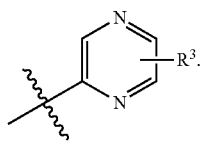

15. The compound of claim 14, wherein $R^1$ is

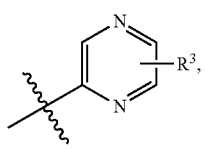

and $R^3$ is

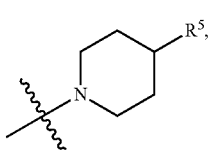

wherein $R^5$ is $C_{1-4}$ alkyl.

16. The compound of claim 13, wherein $R^1$ is selected from

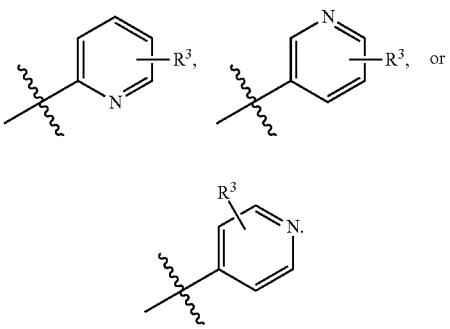

17. The compound of claim 2, wherein $R^1$ is a 9 to 10 membered bicyclic heteroaryl having 1 to 3 heteroatoms independently selected from N, O, or S, wherein the bicyclic heteroaryl is substituted with x occurrences of $R^3$, wherein x is 1.

18. The compound of claim 17, wherein $R^1$ is selected from

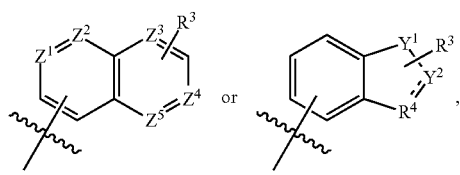 or 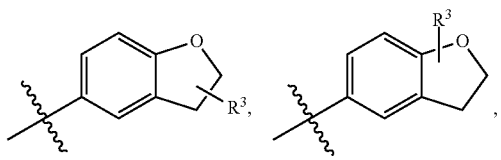, wherein each of $Z^1$, $Z^2$, $Z^3$, $Z^4$, and $Z^5$ is independently $CR^3$ or N, wherein at least one of $Z^1$, $Z^2$, $Z^3$, $Z^4$, and $Z^5$ is N;

each of $Y^1$, $Y^2$, and $Y^3$ is independently CH, $CR^3$, N, $NR^3$, or O, wherein at least one of $Y^1$, $Y^2$, and $Y^3$ are N, $NR^3$, or O; and --- is a bond or is absent, provided that a) no more than three of $Z^1$, $Z^2$, $Z^3$, $Z^4$, and $Z^5$ is N;
b) $R^1$ is substituted with no more than three occurrences of $R^3$;
c) if either of $Y^2$ or $Y^3$ is —O—, then --- is absent; and
d) if --- is a bond, then $Y^2$ is N, CH, or $CR^3$, and $Y^3$ is N, CH, or $CR^3$.

19. The compound of claim 18, wherein $R^1$ is selected from

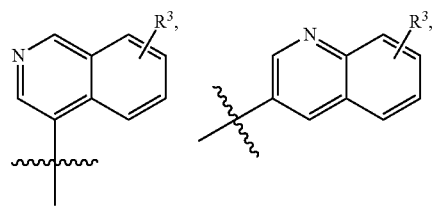

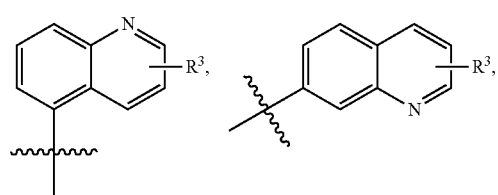

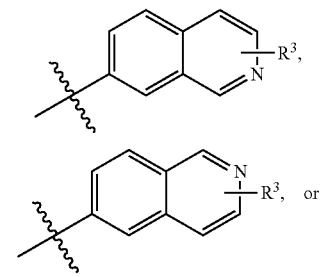

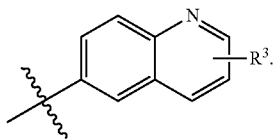

20. The compound of claim 18, wherein $R^1$ is selected from

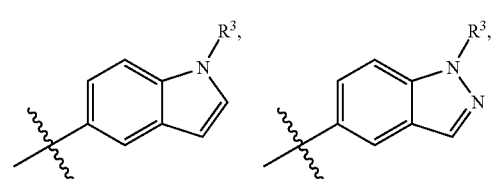

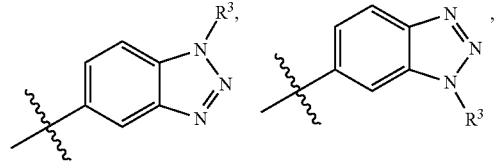

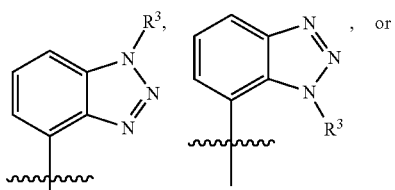

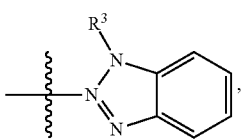

21. The compound of claim 1, which is a compound of Formula I-A:

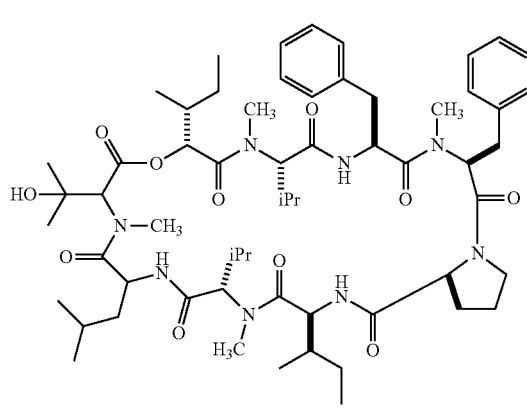

or a pharmaceutically acceptable salt thereof, wherein R¹ is

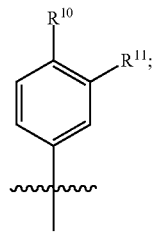

each of $R^{10}$ and $R^{11}$ is independently H or

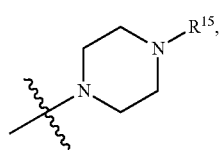

wherein $R^{15}$ is —H or —$C_{1-3}$ alkyl, provided that: when $R^{10}$ is —H, then $R^{11}$ is not —H.

22. The compound of claim 21, wherein R¹ is

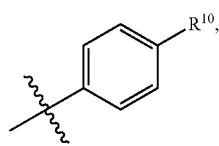

and $R^{10}$ is

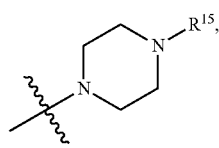

wherein $R^{15}$ is —H or —$C_{1-3}$ alkyl.

23. The compound of claim 21, wherein R¹ is

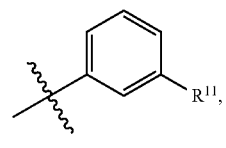

and $R^{11}$ is

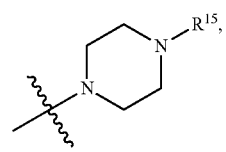

wherein $R^{15}$ is —H or —$C_{1-3}$ alkyl.

24. The compound of claim 1, which is a compound of Formula I-B:

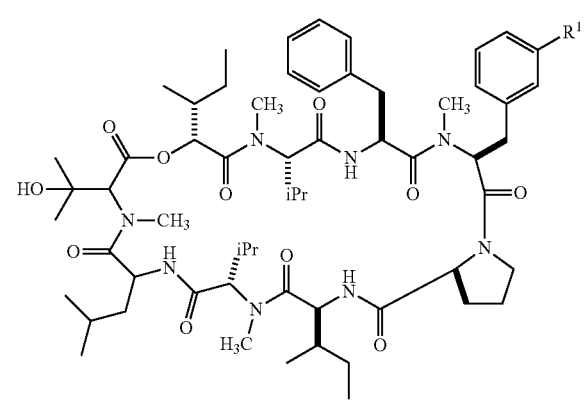

or a pharmaceutically acceptable salt thereof, wherein R¹ is

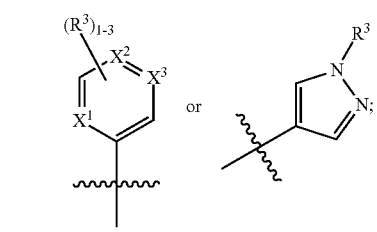

each of $X^1$, $X^2$, and $X^3$ is independently CH, $CR^3$ or N, wherein $R^1$ is substituted with 1 to 3 occurrences of $R^3$;

each $R^3$ is independently selected from

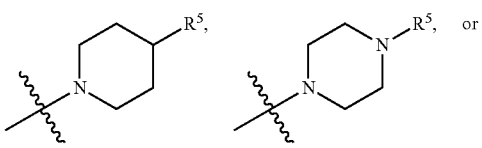

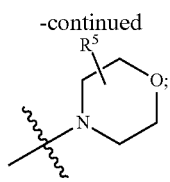
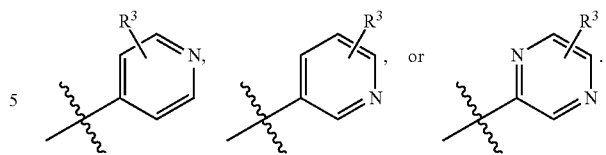
26. The compound of claim 24, wherein R¹ is
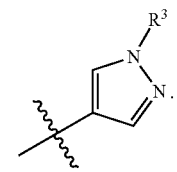
each R⁵ is independently selected from the group consisting of —H, $C_{1-4}$ alkyl, —N(CH₃)₂, —C(O)—CH₃, —C(O)—CH₂—CH₃, and —C(O)—O—C(CH₃)₃;
provided that
  i) when X² is N, then X³ is CH or CR³; and
  ii) when X³ is N, then X² is CH or CR³.
25. The compound of claim 24, wherein R¹ is selected from
27. The compound of claim 1, which is a compound selected from
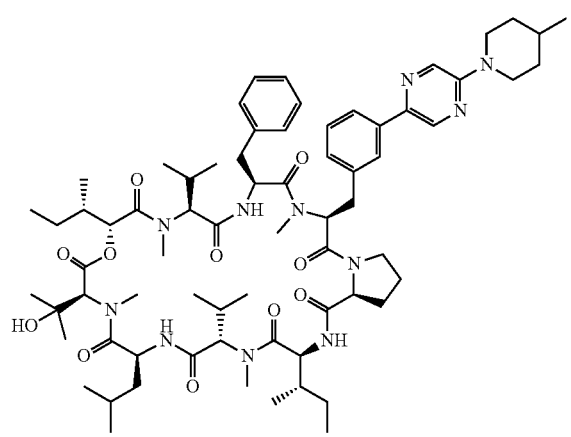
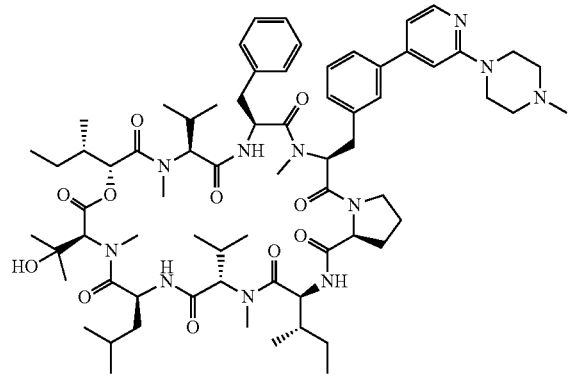
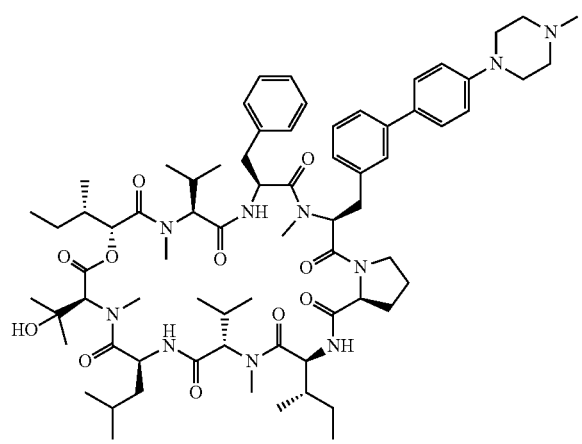
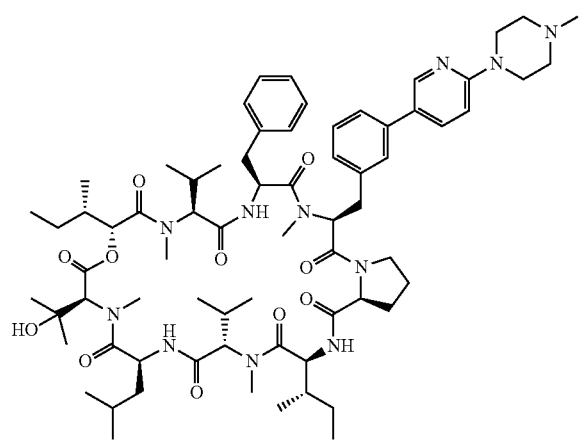

-continued
21
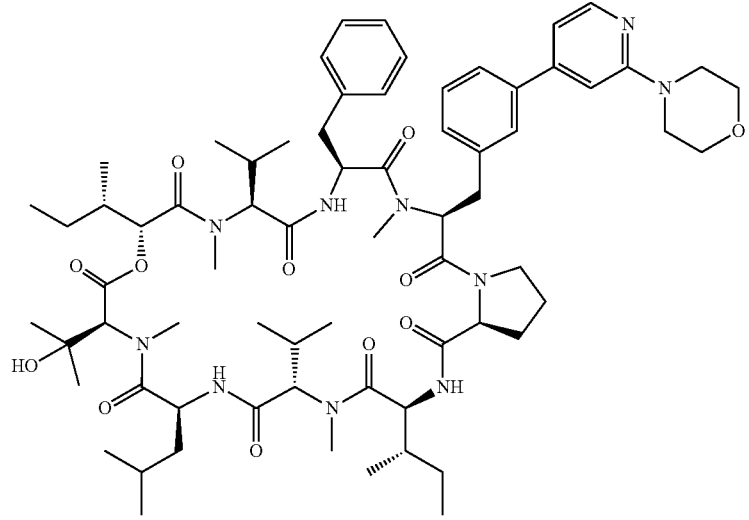
23
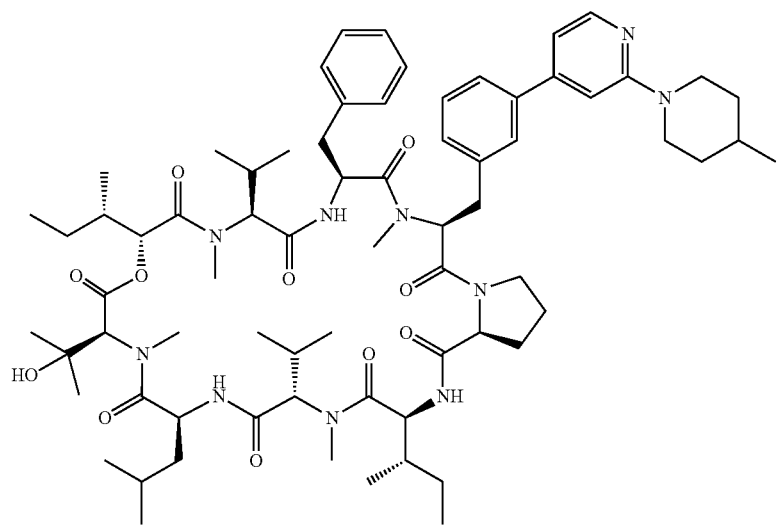
24
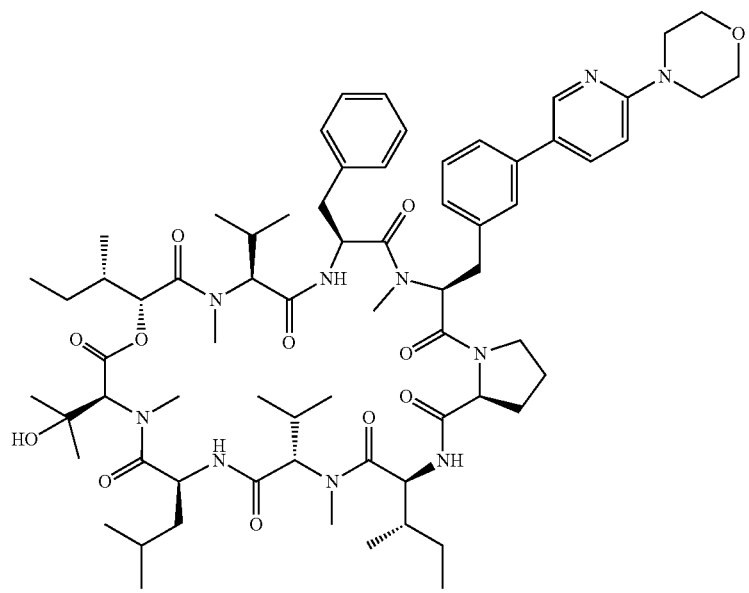

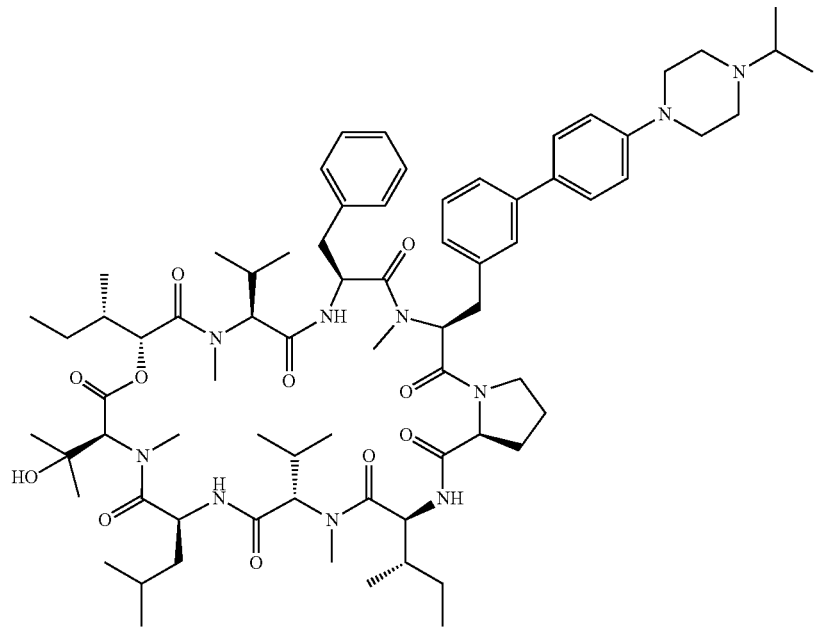
25
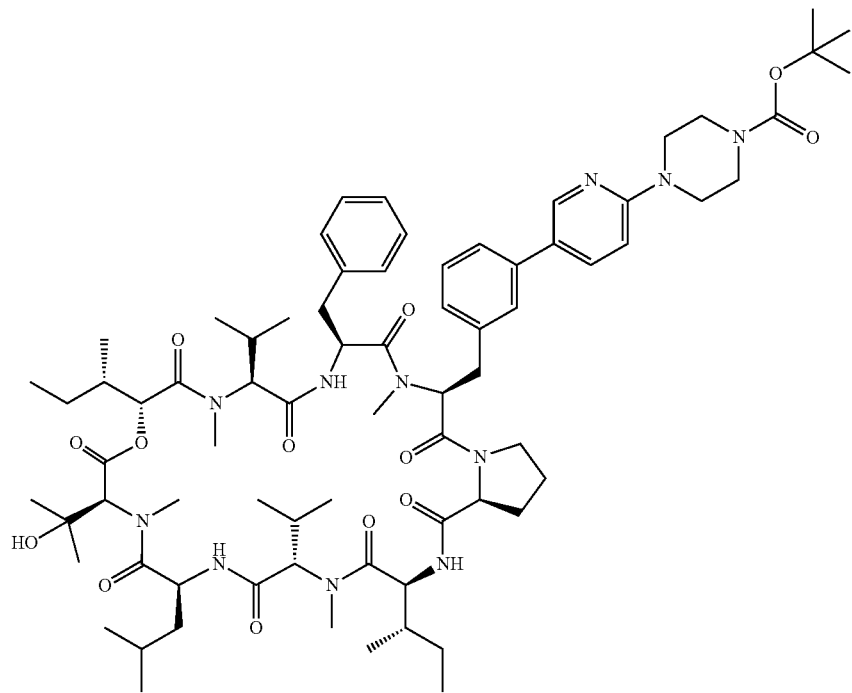
26

30
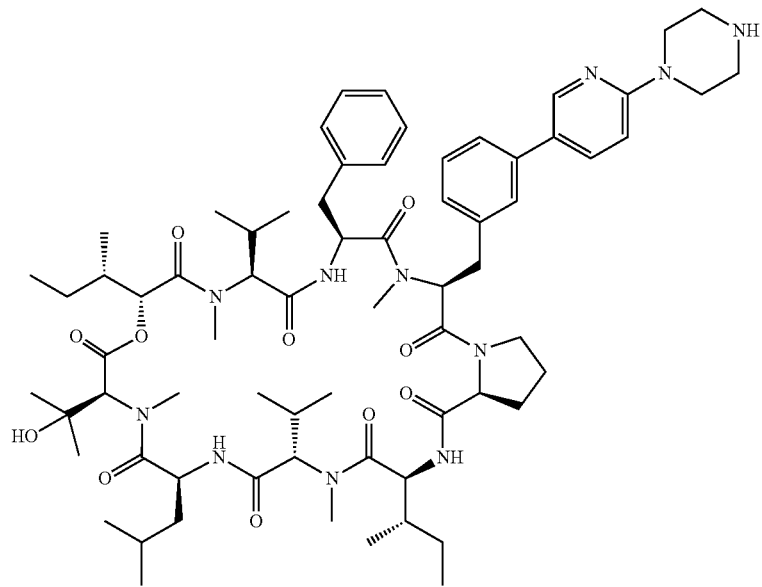
31
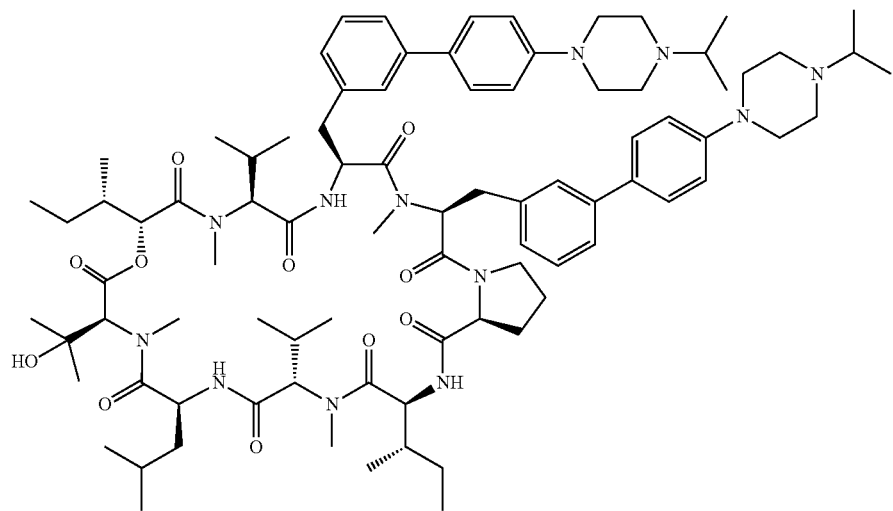

-continued

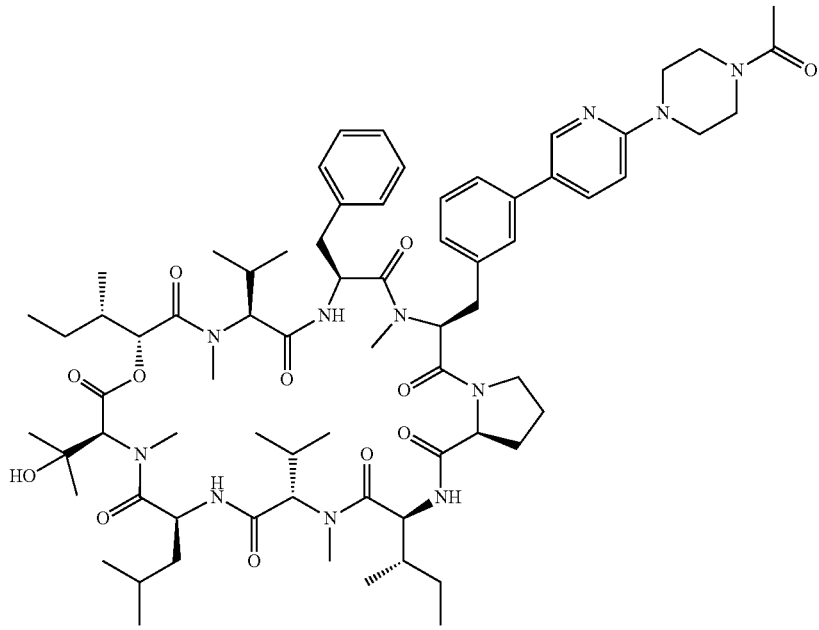

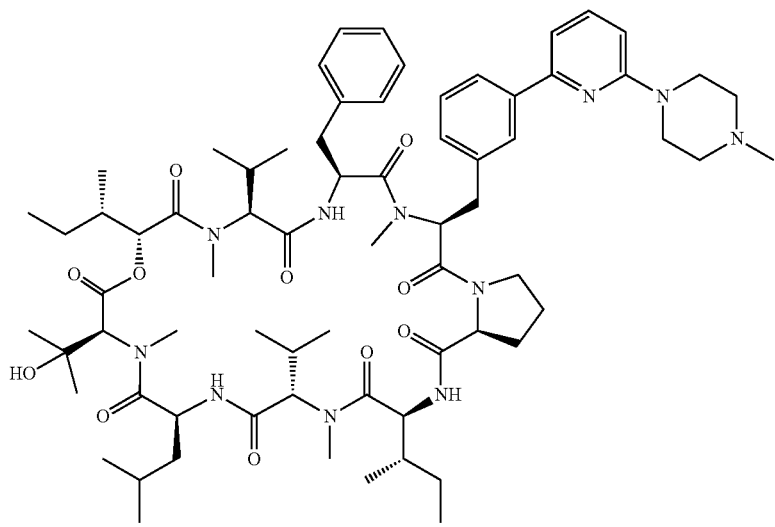

or a pharmaceutically acceptable salt thereof.

28. A pharmaceutical composition comprising a compound of claim 1, and a pharmaceutically acceptable carrier, vehicle, or adjuvant.

29. A method of treating a fungal infection in a patient or of reducing the number of fungi in a biological sample comprising administering to said patient or said biological sample an effective amount of the compound of claim 1.

30. The method of claim 29, wherein the fungi is selected from *Aspergillus, Candida, Cryptococcus, Coccidiodes, Issatchenkia, Saccharomyces, Emericella*, or *Trichophyton*.

* * * * *